(12) United States Patent
Quattropani et al.

(10) Patent No.: US 8,202,856 B2
(45) Date of Patent: Jun. 19, 2012

(54) TRIAZOLE OXADIAZOLES DERIVATIVES

(75) Inventors: Anna Quattropani, Geneva (CH); Christophe Cleva, La Tour (FR); Eric Sebille, Le Poizat (FR); Matthias Schwarz, Thonex (CH); Delphine Marin, Arthaz-Pont-Notre Dame (FR); Agnes Bombrun, Chambesy (CH); Wesley Blackaby, Essex (GB); Charles Baker-Glenn, Essex (GB); Chris Knight, Essex (GB); Craig Rouse, Essex (GB)

(73) Assignee: Merck Serono SA, Coinsins, Vaud (CH)

( * ) Notice: Subject to any disclaimer, the term of this patent is extended or adjusted under 35 U.S.C. 154(b) by 13 days.

(21) Appl. No.: 12/809,816

(22) PCT Filed: Dec. 17, 2008

(86) PCT No.: PCT/EP2008/067776
§ 371 (c)(1),
(2), (4) Date: Jun. 21, 2010

(87) PCT Pub. No.: WO2009/080663
PCT Pub. Date: Jul. 2, 2009

(65) Prior Publication Data
US 2010/0305092 A1 Dec. 2, 2010

Related U.S. Application Data

(60) Provisional application No. 61/066,385, filed on Feb. 20, 2008.

(30) Foreign Application Priority Data

Dec. 21, 2007 (EP) .................................. 07150311

(51) Int. Cl.
| | |
|---|---|
| A61K 31/397 | (2006.01) |
| A61K 31/4545 | (2006.01) |
| A61K 31/444 | (2006.01) |
| A61K 31/5377 | (2006.01) |
| A61K 31/4245 | (2006.01) |
| A61K 31/4439 | (2006.01) |
| A61K 31/4725 | (2006.01) |
| A61K 31/497 | (2006.01) |
| C07D 413/04 | (2006.01) |
| C07D 413/14 | (2006.01) |
| C07D 401/14 | (2006.01) |
| A61P 19/02 | (2006.01) |
| A61P 3/10 | (2006.01) |
| A61P 9/10 | (2006.01) |
| A61P 29/00 | (2006.01) |
| A61P 1/04 | (2006.01) |
| A61P 17/06 | (2006.01) |
| A61P 11/06 | (2006.01) |

(52) U.S. Cl. ............. 514/210.18; 514/210.2; 514/236.2; 514/255; 514/307; 514/318; 514/333; 514/340; 514/364; 544/138; 544/405; 546/144; 546/194; 546/256; 546/269.1; 548/131

(58) Field of Classification Search ...................... None
See application file for complete search history.

(56) References Cited

U.S. PATENT DOCUMENTS
2010/0240658 A1  9/2010  Quattropani et al.
2010/0305104 A1  12/2010  Montagne et al.

FOREIGN PATENT DOCUMENTS
WO    WO 2004/091502    10/2004
WO    WO 2006/131336    12/2006

OTHER PUBLICATIONS

Dimroth et al., caplus an 1907:1692.*
Chawla et al., "Challenges in Polymorphism of Pharmaceuticals", CRIPS vol. 5, No. 1, Jan.-Mar. 2004 (4 Pages.*
Newman et al., "Solid-state analysis of the active pharmaceutical ingredient in drug products", DDT vol. 8, No. 19, Oct. 2003, p. 898-905.*
Collins, Expert Opinion Investig. Drugs 2007, 16(11), 1743-1751.*
Beck et al., caplus an 1974:72087.*
Cyster, J. G. "Chemokines, Sphingosine-1-Phosphate, and Cell Migration in Secondary Lymphoid Organs" *Annu. Rev. Immunol.*, 2005, pp. 127-159, vol. 23.

* cited by examiner

*Primary Examiner* — Sun Jae Loewe
(74) *Attorney, Agent, or Firm* — Saliwanchik, Lloyd & Eisenschenk

(57) ABSTRACT

The invention relates to compounds of formula I:

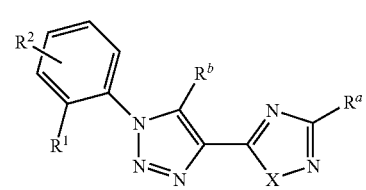

wherein $R^1$, $R^2$, $R^a$, $R^b$, X have the meanings given in claim 16. The compounds are useful e.g. in the treatment of autoimmune disorders, such as multiple sclerosis.

13 Claims, No Drawings

TRIAZOLE OXADIAZOLES DERIVATIVES

CROSS-REFERENCE TO RELATED APPLICATION

This application is the U.S. national stage application of International Patent Application No. PCT/EP2008/067776, filed Dec. 17, 2008, which claims the benefit of U.S. Provisional Patent Application No. 61/066,385, filed Feb. 20, 2008, the disclosures of which are hereby incorporated by reference in their entirety, including all figures, tables and amino acid or nucleic acid sequences.

The present invention relates to triazole oxadiazoles derivatives, their use as medicament and their use for treating multiple sclerosis and other diseases.

In particular, the invention relates to the use of compounds of formula I:

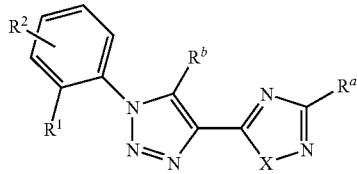

wherein
X is O or S;
$R^1$ denotes H, Hal, $CF_3$, $OCF_3$, CN, or $NO_2$;
$R^2$ is H, A or Hal;
$R^a$ is H, A, Ar, or Het;
$R^b$ is A, Ar, Het, OA, NHA, or $NA_2$, Ar-alkyl, or Het-alkyl;
Hal is F, Cl, Br or I;
A is a branched or linear alkyl having 1 to 12 C-atoms, wherein one or more, preferably 1 to 7H-atoms may be replaced by Hal, $OR^3$, CN, $CO_2R^3$, cycloalkyl having 3 to 7 ring carbon atoms, or $N(R^3)_2$ and wherein one or more, preferably 1 to 7 non-adjacent $CH_2$-groups may be replaced by O, $NR^3$ or S and/or by —CO—, —$NR^3$CO—, —$CONR^3$—, $NR^3CO_2$—, —$NR^3CONR^3$—, —CH=CH—, —C≡C—, groups, or

or denotes cycloalkyl or cycloalkylalkylen having 3-7 ring C atoms;
q is 1, 2, 3, or 4
Ar denotes a monocyclic or bicyclic, unsaturated or aromatic carbocyclic ring having 6 to 14 carbon atoms which may be unsubstituted or monosubstituted, disubstituted or trisubstituted by a substituent selected from $R^4$ and/or $R^5$;
Ar-alkyl denotes an aryl group linked to the rest of the molecule through a $C_1$-$C_{12}$ alkylen chain, preferably $C_1$-$C_6$ alkylen chain. Preferred Ar-alkyl is linked to the rest of the molecule through a methylen or an ethylen group.
Het denotes a monocyclic or bicyclic, saturated, unsaturated or aromatic heterocyclic ring having 1 to 4 N, O and/or S atoms which may be unsubstituted or monosubstituted, disubstituted or trisubstituted by a substituent selected from $R^4$ and/or $R^5$; and wherein one or more $CH_2$ groups may be replaced by —CO—.
Het-alkyl denotes a group Het linked to the rest of the molecule through a $C_1$-$C_{12}$ alkylen chain, preferably $C_1$-$C_6$ alkylen chain. Preferred Het-alkyl are linked to the rest of the molecule through a methylen or an ethylen group.
$R^4$ and $R^5$ are each independently selected from A, Hal, hydroxy, alkoxy, carboxy, carboxy-alkyl, Perfluoro-alkyl, Perfluoro-alkoxy, acyl, alkylsulfonyl, sulfonyl, —$SO_2$($R^3)_2$, cyano, nitro, amino, amido, alkyl optionally substituted by a carboxy, —$N(R^3)_2$, —$CO(NR^3)_2$, —$OR^3$, ($NR^3$) $COR^3$, —$CO_2R^3$, —$COR^3$, or Ar-alkyl or Het-alkyl both optionally substituted by A, Hal, an acyl, alkylsulfonyl, carboxy, —$N(R^3)_2$, —$CON(R^3)_2$, —$OR^3$, ($NR^3$)$COR^3$, —$CO_2R^3$, —$COR^3$, —$SO_2N(R^3)_2$, —$SO_2$alkyl, $NR^3SO_2$alkyl, $NR^3SO_2$alkyl,

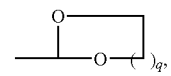

or $C_1$-$C_6$alkyl;
$R^3$ is H or A;
and pharmaceutically acceptable derivatives, solvates, tautomers, salts and stereo-isomers thereof, including mixtures thereof in all ratios as a medicament, especially for treating multiple sclerosis and other diseases.

More Particularly, the invention relates to compounds of formula I:

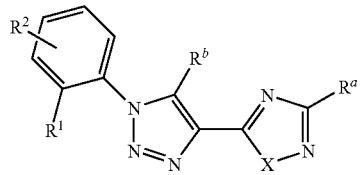

wherein
X, $R^1$, $R^2$, $R^b$ are as above defined and wherein
$R^a$ is H, A, Ar, or Het, provided that $R^a$ is not a benzo[1,3] dioxolyl group, or a phenyl group being unsubstituted or substituted by at least one Methyl, F, Cl, OMe and/or OEt, if $R^b$ is a methyl group;
and pharmaceutically acceptable derivatives, solvates, tautomers, salts and stereoisomers thereof, including mixtures thereof in all ratios and their use for treating multiple sclerosis and other diseases.

The compounds of formula I and related formulae are preferably binding on receptors for sphingosine 1-phosphate (S1P). S1P is a bioactive sphingolipid metabolite that is secreted by hematopoietic cells and stored and released from activated platelets. It acts as an agonist on a family of G protein-coupled receptors (GPCR). Five sphingosine 1-phosphate receptors have been identified ($S1P_1$, $S1P_2$, $S1P_3$, $S1P_4$, and $S1P_5$, also known as endothelial differentiation genes, which are Edg1, Edg5, Edg3, Edg6 and Edg8 respectively), that have widespread cellular and tissue distribution and are well conserved in human and rodent species.

S1P is involved in a number of cellular functions such as survival, proliferation and immunological responses. The compounds of the present invention are preferably acting as $S1P_1$/Edg1 receptor agonists and thus have immunosuppressive activities by modulating leukocyte trafficking, sequestering lymphocytes in secondary lymphoid tissues, and interfering with cell-cell interactions required for an efficient immune response. The invention is also directed to pharmaceutical compositions containing such compounds and methods of treatment or prevention.

FTY720 or fingolimod, a non selective $S1P_1$ agonist, exerts immunosuppressive activity and shows therapeutic effects in the treatment of relapsing-remitting multiple sclerosis. Numerous publications have been already published using this compound: Cyster J G Annu Rev Immunol 23:127-59, 2005, Rosen H Nat Rev Immunol 5:560-570, 2005, Rosen H Trends Immunol 28:102-107, 2007, Yopp A C Clin Transplant 20:788-795, 2006, Kappos L N Engl J Med 355:1124-1140, 2006, Massberg S N Engl J Med 355:1088-1089, 2006.

The patent applications WO 2006/131336 and WO 2004/091502 disclose other compounds active against immunological diseases and rheumatoid arthritis.

Immunosuppressive agents are further useful in a wide variety of autoimmune and chronic inflammatory diseases, including systemic lupus erythematosus, chronic rheumatoid arthritis, type I diabetes mellitus, inflammatory bowel diseases, biliary cirrhosis, uveitis and other disorders such as Crohn's diseases, ulcerative colitis, bullous pemphigoid, sarcoidosis, psoriasis, autoimmune myositis, Wegener's granulomatosis, ichthyosis, Graves opthalmopathy, atopic dermatitis and asthma. They are also useful as part of chemotherapeutic regimens for the treatment of cancers, lymphomas and leukemias.

It has been found that the compounds of the present invention are selective $S1P_1$ agonists with improved pharmacological and/or other properties.

Thus, the present invention preferably comprises compounds which are agonists of the $S1P_1/Edg1$ receptor, especially having selectivity over the $S1P_3/Edg3$ receptor. An $S1P_1/Edg1$ receptor selective agonist has advantages over current therapies and extends the therapeutic window of lymphocyte sequestration agents, allowing better tolerability with higher dosing and thus improving efficacy.

The invention further relates to the manufacture of a medicament for the improvement of vascular function, either alone or in combination with other active compounds or therapies.

The inventions further relates to the use of compounds according to formula I in combination with immunomodulating agents for example Fingolimod; cyclosporins, rapamycins or ascomycins, or their immunosuppressive analogs, e.g. cyclosporin A, cyclosporin G, FK-506, ABT-281, ASM981, rapamycin, 40-O-(2-hydroxy)ethyl-rapamycin etc.; corticosteroids; cyclophosphamide; azathioprene; methotrexate; leflunomide; mizoribine; mycophenolic add; mycophenolate mofetil; 15-deoxyspergualine; diflucortolone valerate; difluprednate; Alclometasone dipropionate; amcinonide; amsacrine; asparaginase; azathioprine; basiliximab; beclometasone dipropionate; betamethasone; betamethasone acetate; betamethasone dipropionate; betamethasone phosphate sodique; betamethasone valerate; budesonide; captopril; chlormethine chlorhydrate; cladribine; clobetasol propionate; cortisone acetate; cortivazol; cyclophosphamide; cytarabine; daclizumab; dactinomycine; desonide; desoximetasone; dexamethasone; dexamethasone acetate; dexamethasone isonicotinate; dexamethasone metasulfobenzoate sodique; dexamethasone phosphate; dexamethasone tebutate; dichlorisone acetate; doxorubicine chlorhydrate; epirubicine chlorhydrate; fluclorolone acetonide; fludrocortisone acetate; fludroxycortide; flumetasone pivalate; flunisolide; fluocinolone acetonide; fluocinonide; fluocortolone; fluocortolone hexanoate; fluocortolone pivalate; fluorometholone; fluprednidene acetate; fluticasone propionate; gemcitabine chlorhydrate; halcinonide; hydrocortisone, hydrocortisone acetate, hydrocortisone butyrate, hydrocortisone hemisuccinate; melphalan; meprednisone; mercaptopurine; methylprednisolone; methylprednisolone acetate; methylprednisolone hemisuccinate; misoprostol; muromonabcd3; mycophenolate mofetil; paramethasone acetate; prednazoline, prednisolone; prednisolone acetate; prednisolone caproate; prednisolone metasulfobenzoate sodique; prednisolone phosphate sodique; prednisone; prednylidene; rifampicine; rifampicine sodique; tacrolimus; thalidomide; thiotepa; tixocortol pivalate; triamcinolone; triamcinolone acetonide hemisuccinate; triamcinolone benetonide; triamcinolone diacetate; triamcinolone hexacetonide; immunosuppressive monoclonal antibodies, e.g., monoclonal antibodies to leukocyte receptors, e.g., MHC, CD2, CD3, CD4, CD7, CD25, CD28, B7, CD40, CD45 or CD58 or their ligands; or other immunomodulatory compounds, e.g. CTLA41g, or other adhesion molecule inhibitors, e.g. mAbs or low molecular weight inhibitors including Selectin antagonists and VLA-4 antagonists. A preferred composition is with Cyclosporin A, FK506, rapamycin or 40-(2-hydroxy)ethyl-rapamycin and Fingolimod.

The triazole oxadiazole derivatives according to formula I and related formulae may be prepared from readily available starting materials using the following general methods and procedures. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures.

The following abbreviations refer respectively to the definitions below: aq (aqueous), h (hour), g (gram), L (liter), mg (milligram), MHz (Megahertz), µM (micormolar) min. (minute), mm (millimeter), mmol (millimole), mM (millimolar), m.p. (melting point), eq (equivalent), mL (milliliter), µL (microliter), ACN (acetonitrile), BINAP (2,2'-bis(disphenylphosphino)-1,1'-binaphthalene, BOC (tert-butoxy-carbonyl), CBZ (carbobenzoxy), $CDCl_3$ (deuterated chloroform), $CD_3OD$ (deuterated methanol), $CH_3CN$ (acetonitrile), c-hex (cyclohexane), DCC (dicyclohexyl carbodiimide), DCM (dichloromethane), DIC (diisopropyl carbodiimide), DIEA (diisopropylethyl-amine), DMF (dimethylformamide), DMSO (dimethylsulfoxide), DMSO-$d_6$ (deuterated dimethylsulfoxide), EDC (1-(3-dimethyl-amino-propyl)-3-ethyl-carbodiimide), ESI (Electro-spray ionization), EtOAc (ethyl acetate), $Et_2O$ (diethyl ether), EtOH (ethanol), FMOC (fluorenylmethyloxycarbonyl), HATU (dimethylamino-([1,2,3]triazolo[4,5-b]pyridin-3-yloxy)methylene]-dimethyl-ammonium hexafluorophosphate), HPLC (High Performance Liquid Chromatography), i-PrOH (2-propanol), $K_2CO_3$ (potassium carbonate), LC (Liquid Chromatography), MeCN (Acetonitrile), MeOH (methanol), $MgSO_4$ (magnesium sulfate), MS (mass spectrometry), MTBE (Methyl tert-butyl ether), Mtr. (4-Methoxy-2,3,6-trimethylbenzensulfonyl), MW (microwave), $NaHCO_3$ (sodium bicarbonate), $NaBH_4$ (sodium borohydride), NMM (N-methyl morpholine), NMR (Nuclear Magnetic Resonance), POA (phenoxyacetate), PyBOP® (benzotriazole-1-yl-oxy-tris-pyrrolidino-phosphonium hexafluorophosphate), RT (room temperature), Rt (retention time), SPE (solid phase extraction), TBTU (2-(1-H-benzotriazole-1-yl)-1,1,3,3-tetramethyluromium tetrafluoro borate), TEA (triethylamine), TFA (trifluoroacetic acid), THF (tetrahydrofuran), TLC (Thin Layer Chromatography), UV (Ultraviolet).

The compounds of invention have been named according to the standards used in the program "ACD/Name Batch"

from Advanced Chemistry Development Inc., ACD/Labs (7.00 Release). Product version: 7.10, build: 15 Sep. 2003.

Depending on the nature of X, $R^a$, $R^b$, $R^1$ and $R^2$, different synthetic strategies may be selected for the synthesis of compounds of formula I and related formulae. In the process illustrated in the following schemes, $R^a$, $R^b$, $R^1$ and $R^2$ are as above defined in the description. Compounds of formula I, wherein X is defined as O or S, can be obtained analogously.

In general, the triazole oxadiazole derivatives according to formula I and related formulae of this invention may be prepared from readily available starting materials. If such starting materials are not commercially available they may be prepared by standard synthetic techniques. The following general methods and procedures described hereinafter in the examples may be employed to prepare compounds of formula I and related formulae.

The process for the preparation of compounds of formula I and related formulae, wherein X, $R^a$, $R^b$, $R^1$ and $R^2$ are defined as above, and as outlined in Scheme 1, is also object of the invention.

More preferably compounds of formula I and related formulae can be obtained in a 2-step protocol as outlined in Schem 1a:

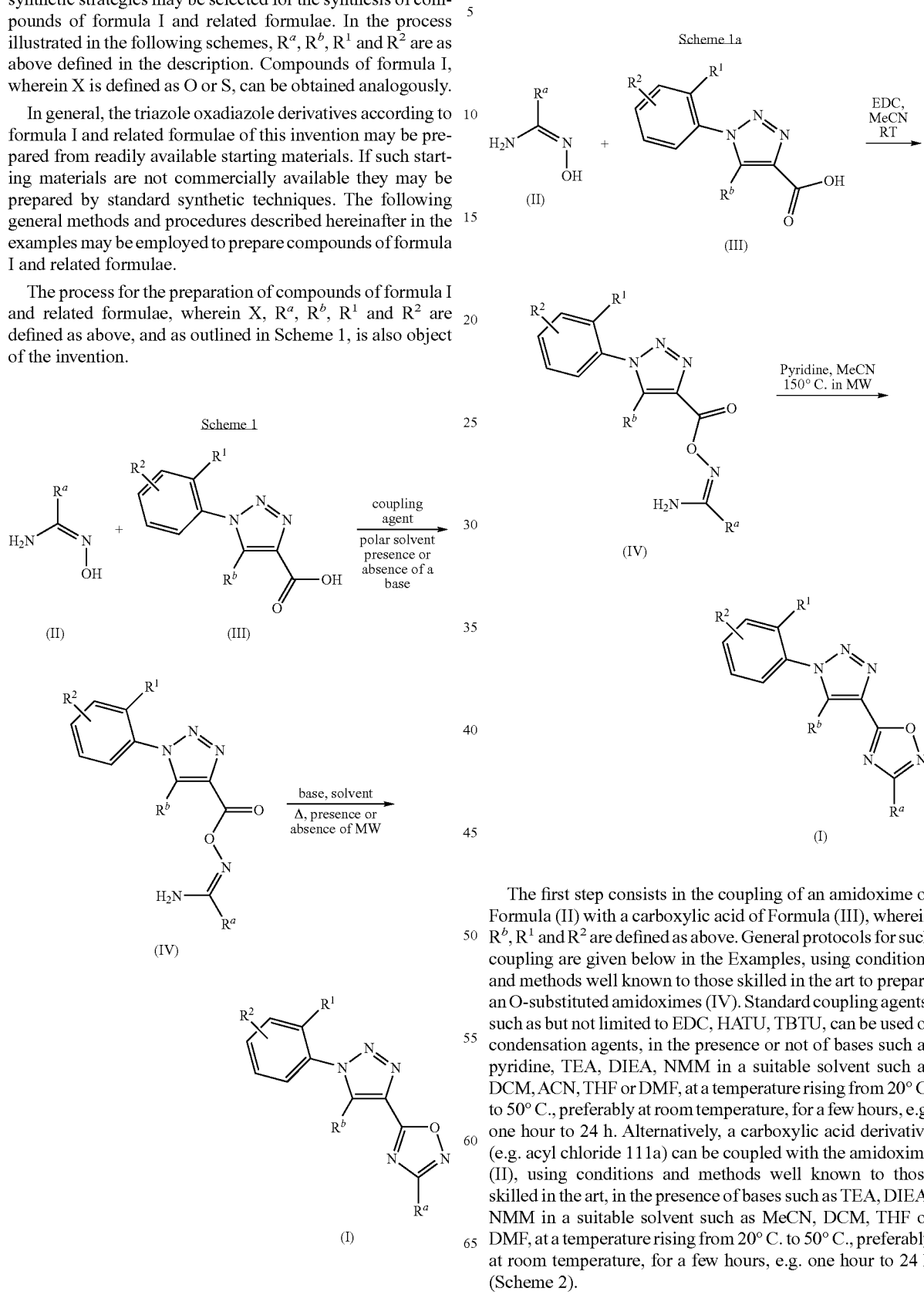

The first step consists in the coupling of an amidoxime of Formula (II) with a carboxylic acid of Formula (III), wherein $R^b$, $R^1$ and $R^2$ are defined as above. General protocols for such coupling are given below in the Examples, using conditions and methods well known to those skilled in the art to prepare an O-substituted amidoximes (IV). Standard coupling agents, such as but not limited to EDC, HATU, TBTU, can be used or condensation agents, in the presence or not of bases such as pyridine, TEA, DIEA, NMM in a suitable solvent such as DCM, ACN, THF or DMF, at a temperature rising from 20° C. to 50° C., preferably at room temperature, for a few hours, e.g. one hour to 24 h. Alternatively, a carboxylic acid derivative (e.g. acyl chloride 111a) can be coupled with the amidoxime (II), using conditions and methods well known to those skilled in the art, in the presence of bases such as TEA, DIEA, NMM in a suitable solvent such as MeCN, DCM, THF or DMF, at a temperature rising from 20° C. to 50° C., preferably at room temperature, for a few hours, e.g. one hour to 24 h (Scheme 2).

Scheme 2

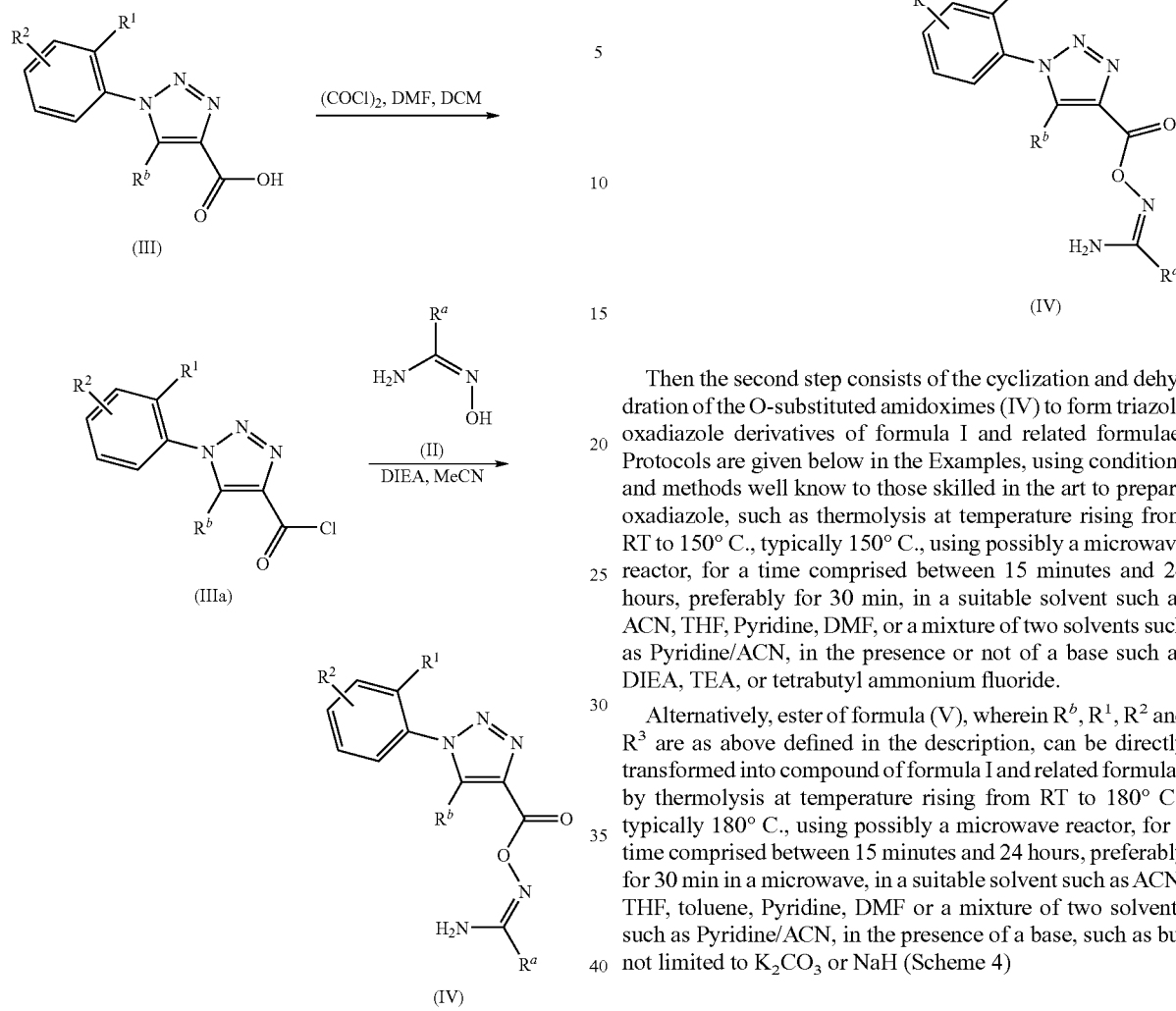

The corresponding salt (IIIb), such as but not limited to lithium, sodium or potassium salt, of the carboxylic acid (III), can be alternatively used to prepare an O-substituted amidoximes (IV). Salts can be activated with isobutylchloroformate at low temperature, typically at −40° C., and then react with an amidoxime (II), affording O-substituted amidoximes (IV) (Scheme 3).

Scheme 3

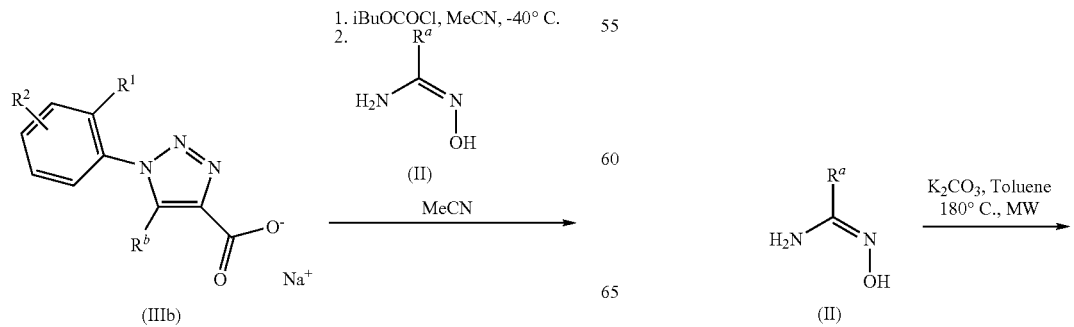

Then the second step consists of the cyclization and dehydration of the O-substituted amidoximes (IV) to form triazole oxadiazole derivatives of formula I and related formulae. Protocols are given below in the Examples, using conditions and methods well know to those skilled in the art to prepare oxadiazole, such as thermolysis at temperature rising from RT to 150° C., typically 150° C., using possibly a microwave reactor, for a time comprised between 15 minutes and 24 hours, preferably for 30 min, in a suitable solvent such as ACN, THF, Pyridine, DMF, or a mixture of two solvents such as Pyridine/ACN, in the presence or not of a base such as DIEA, TEA, or tetrabutyl ammonium fluoride.

Alternatively, ester of formula (V), wherein $R^b$, $R^1$, $R^2$ and $R^3$ are as above defined in the description, can be directly transformed into compound of formula I and related formulae by thermolysis at temperature rising from RT to 180° C., typically 180° C., using possibly a microwave reactor, for a time comprised between 15 minutes and 24 hours, preferably for 30 min in a microwave, in a suitable solvent such as ACN, THF, toluene, Pyridine, DMF or a mixture of two solvents such as Pyridine/ACN, in the presence of a base, such as but not limited to $K_2CO_3$ or NaH (Scheme 4)

Scheme 4

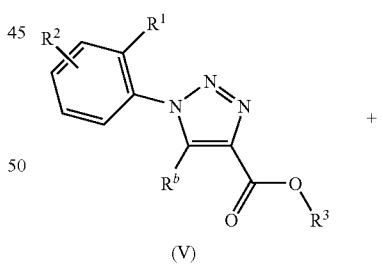

+

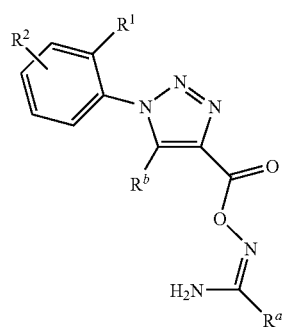

-continued

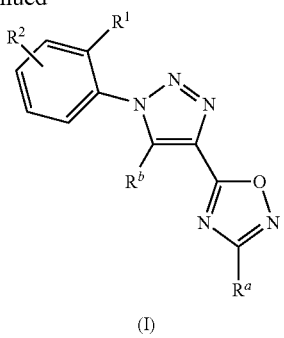
(I)

Compounds of formula I and related formulae, wherein X, $R^a$, $R^b$, $R^1$ and $R^2$ are defined as above, can be converted to alternative compounds of formula I and related formulae, wherein X, $R^a$, $R^b$, $R^1$ and $R^2$ are defined as above, employing suitable interconversion techniques well known by a person skilled in the art.

Typically, when $R^a$ is a benzyl alcohol, compound of Formula (Ia) can be further modified into compound of Formula (Ib), wherein $R^a$ is a benzyl amine, as illustrated on Scheme 5. It can be first be transformed into the corresponding mesyl or tosyl groups (Ic), which can then react with an amine HN$(R^3)_2$, affording compounds of formula (Ib) wherein X, $R^a$, $R^b$, $R^1$, $R^2$ and $R^3$ are defined as above (Scheme 5). Alcohol (Ia) can be oxidized into the corresponding aldehyde (Id), using conditions well known to those skilled in the art, such as but not limited to Swern oxydation conditions, or the use of $MnO_2$ as oxydative agent, as illustrated on Scheme 5. Then a reductive amination of the compounds of formula (Id) with a suitable amine $HN(R^3)_2$, affords compounds of formula (Ib), wherein $R^a$ is a benzyl amine and wherein X, $R^b$, $R^1$, $R^2$ and $R^3$ are defined as above.

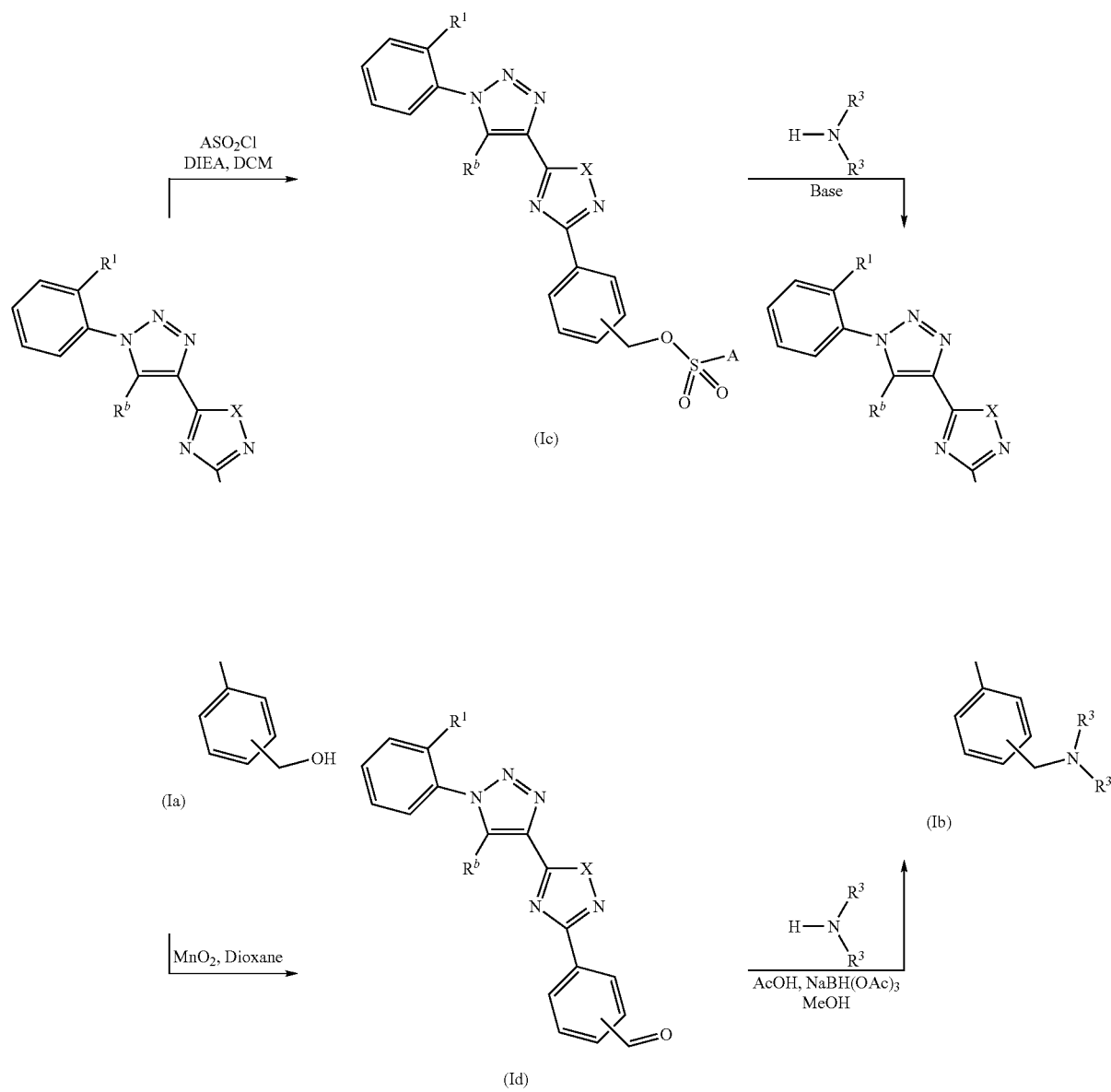

Scheme 5

Compounds of Formula (II), wherein $R^a$ is defined as above, are either commercially available or may be prepared by standard synthetic techniques well known to those skilled in the art. Typically, it can be prepared according to Scheme 6 by addition of hydroxylamine into a solution of the corresponding substituted benzonitrile of Formula (VI) in a solvent or a mixture of solvents, such as EtOH, water, at a temperature rising from 20° C. to 50° C., preferably at room temperature, for a few hours, e.g. one hour to 24 h.

Scheme 6

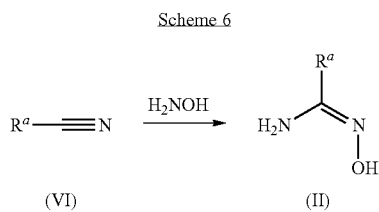

The method for preparing the compounds of Formula (II) selected below:
Methyl 4-[amino(hydroxyimino)methyl]-2-fluorobenzoate;
Methyl 4-[amino(hydroxyimino)methyl]-3-fluorobenzoate;
Methyl 3-[amino(hydroxyimino)methyl]benzoate;
2-Fluoro-N-hydroxybenzenecarboximidamide;
2,6-Difluoro-N-hydroxybenzenecarboximidamide;
2-Fluoro-N,4-dihydroxybenzenecarboximidamide;
tert-Butyl 3-{4-[amino(hydroxyimino)methyl]-3-methoxyphenyl}propanoate;
tert-Butyl 3-{4-[amino(hydroxyimino)methyl]-3-methylphenyl}propanoate;
N-Hydroxy-1H-indole-5-carboxamidine;
N'-hydroxy-1H-indole-5-carboximidamide;
4-[amino(hydroxyimino)methyl]benzamide
tert-butyl {4-[amino(hydroxyimino)methyl]benzyl}carbamate
4-(aminosulfonyl)-N'-hydroxybenzenecarboximidamide
N'-hydroxy-1H-indazole-5-carboximidamide
N'-hydroxyfuran-2-carboximidamide
N'-hydroxy-4-(hydroxymethyl)benzenecarboximidamide
N'-hydroxy-3-(hydroxymethyl)benzenecarboximidamide
N',3-dihydroxybenzenecarboximidamide
2-bromo-5-fluoro-N'-hydroxybenzenecarboximidamide
1-acetyl-N'-hydroxyindoline-5-carboximidamide
N'-hydroxy-1,2,3,4-tetrahydroisoquinoline-7-carboximidamide
2-ethyl-N'-hydroxy-1,2,3,4-tetrahydroisoquinoline-7-carboximidamide
1-acetyl-N'-hydroxyindoline-6-carboximidamide
N'-hydroxy-3-(methylsulfonyl)benzenecarboximidamide
N'-hydroxy-3-(1H-1,2,4-triazol-1-ylmethyl)benzenecarboximidamide
N'-hydroxyfuran-3-carboximidamide
N'-hydroxy-1H-indole-4-carboximidamide
3-(aminosulfonyl)-N'-hydroxybenzenecarboximidamide
N'-hydroxy-2-oxoindoline-5-carboximidamide
5-fluoro-N'-hydroxy-2-methoxybenzenecarboximidamide
N'-hydroxy-4-(2-hydroxyethyl)benzenecarboximidamide
tert-butyl {4-[amino(hydroxyimino)methyl]pyridin-2-yl}carbamate
N'-hydroxy-4-(1H-pyrazol-1-ylmethyl)benzenecarboximidamide
N'-hydroxy-1H-benzimidazole-5-carboximidamide
Tert-butyl 4-[(hydroxyamino)(imino)methyl]-1-piperidinecarboxylate;
tert-butyl {3-[amino(hydroxyimino)methyl]benzyl}carbamate;
is more particularly described in the Examples.

Compounds of Formula (VI), wherein $R^a$ is defined as above, are either commercially available or may be prepared by standard synthetic techniques well known to those skilled in the art.

Compounds of Formula (III), wherein $R^b$, $R^1$ and $R^2$ is defined as above, are either commercially available or may be prepared by standard synthetic techniques well known to those skilled in the art. Treatment of azide derivative of Formula (VII) wherein $R^1$ and $R^2$ are as above defined with substituted alkyl acetoacetate (VIII) wherein $R^b$ and $R^3$ are as above defined gives access to functionalized [1,2,3]-triazole of Formula (V). This transformation take place in the presence of a base, such as but not limited to DBU, TEA, $K_2CO_3$, EtONa or MeONa, in a suitable solvent such as DMF, THF, methanol or ethanol, at a temperature rising from 0° C. to 100° C., preferably at 70° C., for a few hours, e.g. one hour to 24 h (Scheme 7).

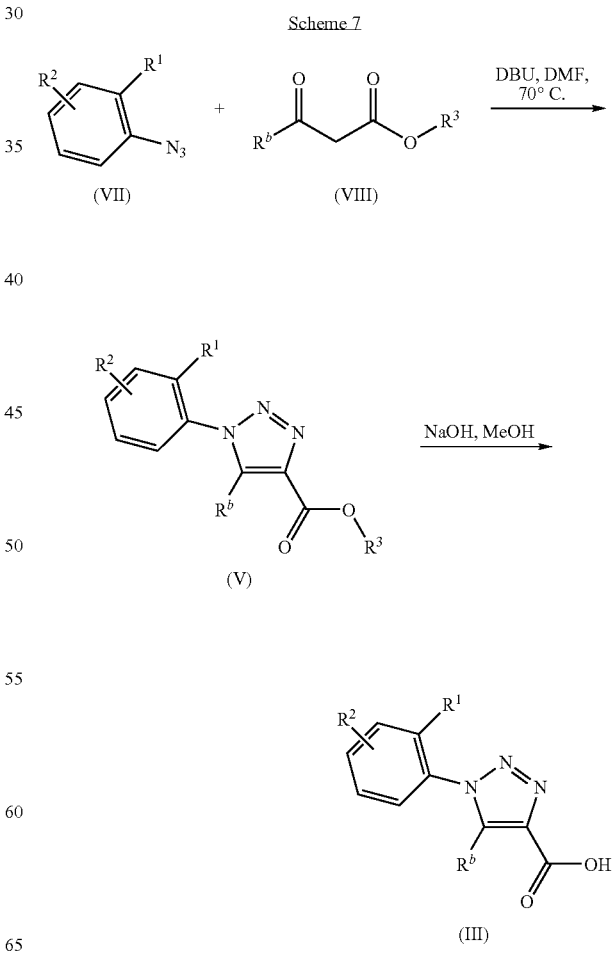

The method for preparing the compounds of Formula (V) selected below:

Ethyl 1-(2-fluorophenyl)-5-pyridin-4-yl-1H-1,2,3-triazole-4-carboxylate is more particularly described in the Examples.

[1,2,3]-Triazole of Formula (V) can be saponified into carboxylic acid of Formula (III) using conditions well known to those skilled in the art, such as but not limited to the use of a metal hydroxide, e.g. lithium hydroxide, sodium hydroxide or potassium hydroxide, in a suitable solvent such as THF, methanol, ethanol or water or mixtures thereof, at a temperature rising from 20° C. to 50° C., preferably at room temperature, for few hours, e.g. one hour to 24 h.

The method for preparing the compounds of Formula (III) selected below:

1-(2-Fluorophenyl)-5-methyl-1H-1,2,3-triazole-4-carboxylic acid;

5-Ethyl-1-(2-fluorophenyl)-1H-1,2,3-triazole-4-carboxylic acid;

1-(2-Fluorophenyl)-5-(methoxymethyl)-1H-1,2,3-triazole-4-carboxylic acid;

5-Butyl-1-(2-fluorophenyl)-1H-1,2,3-triazole-4-carboxylic acid;

5-Phenyl-1-(2-fluorophenyl)-1H-1,2,3-triazole-4-carboxylic acid;

1-(2-Fluorophenyl)-5-pyridin-3-yl-1H-1,2,3-triazole-4-carboxylic acid;

1-(2-Fluorophenyl)-5-pyridin-2-yl-1H-1,2,3-triazole-4-carboxylic acid;

1-(2-Fluorophenyl)-5-pyridin-4-yl-1H-1,2,3-triazole-4-carboxylic acid;

Ethyl 1-(2-fluorophenyl)-5-pyridin-4-yl-1H-1,2,3-triazole-4-carboxylate 1-(2-Fluorophenyl)-5-(2-methoxyethyl)-1H-1,2,3-triazole-4-carboxylic acid;

1-(2-fluorophenyl)-5-(morpholin-4-ylmethyl)-1H-1,2,3-triazole-4-carboxylic acid

5-Cyclopentyl-1-(2-fluorophenyl)-1H-1,2,3-triazole-4-carboxylic acid;

5-Cyclopropyl-1-(2-fluorophenyl)-1H-1,2,3-triazole-4-carboxylic acid;

1-(2-Fluorophenyl)-5-(tetrahydrofuran-2-yl)-1H-1,2,3-triazole-4-carboxylic acid;

5-Benzyl-1-(2-fluorophenyl)-1H-1,2,3-triazole-4-carboxylic acid;

1-(2-Fluorophenyl)-5-(tetrahydro-2H-pyran-4-yl)-1H-1,2,3-triazole-4-carboxylic acid;

1-(2-Fluorophenyl)-5-isopropyl-1H-1,2,3-triazole-4-carboxylic acid;

Ethyl 1-(2-fluorophenyl)-5-(morpholinomethyl)-1H-1,2,3-triazole-4-carboxylate

Ethyl 1-(2-fluorophenyl)-5-pyridin-2-yl-1H-1,2,3-triazole-4-carboxylate;

is more particularly described in the Examples.

Compounds of Formula (VIII), wherein $R^3$ and $R^b$ are defined as above, are either commercially available or may be prepared by standard synthetic techniques well known to those skilled in the art.

Compounds of Formula (V), wherein $R^b$, $R^1$, $R^2$ and $R^3$ are defined as above, can be converted to alternative compounds of Formula (V), wherein $R^b$, $R^1$, $R^2$ and $R^3$ are defined as above, employing suitable interconversion techniques well known by a person skilled in the art. For instance, [1,2,3]-triazole of Formula (Va), wherein $R^b$ is Me, may be halogenated into [1,2,3]-triazole of Formula (Vb), wherein Hal is defined as above, which can be further transformed by addition of amines or alcohols, affording [1,2,3]-triazole of Formula (Vc) or (Vd) respectively wherein A is as above defined, as depicted in Scheme 8, following a protocol reported in L'Abbe, G. et al *Tetrahedron* 1988, 44, 461.

Scheme 8

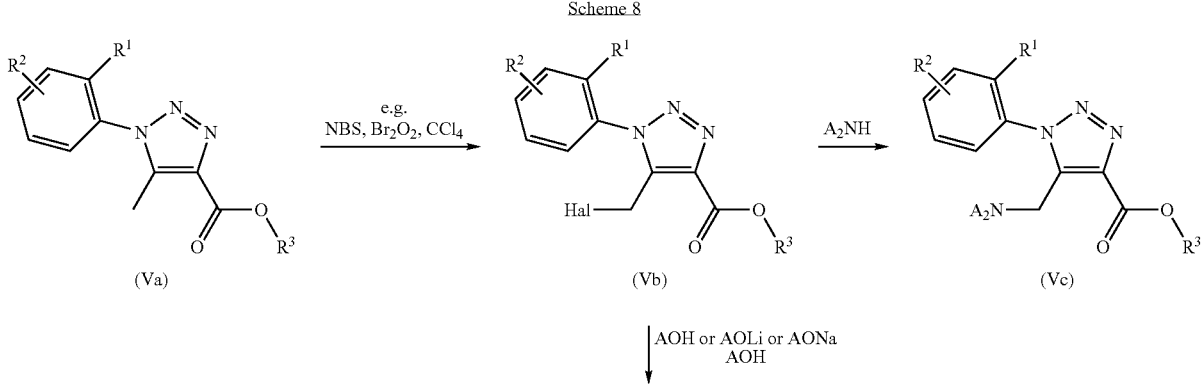

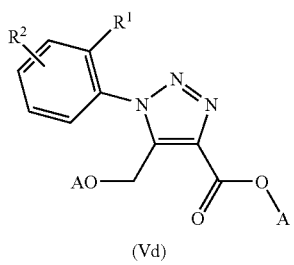

(Vd)

Alternatively, [1,2,3]-triazole of Formula (Vc) and (Vd) may be directly obtained by the treatment of azide (VII) with a halogenated acetoacetate (VIIIa), such as methyl 4-chloroacetoacetate, in the presence of an amine or an alcohol. The reaction may be performed in a solvent, such as DMF or ACN, or in the selected amine or alcohol, $A_2NH$ or AOH respectively, at a temperature rising from RT to 100° C., preferably at 50° C., for a few hours, e.g. one hour to 24 h (Scheme 9). [1,2,3]-Triazole of Formula (Vc) or (Vd) can be saponified into carboxylic acid of Formula (IIIa) or (IIIb) using conditions well known to those skilled in the art, such as but not limited to the one described in the examples below.

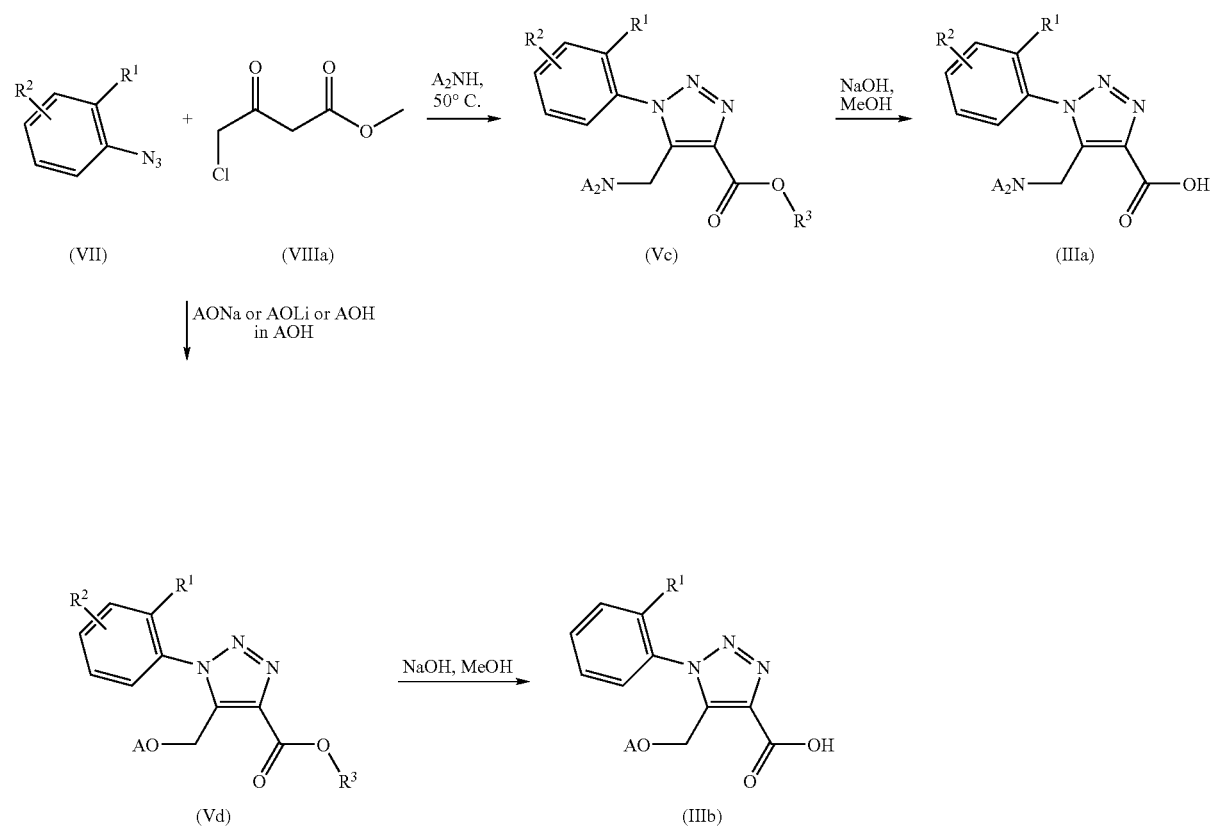

The method for preparing the compound of Formula (IIIa) selected below:
1-(2-fluorophenyl)-5-(morpholin-4-ylmethyl)-1H-1,2,3-triazole-4-carboxylic acid;
Ethyl 1-(2-fluorophenyl)-5-(morpholinomethyl)-1H-1,2,3-triazole-4-carboxylate;
is more particularly described in the Examples.

Alternatively, [1,2,3]-triazole of Formula (Ve), wherein $R^1$, $R^2$ and $R^3$ are as above defined and $R^b$ is H, may be transformed into [1,2,3]-triazole of Formula (Vf), wherein $R^b$ is aromatic Ar or aromatic Het as define above, and is introduced via a direct Pd-catalyzed C-5 arylation as described in Scheme 10 and reported in Gevorgyan, V. et al. *Org. Lett.* 2007, 9, 2333. Different palladium catalysts may be used, such as but not limited to $Pd(PPh_3)_2Cl_2$, $Pd(OAc)_2$ or $Pd_2(dba)_3 \cdot CHCl_3$.

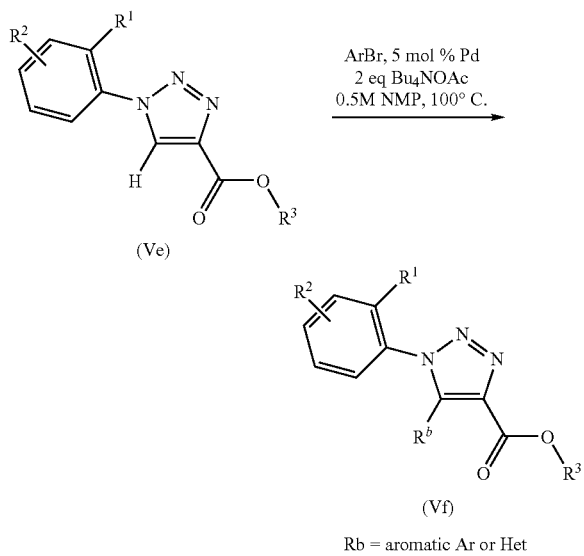

Rb = aromatic Ar or Het

Azides of Formula (VII), wherein $R^1$ and $R^2$ are defined as above, are either commercially available or may be prepared by standard synthetic techniques well known to those skilled in the art. Typically an amine of Formula (IX), where $R^1$ and $R^2$ are defined as above, is reacted with sodium nitrite in an aqueous HCl solution at 0° C. An aqueous solution of sodium azide is then added, keeping the temperature at 0° C., affording azides of Formula (VII) (Scheme 11).

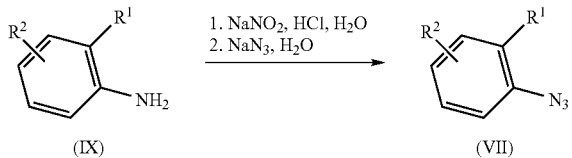

Amines of Formula (IX), wherein $R^1$ and $R^2$ are defined as above, are either commercially available or may be prepared by standard synthetic techniques well known to those skilled in the art.

If the above set out general synthetic methods are not applicable for the obtention of compounds of formula I and related formulae, suitable methods of preparation known by a person skilled in the art should be used.

The pharmaceutically acceptable cationic salts of compounds of the present invention are readily prepared by reacting the acid forms with an appropriate base, usually one equivalent, in a co-solvent. Typical bases are sodium hydroxide, sodium methoxide, sodium ethoxide, sodium hydride, potassium hydroxide, potassium methoxide, magnesium hydroxide, calcium hydroxide, benzathine, choline, diethanolamine, ethylenediamine, meglumine, benethamine, diethylamine, piperazine and tromethamine. The salt is isolated by concentration to dryness or by addition of a non-solvent. In some cases, salts can be prepared by mixing a solution of the acid with a solution of the cation (sodium ethylhexanoate, magnesium oleate), employing a solvent in which the desired cationic salt precipitates, or can be otherwise isolated by concentration and addition of a non-solvent.

According to a further general process, compounds of formula I and related formulae, (II), (III) and (V) can be converted to alternative compounds of formula I and related formulae, (II), (III) and (V), employing suitable interconversion techniques well known by a person skilled in the art.

In general, the synthesis pathways for any individual compound of formula I and related formulae will depend on the specific substituents of each molecule and upon the ready availability of intermediates necessary; again such factors being appreciated by those of ordinary skill in the art. For all the protection and deprotection methods, see Philip J. Kocienski, in "*Protecting Groups*", Georg Thieme Verlag Stuttgart, New York, 1994 and, Theodora W. Greene and Peter G. M. Wuts in "*Protective Groups in Organic Synthesis*", Wiley Interscience, $3^{rd}$ Edition 1999.

Compounds of this invention can be isolated in association with solvent molecules by crystallization from evaporation of an appropriate solvent. The pharmaceutically acceptable acid addition salts of the compounds of formula I and related formulae, which contain a basic center, may be prepared in a conventional manner. For example, a solution of the free base may be treated with a suitable acid, either neat or in a suitable solution, and the resulting salt isolated either by filtration or by evaporation under vacuum of the reaction solvent. Pharmaceutically acceptable base addition salts may be obtained in an analogous manner by treating a solution of compound of formula (I), which contain an acid center, with a suitable base. Both types of salts may be formed or interconverted using ion-exchange resin techniques.

Depending on the conditions used, the reaction times are generally between a few minutes and 14 days, and the reaction temperature is between about −30° C. and 140° C., normally between −10° C. and 90° C., in particular between about 0° C. and about 70° C.

Compounds of the formula I and related formulae can furthermore be obtained by liberating compounds of the formula I from one of their functional derivatives by treatment with a solvolysing or hydrogenolysing agent.

Preferred starting materials for the solvolysis or hydrogenolysis are those which conform to the formula I and related formulae, but contain corresponding protected amino and/or hydroxyl groups instead of one or more free amino and/or hydroxyl groups, preferably those which carry an amino-protecting group instead of an H atom bonded to an N atom, in particular those which carry an R'—N group, in which R' denotes an amino-protecting group, instead of an HN group, and/or those which carry a hydroxyl-protecting group instead of the H atom of a hydroxyl group, for example those which conform to the formula I, but carry a —COOR" group, in which R" denotes a hydroxyl-protecting group, instead of a —COON group.

It is also possible for a plurality of—identical or different—protected amino and/or hydroxyl groups to be present in the molecule of the starting material. If the protecting groups present are different from one another, they can in many cases be cleaved off selectively.

The term "amino-protecting group" is known in general terms and relates to groups which are suitable for protecting (blocking) an amino group against chemical reactions, but which are easy to remove after the desired chemical reaction has been carried out elsewhere in the molecule. Typical of such groups are, in particular, unsubstituted or substituted acyl, aryl, aralkoxymethyl or aralkyl groups. Since the amino-protecting groups are removed after the desired reaction (or reaction sequence), their type and size are furthermore not crucial; however, preference is given to those having 1-20, in particular 1-8, carbon atoms. The term "acyl group" is to be understood in the broadest sense in connection with the present process. It includes acyl groups derived from aliphatic, araliphatic, aromatic or heterocyclic carboxylic acids or sulfonic acids, and, in particular, alkoxycarbonyl, aryloxycarbonyl and especially aralkoxycarbonyl groups. Examples of such acyl groups are alkanoyl, such as acetyl, propionyl and butyryl; aralkanoyl, such as phenylacetyl; aroyl, such as benzoyl and tolyl; aryloxyalkanoyl, such as POA; alkoxycarbonyl, such as methoxycarbonyl, ethoxycarbonyl, 2,2,2-trichloroethoxycarbonyl, BOC (tert-butoxycarbonyl) and 2-iodoethoxycarbonyl; aralkoxycarbonyl, such as CBZ ("carbobenzoxy"), 4-methoxybenzyloxycarbonyl and FMOC; and arylsulfonyl, such as Mtr. Preferred amino-protecting groups are BOC and Mtr, furthermore CBZ, Fmoc, benzyl and acetyl.

The term "hydroxyl-protecting group" is likewise known in general terms and relates to groups which are suitable for protecting a hydroxyl group against chemical reactions, but are easy to remove after the desired chemical reaction has been carried out elsewhere in the molecule. Typical of such groups are the above-mentioned unsubstituted or substituted aryl, aralkyl or acyl groups, furthermore also alkyl groups. The nature and size of the hydroxyl-protecting groups are not crucial since they are removed again after the desired chemical reaction or reaction sequence; preference is given to groups having 1-20, in particular 1-10, carbon atoms. Examples of hydroxyl-protecting groups are, inter alia, benzyl, 4-methoxybenzyl, p-nitrobenzoyl, p-toluenesulfonyl, tert-butyl and acetyl, where benzyl and tert-butyl are particularly preferred.

The compounds of the formula I and related formulae are liberated from their functional derivatives—depending on the protecting group used—for example using strong acids, advantageously using TFA or perchloric acid, but also using other strong inorganic acids, such as hydrochloric acid or sulfuric acid, strong organic carboxylic acids, such as trichloroacetic acid, or sulfonic acids, such as benzene- or p-toluenesulfonic acid. The presence of an additional inert solvent is possible, but is not always necessary. Suitable inert solvents are preferably organic, for example carboxylic acids, such as acetic acid, ethers, such as tetrahydrofuran or dioxane, amides, such as DMF, halogenated hydrocarbons, such as dichloromethane, furthermore also alcohols, such as methanol, ethanol or isopropanol, and water. Mixtures of the above-mentioned solvents are furthermore suitable. TFA is preferably used in excess without addition of a further solvent, and perchloric acid is preferably used in the form of a mixture of acetic acid and 70% perchloric acid in the ratio 9:1. The reaction temperatures for the cleavage are advantageously between about 0 and about 50° C., preferably between 15 and 30° C. (room temperature).

The BOC, OBut and Mtr groups can, for example, preferably be cleaved off using TFA in dichloromethane or using approximately 3 to 5N HCl in dioxane at 15-30° C., and the FMOC group can be cleaved off using an approximately 5 to 50% solution of dimethylamine, diethylamine or piperidine in DMF at 15-30° C.

Protecting groups which can be removed hydrogenolytically (for example CBZ, benzyl or the liberation of the amidino group from the oxadiazole derivative thereof) can be cleaved off, for example, by treatment with hydrogen in the presence of a catalyst (for example a noble-metal catalyst, such as palladium, advantageously on a support, such as carbon). Suitable solvents here are those indicated above, in particular, for example, alcohols, such as methanol or ethanol, or amides, such as DMF. The hydrogenolysis is generally carried out at temperatures between about 0 and 100° C. and pressures between about 1 and 200 bar, preferably at 20-30° C. and 1-10 bar. Hydrogenolysis of the CBZ group succeeds well, for example, on 5 to 10% Pd/C in methanol or using ammonium formate (instead of hydrogen) on Pd/C in methanol/DMF at 20-30° C.

Examples of suitable inert solvents are hydrocarbons, such as hexane, petroleum ether, benzene, toluene or xylene; chlorinated hydrocarbons, such as trichloroethylene, 1,2-dichloroethane, tetrachloromethane, trifluoromethylbenzene, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether or ethylene glycol dimethyl ether (diglyme); ketones, such as acetone or butanone; amides, such as acetamide, dimethylacetamide, N-methylpyrrolidone (NMP) or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Esters can be saponified, for example, using acetic acid or using LiOH, NaOH or KOH in water, water/THF, water/THF/ethanol or water/dioxane, at temperatures between 0 and 100° C.

Free amino groups can furthermore be acylated in a conventional manner using an acid chloride or anhydride or alkylated using an unsubstituted or substituted alkyl halide or reacted with $CH_3$—C(=NH)—OEt, advantageously in an inert solvent, such as dichloromethane or THF and/or in the presence of a base, such as triethylamine or pyridine, at temperatures between −60° C. and +30° C.

Throughout the specification, the term leaving group preferably denotes Cl, Br, I or a reactively modified OH group, such as, for example, an activated ester, an imidazolide or alkylsulfonyloxy having 1-6 carbon atoms (preferably methylsulfonyloxy or trifluoro-methylsulfonyloxy) or arylsulfonyloxy having 6-10 carbon atoms (preferably phenyl- or p-tolylsulfonyloxy).

Radicals of this type for activation of the carboxyl group in typical acylation reactions are described in the literature (for example in the standard works, such as Houben-Weyl, Methoden der organischen Chemie [Methods of Organic Chemistry], Georg-Thieme-Verlag, Stuttgart).

Activated esters are advantageously formed in situ, for example through addition of HOBt or N-hydroxysuccinimide.

The formula I and related formulae also encompasses the optically active forms (stereoisomers), the enantiomers, the racemates, the diastereomers and the hydrates and solvates of these compounds. The term "solvates of the compounds" is taken to mean adductions of inert solvent molecules onto the compounds which form owing to their mutual attractive force. Solvates are, for example, mono- or dihydrates or alcoholates.

The term "pharmaceutically usable derivatives" is taken to mean, for example, the salts of the compounds of the formula I and so-called prodrug compounds.

The term "prodrug derivatives" is taken to mean compounds of the formula I which have been modified with, for example, alkyl or acyl groups, sugars or oligopeptides and which are rapidly cleaved in the organism to form the active compounds.

These also include biodegradable polymer derivatives of the compounds according to the invention, as described, for example, in Int. J. Pharm. 115, 61-67 (1995).

The formula I and related formulae also encompasses mixtures of the compounds of the formula I, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

Very particularly, preferred embodiments of formula I are the compounds of formula IA, IB, IC, ID, IE:

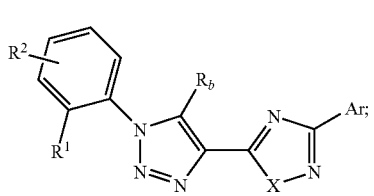

IA

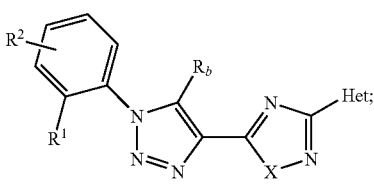

IB

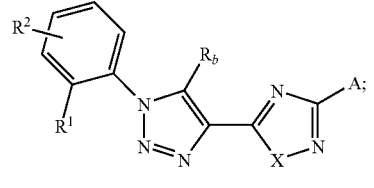

IC

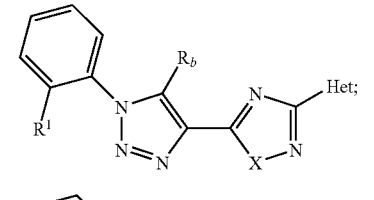

ID

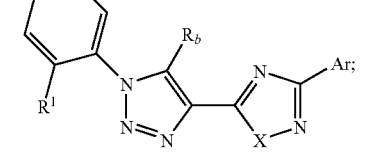

IE

Wherein X, $R^1$, $R^2$, $R^b$Het, Ar, A are defined as above. Formula IA wherein $R^2$ is H, is especially preferred. Preferably, $R^1$ is selected from F or Br, and is especially F.

Preference is given to the compounds of the present invention selected from the following group 1 to 193:

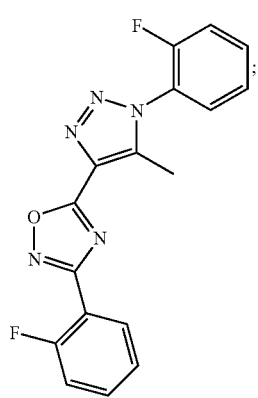

1

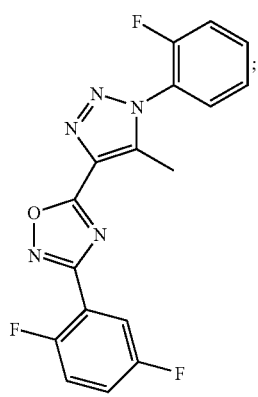

2

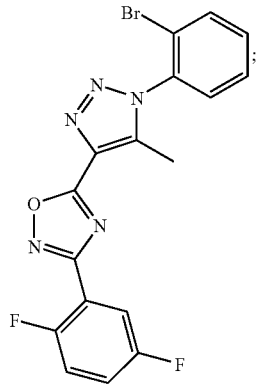

3

4
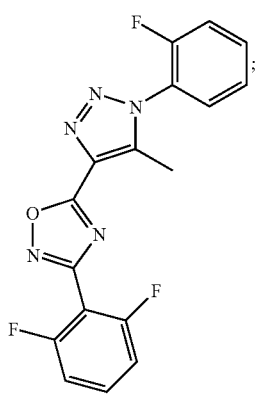
5
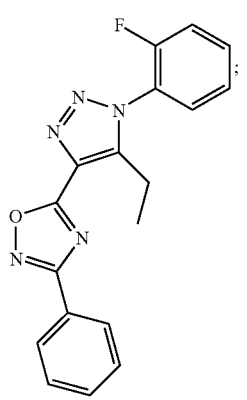
6
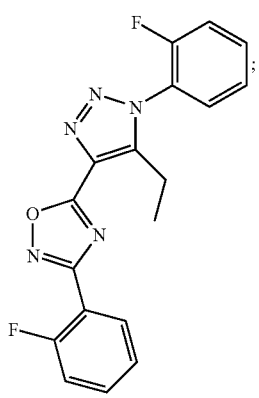
7
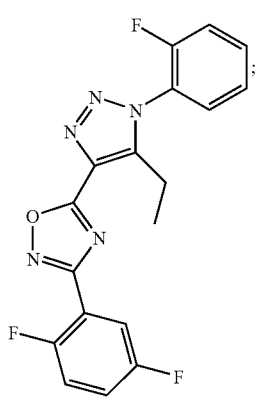
8
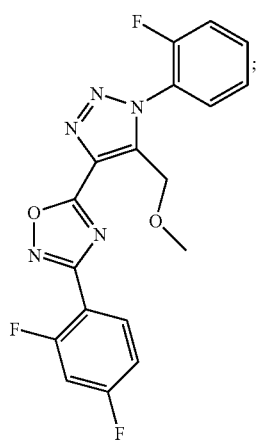
9
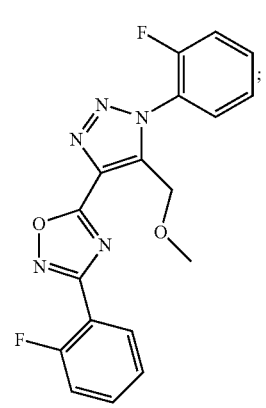
10
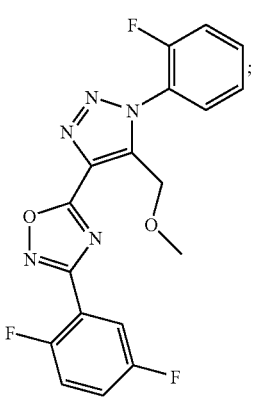
11
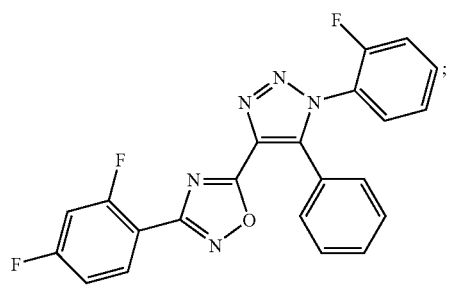

-continued
12
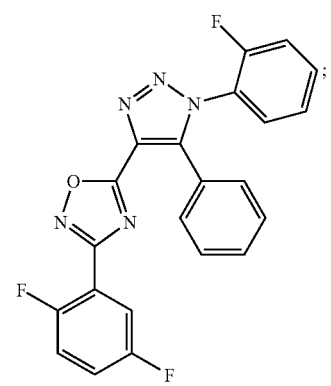
13
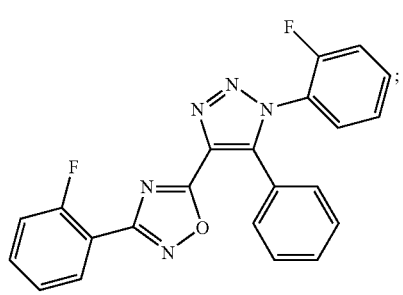
14
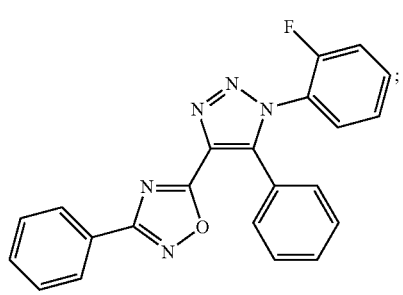
15
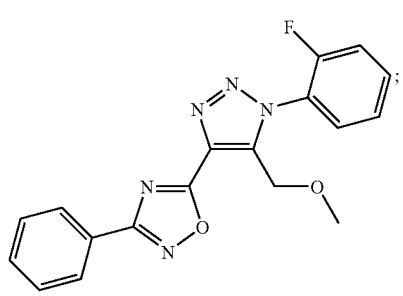
16
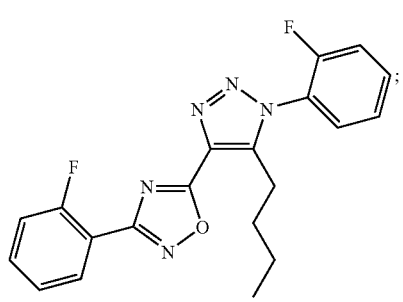
-continued
17
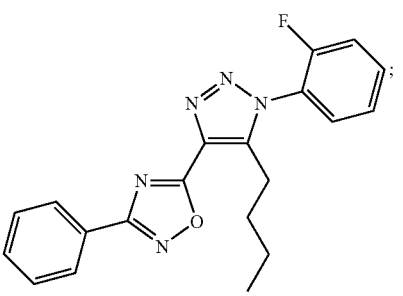
18
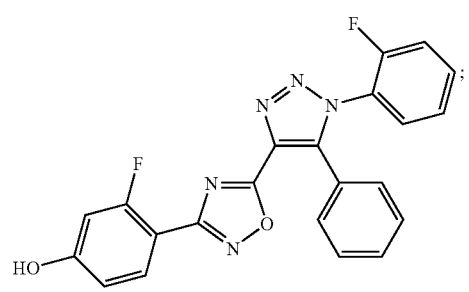
19
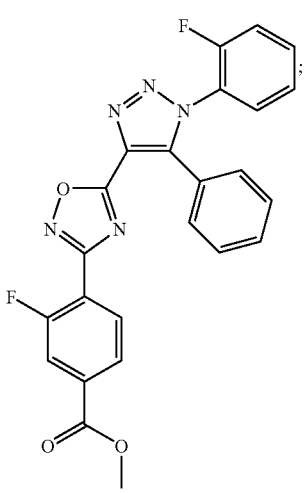
20
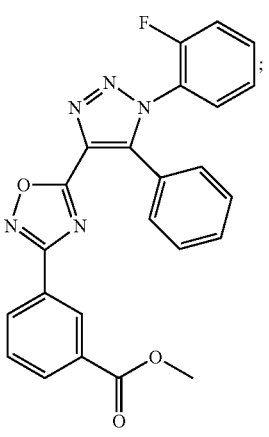

21
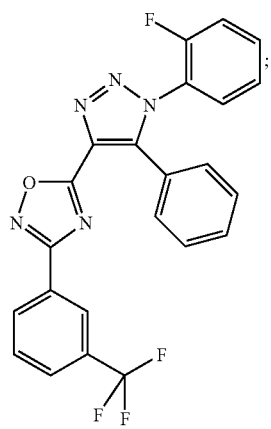
22
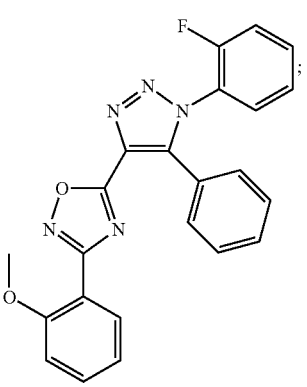
23
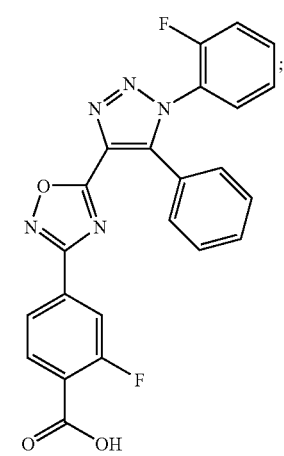
24
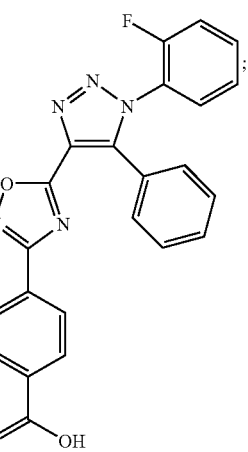
25
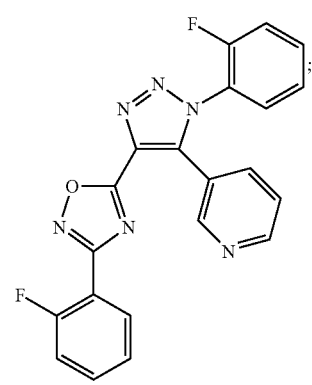
26
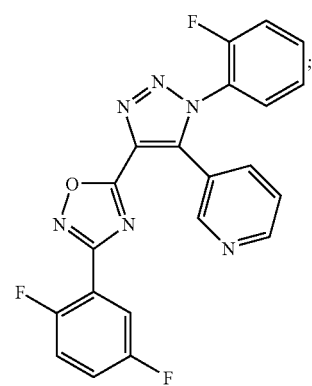
27
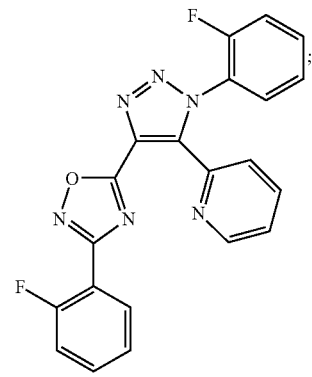

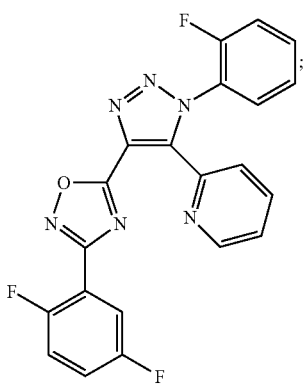
28
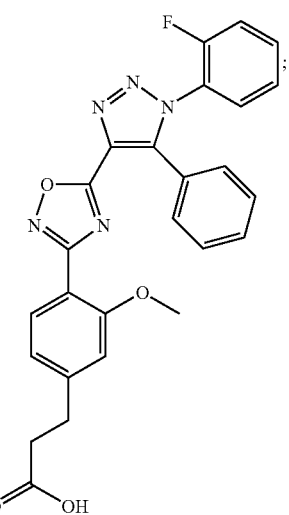
29
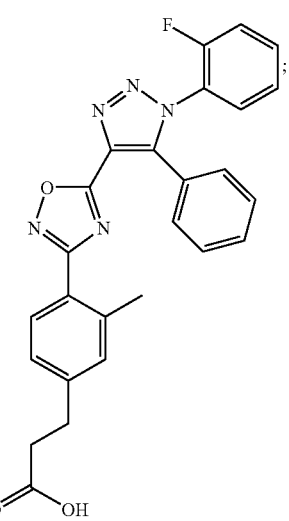
30
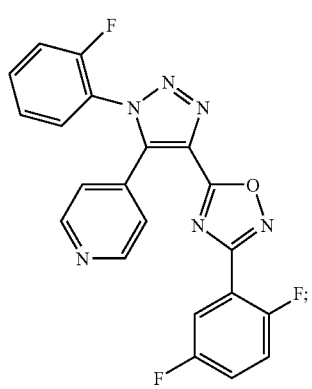
31
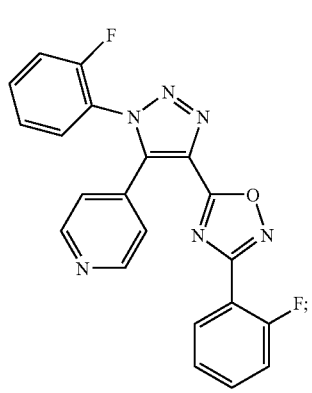
32
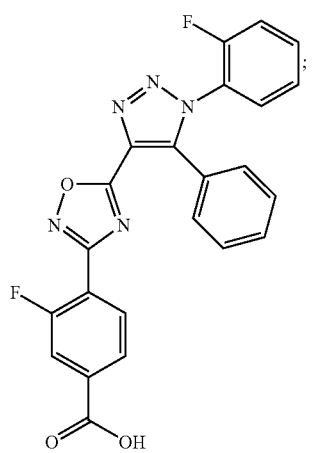
33
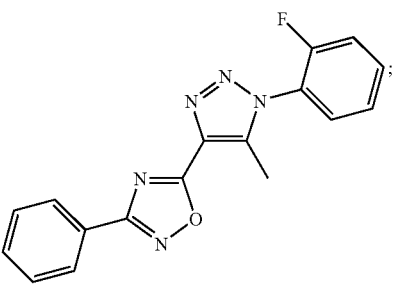
34

35
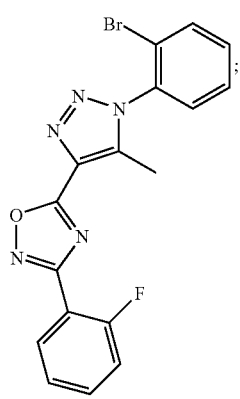
36
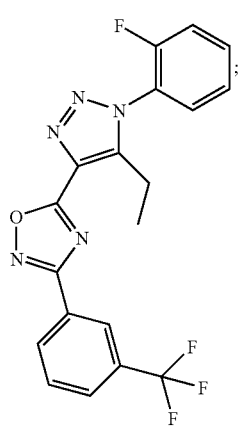
37
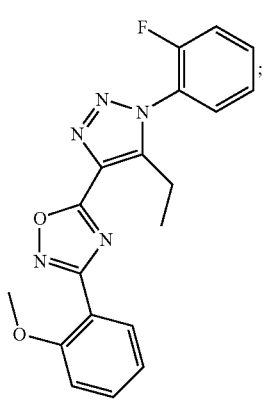
38
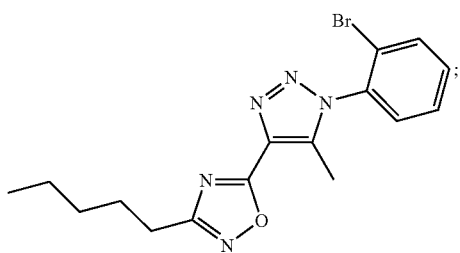
39
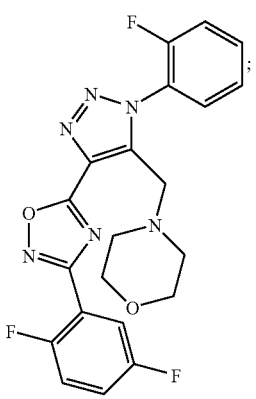
40
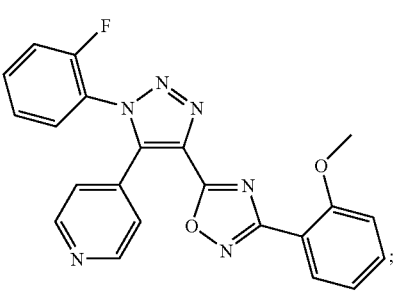
41
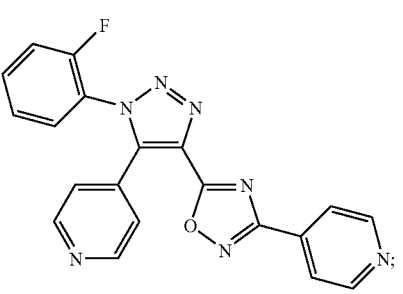
42
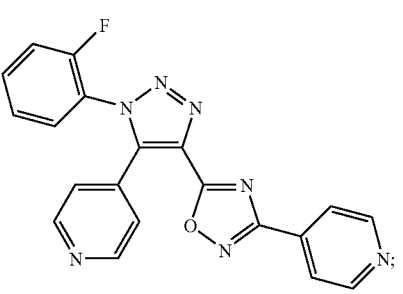
43
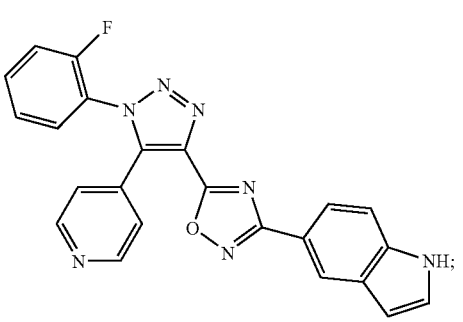

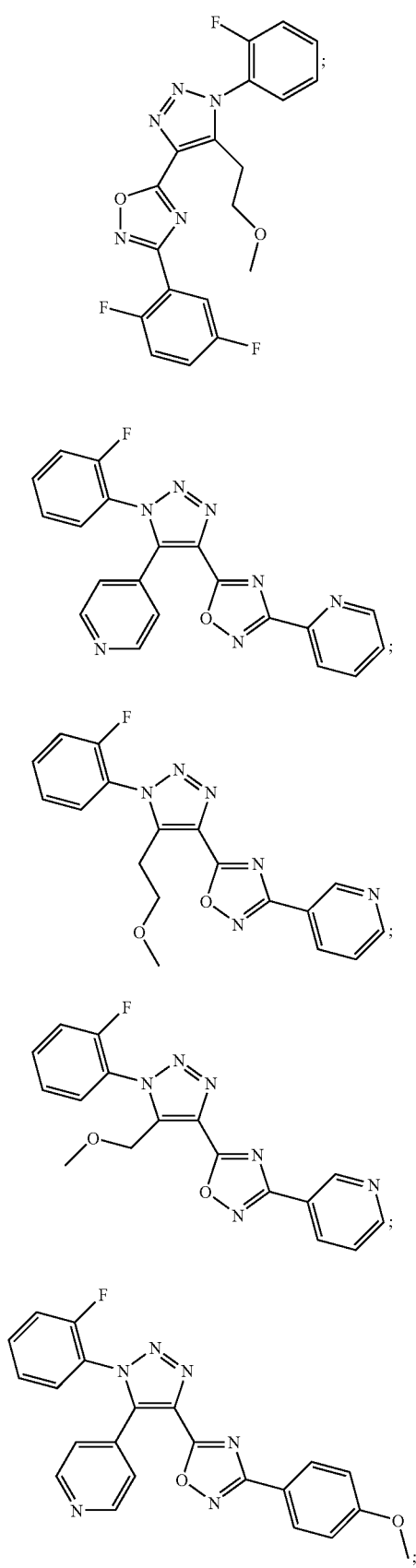
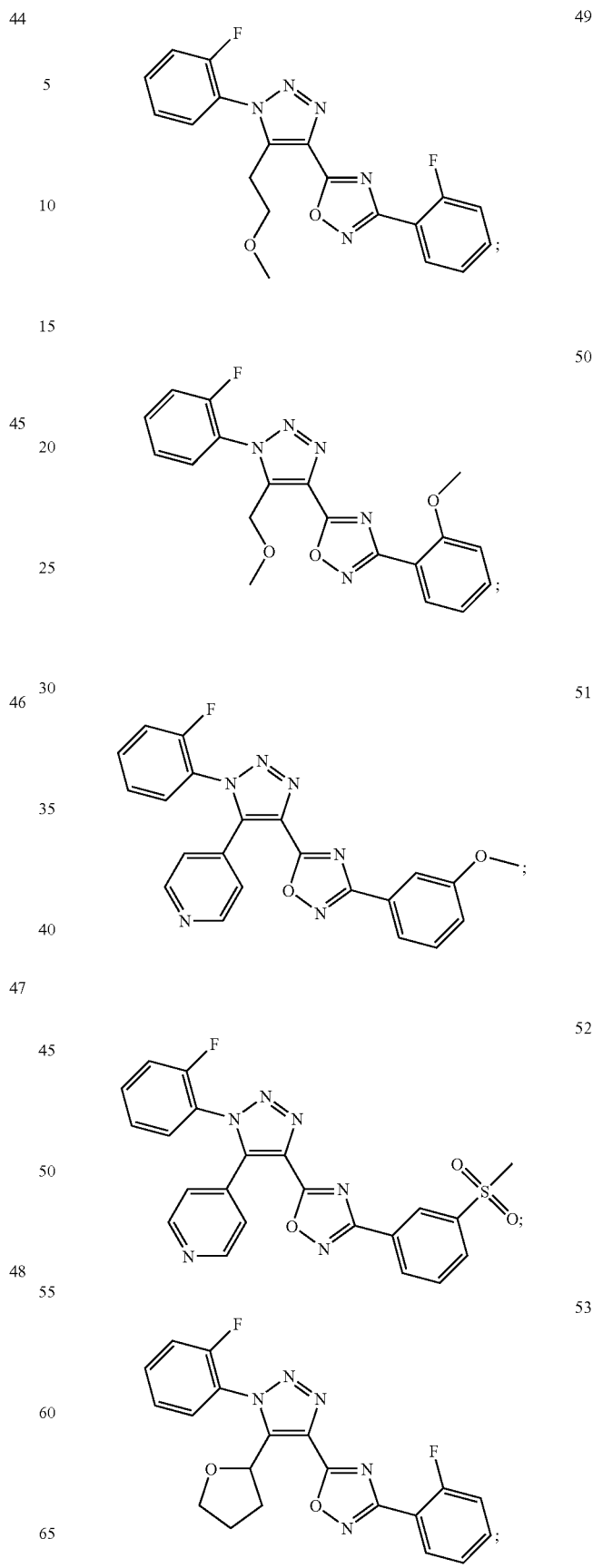

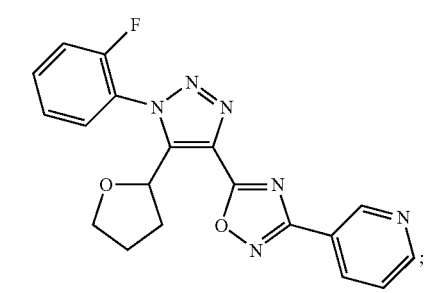
54
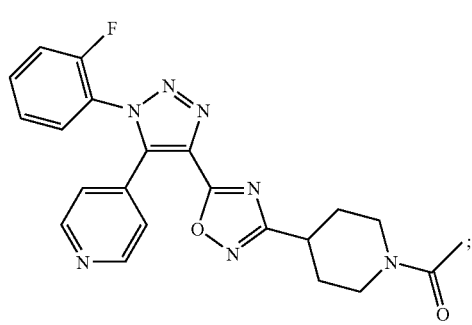
55
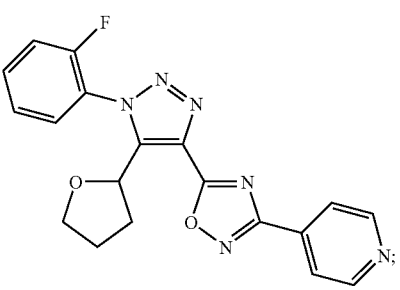
56
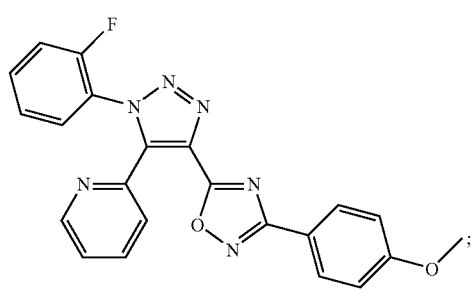
57
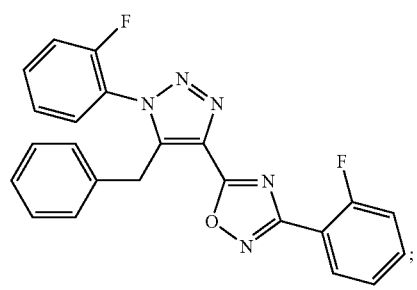
58
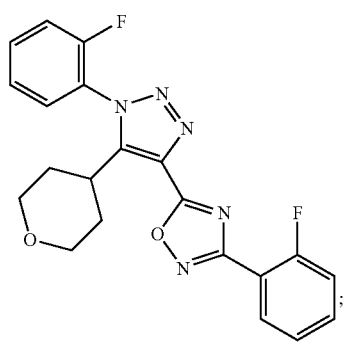
59
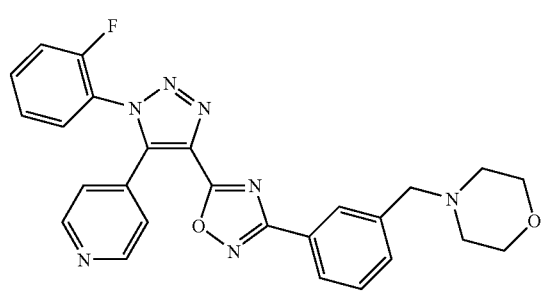
60
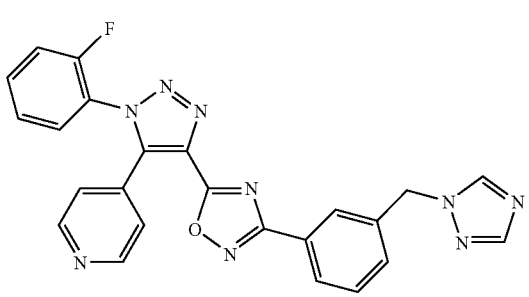
61
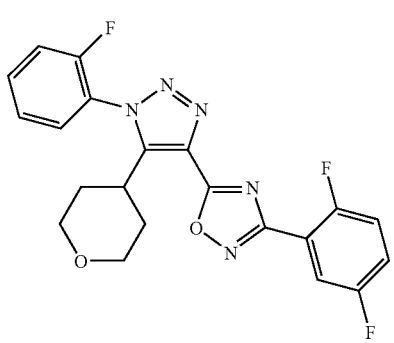
62
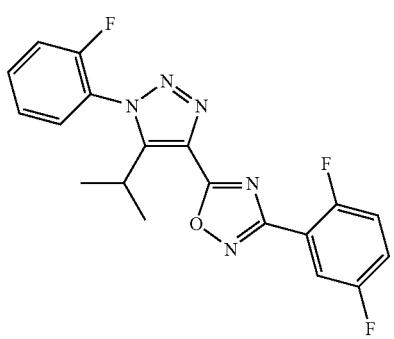
63

| | |
|---|---|
| 64 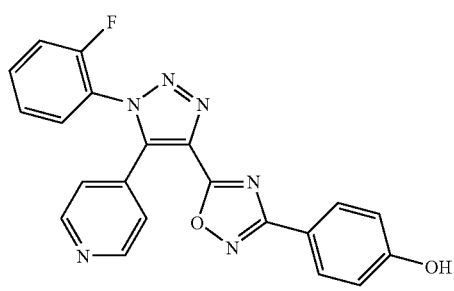 | 69 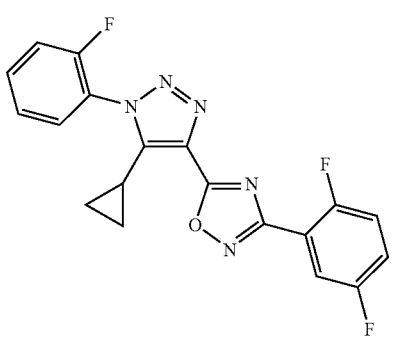 |
| 65 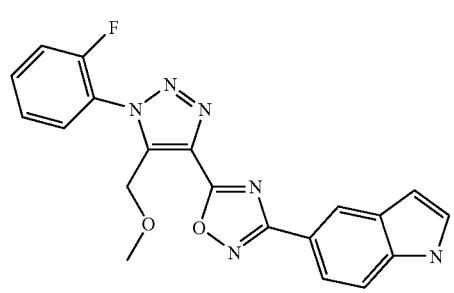 | 70 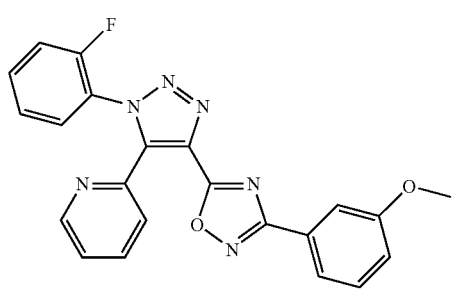 |
| 66 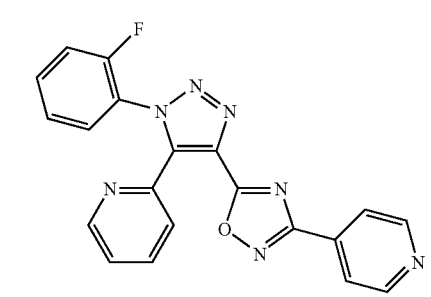 | 71 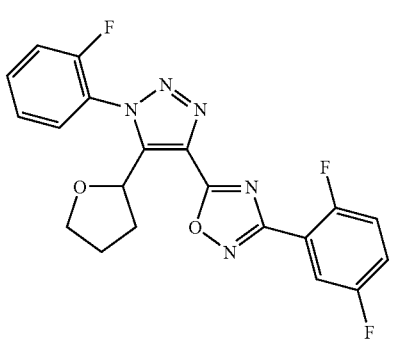 |
| 67 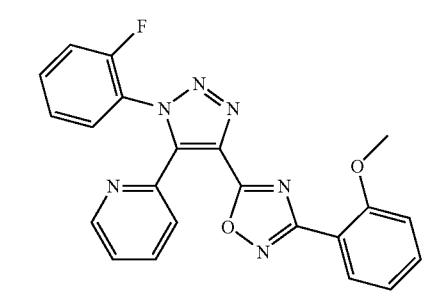 | 72 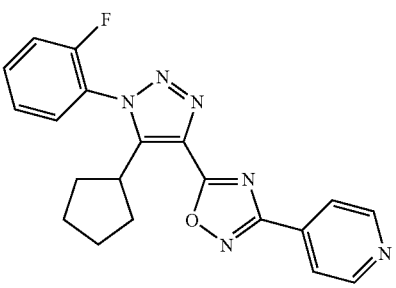 |
| 68 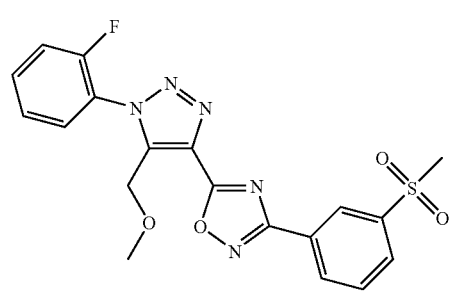 | 73 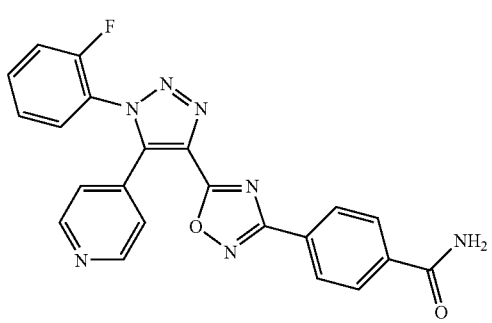 |

74 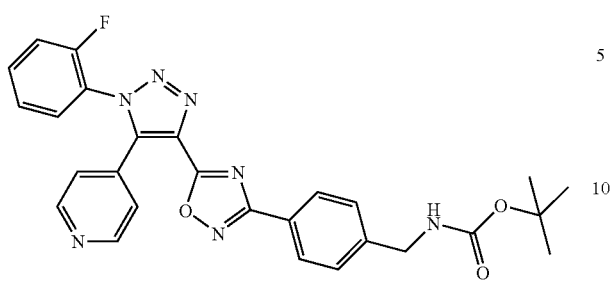
75 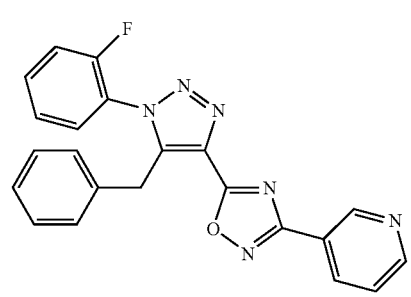
76 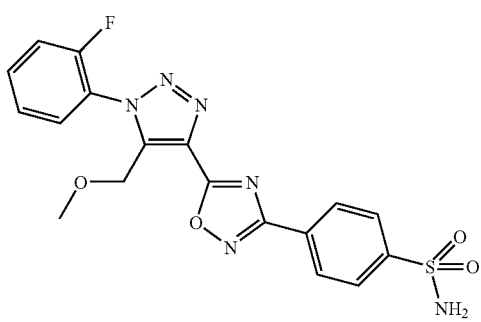
77 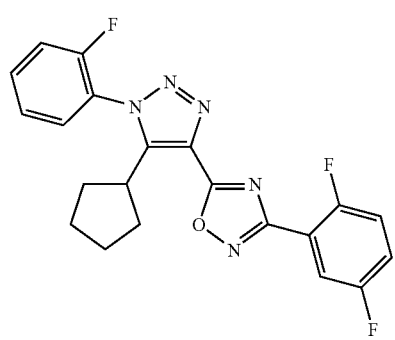
78 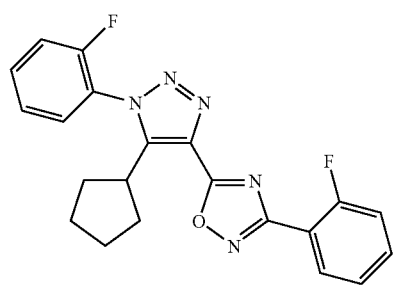
79 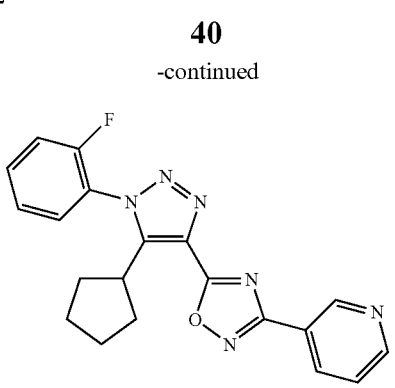
80 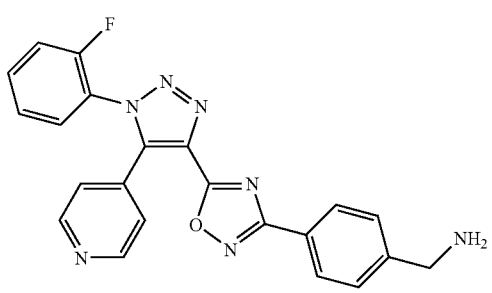
81 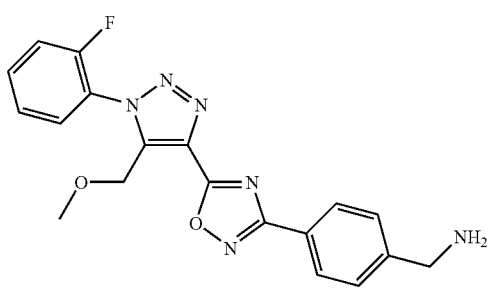
82 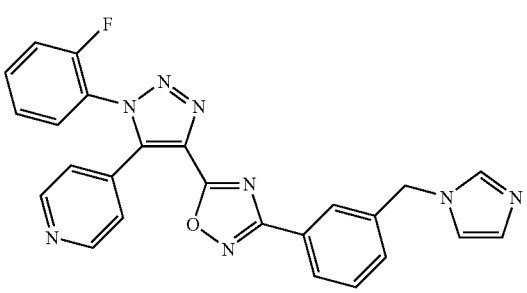
83 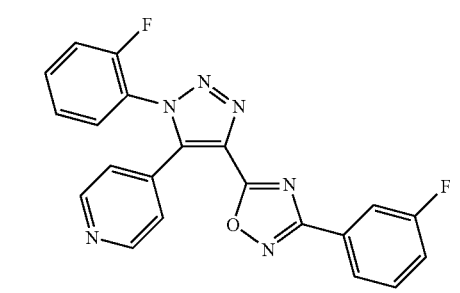

84
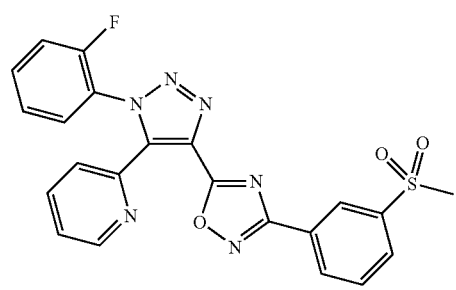
85
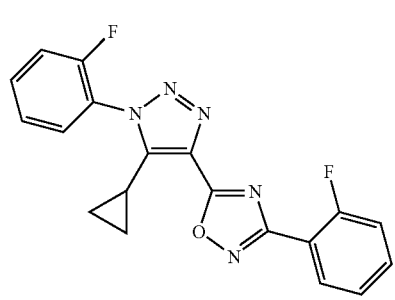
86
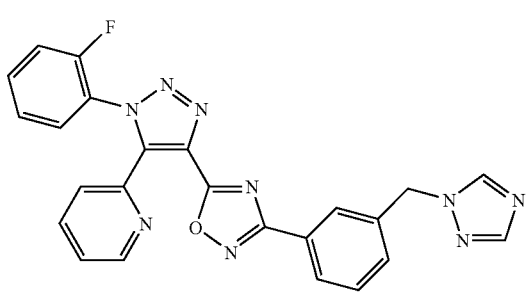
87
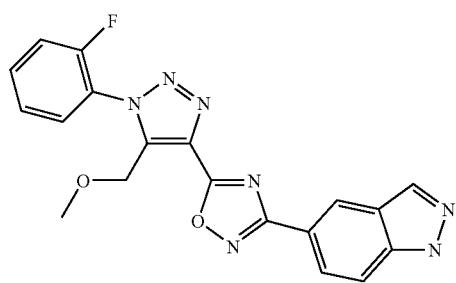
88
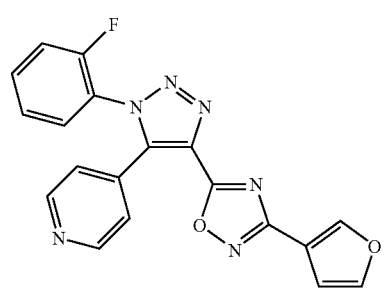
89
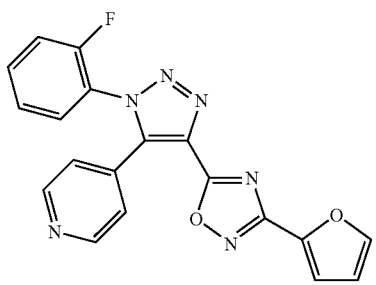
90
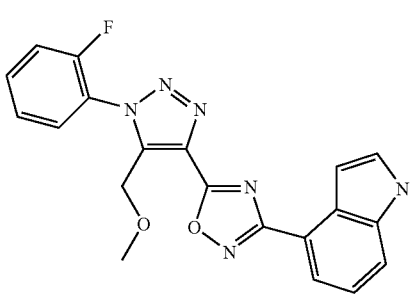
91
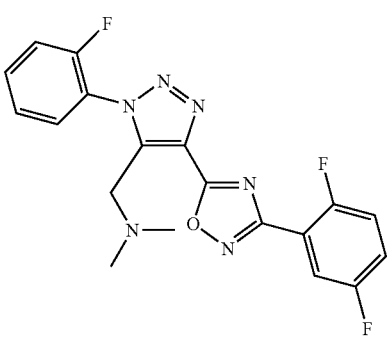
92
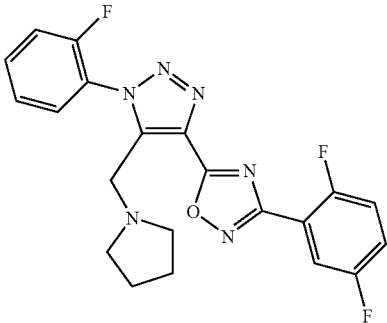
93
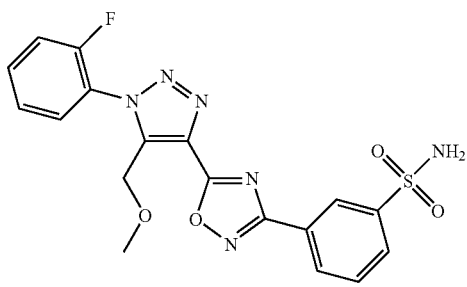

94
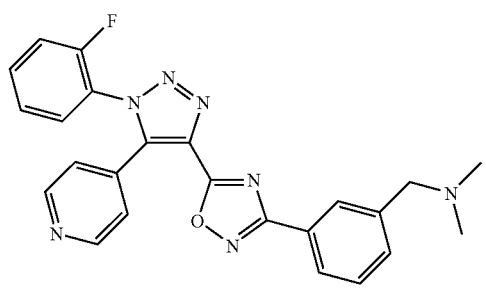
95
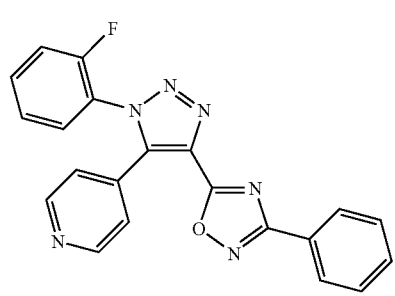
96
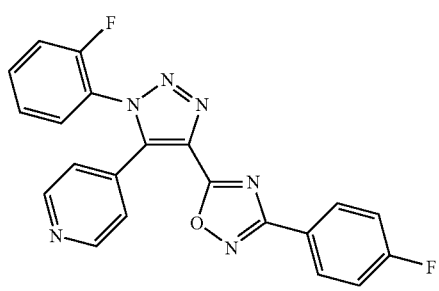
97
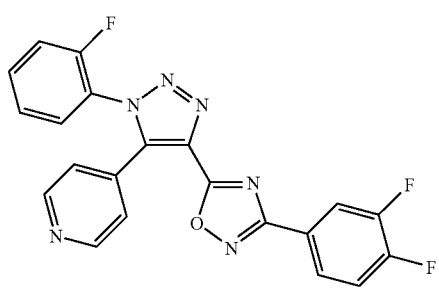
98
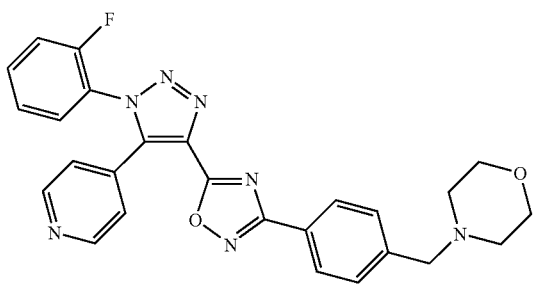
99
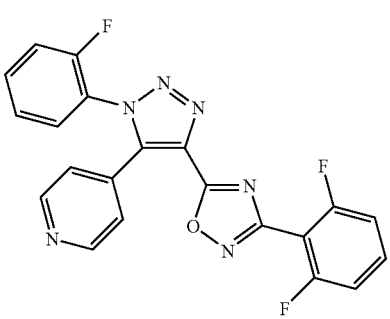
100
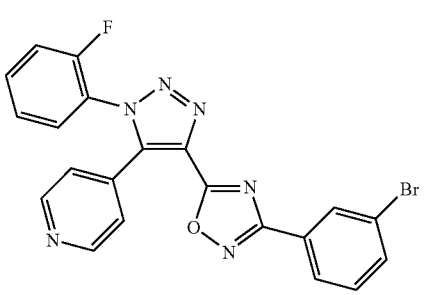
101
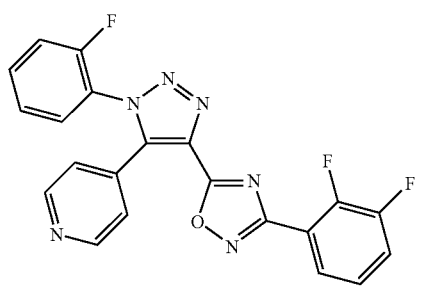
102
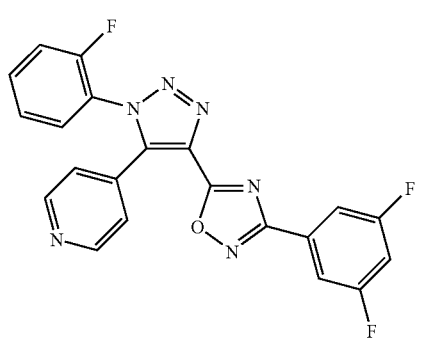
103
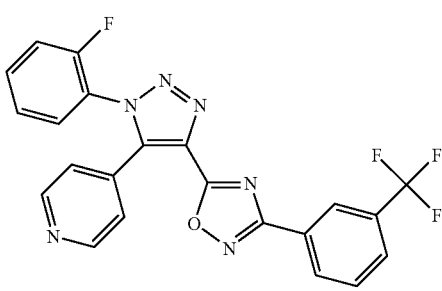

104
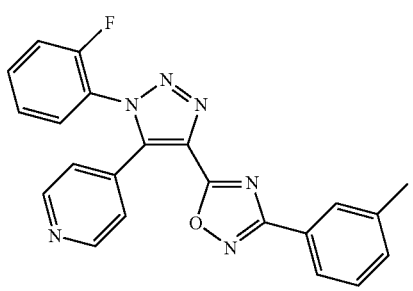
109
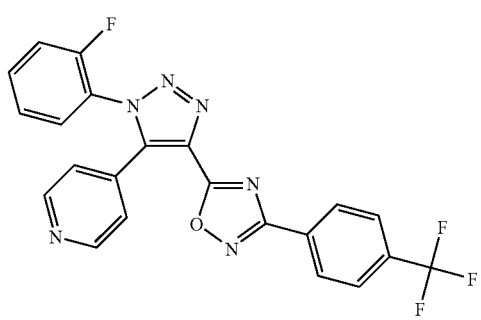
105
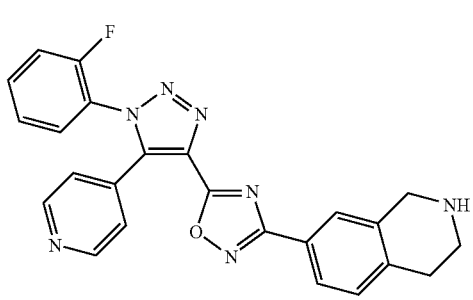
110
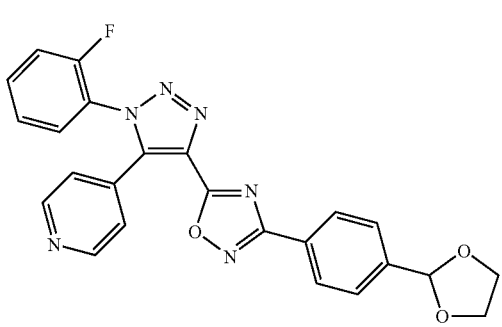
106
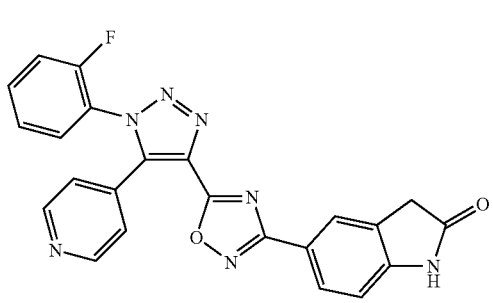
111
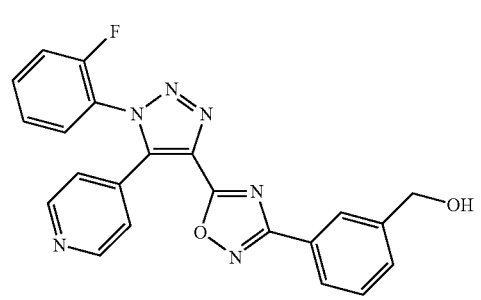
107
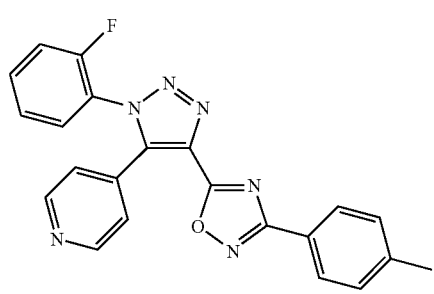
112
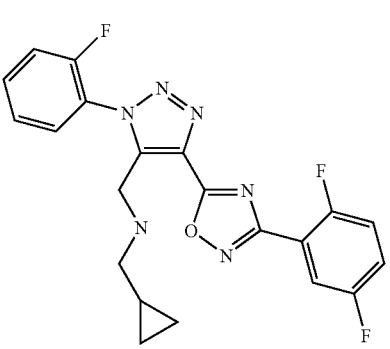
108
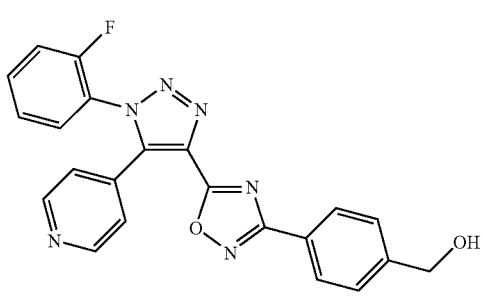
113
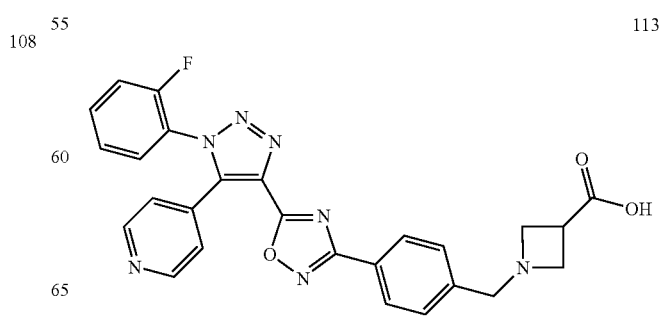

114
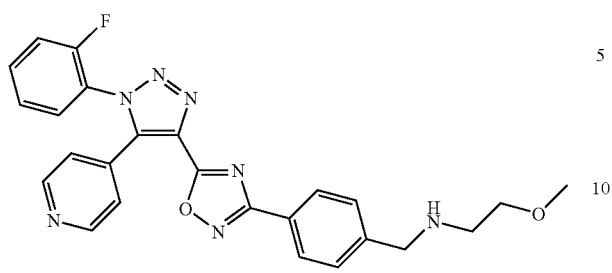
115
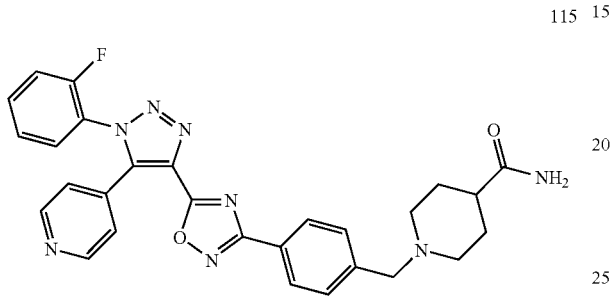
116
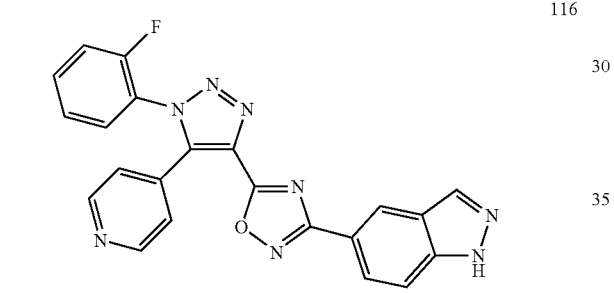
117
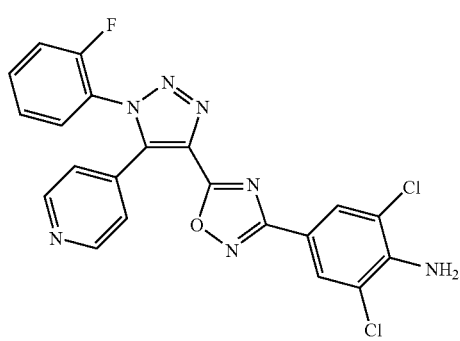
118
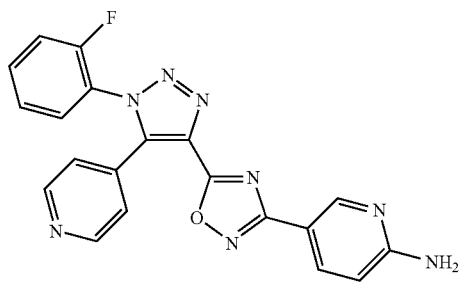
119
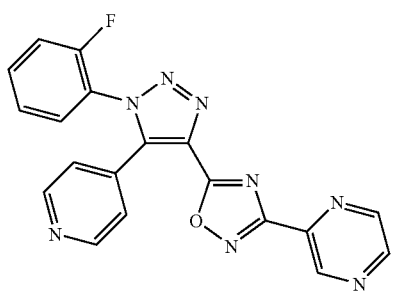
120
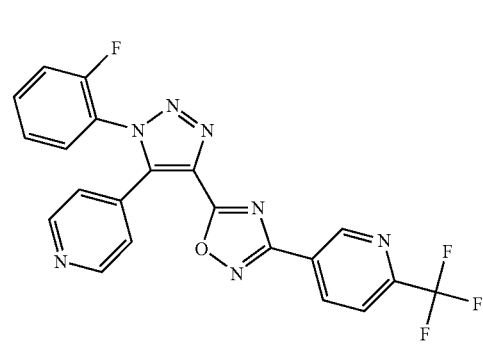
121
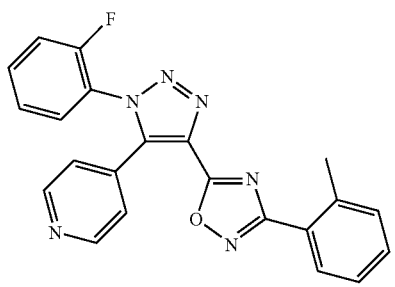
122
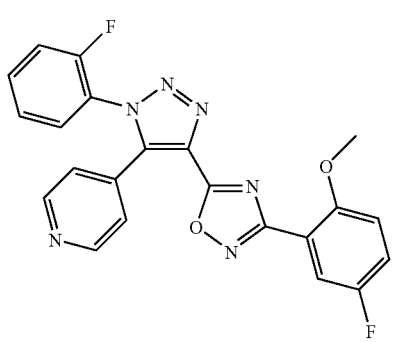
123
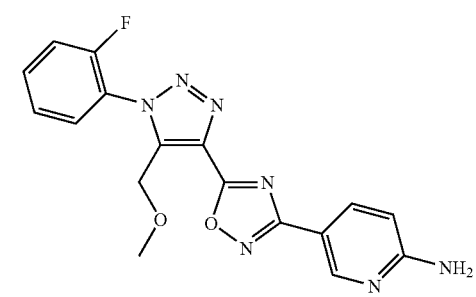

124
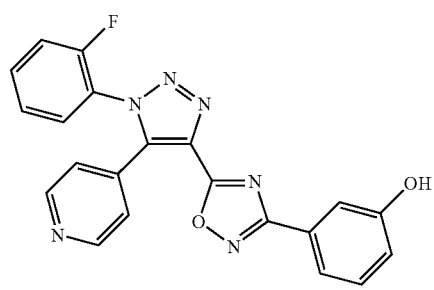
125
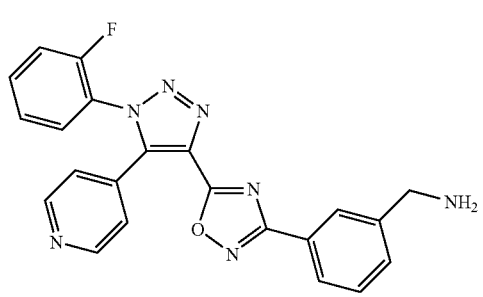
126
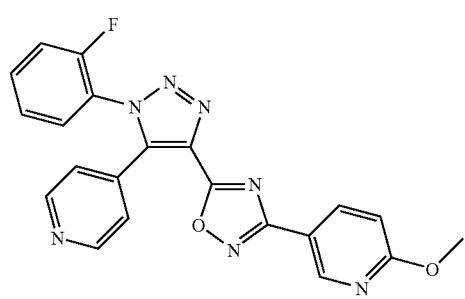
127
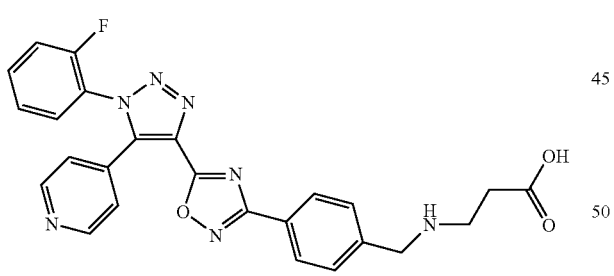
128
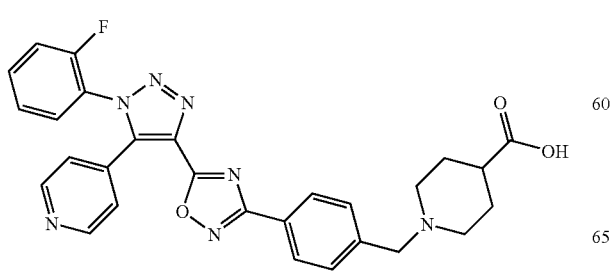
129
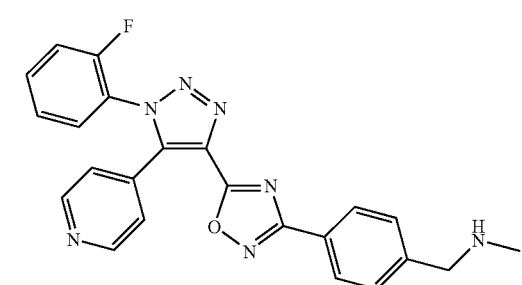
130
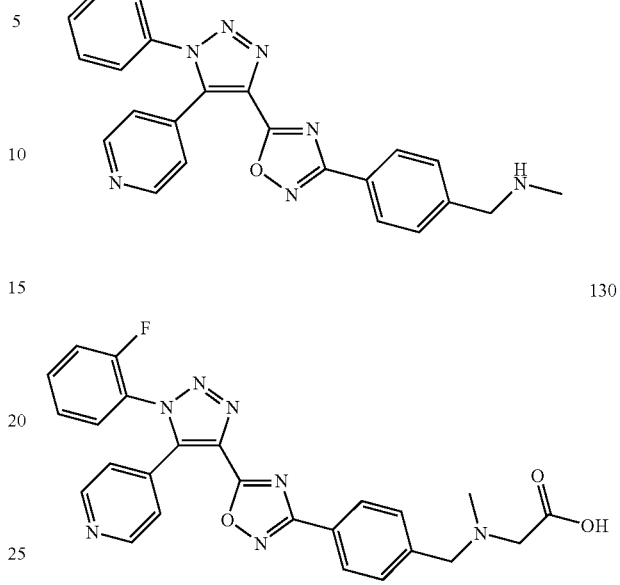
131
132
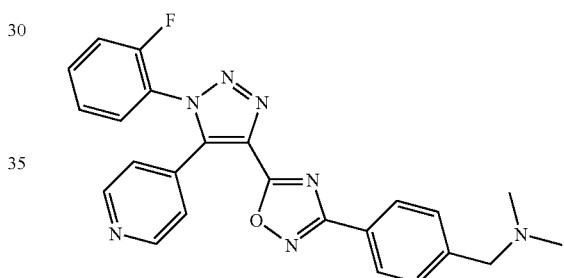
133
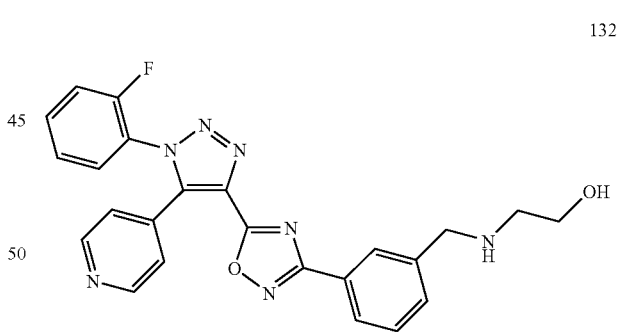

134
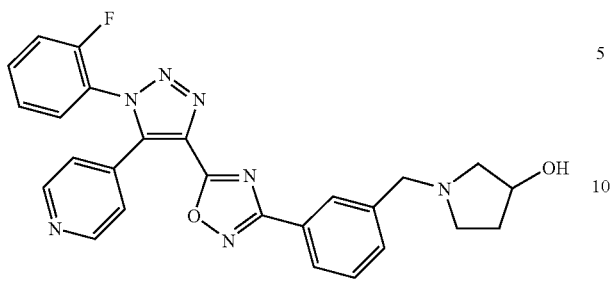
135
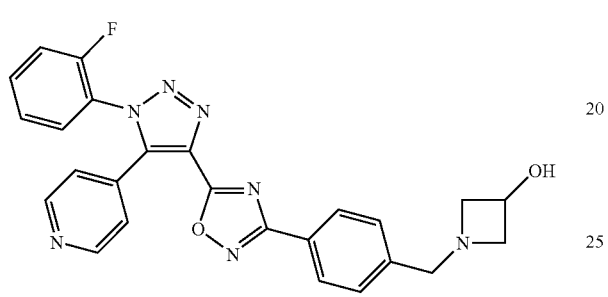
136
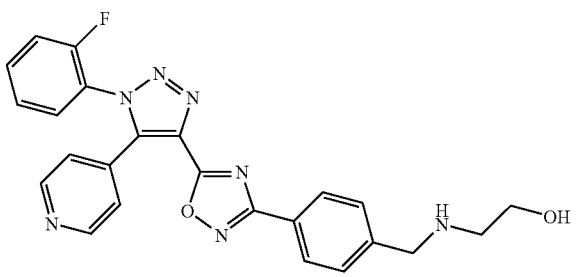
137
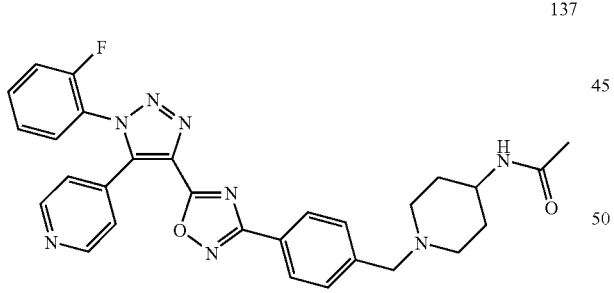
138
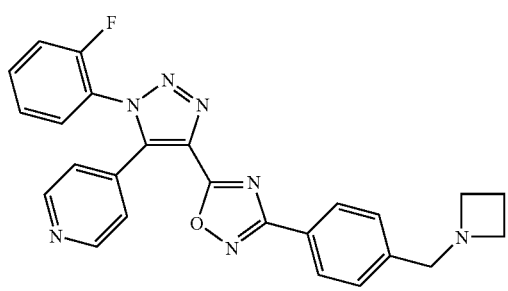
139
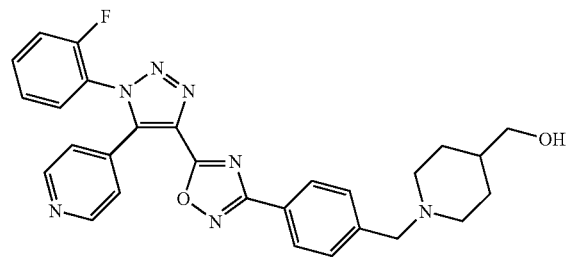
140
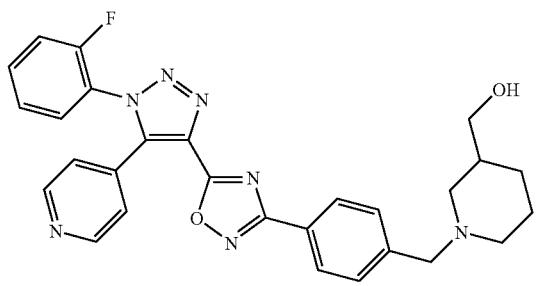
141
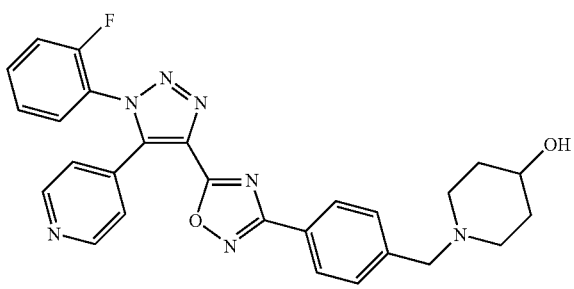
142
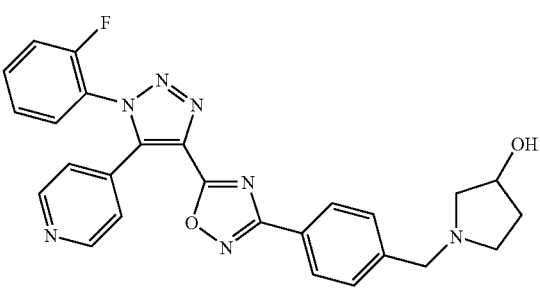
143
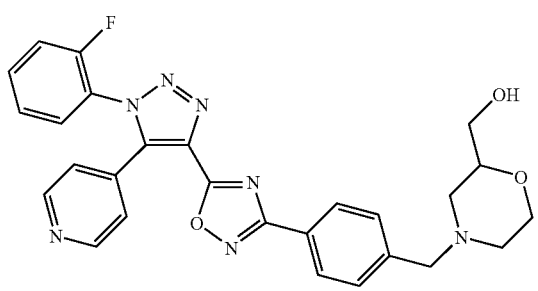

-continued
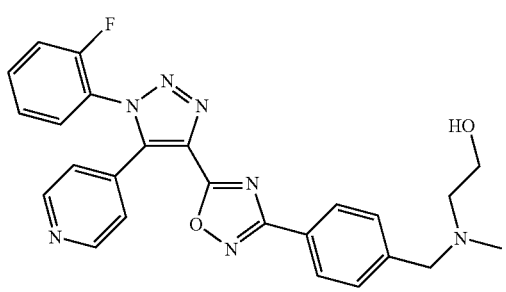
144
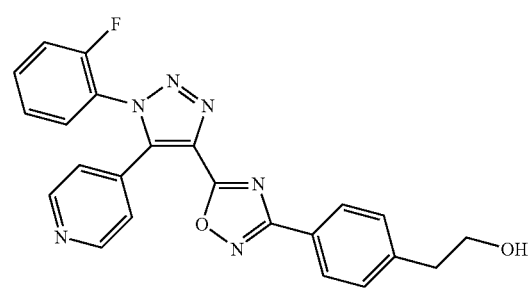
149
145
150
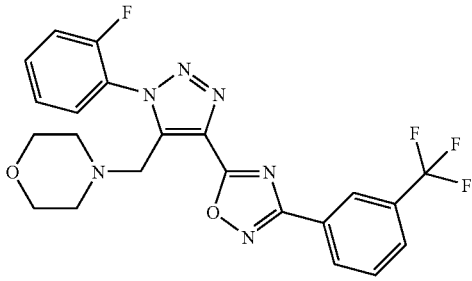
146
151
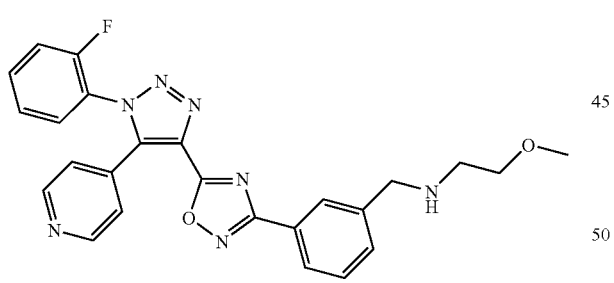
147
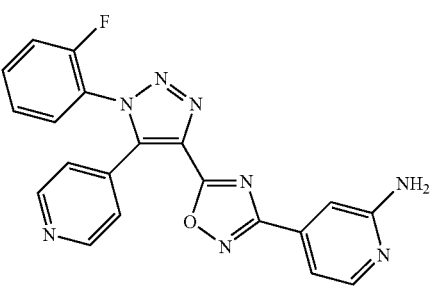
152
148
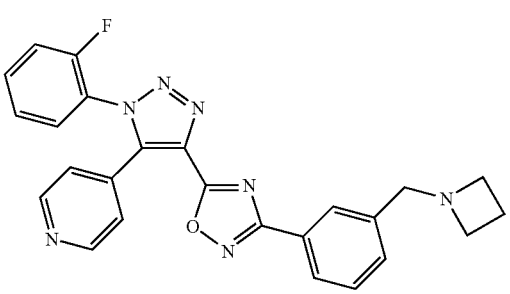
153
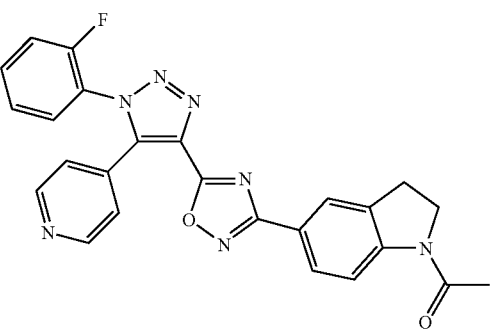

154
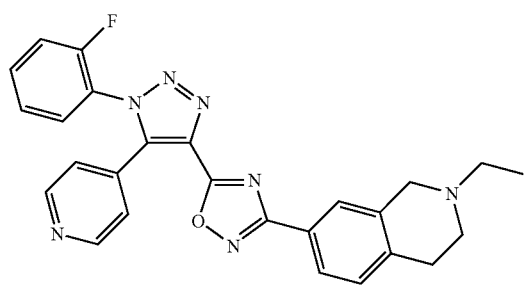
155
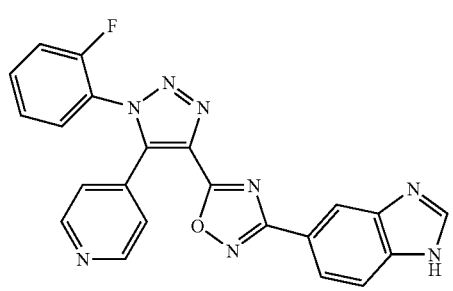
156
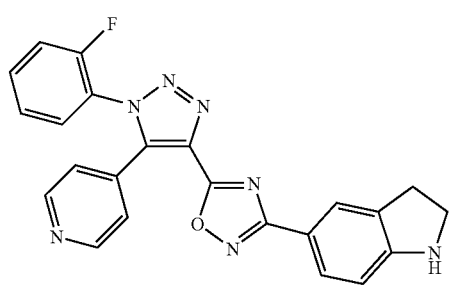
157
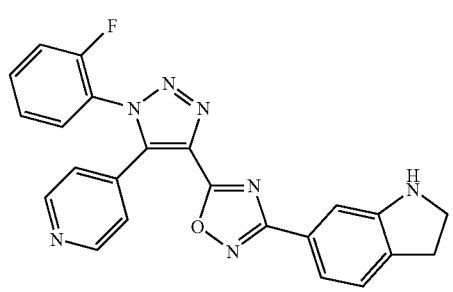
158
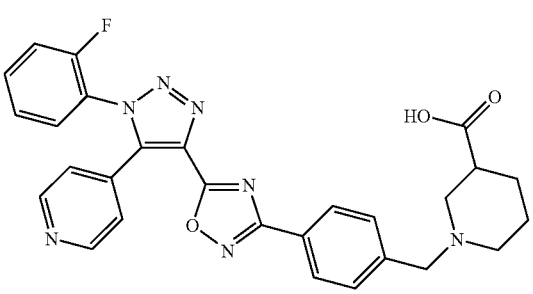
159
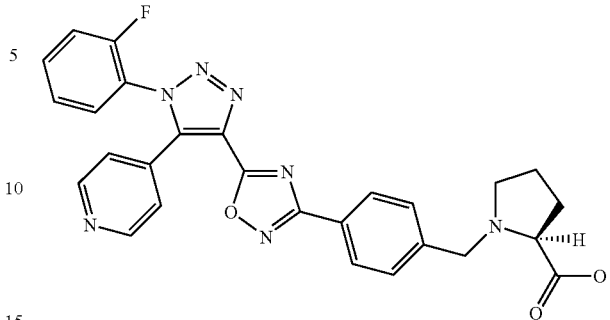
160
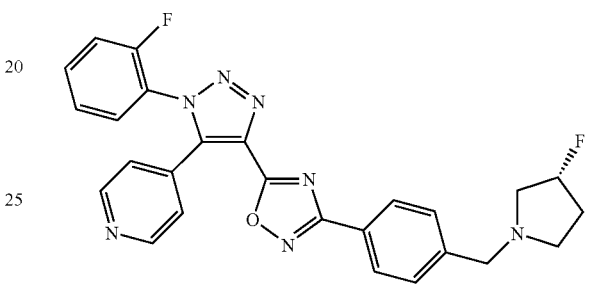
161
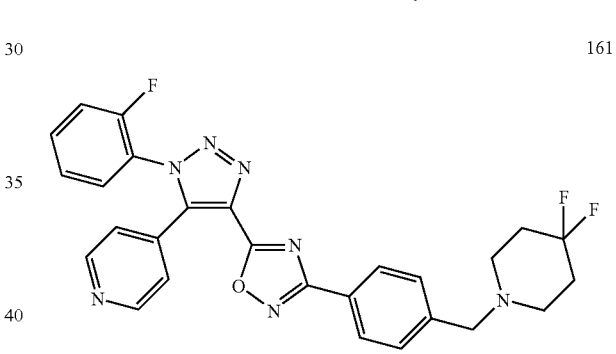
162
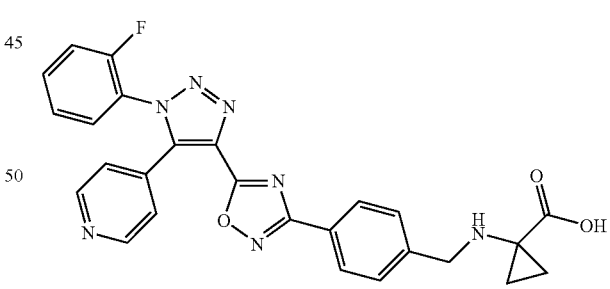
163
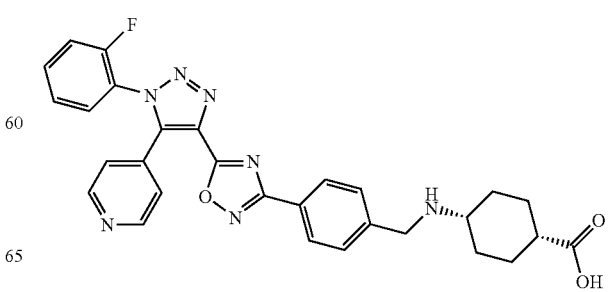

164
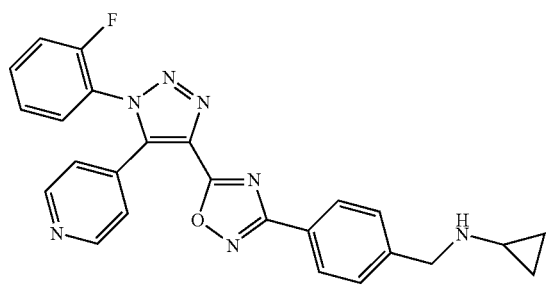
165
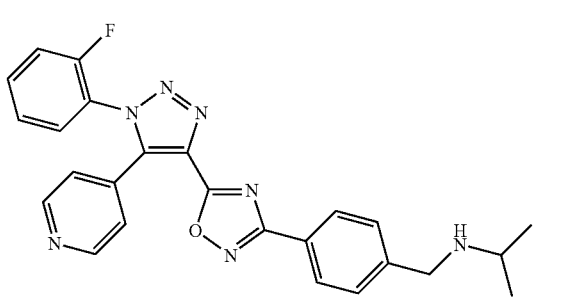
166
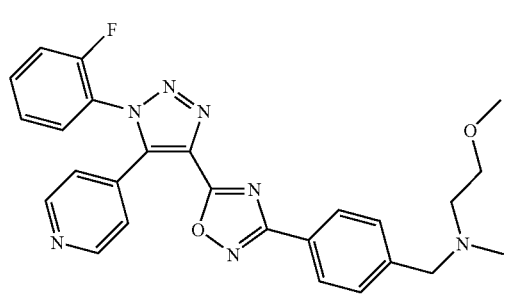
167
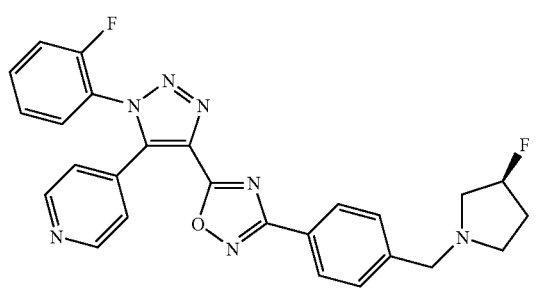
168
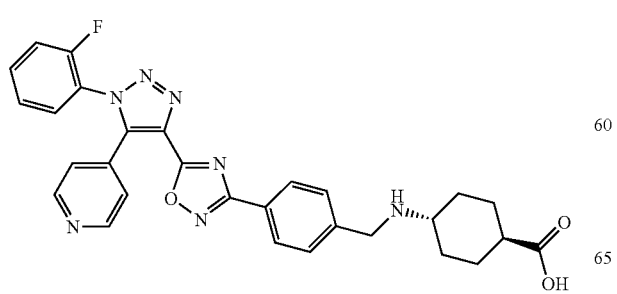
169 Chiral
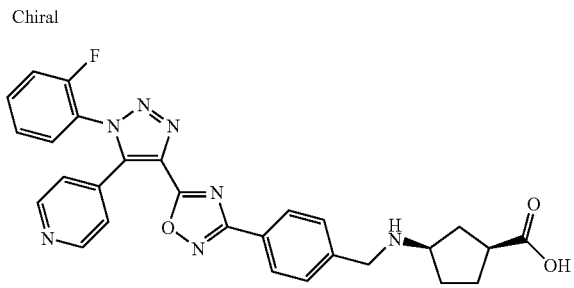
170
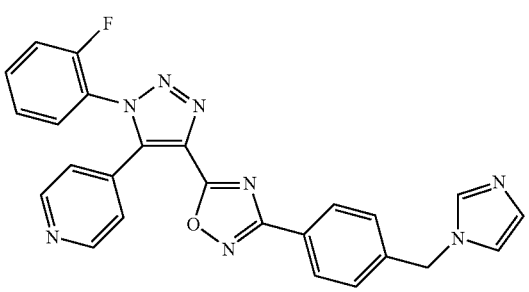
171
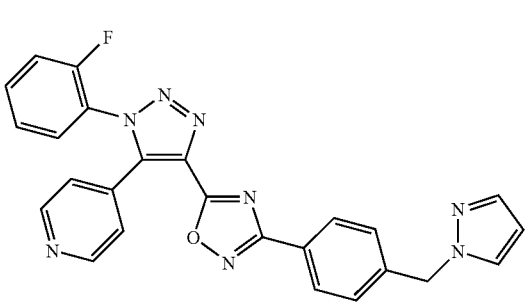
172
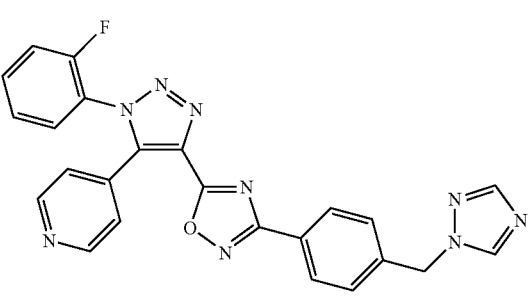
173
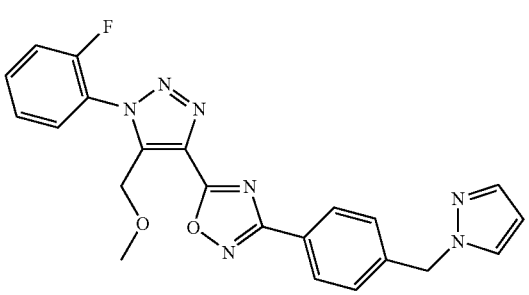

174
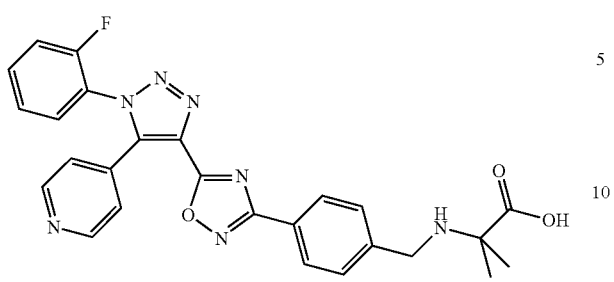
175
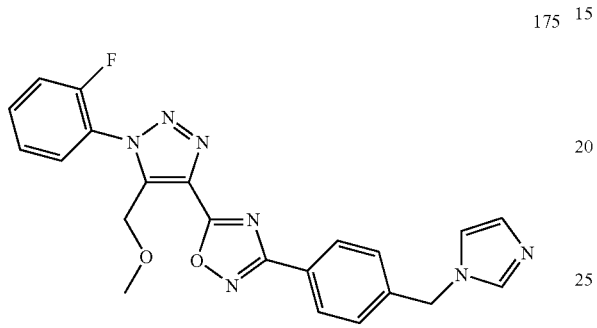
176
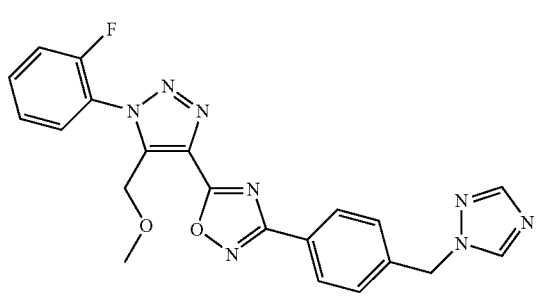
177
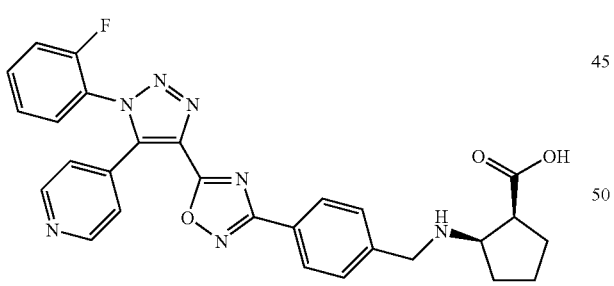
178
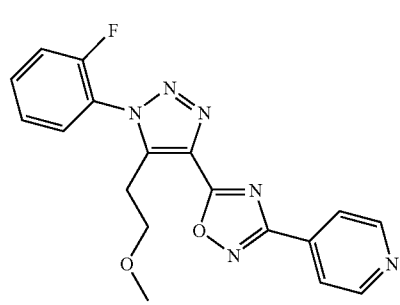
179
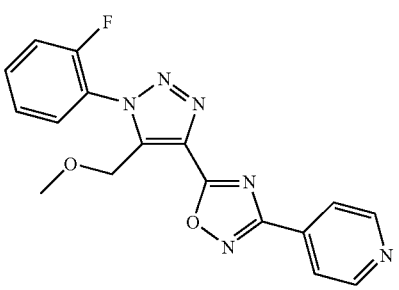
180
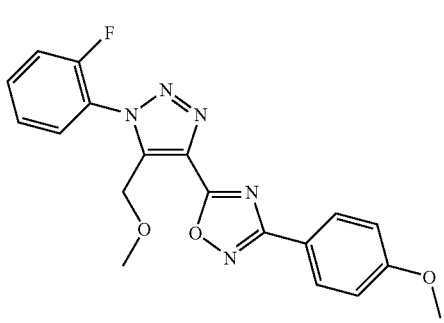
181
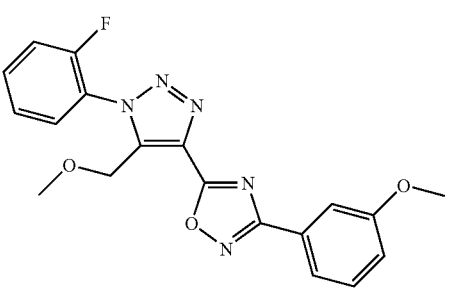
182
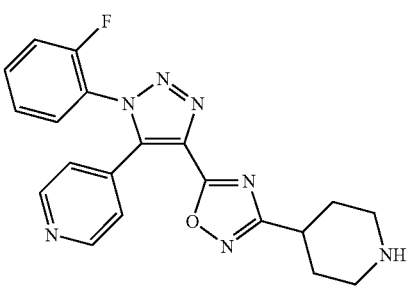
183
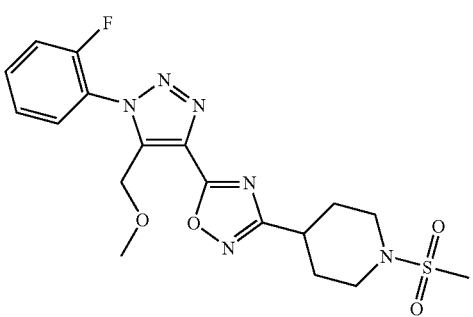

184 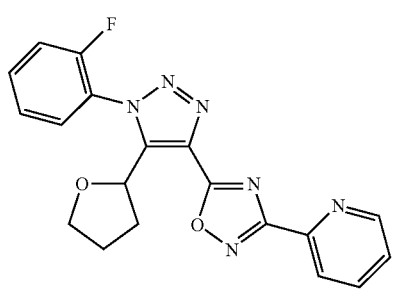
185 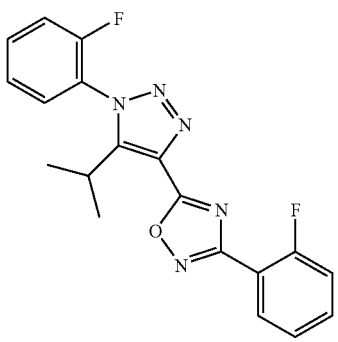
186
187
188
189 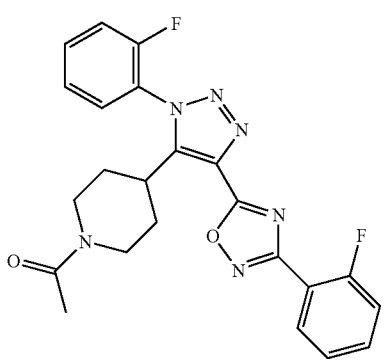
190
191 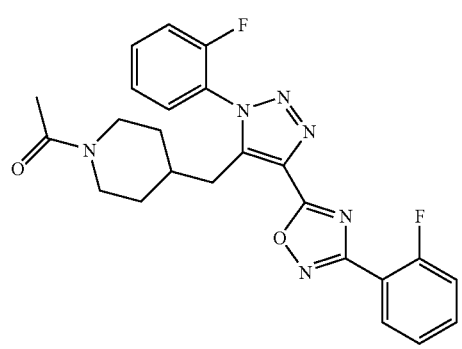
192 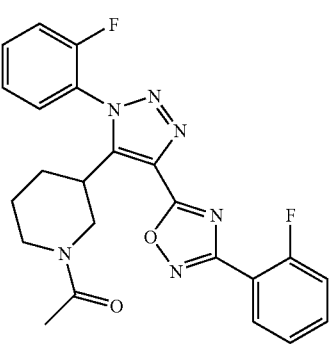

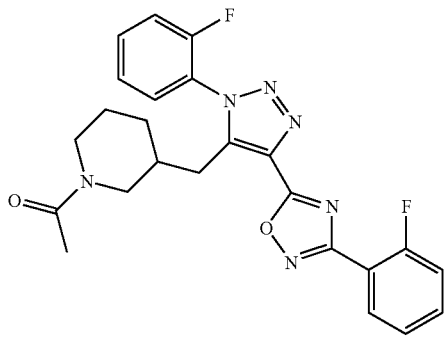

and pharmaceutically usable derivatives, solvates, salts and stereoisomers thereof, including mixtures thereof in all ratios.

Above and below, all radicals, such as X, $R^1$, $R^2$, $R^3$, $R^4$, $R^5$, $R^a$, $R^b$, A, Het, Ar, have the meaning indicated under the formula I, unless expressly stated otherwise.

Generally, compounds of formula I are the more preferred, the more preferred substituents they carry.

X is preferably O.

$R^1$ preferably denotes Hal; especially F or Br.

$R^2$ preferably denotes H, A or Hal; especially H.

$R^a$ preferably denotes A, Ar or Het.

$R^a$ more preferably denotes Ar or Het.

$R^b$ preferably denotes A, Ar, Het or Het-alkyl;

$R^b$ preferably denotes A, Ar, Het or Het-alykl.

$R^b$ more preferably denotes A, Het or Het-alkyl.

$R^b$ very most preferably denotes A wherein A is linear or branched alkyl having 1 to 12 C-atoms, wherein one or more, preferably 1 to H-atoms may be replaced by $OR^3$.

$R^b$ very most preferably denotes Het wherein Het is pyridinyl.

$R^b$ very most preferably denotes Het-alkyl wherein Het is piperidinyl, morpholino or piperazinyl.

Alkyl denotes a carbon chain having 1 to 12 carbon atoms, preferably 1 to 8 carbon atoms and most preferably 1 to 6 carbon atoms. Alkyl very preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl $N(R^3)_2$ may also denote Het.

A preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, furthermore preferably, for example, trifluoromethyl.

A very particularly preferably denotes alkyl having 1, 2, 3, 4, 5 or 6 carbon atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoroethyl. A furthermore denotes $(CH_2)_nO(CH_2)_nCH_3$, $(CH_2)_nO(CH_2)_n OR^3$, $(CH_2)_nNR^3(CH_2)_2N(R^3)_2$, especially, $CH_2-OCH_3$, $(CH_2)_n-OCH_3$, $(CH_2)_2O(CH_2)_2OR^3$, $(CH_2)_nN(R^3)_2$ or $(CH_2)_2NH(CH_2)_2N(R^3)_2$, wherein n is 1, 2, 3 or 4.

Cycloalkyl preferably denotes cyclopropyl, cyclobutyl, cyclopentyl, cyclohexyl or cycloheptyl.

Cycloalkylalkylene preferably denotes cyclopropylmethylene, cyclobutylmethylene, cyclopentylmethylene, cyclohexylmethylene or cycloheptylmethylene.

Alkylene is preferably methylene, ethylene, propylene, butylene, pentylene or hexylene, furthermore branched alkylene.

Perfluoroalkyl preferably denotes $CF_3$.

Perfluoro-alkoxy preferably denotes $OCF_3$.

Hal denotes Cl, Br, I, F and preferably F, Br or Cl.

Alkoxy denotes a group $-O-(CH_2)_n-CH_3$, wherein n is 0, 1, 2, 3 or 4, preferably Methoxy or Ethoxy.

Carboxy denotes a group $-COON$.

Carboxyalkyl denotes an ester group preferably COOMe or COOEt.

Alkylsulfonyl denotes a group $-S(O)_2$-alkyl preferably Methylsulfonyl or Ethylsulfonyl.

Acyl denotes a group $-C(O)R$ wherein R can be A, Ar, Het as defined above, preferably Acyl denotes a group Acetyl $-C(O)CH_3$.

Amino denotes the group $-NR*R'''$ where each $R*$, $R'''$ is independently hydrogen or alkyl or Ar or Het or A or Het-alkyl or Ar-alkyl, and where $R*$ and $R'''$, together with the nitrogen atom to which they are attached, can optionally form a 3-8-membered Het ring.

Amido refers to the group $-C(O)NR*R'''$ where each $R*$, $R'''$ is independently hydrogen or alkyl or Ar or Het or A or Het-alkyl or Ar-alkyl, and where $R*$ and $R'''$, together with the nitrogen atom to which they are attached, can optionally form a 3-8-membered Het ring.

Ar, additionally to the above meaning, can also denote a saturated carbocyclic ring having 6 to 14 carbon atoms which may be unsubstituted or monosubstituted, disubstituted or trisubstituted by a substituent selected from $R^4$ and/or $R^5$.

Ar preferably denotes phenyl, which may be unsubstituted or monosubstituted, disubstituted or trisubstituted by a substituent selected from $R^4$ and/or $R^5$.

Ar very particularly preferably denotes one of the following groups:

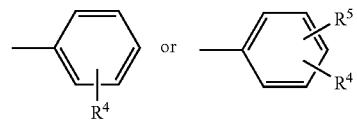

wherein $R^4$ and $R^5$ are as defined above.

More particularly, Ar is one of the following groups:

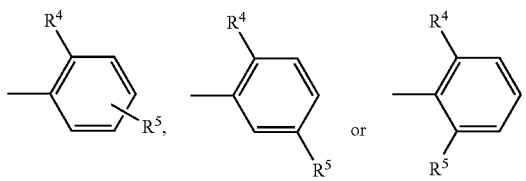

wherein $R^4$, $R^5$ is as defined above and preferably, wherein $R^4$ is Hal and $R^5$ is Hal or H.

Furthermore, Ar is preferably unsubstituted or

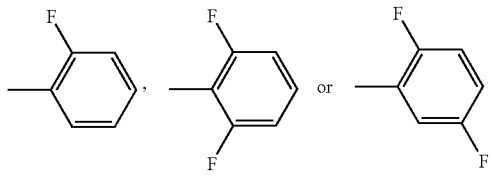

Het preferably denotes a monocyclic or bicyclic, saturated, unsaturated or aromatic heterocyclic ring having 1 to 3 N atoms which may be unsubstituted or monosubstituted, disubstituted or trisubstituted by a substituent selected from $R^4$ and/or $R^5$; or bicyclic, saturated, unsaturated or aromatic heterocyclic ring having 1 oxygen atom which may be unsubstituted or monosubstituted, disubstituted or trisubstituted by a substituent selected from $R^4$ and/or $R^5$.

Het is preferably a 6 to 14 membered ring system and denotes, not withstanding further substitutions, for example, 2- or 3-furyl, 2- or 3-thienyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, indazolyl, 4- or 5-isoindolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxa-diazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, furthermore preferably 1,3-benzodioxol-5-yl, 1,4-benzodioxane-6-yl, 2,1,3-benzothiadiazol-4- or -5-yl or 2,1,3-benzoxadiazol-5-yl.

The heterocyclic radicals may also be partially or fully hydrogenated.

Het can thus also denote, for example, 2,3-dihydro-2-, -3-, -4- or -5-furyl, 2,5-dihydro-2-, -3-, -4- or -5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxaneyl, 1,3-dioxane-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl, furthermore preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or -6-yl, 2,3-(2-oxomethylenedioxy)phenyl or also 3,4-dihydro-2H-1,5-benzodioxepin-6- or -7-yl, furthermore preferably 2,3-dihydrobenzofuranyl or 2,3-dihydro-2-oxofuranyl.

Het very particularly denotes one of the following groups:

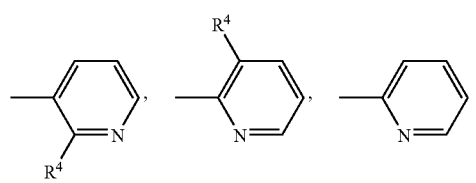

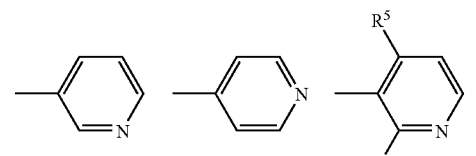

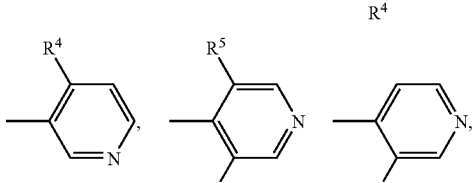

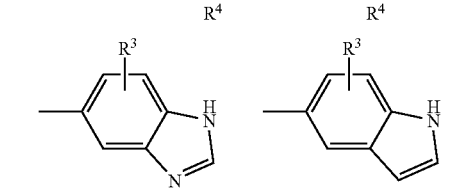

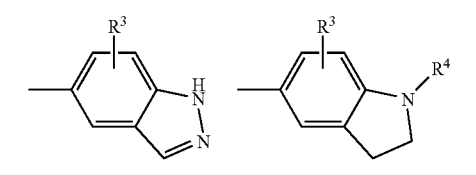

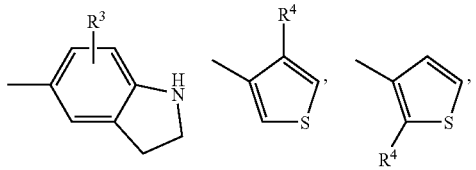

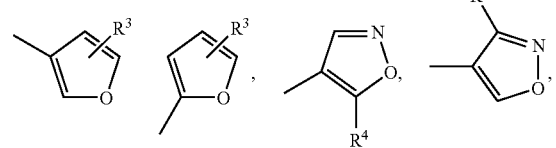

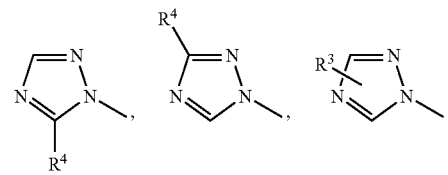

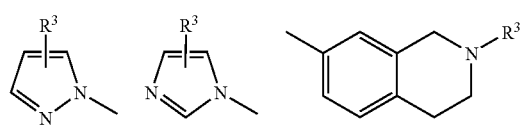

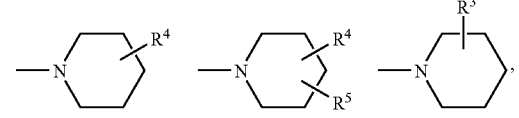

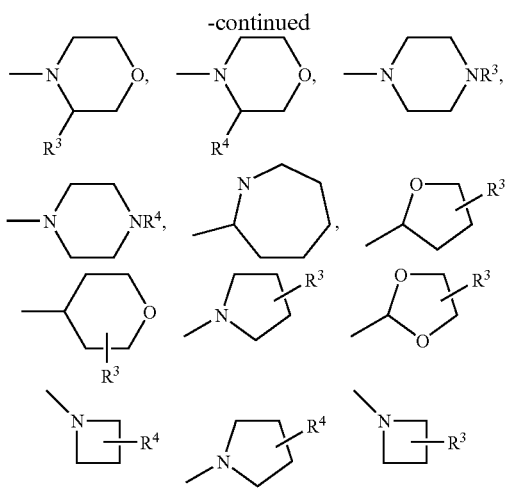

Wherein R³, R⁴ and R⁵ are as defined above.

Preferably, R⁴ and R⁵ are each independently selected from A, Hal, hydroxy, alkoxy, carboxy, carboxy-alkyl, Perfluoro-alkyl, Perfluoro-alkoxy, acyl, alkylsulfonyl, sulfonyl, —SO₂(R³)₂, cyano, nitro, amino, amido, alkyl optionally substituted by a carboxy, —N(R³)₂, —CO(NR³)₂, —OR³, (NR³)COR³, —CO₂R³, —COR³, or Het-alkyl optionally substituted by A, Hal, an acyl, alkylsulfonyl, carboxy, —N(R³)₂, —CON(R³)₂, —OR³, (NR³)COR³, —CO₂R³, —COR³, —SO₂N(R³)₂, —SO₂(C₁-C₆)alkyl, NR³SO₂(C₁-C₆)alkyl,

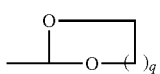

wherein q is as above defined, or C₁-C₆alkyl; wherein R³ is H or (C₁-C₆)alkyl.

Very particularly, R⁴ and R⁵ are selected from the following groups:

Hal, C₁-C₆alkyl, —CF₃, —(CH₂)ₙOR³, —(CH₂)ₙCOOR³, —SO₂Me, —SO₂N(R³)₂, —COR^S, —CO(NR³)₂, —(CH₂)ₙCOOtBu, —(CH₂)ₙN(R³)₂, —(CH₂)ₙOH, —(CH₂)ₙN(R³)(CH₂)ₚOR³, (CH₂)ₙN(R³)(CH₂)ₚCOOR³, —NHCOR³, NHSO₂R³, NHSO₂R³, —(CH₂)ₙN(R³)(CH₂)ₚCOOR³, —NHCOR³, NHSO₂R³,

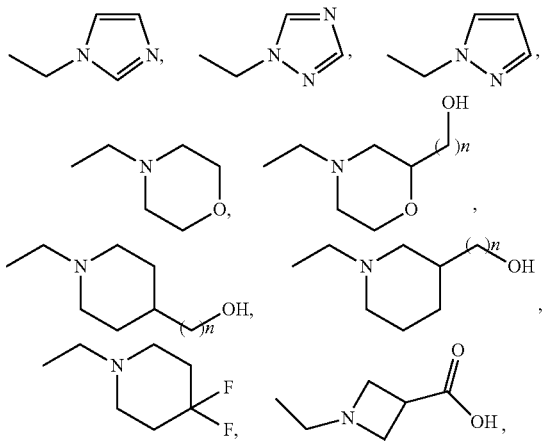

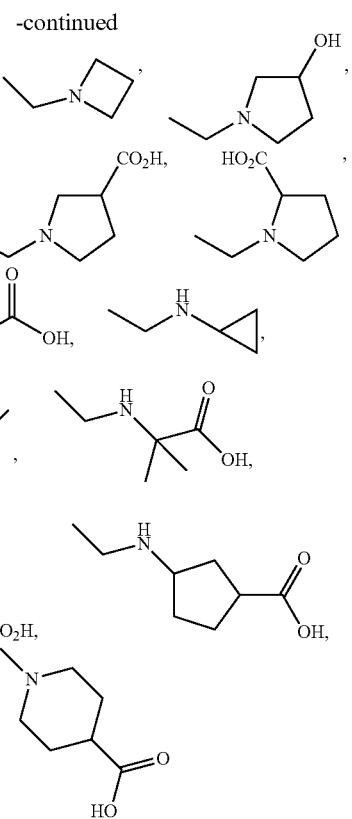

wherein n and p are independently from one other 0, 1, 2, 3 or 4 and R³ is as above defined. Preferably R³ is H or C₁-C₆ alkyl.

In another specific embodiment, the invention provides compounds of formula I wherein X is O;

In another specific embodiment, the invention provides compounds of formula I wherein X is S;

In another specific embodiment, the invention provides compounds of formula I wherein R² is H or Hal and X is O or S;

In another specific embodiment, the invention provides compounds of formula I wherein R² is H or Hal and X is O;

In another specific embodiment, the invention provides compounds of formula I wherein R² is H or Hal and X is S;

In another specific embodiment, the invention provides compounds of formula I wherein R² is H, X is O and S;

In another specific embodiment, the invention provides compounds of formula I wherein R² is H, X is O;

In another specific embodiment, the invention provides compounds of formula I wherein R² is H, X is S;

In another specific embodiment, the invention provides compounds of formula I wherein R² is H, X is O or S and R^b is A, Ar, Ar-alkyl, Het, or Het-alkyl;

In another specific embodiment, the invention provides compounds of formula I wherein R² is H, X is O and R^b is A, Ar, Ar-alkyl, Het, or Het-alkyl;

In another specific embodiment, the invention provides compounds of formula I wherein R² is H, X is S and R^b is A, Ar, Ar-alkyl, Het, or Het-alkyl;

In another specific embodiment, the invention provides compounds of formula I wherein R₂ is H, X is O or S, R^b is A, Ar, Ar-alkyl, Het, or Het-alkyl, R¹ is F or Br;

In another specific embodiment, the invention provides compounds of formula I wherein R² is H, X is O, R^b is A, Ar, Ar-alkyl, Het, or Het-alkyl, R¹ is F or Br;

In another specific embodiment, the invention provides compounds of formula I wherein $R^2$ is H, X is S, $R^b$ is A, Ar, Ar-alkyl, Het, or Het-alkyl, $R^1$ is F or Br;

In another specific embodiment, the invention provides compounds of formula I wherein $R^2$ is H, X is O or S, $R^a$ is Ar and Het, $R^b$ is A, Ar, Ar-alkyl, Het, or Het-alkyl, $R^1$ is F or Br;

In another specific embodiment, the invention provides compounds of formula I wherein $R^2$ is H, X is O, $R^a$ is Ar and Het, $R^b$ is A, Ar, Ar-alkyl, Het, or Het-alkyl, $R^1$ is F or Br;

In another specific embodiment, the invention provides compounds of formula I wherein $R^2$ is H, X is S, $R^a$ is Ar and Het, $R^b$ is A, Ar, Ar-alkyl, Het, or Het-alkyl, $R^1$ is F or Br;

In another specific embodiment, the invention provides compounds of formula I wherein $R^2$ is H, X is O or S, $R^a$ is Phenyl and Het wherein Het is selected from pyridinyl, indolyl, piperazinyl, piperidinyl, $R^b$ is A, Phenyl, Benzyl Het, or Het-alkyl wherein Het is selected from pyridinyl, piperazinyl, piperidinyl, morpholino, $R^1$ is F or Br, and wherein $R^a$ and $R^b$ as defined may be unsubstituted or monosubstituted, disubstituted or trisubstituted by a substituent selected from $R^4$ and/or $R^5$;

In another specific embodiment, the invention provides compounds of formula I wherein $R^2$ is H, X is O, $R^a$ is Phenyl and Het wherein Het is selected from pyridinyl, indolyl, piperazinyl, piperidinyl, $R^b$ is A, Phenyl, Benzyl, Het, or Het-alkyl wherein Het is selected from pyridinyl, piperazinyl, piperidinyl, morpholino, $R^1$ is F or Br, and wherein $R^a$ and $R^b$ as defined may be unsubstituted or monosubstituted, disubstituted or trisubstituted by a substituent selected from $R^4$ and/or $R^5$;

In another specific embodiment, the invention provides compounds of formula I wherein $R^2$ is H, X is S, $R^a$ is Phenyl and Het wherein Het is selected from pyridinyl, indolyl, piperazinyl, piperidinyl, $R^b$ is A, Phenyl, Benzyl, Het, or Het-alkyl wherein Het is selected from pyridinyl, piperazinyl, piperidinyl, morpholino, $R^1$ is F or Br, and wherein $R^a$ and $R^b$ as defined may be unsubstituted or monosubstituted, disubstituted or trisubstituted by a substituent selected from $R^4$ and/or $R^5$;

In a more particular embodiment, the invention provides compounds of formula I wherein $R^2$ is H, X is O or S, $R^a$ is Phenyl and Het wherein Het is selected from pyridinyl, indolyl, piperazinyl, piperidinyl, $R^b$ is A, Phenyl, Het, or Het-alkyl wherein Het is selected from pyridinyl, piperazinyl, piperidinyl, morpholino, $R^1$ is F or Br, and wherein $R^a$ and $R^b$ as defined may be unsubstituted or monosubstituted, disubstituted or trisubstituted by a substituent selected from $R^4$ and/or $R^5$ wherein $R^4$ and $R^5$ are each independently selected from Hal, hydroxy, OMe, OEt, carboxy, COOMe, COOEt, $CF_3$, $OCF_3$, acetyl, methylsulfonyl, $C_1$-$C_6$alkyl optionally substituted by a carboxy, or Het-alkyl optionally substituted by an acetyl, methylsulfonyl or $C_1$-$C_6$alkyl;

In a more particular embodiment, the invention provides compounds of formula I wherein $R^2$ is H, X is O, $R^a$ is Phenyl and Het wherein Het is selected from pyridinyl, indolyl, piperazinyl, piperidinyl, $R^b$ is A, Phenyl, Het, or Het-alkyl wherein Het is selected from pyridinyl, piperazinyl, piperidinyl, morpholino, $R^1$ is F or Br, and wherein $R^a$ and $R^b$ as defined may be unsubstituted or monosubstituted, disubstituted or trisubstituted by a substituent selected from $R^4$ and/or $R^5$ wherein $R^4$ and $R^5$ are each independently selected from Hal, hydroxy, OMe, OEt, carboxy, COOMe, COOEt, $CF_3$, $OCF_3$, acetyl, methylsulfonyl, $C_1$-$C_6$alkyl optionally substituted by a carboxy, or Het-alkyl optionally substituted by an acetyl, methylsulfonyl or $C_1$-$C_6$alkyl;

In a more particular embodiment, the invention provides compounds of formula I wherein $R^2$ is H, X is S, $R^a$ is Phenyl and Het wherein Het is selected from pyridinyl, indolyl, piperazinyl, piperidinyl, $R^b$ is A, Phenyl, Het, or Het-alkyl wherein Het is selected from pyridinyl, piperazinyl, piperidinyl, morpholino, $R^1$ is F or Br, and wherein $R^a$ and $R^b$ as defined may be unsubstituted or monosubstituted, disubstituted or trisubstituted by a substituent selected from $R^4$ and/or $R^5$ wherein $R^4$ and $R^5$ are each independently selected from Hal, hydroxy, OMe, OEt, carboxy, COOMe, COOEt, $CF_3$, $OCF_3$, acetyl, methylsulfonyl, $C_1$-$C_6$alkyl optionally substituted by a carboxy, or Het-alkyl optionally substituted by an acetyl, methylsulfonyl or $C_1$-$C_6$alkyl;

In a more particular embodiment A as described above in the specific embodiment are selected from a branched or linear alkyl having 1 to 12 C-atoms, wherein one or more, preferably 1 to 7 H-atoms may be replaced by Hal, $OR^3$, CN or $N(R^3)_2$ and wherein one or more, preferably 1 to 7 non-adjacent $CH_2$-groups may be replaced by O, $NR^3$ or S and/or by —CH=CH— or —C≡C— groups, or denotes cycloalkyl or cycloalkylalkylen having 3-7 ring C atoms;

In a very most preferred embodiment A as described above in the specific embodiment are selected from a branched or linear alkyl having 2 to 12 C-atoms, wherein one or more, preferably 1 to 7 H-atoms may be replaced by Hal, $OR^3$, CN or $N(R^3)_2$ and wherein one or more, preferably 1 to 7 non-adjacent $CH_2$-groups may be replaced by O, $NR^3$ or S and/or by —CH=CH— or —C≡C— groups, or denotes cycloalkyl or cycloalkylalkylen having 3-7 ring C atoms.

In Particular, the invention also relates to compounds of formula IF:

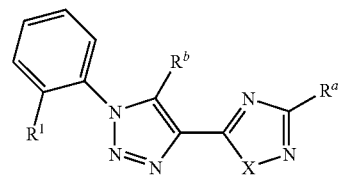

IF

Wherein X, $R^1$, $R^b$ are as defined above and $R^a$ denotes Ar and Het, A is as defined above, and wherein A is more particularly a branched or linear alkyl having 2 to 12 C-atoms, wherein one or more, preferably 1 to 7 H-atoms may be replaced by Hal, $OR^3$, CN or $N(R^3)_2$ and wherein one or more, preferably 1 to 7 non-adjacent $CH_2$-groups may be replaced by O, $NR^3$ or S and/or by —CH=CH— or —C≡C— groups, or denotes cycloalkyl or cycloalkylalkylen having 3-7 ring C atoms.

In another specific embodiment, the invention provides compounds of formula IF wherein X is O or S and $R^b$ is A, Ar, Ar-alkyl, Het, or Het-alkyl;

In another specific embodiment, the invention provides compounds of formula IF wherein X is O and $R^b$ is A, Ar, Ar-alkyl, Het, or Het-alkyl;

In another specific embodiment, the invention provides compounds of formula IF wherein X is S and $R^b$ is A, Ar, Ar-alkyl, Het, or Het-alkyl;

In another specific embodiment, the invention provides compounds of formula IF wherein X is O or S, $R^b$ is A, Ar, Ar-alkyl, Het, or Het-alkyl, $R^1$ is F or Br;

In another specific embodiment, the invention provides compounds of formula IF wherein X is O, $R^b$ is A, Ar, Ar-alkyl, Het, or Het-alkyl, $R^1$ is F or Br;

In another specific embodiment, the invention provides compounds of formula IF wherein X is S, $R^b$ is A, Ar, Ar-alkyl, Het, or Het-alkyl, $R^1$ is F or Br;

In another specific embodiment, the invention provides compounds of formula IF wherein X is O or S, $R^a$ is Ar and Het, $R^b$ is A, Ar, Ar-alkyl, Het, or Het-alkyl, $R^1$ is F or Br;

In another specific embodiment, the invention provides compounds of formula IF wherein X is O, $R^a$ is Ar and Het, $R^b$ is A, Ar, Ar-alkyl, Het, or Het-alkyl, $R^1$ is F or Br;

In another specific embodiment, the invention provides compounds of formula IF wherein X is S, $R^a$ is Ar and Het, $R^b$ is A, Ar, Ar-alkyl, Het, or Het-alkyl, $R^1$ is F or Br;

In another specific embodiment, the invention provides compounds of formula IF wherein X is O or S, $R^a$ is Phenyl and Het wherein Het is selected from pyridinyl, indolyl, piperazinyl, piperidinyl, $R^b$ is A, Phenyl, Benzyl Het, or Het-alkyl wherein Het is selected from pyridinyl, piperazinyl, piperidinyl, morpholino, $R^1$ is F or Br, and wherein $R^a$ and $R^b$ as defined may be unsubstituted or monosubstituted, disubstituted or trisubstituted by a substituent selected from $R^4$ and/or $R^5$;

In another specific embodiment, the invention provides compounds of formula IF wherein X is O, $R^a$ is Phenyl and Het wherein Het is selected from pyridinyl, indolyl, piperazinyl, piperidinyl, $R^b$ is A, Phenyl, Benzyl, Het, or Het-alkyl wherein Het is selected from pyridinyl, piperazinyl, piperidinyl, morpholino, $R^1$ is F or Br, and wherein $R^a$ and $R^b$ as defined may be unsubstituted or monosubstituted, disubstituted or trisubstituted by a substituent selected from $R^4$ and/or $R^5$;

In another specific embodiment, the invention provides compounds of formula IF wherein X is S, $R^a$ is Phenyl and Het wherein Het is selected from pyridinyl, indolyl, piperazinyl, piperidinyl, $R^b$ is A, Phenyl, Benzyl, Het, or Het-alkyl wherein Het is selected from pyridinyl, piperazinyl, piperidinyl, morpholino, $R^1$ is F or Br, and wherein $R^a$ and $R^b$ as defined may be unsubstituted or monosubstituted, disubstituted or trisubstituted by a substituent selected from $R^4$ and/or $R^5$;

In a more particular embodiment, the invention provides compounds of formula IF wherein X is O or S, $R^a$ is Phenyl and Het wherein Het is selected from pyridinyl, indolyl, piperazinyl, piperidinyl, $R^b$ is A, Phenyl, Het, or Het-alkyl wherein Het is selected from pyridinyl, piperazinyl, piperidinyl, morpholino, $R^1$ is F or Br, and wherein $R^a$ and $R^b$ as defined may be unsubstituted or monosubstituted, disubstituted or trisubstituted by a substituent selected from $R^4$ and/or $R^5$ wherein $R^4$ and $R^5$ are each independently selected from Hal, hydroxy, OMe, OEt, carboxy, COOMe, COOEt, $CF_3$, $OCF_3$, acetyl, methylsulfonyl, $C_1$-$C_6$alkyl optionally substituted by a carboxy, or Het-alkyl optionally substituted by an acetyl, methylsulfonyl or $C_1$-$C_6$alkyl;

In a more particular embodiment, the invention provides compounds of formula IF wherein X is O, $R^a$ is Phenyl and Het wherein Het is selected from pyridinyl, indolyl, piperazinyl, piperidinyl, $R^b$ is A, Phenyl, Het, or Het-alkyl wherein Het is selected from pyridinyl, piperazinyl, piperidinyl, morpholino, $R^1$ is F or Br, and wherein $R^a$ and $R^b$ as defined may be unsubstituted or monosubstituted, disubstituted or trisubstituted by a substituent selected from $R^4$ and/or $R^5$ wherein $R^4$ and $R^5$ are each independently selected from Hal, hydroxy, OMe, OEt, carboxy, COOMe, COOEt, $CF_3$, $OCF_3$, acetyl, methylsulfonyl, $C_1$-$C_6$alkyl optionally substituted by a carboxy, or Het-alkyl optionally substituted by an acetyl, methylsulfonyl or $C_1$-$C_6$alkyl;

In a more particular embodiment, the invention provides compounds of formula IF wherein $R^2$ is H, X is S, $R^a$ is Phenyl and Het wherein Het is selected from pyridinyl, indolyl, piperazinyl, piperidinyl, $R^b$ is A, Phenyl, Het, or Het-alkyl wherein Het is selected from pyridinyl, piperazinyl, piperidinyl, morpholino, $R^1$ is F or Br, and wherein $R^a$ and $R^b$ as defined may be unsubstituted or monosubstituted, disubstituted or trisubstituted by a substituent selected from $R^4$ and/or $R^5$ wherein $R^4$ and $R^5$ are each independently selected from Hal, hydroxy, OMe, OEt, carboxy, COOMe, COOEt, $CF_3$, $OCF_3$, acetyl, methylsulfonyl, $C_1$-$C_6$alkyl optionally substituted by a carboxy, or Het-alkyl optionally substituted by an acetyl, methylsulfonyl or $C_1$-$C_6$alkyl.

In particular, the invention also relates to compounds of Formula IF wherein X, $R^1$, $R^b$ are defined as above and $R^a$ denotes A and Het; Wherein A is a branched or linear alkyl having 1 to 12 C-atoms, wherein one or more, preferably 1 to 7H-atoms may be replaced by Hal, $OR^3$, CN or $N(R^3)_2$ and wherein one or more, preferably 1 to 7 non-adjacent $CH_2$-groups may be replaced by O, $NR^3$ or S and/or by —CH=CH— or —C≡C— groups, or denotes cycloalkyl or cycloalkylalkylen having 3-7 ring C atoms;

Wherein Het denotes a monocyclic or bicyclic, saturated heterocyclic ring having 1 to 4 N, O and/or S atoms which may be unsubstituted or monosubstituted, disubstituted or trisubstituted by a substituent selected from $R^4$ and/or $R^5$ wherein $R^4$ and $R^5$ are defined as above;

$R^3$ is H or A;

and pharmaceutically acceptable derivatives, solvates, tautomers, salts and stereoisomers thereof, including mixtures thereof in all ratios.

In another specific embodiment, the invention provides compounds of formula IF wherein X is O;

In another specific embodiment, the invention provides compounds of formula IF wherein X is S;

In another specific embodiment, the invention provides compounds of formula IF wherein X is O or S, and $R^a$ denotes A and more particularly a branched or linear alkyl having 1 to 12 C-atoms, wherein one or more, preferably 1 to 7H-atoms may be replaced by Hal, $OR^3$, CN or $N(R^3)_2$ and wherein one or more, preferably 1 to 7 non-adjacent $CH_2$-groups may be replaced by O, $NR^3$ or S and/or by —CH=CH— or —C≡C— groups, or denotes cycloalkyl or cycloalkylalkylen having 3-7 ring C atoms.

In another specific embodiment, the invention provides compounds of formula IF wherein X is O, and $R^a$ denotes A and more particularly a branched or linear alkyl having 1 to 12 C-atoms, wherein one or more, preferably 1 to 7H-atoms may be replaced by Hal, $OR^3$, CN or $N(R^3)_2$ and wherein one or more, preferably 1 to 7 non-adjacent $CH_2$-groups may be replaced by O, $NR^3$ or S and/or by —CH=CH— or —C≡C— groups, or denotes cycloalkyl or cycloalkylalkylen having 3-7 ring C atoms.

In another specific embodiment, the invention provides compounds of formula IF wherein X is S, and $R^a$ denotes A and more particularly a branched or linear alkyl having 1 to 12 C-atoms, wherein one or more, preferably 1 to 7H-atoms may be replaced by Hal, $OR^3$, CN or $N(R^3)_2$ and wherein one or more, preferably 1 to 7 non-adjacent $CH_2$-groups may be replaced by O, $NR^3$ or S and/or by —CH=CH— or —C≡C— groups, or denotes cycloalkyl or cycloalkylalkylen having 3-7 ring C atoms.

In another specific embodiment, the invention provides compounds of formula IF wherein X is O or S, and $R^a$ denotes Het wherein Het is a monocyclic or bicyclic, saturated heterocyclic ring having 1 to 4 N, O and/or S atoms which may be unsubstituted or monosubstituted, disubstituted or trisubstituted by a substituent selected from $R^4$ and/or $R^5$, wherein $R^4$ and $R^5$ are defined as above.

In another specific embodiment, the invention provides compounds of formula IF wherein X is O or S, and R$^a$ denotes Het wherein Het is a monocyclic or bicyclic, saturated heterocyclic ring having 1 to 4 N, O and/or S atoms which may be unsubstituted or monosubstituted, disubstituted or trisubstituted by a substituent selected from R$^4$ and/or R$^5$ wherein R$^4$ and R$^5$ are defined as above.

In another specific embodiment, the invention provides compounds of formula IF wherein X is O, and R$^a$ denotes Het wherein Het is a monocyclic or bicyclic, saturated heterocyclic ring having 1 to 4 N, O and/or S atoms which may be unsubtituted or monosubstituted, disubstituted or trisubstituted by a substituent selected from R$^4$ and/or R$^5$ wherein R$^4$ and R$^5$ are defined as above.

In another specific embodiment, the invention provides compounds of formula IF wherein X is S, and R$^a$ denotes Het wherein Het is a monocyclic or bycyclic, saturated heterocyclic ring having 1 to 4 N, O and/or S atoms which may be unsubstituted or monosubstituted, disubstituted or trisubstituted by a substituent selected from R$^4$ and/or R$^5$ wherein R$^4$ and R$^5$ are defined as above.

In another specific embodiment, the invention provides compounds of formula IF wherein X is O or S, and R$^a$ denotes Het wherein Het is a monocyclic saturated heterocyclic ring having 1 to 4 N, O and/or S atoms which may be unsubstituted or monosubstituted, disubstituted or trisubstituted by a substituent selected from R$^4$ and/or R$^5$ wherein R$^4$ and R$^5$ are defined as above;

In another specific embodiment, the invention provides compounds of formula IF wherein X is O, and R$^a$ denotes Het wherein Het is a heterocyclic ring having 1 to 4 N, O and/or S atoms which may be unsubstituted or monosubstituted, disubstituted or trisubstituted by a substituent selected from R$^4$ and/or R$^5$ wherein R$^4$ and R$^5$ are defined as above;

In another specific embodiment, the invention provides compounds of formula IF wherein X is S, and R$^a$ denotes Het wherein Het is a monocyclic saturated heterocyclic ring having 1 to 4 N, O and/or S atoms which may be unsubstituted or monosubstituted or trisubstituted by a substituent selected from R$^4$ and/or R$^5$ wherein R$^4$ and R$^5$ are defined as above;

In another specific embodiment, the invention provides compounds of formula IF wherein X is O S and R$^a$ denotes Het wherein Het is a piperidinyl or a piperazinyl which may be unsubstituted or monosubstituted, disubstituted or trisubstituted by a substituent selected from R$^4$ and/or R$^5$ wherein R$^4$ and R$^5$ are defined as above;

In another specific embodiment, the invention provides compounds of formula IF wherein X is O, and R$^a$ denotes Het wherein Het is a piperidinyl or a piperizinyl which may be unsubstituted or monosubstituted, disubstituted or trisubstituted by a substituent selected from R$^4$ and/or R$^5$ wherein R$^4$ and R$^5$ are defined as above;

In another specific embodiment, the invention provides compounds of formula IF wherein X is S, and R$^a$ denotes Het wherein Het is a piperidinyl or a piperzinyl which may be unsubstituted or monosubstituted, disubstituted or trisubstituted by a substituent selected from R$^4$ and/or R$^5$ wherein R$^4$ and R$^5$ are defined as above;

In another specific embodiment, the invention provides compounds of formula IF wherein X is O or S, and R$^a$ denotes Het wherein Het is a piperidinyl or a piperzinyl which may be unsubstituted or monosubstituted, disubstituted or trisubstituted by a substituent selected from R$^4$ and/or R$^5$ wherein R$^4$ and R$^5$ are selected from alkyl alkylsulonyl or acyl;

In another specific embodiment, the invention provides compounds of formula IF wherein X is O, and R$^a$ denotes Het wherein Het is a piperidinyl or a piperzinyl which may be unsubstituted or monosubstituted, disubstituted or trisubstituted by a substituent selected from R$^4$ and/or R$^5$ wherein R$^4$ and R$^5$ are selected from alkyl alkylsulonyl or acyl;

In another specific embodiment, the invention provides compounds of formula IF wherein X is S, and R$^a$ denotes Het wherein Het is a piperidinyl or a piperzinyl which may be unsubstituted or monosubstituted, disubstituted or trisubstituted by a substituent selected from R$^4$ and/or R$^5$ wherein R$^4$ and R$^5$ are selected from alkyl alkylsulonyl or acyl;

The invention also relates to compounds of Formula IG

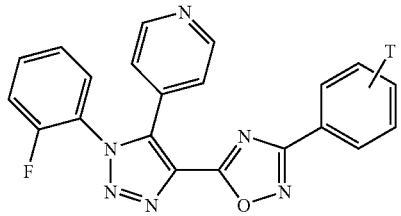

IG wherein T is Het-alky, A, SO$_2$Me, R$^4$ or R$^5$.

In another specific embodiment, the invention relates to Formula IG wherein T is selected from the following groups:
—SO$_2$Me, —(CH$_2$)NH Me, —(CH$_2$)NH(CH$_2$)$_2$COOH,

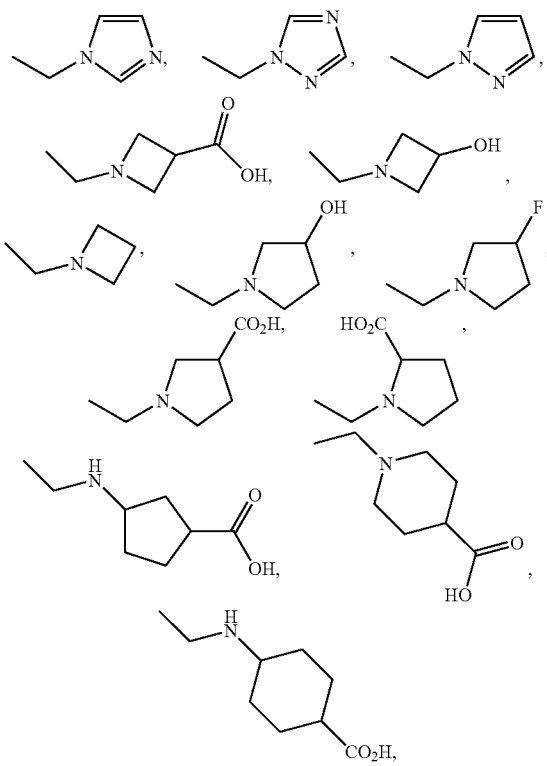

In another specific embodiment, the invention provides compounds of Formula I and related Formulae wherein R$^1$ is F or Br.

In another specific embodiment, the invention provides compounds of Formula I and related Formulae wherein R$^2$ is H or Hal.

In another specific embodiment, the invention provides compounds of Formula I and related Formulae wherein R$^b$ is selected from an Ar, Ar-alkyl, an Het, or Het-alkyl, a branched of linear alkyl having 1 to 12 C-atoms, wherein one or more, preferably 1 to 7H-atoms may be replaced by Hal, $OR^3$, CN or $N(R^3)_2$ and wherein one or more, preferably 1 to 7 non-adjacent $CH_2$-groups may be replaced by O, $NR^3$;

In another specific embodiment, the invention provides compounds of Formula I and related Formulae wherein $R^b$ is selected from a Phenyl, Benzyl, cyclopropyl, a pyridinyl, a Het-alkyl, wherein Het is selected from morpholino, tetrahydrofuranyl, tetrahydropyranyl, piperazinyl or piperidinyl, a branched of linear alkyl having 1 to 12 C-atoms, wherein one or more, preferably 1 to 7 H-atoms may be replaced by Hal, $OR^3$, CN or $N(R^3)_2$ and wherein one or more, preferably 1 to 7 non-adjacent $CH_2$-groups may be replaced by O;
wherein Phenyl, Benzyl, pyridinyl or Het-alkyl groups may be unsubstituted or monosubstituted, disubstituted or trisubstituted by a substituent selected from $R^4$ and/or $R^5$.

In another specific embodiment, the invention provides compounds of Formula I and related Formulae, wherein $R^b$ is selected from a Phenyl, a pyridinyl, a Het-alkyl wherein Het is morpholino, a branched or linear alkyl having 1 to 12 C-atoms, wherein one or more, preferably 1 to 7H-atoms may be replaced by Hal, $OR^3$, CN or $N(R^3)_2$ and wherein one or more, preferably 1 to 7 non-adjacent $CH_2$-groups may be replaced by O; wherein Phenyl, pyridinyl or Het-alkyl groups may be unsubstituted or monosubstituted, disubstituted or trisubstituted by a substituent selected from $R^4$ and/or $R^5$.

In another specific embodiment, the invention provides compounds of Formula I and related Formulae wherein $R^4$ and $R^5$ are each independently selected from Hal, hydroxy, alkoxy, carboxy, carboxy-alkyl, Perfluoro-alkyl, acyl, alkylsulfonyl, sulfonyl, cyano, nitro, amino, amido, alkyl optionally substituted by a carboxy, or Het-alkyl optionally substituted by an acyl, alkylsulfonyl or alkyl. Preferably, $R^4$ and $R^5$ are each independently selected from F, OH, OMe, COOH, COOMe, $CF_3$, acetyl, methylsulfonyl, sulfonyl, cyano, nitro, amino, amido, methyl optionally substituted by a carboxy, or Het-alkyl optionally substituted by an acetyl, methylsulfonyl or methyl wherein Het is selected from pipetidinyl, piperazinyl or [1,2,4]triazolyl.

In a very more preferred embodiment, the invention provides compounds of formula I wherein X is O, $R^2$ is H, $R^1$ is Hal, $R^a$ is H, A, Ar, or Het and $R^b$Het wherein Het is selected from pyridinyl;

In a very more preferred embodiments the invention provides compounds of formula I wherein X is O, $R^2$ is H, $R^1$ is Hal, $R^a$ is H, A, Ar, or Het and $R^b$ is A wherein A selected from a branched or linear alkyl having 1 to 12 C-atoms, wherein one or more, preferably 1 to 7H-atoms may be replaced by Hal, $OR^3$, CN or $N(R^3)_2$ and wherein one or more, preferably 1 to 7 non-adjacent $CH_2$-groups may be replaced by O, $NR^3$ or S and/or by —CH═CH— or —C≡C-groups, or denotes cycloalkyl or cycloalkylalkylen having 3-7 ring C atoms;

In a very more preferred embodiments the invention provides compounds of formula I wherein X is O, $R^2$ is H, $R^1$ is Hal, $R^a$ is H, A, Ar, or Het and $R^b$ is A wherein A selected from a branched or linear alkyl having 2 to 12 C-atoms, wherein one or more, preferably 1 to 7H-atoms may be replaced by Hal, $OR^3$, CN or $N(R^3)_2$ and wherein one or more, preferably 1 to 7 non-adjacent $CH_2$-groups may be replaced by O, $NR^3$ or S and/or by —CH═CH— or —C≡C-groups, or denotes cycloalkyl or cycloalkylalkylen having 3-7 ring C atoms;

In a very more preferred embodiments the invention provides compounds of formula I wherein X is O, $R^2$ is H, $R^1$ is Hal, $R^a$ is H, A, Ar, or Het and $R^b$ is Het-alkyl;

In a more preferred embodiments the invention provides compounds of formula I wherein X is O, $R^2$ is H, $R^1$ is Hal, $R^a$ is H, A, Ar, or Het and $R^b$ is Aryl;

In a more preferred embodiments the invention provides compounds of formula I wherein X is O, $R^2$ is H, $R^1$ is Hal, $R^b$ is A, Ar, Het, OA, NHA, or $NA_2$, Ar-alkyl, or Het-alkyl and $R^a$ is A;

In a more preferred embodiments the invention provides compounds of formula I wherein X is O, $R^2$ is H, $R^1$ is Hal, $R^b$ is A or Ar, $R^a$ is A;

In a more preferred embodiments the invention provides compounds of formula I wherein X is O, $R^2$ is H, $R^1$ is Hal, $R^b$ is Ar, $R^a$ is A;

In a more preferred embodiments the invention provides compounds of formula I wherein X is O, $R^2$ is H, $R^1$ is Hal, $R^b$ is A and $R^a$ is A;

The compounds of the formula I, IA, IB, IC, ID, IE, IF, IG, II, III and also the starting materials for the preparation thereof are, in addition, prepared by methods known per se, as described in the literature (for example in the standard works, such as Houben-Weyl, Methoden der organischen Chemie [Methods of Organic Chemistry], Georg-Thieme-Verlag, Stuttgart), under reaction conditions which are known and suitable for the said reactions. For all the protection and deprotection methods, see Philip J. Kocienski, in "*Protecting Groups*", Georg Thieme Verlag Stuttgart, New York, 1994 and, Theodora W. Greene and Peter G. M. Wuts in "*Protective Groups in Organic Synthesis*", Wiley Interscience, $3^{rd}$ Edition 1999. Use can also be made here of variants which are known per se, but are not mentioned here in greater detail.

If desired, the starting materials can also be formed in situ so that they are not isolated from the reaction mixture, but instead are immediately converted further into the compounds of the formula I.

The starting compounds for the preparation of compounds of formula I are generally known. If they are novel, they can, however, be prepared by methods known per se.

The reactions are preferably carried out in an inert solvent.

Examples of suitable inert solvents are hydrocarbons, such as hexane, petroleum ether, benzene, toluene or xylene; chlorinated hydrocarbons, such as trichloroethylene, 1,2-dichloroethane, tetrachloromethane, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether or ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Accordingly, the invention relates, in particular, to the use of compounds of the formula I, IA, IB, IC, ID, IE, IF, IG as defined above, wherein X, $R^1$, $R^2$, $R^3$, $R^a$ and $R^b$ are as defined above as a medicament.

Accordingly, the invention relates, in particular, to the use of compounds of the formula I, IA, IB, IC, ID, IE, IF, IG as defined above, wherein X, $R^1$, $R^2$, $R^3$, $R^a$ and $R^b$ are as defined above for the preparation of pharmaceutical formulation for the prevention and/or the treatment of multiple sclerosis and related disorders.

The said compounds of the formula I and related formulae such as IA, IB, IC, ID, IE, IF, IG, II, III can be used in their final non-salt form. On the other hand, the present invention also relates to the use of these compounds in the form of their pharmaceutically acceptable salts, which can be derived from various organic and inorganic acids and bases by procedures known in the art. Pharmaceutically acceptable salt forms of the compounds of the formula I are for the most part prepared by conventional methods. If the compound of the formula I contains an acidic center, such as a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline earth metal hydroxides, such as barium hydroxide and calcium hydroxide; alkali metal alkoxides, for example sodium- or potassium methoxide and sodium or potassiumpropoxide, alkalihydrides, such as sodium- or potassiumhydride; and various organic bases, such as piperidine, diethanolamine and N-methyl-glutamine, benzathine, choline, diethanolamine, ethylenediamine, meglumine, benethamine, diethylamine, piperazine and tromethamine. The aluminium salts of the compounds of the formula I and related formulae such as IA, IB, IC, ID, IE, IF, IG, II, III are likewise included. In the case of certain compounds of the formula I and related formulae, which contain a basic center, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzene-sulfonate, and other organic acids and corresponding salts thereof, such as acetate, trifluoro-acetate, tartrate, maleate, succinate, citrate, benzoate, salicylate, ascorbate and the like. Accordingly, pharmaceutically acceptable acid-addition salts of the compounds of the formula I and related formulae include the following: acetate, adipate, alginate, arginate, aspartate, benzoate, benzene-sulfonate (besylate), bisulfate, bisulfite, bromide, butyrate, camphorate, camphorsulfonate, caprylate, chloride, chlorobenzoate, citrate, cyclopentane-propionate, digluconate, dihydrogen-phosphate, dinitrobenzoate, dodecyl-sulfate, ethanesulfonate, fumarate, galacterate (from mucic acid), galacturonate, glucoheptanoate, gluco-nate, glutamate, glycerophosphate, hemi-succinate, hemisulfate, heptanoate, hexanoate, hippurate, hydrochloride, hydrobromide, hydroiodide, 2-hydroxy-ethane-sulfonate, iodide, isethionate, isobutyrate, lactate, lactobionate, malate, maleate, malonate, mandelate, metaphosphate, methanesulfonate, methylbenzoate, mono-hydrogen-phosphate, 2-naphthalenesulfonate, nicotinate, nitrate, oxalate, oleate, palmo-ate, pectinate, persulfate, phenylacetate, 3-phenylpropionate, phosphate, phosphonate, phthalate, but this does not represent a restriction. Both types of salts may be formed or interconverted preferably using ion-exchange resin techniques.

Furthermore, the base salts of the compounds of the formula I and related formulae such as IA, IB, IC, ID, IE, IF, IG include aluminum, ammonium, calcium, copper, iron(III), iron(II), lithium, magne-sium, manganese(III), manganese (II), potassium, sodium and zinc salts, but this is not intended to represent a restriction. Of the above-mentioned salts, preference is given to ammonium; the alkali metal salts sodium and potassium, and the alkaline earth metal salts calcium and magnesium. salts of the compounds of the formula I which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzyl-ethylen-ediamine (benzathine), dicyclohexylamine, diethanol-amine, diethylamine, 2-diethyl-amino-ethanol, 2-dimethyl-amino-ethanol, ethanolamine, thylenediamine, N-ethylmorpholine, N-ethyl-piperidine, glucamine, glucosamine, histidine, hydrabamine, isopropyl-amine, lidocaine, lysine, meglumine (N-methyl-D-glucamine), morpholine, piperazine, piperidine, polyamine resins, procaine, purines, theobromine, triethanol-amine, triethylamine, trimethylamine, tripropyl-amine and tris(hydroxy-methyl)-methylamine (tromethamine), but this is not intended to represent a restriction.

Compounds of the formula I and related formulae such as IA, IB, IC, ID, IE, IF, IG of the present invention which contain basic nitrogen-containing groups can be quaternised using agents such as $(C_1\text{-}C_4)$-alkyl halides, for example methyl, ethyl, isopropyl and tert-butyl chloride, bromide and iodide; di($C_1\text{-}C_4$)alkyl sulfates, for example dimethyl, diethyl and diamyl sulfate; $(C_{10}\text{-}C_{18})$alkyl halides, for example decyl, do-decyl, lauryl, myristyl and stearyl chloride, bromide and iodide; and aryl-$(C_1\text{-}C_4)$alkyl halides, for example benzyl chloride and phenethyl bromide. Both water- and oil-soluble compounds of the formula I can be prepared using such salts.

The above-mentioned pharmaceutical salts, which are preferred, include acetate, trifluoroacetate, besylate, citrate, fumarate, gluconate, hemisuccinate, hippurate, hydrochloride, hydrobromide, isethionate, mandelate, me-glumine, nitrate, oleate, phosphonate, pivalate, sodium phosphate, stea-rate, sulfate, sulfosalicylate, tartrate, thiomalate, tosylate and tro-meth-amine, but this is not intended to represent a restriction.

The acid-addition salts of basic compounds of the formula I and related formulae such as IA, IB, IC, ID, IE, IF, IG are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts other-wise correspond to the respective free base forms thereof.

As mentioned, the pharmaceutically acceptable base-addition salts of the compounds of the formula I are formed with metals or amines, such as alkali metals and alkaline earth metals or organic amines. Preferred metals are sodium, potassium, magnesium and calcium. Preferred organic amines are N,N'-dibenzylethylenediamine, chloroprocaine, choline, diethanol-amine, ethylenediamine, N-methyl-D-glucamine and procaine.

The base-addition salts of acidic compounds of the formula I, IA, IB, IC, ID, IE, IF, IG are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts other-wise correspond to the respective free acid forms thereof.

If a compound of the formula I, IA, IB, IC, ID, IE, IF, IG contains more than one group which is capable of forming pharmaceutically acceptable salts of this type, the formula I also encompasses multiple salts. Typical multiple salt forms include, for example, bitartrate, diacetate, difumarate, dimeglumine, di-phosphate, disodium and trihydrochloride, but this is not intended to represent a restriction.

With regard to that stated above, it can be seen that the term "pharmaceutically acceptable salt" in the present connection is taken to mean an active ingredient which comprises a compound of the formula I, IA, IB, IC, ID, IE, IF, IG, II, III in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

Owing to their molecular structure, the compounds of the formula I, IA, IB, IC, ID, IE, IF, IG can be chiral and can accordingly occur in various enantiomeric forms. They can therefore exist in racemic or in optically active form.

Since the pharmaceutical activity of the racemates or stereoisomers of the compounds according to the invention may differ, it may be desirable to use the enantiomers. In these cases, the end product or even the intermediates can be separated into enantiomeric compounds by chemical or physical measures known to the person skilled in the art or even employed as such in the synthesis.

In the case of racemic amines, diastereomers are formed from the mixture by reaction with an optically active resolving agent. Examples of suitable resolving agents are optically active acids, such as the R and S forms of tartaric acid, diacetyltartaric acid, dibenzoyltartaric acid, mandelic acid, malic acid, lactic acid, suitable N-protected amino acids (for example N-benzoylproline or N-benzenesulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel). Suitable eluents for this purpose are aqueous or alcoholic solvent mixtures, such as, for example, hexane/isopropanol/acetonitrile, for example in the ratio 82:15:3.

The invention furthermore relates to the use of compounds of formula I, IA, IB, IC, ID, IE, IF, IG in combination with at least one further medicament active ingredient, preferably medicaments used in the treatment of multiple sclerosis such as cladribine or another co-agent, such as interferon, e.g. pegylated or non-pegylated interferons, preferably interferon beta and/or with compounds improving vascular function or in combination with immunomodulating agents for example Fingolimod; cyclosporins, rapamycins or ascomycins, or their immunosuppressive analogs, e.g. cyclosporin A, cyclosporin G, FK-506, ABT-281, ASM981, rapamycin, 40-O-(2-hydroxy)ethyl-rapamycin etc.; corticosteroids; cyclophosphamide; azathioprene; methotrexate; leflunomide; mizoribine; mycophenolic add; mycophenolate mofetil; 15-deoxyspergualine; diflucortolone valerate; diflu prednate; Alclometasone dipropionate; amcinonide; amsacrine; asparaginase; azathioprine; basiliximab; beclometasone dipropionate; betamethasone; betamethasone acetate; betamethasone dipropionate; betamethasone phosphate sodique; betamethasone valerate; budesonide; captopril; chlormethine chlorhydrate; cladribine; clobetasol propionate; cortisone acetate; cortivazol; cyclophosphamide; cyt- arabine; daclizumab; dactinomycine; desonide; desoximetasone; dexamethasone; dexamethasone acetate; dexamethasone isonicotinate; dexamethasone metasulfobenzoate sodique; dexamethasone phosphate; dexamethasone tebutate; dichlorisone acetate; doxorubicine chlorhydrate; epirubicine chlorhydrate; fluclorolone acetonide; fludrocortisone acetate; fludroxycortide; flumetasone pivalate; flunisolide; fluocinolone acetonide; fluocinonide; fluocortolone; fluocortolone hexanoate; fluocortolone pivalate; fluorometholone; fluprednidene acetate; fluticasone propionate; gemcitabine chlorhydrate; halcinonide; hydrocortisone, hydrocortisone acetate, hydrocortisone butyrate, hydrocortisone hemisuccinate; melphalan; meprednisone; mercaptopurine; methylprednisolone; methylprednisolone acetate; methylprednisolone hemisuccinate; misoprostol; muromonabcd3; mycophenolate mofetil; paramethasone acetate; prednazoline, prednisolone; prednisolone acetate; prednisolone caproate; prednisolone metasulfobenzoate sodique; prednisolone phosphate sodique; prednisone; prednylidene; rifampicine; rifampicine sodique; tacrolimus; thalidomide; thiotepa; tixocortol pivalate; triamcinolone; triamcinolone acetonide hemisuccinate; triamcinolone benetonide; triamcinolone diacetate; triamcinolone hexacetonide; immunosuppressive monoclonal antibodies, e.g., monoclonal antibodies to leukocyte receptors, e.g., MHC, CD2, CD3, CD4, CD7, CD25, CD28, B7, CD40, CD45 or CD58 or their ligands; or other immunomodulatory compounds, e.g. CTLA4Ig, or other adhesion molecule inhibitors, e.g. mAbs or low molecular weight inhibitors including Selectin antagonists and VLA-4 antagonists. A preferred composition is with Cyclosporin A, FK506, rapamycin or 40-(2-hydroxy)ethyl-rapamycin and Fingolimod. These further medicaments, such as interferon beta, may be administered concomitantly or sequentially, e.g. by subcutaneous, intramuscular or oral routes. These compositions can be used as medicaments in human and veterinary medicine.

In a further aspect, the invention provides the use of compounds of Formula I and related formulae, as well as pharmaceutically usable derivatives, salts, tautomers, solvates and stereoisomers thereof, including mixtures thereof in all ratios, for the preparation of a medicament for the treatment and/or prophylaxis of diseases in which the inhibition, activation, regulation, and/or modulation of $S1P_1$ receptor signal transduction plays a role.

In a further aspect, the invention provides the use of compounds of Formula I and related Formulae for the preparation of a medicament for the treatment and/or prophylaxis of autoimmune disorder or condition associated with an overactive immune response.

In another aspect, the present invention provides the use of compounds of Formula I wherein X is O or S; $R^1$ denotes H, Hal, $CF_3$, $OCF_3$, CN or $NO_2$; $R^2$ is H; as a medicament.

Pharmaceutical formulations can be administered in the form of dosage units, which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the disease condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process, which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medica-ment after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinyl-pyrrolidone, a dissolution retardant, such as, for example, paraffin, an absorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tabletting machine, giving lumps of non-uniform shape which are broken up to form granules. The granules can be lubricated by addition of stearic acid, a stearate salt, talc or mineral oil in order to prevent sticking to the tablet casting moulds. The lubricated mixture is then pressed to give tablets. The active ingredients can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compounds. Syrups can be prepared by dissolving the compounds in an aqueous solution with a suitable flavour, while elixirs are prepared using a non-toxic alcoholic vehicle. Suspensions can be for-mulated by dispersion of the compounds in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds of the formula I and related formulae such as IA, IB, IC, ID, IE, IF, IG and salts, solvates and physiologically functional derivatives thereof and the other active ingredients can also be administered in the form of liposome delivery systems, such as, for exam-ple, small unilamellar vesicles, large unilamellar vesicles and multilamellar vesicles. Liposomes can be formed from various phospholipids, such as, for example, cholesterol, stearylamine or phosphatidylcholines.

The compounds of the formula I and related formulae such as IA, IB, IC, ID, IE, IF, IG and the salts, solvates and physiologically functional derivatives thereof and the other active ingredients can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropyl-methacrylamidophenol, polyhydroxyethylaspartamido-phenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, poly-orthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or sus-pended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary.

Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the formula I and related formulae and of the other active ingredient depends on a number of factors, including, for example, the age and weight of the animal, the precise disease condition which requires treatment, and its severity, the nature of the formulation and the method of administration, and is ultimately determined by the treating doctor or vet. However, an effective amount of a compound is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as an individual dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound per se.

The present invention also relates to a kit comprising at least one compound of formula (I) and/or pharmaceutically usable derivatives, tautomers, salts, solvates and stereoisomers thereof, including mixtures thereof in all ratios, and at least one further active ingredient.

The present invention furthermore relates to a method for treating a subject suffering from a sphingosine 1-phosphate associated disorder, comprising administering to said subject an effective amount of a compound of formula I. The present invention preferably relates to a method, wherein the sphingosine 1-phosphate-1 associated disorder is an autoimmune disorder or condition associated with an overactive immune response.

The present invention furthermore relates to a method of treating a subject suffering from an immunoregulatory abnormality, comprising administering to said subject a compound of formula I in an amount that is effective for treating said immunoregulatory abnormality. The present invention preferably relates to a method wherein the immunoregulatory abnormality is an autoimmune or chronic inflammatory disease selected from the group consisting of: amyotrophic lateral sclerosis (ALS), systemic lupus erythematosus, chronic rheumatoid arthritis, type I diabetes mellitus, inflammatory bowel disease, biliary cirrhosis, uveitis, multiple sclerosis, Crohn's disease, ulcerative colitis, bullous pemphigoid, sarcoidosis, psoriasis, autoimmune myositis, Wegener's granulomatosis, ichthyosis, Graves opthalmopathy and asthma. The present invention furthermore relates to a method wherein the immunoregulatory abnormality is bone marrow or organ transplant rejection or graft-versus-host disease. The present invention furthermore relates to a method wherein the immunoregulatory abnormality is selected from the group consisting of: transplantation of organs or tissue, graft-versus-host diseases brought about by transplantation, autoimmune syndromes including rheumatoid arthritis, systemic lupus erythematosus, Hashimoto's thyroiditis, multiple sclerosis, myasthenia gravis, type I diabetes, uveitis, posterior uveitis, allergic encephalomyelitis, glomerulonephritis, post-infectious autoimmune diseases including rheumatic fever and post-infectious glomerulonephritis, inflammatory and hyperproliferative skin diseases, psoriasis, atopic dermatitis, contact dermatitis, eczematous dermatitis, seborrhoeic dermatitis, lichen planus, pemphigus, bullous pemphigoid, epidermolysis bullosa, urticaria, angioedemas, vasculitis, erythema, cutaneous eosinophilia, lupus erythematosus, acne, alopecia greata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns, coeliac diseases, proctitis, eosinophilic gastroenteritis, mastocytosis, Crohn's disease, ulcerative colitis, migraine, rhinitis, eczema, interstitial nephritis, Goodpasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, chronic lymphocytic leukemia, arteriosclerosis, atherosclerosis, aortitis syndrome, polyarteritis nodosa, myocardosis, scleroderma, Wegener's granuloma, Sjogren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth, muscular dystrophy, pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis pigmentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenesis, metastasis of carcinoma and hypobaropathy, disease caused by histamine or leukotriene-$C_4$ release, Behcet's disease, autoimmune hepatitis, primary biliary cirrhosis, sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augmentation of chemotherapeutic effect, cytomegalovirus infection, HCMV infection, AIDS, cancer, senile dementia, trauma, and chronic bacterial infection.

In the embodiment 1, the present invention relates to a compound according to formula IF

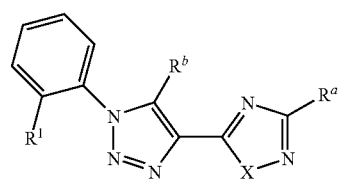

IF wherein
X is O, S;
$R^1$ is selected from F, Cl, Br, I;
$R^b$ is selected from an Ar, Ar-alkyl, an Het, a Het-alkyl, a branched of linear alkyl having 2 to 12 C-atoms, wherein one or more, preferably 1 to 7H-atoms may be replaced by Hal, $OR^3$, CN or $N(R^3)_2$ and wherein one or more, preferably 1 to 7 non-adjacent $CH_2$-groups may be replaced by O, $NR^3$ or S and/or by —CH=CH— or —C≡C— groups, or denotes cycloalkyl or cycloalkylalkylen having 3-7 ring C atoms;
$R^a$ denotes Ar or Het;
$R^3$ is H or A;
Ar denotes a monocyclic or bicyclic, saturated, unsaturated or aromatic carbocyclic ring having 6 to 14 carbon atoms, which may be unsubstituted or monosubstituted, disubstituted or trisubstituted by a substituent selected from $R^4$ and/or $R^5$;
Het denotes a monocyclic or bicyclic, saturated, unsaturated or aromatic heterocyclic ring having 1 to 4 N, O and/or S atoms, which may be unsubstituted or monosubstituted, disubstituted or trisubstituted by a substituent selected from $R^4$ and/or $R^5$;
$R^4$ and $R^5$ are each independently selected from Hal, hydroxy, alkoxy, carboxy, carboxy-alkyl, Perfluoro-alkyl, acyl, alkylsulfonyl, sulfonyl, cyano, nitro, amino, amido, alkyl optionally substituted by a carboxy, or Het-alkyl optionally substituted by an acyl, alkylsulfonyl or alkyl;
and pharmaceutically acceptable derivatives, solvates, tautomers, salts and stereoisomers thereof, including mixtures thereof in all ratios.

In the embodiment 2, the invention relates to a compound according to formula IF:

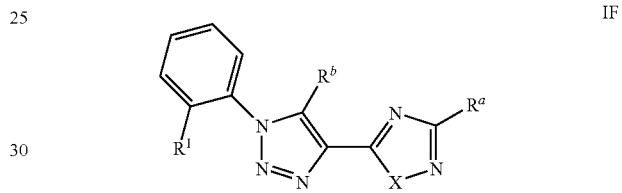

IF wherein
X is O, S;
$R^1$ is selected from F, Cl, Br, I;
$R^b$ is selected from an Ar, Ar-alkyl, an Het, a Het-alkyl, A;
$R^a$ denotes A or a monocyclic or bicyclic, saturated heterocyclic ring having 1 to 4 N, O and/or S atoms, which may be unsubstituted or monosubstituted, disubstituted or trisubstituted by a substituent selected from $R^4$ and/or $R^5$;
A is a branched or linear alkyl having 1 to 12 C-atoms, wherein one or more, preferably 1 to 7 H-atoms may be replaced by Hal, $OR^3$, CN or $N(R^3)_2$ and wherein one or more, preferably 1 to 7 non-adjacent $CH_2$-groups may be replaced by O, $NR^3$ or S and/or by —CH=CH— or —C≡C-groups, or denotes cycloalkyl or cycloalkylalkylen having 3-7 ring C atoms;
Het denotes a monocyclic or bicyclic, saturated, unsaturated or aromatic heterocyclic ring having 1 to 4 N, O and/or S atoms, which may be unsubstituted or monosubstituted, disubstituted or trisubstituted by a substituent selected from $R^4$ and/or $R^5$;
$R^3$ is H or A;
$R^4$ and $R^5$ are each independently selected from Hal, hydroxy, alkoxy, carboxy, carboxy-alkyl, Perfluoro-alkyl, acyl, alkylsulfonyl, sulfonyl, cyano, nitro, amino, amido, alkyl optionally substituted by a carboxy, or Het-alkyl optionally substituted by an acyl, alkylsulfonyl or alkyl;
and pharmaceutically acceptable derivatives, solvates, tautomers, salts and stereoisomers thereof, including mixtures thereof in all ratios.

In the embodiment 3, the invention relates to a compound according to any one of embodiments 1 or 2, wherein X is O.

In the embodiment 4, the invention relates to a compound according to any one of embodiments 1 to 3, wherein $R^1$ is F or Br.

In the embodiment 5, the invention provides a compound according to any one of embodiment 1 to 4, wherein $R^2$ is H or Hal.

In the embodiment 6, the invention provide a compound according to any one of embodiment 1 to 5, wherein $R^b$ is selected from an Ar, Ar-alkyl, an Het, or Het-alkyl, a branched of linear alkyl having 1 to 12 C-atoms, wherein one or more, preferably 1 to 7 H-atoms may be replaced by Hal, $OR^3$, CN or $N(R^3)_2$ and wherein one or more, preferably 1 to 7 non-adjacent $CH_2$-groups may be replaced by O, $NR^3$;

Ar denotes a monocyclic or bicyclic, saturated, unsaturated or aromatic carbocyclic ring having 6 to 14 carbon atoms which may be unsubstituted or monosubstituted, disubstituted or trisubstituted by a substituent selected from $R^4$ and/or $R^5$;

Het denotes a monocyclic or bicyclic, saturated, unsaturated or aromatic heterocyclic ring having 1 to 4 N, O and/or S atoms, which may be unsubstituted or monosubstituted, disubstituted or trisubstituted by a substituent selected from $R^4$ and/or $R^5$.

In the embodiment 7, the invention provides a compound according to embodiment 6, wherein $R^b$ is selected from a Phenyl, Benzyl, cyclopropyl, a pyridinyl, a Het-alkyl, wherein Het is selected from morpholino, tetrahydrofuranyl, tetrahydropyranyl, piperazinyl or piperidinyl, a branched of linear alkyl having 1 to 12 C-atoms, wherein one or more, preferably 1 to 7 H-atoms may be replaced by Hal, $OR^3$, CN or $N(R^3)_2$ and wherein one or more, preferably 1 to 7 non-adjacent $CH_2$-groups may be replaced by O;

wherein Phenyl, Benzyl, pyridinyl or Het-alkyl groups may be unsubstituted or monosubstituted, disubstituted or trisubstituted by a substituent selected from $R^4$ and/or $R^5$.

In the embodiment 8, the invention provides a compound according to the embodiment 7, wherein $R^b$ is selected from a Phenyl, a pyridinyl, a Het-alkyl wherein Het is morpholino, a branched of linear alkyl having 1 to 12 C-atoms, wherein one or more, preferably 1 to 7 H-atoms may be replaced by Hal, $OR^3$, CN or $N(R^3)_2$ and wherein one or more, preferably 1 to 7 non-adjacent $CH_2$-groups may be replaced by 0;

wherein Phenyl, pyridinyl or Het-alkyl groups may be unsubstituted or monosubstituted, disubstituted or trisubstituted by a substituent selected from $R^4$ and/or $R^5$.

In the embodiment 9, the invention provides compound according to the previous embodiments, wherein $R^4$ and $R^5$ are each independently selected from Hal, hydroxy, alkoxy, carboxy, carboxy-alkyl, Perfluoro-alkyl, acyl, alkylsulfonyl, sulfonyl, cyano, nitro, amino, amido, alkyl optionally substituted by a carboxy, or Het-alkyl optionally substituted by an acyl, alkylsulfonyl or alkyl.

In the embodiment 10, the invention provides compound according to embodiment 9, wherein $R^4$ and $R^5$ are each independently selected from F, OH, OMe, COOH, COOMe, $CF_3$, acetyl, methylsulfonyl, sulfonyl, cyano, nitro, amino, amido, methyl optionally substituted by a carboxy, or Het-alkyl optionally substituted by an acetyl, methylsulfonyl or methyl wherein Het is selected from pipetidinyl, piperazinyl or [1,2,4]triazolyl.

In the embodiment 11, the invention provides a compound according to the previous embodiments, wherein X is O, $R^2$ is H, $R^1$ is Hal, $R^a$ is H, A, Ar, or Het and $R^b$ Het wherein Het is selected from pyridinyl.

In the embodiment 12, the invention provides a compound according to the previous embodiments, wherein X is O, $R^2$ is H, $R^1$ is Hal, $R^a$ is H, A, Ar, or Het and $R^b$ is A.

In the embodiment 13, the invention provides a compound according to the previous embodiments wherein X is O, $R^2$ is H, $R^1$ is Hal, $R^a$ is H, A, Ar, or Het and $R^b$ is Het-alkyl.

In the embodiments 14, the invention provides a compound according to the previous embodiments wherein X is O, $R^2$ is H, $R^1$ is Hal, $R^a$ is H, A, Ar, or Het and $R^b$ is Aryl.

In the embodiment 15, the invention provides a compound according to the previous embodiments wherein X is O, $R^2$ is H, $R^1$ is Hal, $R^b$ is A, Ar, Het, OA, NHA, or $NA_2$, Ar-alkyl, or Het-alkyl and $R^a$ is A.

In the embodiment 16, the invention provides a compound according to the previous embodiments wherein X is O, $R^2$ is H, $R^1$ is Hal, $R^b$ is A or Ar, $R^a$ is A.

In the embodiment 17, the invention provides a compound according to the previous embodiments wherein X is O, $R^2$ is H, $R^1$ is Hal, $R^b$ is Ar, $R^a$ is A.

In the embodiment 18, the invention provides a compound according to the previous embodiments wherein X is O, $R^2$ is H, $R^1$ is Hal, $R^b$ is A and $R^a$ is A.

In the embodiment 19, the invention provides the use of compounds of formula I:

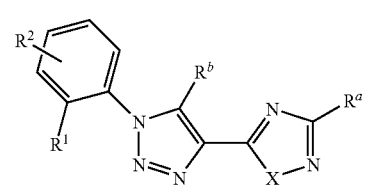

wherein
X is O or S;
$R^1$ denotes H, Hal, $CF_3$, $OCF_3$, CN, or $NO_2$;
$R^2$ is H, A or Hal;
$R^a$ is H, A, Ar, or Het;
$R^b$ is A, Ar, Het, OA, NHA, or $NA_2$, Ar-alkyl, or Het-alkyl;
Hal is F, Cl, Br or I;
A is a branched or linear alkyl having 1 to 12 C-atoms, wherein one or more, preferably 1 to 7 H-atoms may be replaced by Hal, $OR^3$, CN or $N(R^3)_2$ and wherein one or more, preferably 1 to 7 non-adjacent $CH_2$-groups may be replaced by O, $NR^3$ or S and/or by —CH=CH— or —C≡C— groups, or denotes cycloalkyl or cycloalkylalkylen having 3-7 ring C atoms;

Ar denotes a monocyclic or bicyclic, saturated, unsaturated or aromatic carbocyclic ring having 6 to 14 carbon atoms which may be unsubstituted or monosubstituted, disubstituted or trisubstituted by a substituent selected from $R^4$ and/or $R^5$;

Het denotes a monocyclic or bicyclic, saturated, unsaturated or aromatic heterocyclic ring having 1 to 4 N, O and/or S atoms which may be unsubstituted or monosubstituted, disubstituted or trisubstituted by a substituent selected from $R^4$ and/or $R^5$;

$R^4$ and $R^5$ are each independently selected from Hal, hydroxy, alkoxy, carboxy, carboxy-alkyl, Perfluoro-alkyl, Perfluoro-alkoxy, acyl, alkylsulfonyl, sulfonyl, cyano, nitro, amino, amido, alkyl optionally substituted by a carboxy, or Het-alkyl optionally substituted by an acyl, alkylsulfonyl or alkyl;

$R^3$ is H or A;

and pharmaceutically acceptable derivatives, solvates, tautomers, salts and stereoisomers thereof, including mixtures thereof in all ratios as a medicament.

In the embodiment 20, the invention provides the use of compounds according to the previous embodiments:

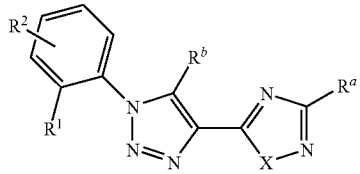

wherein
X is O or S;
R¹ denotes H, Hal, CF$_3$, OCF$_3$, CN or NO$_2$;
R² is H;
as a medicament.

In the embodiment 21, the invention provides the use of compounds according to one or more of the previous embodiments, and pharmaceutically usable derivatives, salts, tautomers, solvates and stereoisomers thereof, including mixtures thereof in all ratios, for the preparation of a medicament for the treatment and/or prophylaxis of diseases in which the inhibition, activation, regulation, and/or modulation of S1P$_1$ receptor signal transduction plays a role.

In the embodiment 22, the invention provides the use of compounds according to one or more of the previous embodiments, and pharmaceutically usable derivatives, salts, tautomers, solvates and stereoisomers thereof, including mixtures thereof in all ratios, for the preparation of a medicament for the treatment and/or prophylaxis of a sphingosine 1-phosphate associated disorder.

In the embodiment 23, the invention provides the use of the previous embodiments, wherein the sphingosine 1-phosphate-(1) associated disorder is an autoimmune disorder or condition associated with an overactive immune response.

In the embodiment 24, the invention provides a process for the preparation of compounds of formula I, comprising
(i) the step of reacting compounds of formula II

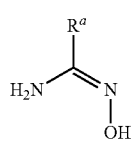

(II)

with compounds of formula III

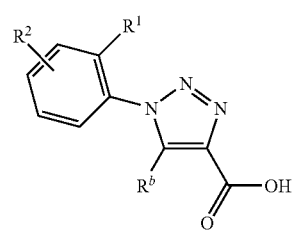

(III)

with a coupling agent in a polar solvent in a presence or absence of a base to obtain the compound of formula IV;

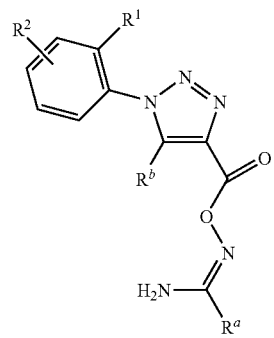

(IV)

(ii) and the step of cyclizing compounds of formula IV in a suitable solvent and a suitable base in the presence or absence of Microwave radiation at elevated temperature

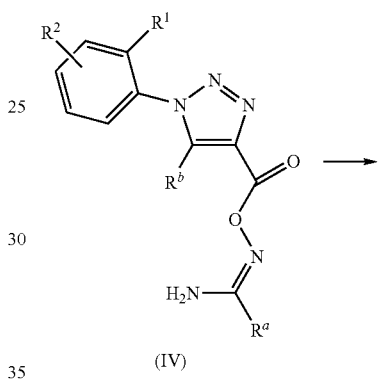

(IV)

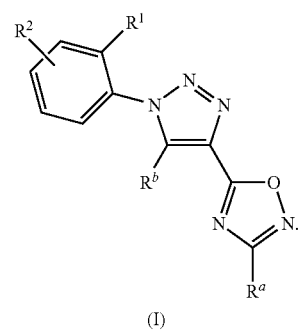

(I)

In the embodiment 25, the invention provides the process according to embodiment 24, wherein the coupling agent is chosen from EDC, HATU, TBTU.

In the embodiment 26, the invention provides the process according to the embodiment 24 wherein the base is chosen from pyridine, TEA, DIEA, NMM.

In the embodiment 27, the invention provides the process according to embodiment 24, wherein the solvent is chosen from a polar solvent, preferably MeCN, THF, DMF, DMC.

Preferred compounds of formula I and related formulae exhibit a EC$_{50}$ in GTPTS for the binding to the S1P$_1$ receptor of less than about 5 μM, preferably less than about 1 μM and even more preferred less than about 0.1 μM.

In the following the present invention shall be illustrated by means of some examples, which are not construed to be viewed as limiting the scope of the invention.

The triazole oxadiazole compounds according to formula I, IA, IB, IC, ID, IE, IF, IG may be prepared from readily available starting materials using the following general methods and procedures. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures.

In the following the present invention shall be illustrated by means of some examples, which are not construed to be viewed as limiting the scope of the invention.

The triazole oxadiazole compounds according to formula I and related formulae can be prepared from readily available starting materials by several synthetic approaches, using both solution-phase and solid-phase chemistry protocols or mixed solution and solid phase protocols.

EXAMPLES

The commercially available starting materials used in the following experimental description were purchased from Aldrich or Fluka unless otherwise reported.

1-Azido-2-fluorobenzene was synthesized following the procedure described in Platz, M. S. et al. *J. Org. Chem.* 1989, 54, 5938-5945.

The HPLC, NMR and MS data provided in the examples described below are obtained as followed:

The HPLC Data:
Method A: HPLC columns: Xbridge™ C8 column 50 mm×4.6 mm at a flow of 2 mL/min; 8 min gradient from 0.1% TFA in $H_2O$ to 0.07% TFA in ACN.
Method B: HPLC columns: Xbridge™ C8 column 50 mm×4.6 mm at a flow of 1 mL/min; 8 min gradient $H_2O$ ammonium acetate (10 μM, pH 9)—ACN from 95:5 to 0:100.
Method C: HPLC columns: ATLANTIS C18 75×4.6 mm 5U at a flow of 0.8 mL/min; A-0.1%HCOOH B-ACN
Method D: HPLC columns: C18 BDS, 50×4.6 mm, SC\307 at a flow of 0.8 mL/min; A-0.1% TFA, B-ACN: Flow—0.8 mL/min.
Method E: HPLC columns: Phenomenex Luna 5μ C18 (2), 100×4.6 mm. (Plus guard cartridge) at a flow of 2 ml/min; 5 min gradient from 95:5 ([0.1% (V/V) formic acid in $H_2O$]: [0.1% (V/V) formic acid in MeCN]) to 5:95% ([0.1% (V/V) formic acid in $H_2O$]:[0.1% (V/V) formic acid in MeCN]).
Method F: HPLC columns: Waters Xterra MS 5μ C18, 100× 4.6 mm. (Plus guard cartridge) at a flow of 2 ml/min; 5 min gradient from 95:5 ([10 mM ammonium bicarbonate in $H_2O$]: MeCN) to 5:95% ([10 mM ammonium bicarbonate in $H_2O$]:MeCN).
Method G: HPLC columns:Waters Sunfire 5μ C18, 150×4.6 mm at a flow of 1 ml/min; 30 min gradient from 95:5 ([0.1% (V/V) formic acid in $H_2O$]:[0.1% (V/V) formic acid in MeCN]) to 0.1% (V/V) formic acid in MeCN.
Method H: HPLC columns:Waters Xterra 5μ C18 (2), 250× 4.6 mm at a flow of 1 ml/min; 30 min gradient from 95:5 ([10 mM ammonium bicarbonate in $H_2O$]:MeCN) to MeCN.
Method I: HPLC columns: Waters Sunfire 5μ C18, 150×4.6 mm at a flow of 1 ml/min; 20 min gradient from 98:2 ([0.1% (V/V) formic acid in $H_2O$]:[0.1% (V/V) formic acid in MeCN]) to 0.1% (V/V) formic acid in MeCN.
UV detection (maxplot) for all methods. Optional ELS detection using Polymer Labs ELS-1000.

Mass Spectrum Data:
Method A: LC/MS Waters ZMD (ESI);
Method B: LC/MS Waters Acquity, column Waters Acquity HPLC BEH C18 1.7 m 2.1×50 mm, conditions: solvent A (10 mM ammonium acetate in water+5% ACN), solvent B (ACN), gradient 5% B to 100% B over 3 min, UV detection (PDA, 230-400 nm) and MS detection (SQ detector, positive and negative ESI modes, cone voltage 30 V).
Method C: UV detection (HP or Waters DAD, 210-400 nm) and MS detection (Micromass ZQ single quadrapole LC-MS, positive and negative ESI or APCI modes, cone voltage 25 V). GC/MS: GC Agilent 6890N & MS Agilent 5973.
$^1$H-NMR data: Bruker DPX-300 MHz unless otherwise reported.

The preparative HPLC purifications are performed with HPLC waters Prep LC 4000 System equipped with columns®PrepMS C18 10 μm, 50×300 mm, unless otherwise reported. All HPLC purifications were performed with a gradient of ACN/$H_2O$ or ACN/$H_2O$/TFA (0.1%).

The microwave chemistry is performed on a single mode microwave reactor Emrys™ Optimiser of or Smith Creator™ from Personal Chemistry or Initiator™ Sixty from Biotage.

Intermediate 1 methyl 4-[amino(hydroxyimino)methyl]-2-fluorobenzoate

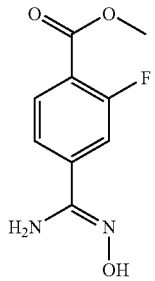

Step 1: methyl-4-cyano-2-fluorobenzoate
4-Cyano-2-fluorobenzoic acid (1 g; 6.06 mmol) was suspended in MeOH (10 mL) and 1-(3-dimethyl aminopropyl)-3-ethylcarbodiimide hydrochloride (EDC) (1.39 g; 7.27 mmol; 1.20 eq.) and 4-dimethylaminopyridine (70 mg; 0.61 mmol; 0.10 eq.) were added. The mixture was stirred at RT overnight.

Solvents were concentrated and the resulting mixture was taken up into EtOAc (20 mL) and washed with 0.1 N HCl solution (10 mL), 0.1 N NaOH solution (10 mL) and brine (2×10 mL), dried over $MgSO_4$ and evaporated. The isolated solid was washed with cyclohexane and a mixture of cyclohexane/EtOAc (3:1) then dried, affording the title compound as an off-white solid. $^1$H-NMR (DMSO-$d_6$, 300 MHz) δ 8.12-8.05 (m, 2H), 7.87 (dd, J=1.32 Hz, J=8.10 Hz, 1H), 3.93 (s, 3H). GC/MS Rt 3.08 min: 179 (M+H)$^+$. HPLC (Method A) Rt 2.83 min (Purity: 97%).

Step 2: methyl 4-[amino(hydroxyimino)methyl]-2-fluorobenzoate
To a solution of methyl 4-cyano-2-fluorobenzoate, obtained in Step 1 (486.8 mg; 2.72 mmol) in abs. EtOH (6 mL) was added hydroxylamine (0.8 mL; 13.6 mmol; 5 eq.) (50% in water) and the mixture was heated at 74° C. overnight. After cooling, a product precipitated. The precipitate was filtered off and dried under vacuum to afford Intermediate 1 as an off-white solid (267.10 mg; 46%). $^1$H-NMR (DMSO-d$_6$, 300 MHz) δ 10.09 (s, 1H), 7.92 (t, J=7.91 Hz, 1H), 7.69 (dd, J=1.70 Hz, J=8.10 Hz, 1H), 7.64 (dd, J=1.51, J=12.81, 1H), 6.05 (s, 2H), 3.90 (s, 3H). HPLC (Method B) Rt 2.99 min (Purity: 100%).

Intermediate 2 methyl 4-[amino(hydroxyimino)methyl]-3-fluorobenzoate

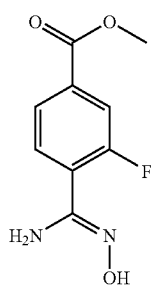

Step 1: methyl-4-cyano-3-fluorobenzoate

4-Cyano-3-fluorobenzoic acid (1 g; 6.06 mmol) was suspended in MeOH (10 mL) and 1-(3-dimethyl aminopropyl)-3-ethylcarbodiimide hydrochloride (EDC) (1.39 g; 7.27 mmol; 1.20 eq.) and 4-dimethylaminopyridine (70 mg; 0.61 mmol; 0.10 eq.) were added. The mixture was stirred at RT overnight.

Solvents were concentrated and the resulting mixture was taken up into EtOAc (20 mL) and washed with 0.1 N HCl solution (10 mL), 0.1 N NaOH solution (10 mL) and brine (2×10 mL), dried over MgSO$_4$ and evaporated. The title product was isolated as an off-white solid (0.95 g; 87%). $^1$H-NMR (DMSO-d$_6$, 300 MHz) δ 8.16 (dd, J=6.40 Hz, J=7.91 Hz, 1H), 8.02 (dd, J=1.50 Hz, J=9.80 Hz, 1H), 7.97 (dd. J=1.50 Hz, J=7.91, 1H), 3.95 (s, 3H). GC/MS R$_t$ 3.10 min: 179 (M+H)$^+$. HPLC (Method A) Rt 3.17 min (Purity: 87%).

Step 2: methyl 4-[amino(hydroxyimino)methyl]-3-fluorobenzoate

To a solution of methyl 4-cyano-3-fluorobenzoate, obtained in Step 1 (834.50 mg; 4.66 mmol) in abs. EtOH (10 mL) was added hydroxylamine (1.37 mL; 23.3 mmol; 5 eq.) (50% in water) and the mixture was heated at 74° C. overnight. After cooling, the solvents were evaporated and the residue was dissolved in EtOAc (15 mL), extracted with brine (3×10 mL), dried over MgSO$_4$ and evaporated. Intermediate 2 was isolated as a yellow solid and used without further purification in the next step. $^1$H-NMR (DMSO-d$_6$, 300 MHz) δ 9.89 (s, 1H), 7.92 (t, J=7.91 Hz, 1H), 7.69 (dd, J=1.70 Hz, J=8.10 Hz, 1H), 7.64 (dd, J=1.51 Hz, J=12.81 Hz, 1H), 5.97 (s, 2H), 3.92 (s, 3H). HPLC (Method B) Rt 2.90 min (Purity: 90%).

Intermediate 3 methyl 3-[amino(hydroxyimino)methyl]benzoate

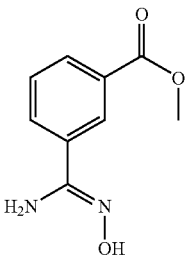

Step 1: methyl-3-cyanobenzoate

4-Cyanobenzoic acid (1 g; 6.80 mmol) was suspended in MeOH (10 mL) and 1-(3-dimethyl aminopropyl)-3-ethylcarbodiimide hydrochloride (EDC) (1.56 g; 8.16 mmol; 1.20 eq.) and 4-dimethylaminopyridine (83 mg, 0.68 mmol; 0.10 eq.) were added. The mixture was stirred at RT overnight.

Solvents were concentrated and the resulting mixture was taken up into EtOAc (20 mL) and washed with 0.1 N HCl solution (10 mL), 0.1 N NaOH solution (10 mL) and brine (2×10 mL), dried over MgSO$_4$ and evaporated. The title product was isolated as an off-white solid (0.85 g; 77%). $^1$H-NMR (DMSO-d$_6$, 300 MHz) δ 8.36 (s, 1H), 8.29 (d, J=7.91 Hz, 1H), 8.18 (d, J=7.91 Hz, 1H), 7.79 (t, J=7.91 Hz, 1H), 3.93 (s, 3H). LC/MS: 161.95 (M+H)$^+$. HPLC (Method A) Rt 2.75 min (Purity: 98%).

Step 2: methyl 3-[amino(hydroxyimino)methyl]benzoate

To a solution of methyl 3-cyanobenzoate, obtained in Step 1 (0.84 g; 5.19 mmol) in abs. EtOH (10 mL) was added hydroxylamine (0.77 mL; 26 mmol; 5 eq.) (50% in water) and the mixture was heated at 74° C. overnight. After cooling, the solvents were evaporated and the residue was dissolved in EtOAc (15 mL), extracted with brine (3×10 mL), dried over MgSO$_4$ and evaporated. Intermediate 3 was isolated as a white solid (0.84 g; 83%) and was used without further purification in the next step. $^1$H-NMR (DMSO-d$_6$, 300 MHz) δ 9.81 (s, 1H), 8.33 (s, 1H) 7.98 (t, J=6.59 Hz, 2H), 7.57 (t, J=7.72 Hz, 1H), 5.98 (s, 2H), 3.91 (s, 3H). HPLC (Method B) Rt 1.01 min (Purity: 96%).

Intermediate 4

2-fluoro-N-hydroxybenzenecarboximidamide

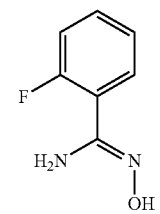

The title compound was prepared following procedure described for Intermediate 3, Step 2, but starting from 2-fluorobenzonitrile (1 g; 8.26 mmol), and isolated as a colorless oil (1.098 g; 86%). $^1$H-NMR (DMSO-d$_6$, 300 MHz) δ 9.67 (s, 1H); 7.57-7.43 (m, 2H); 7.29-7.22 (m, 2H); 5.84 (s, 2H). HPLC (Method B) Rt 2.17 min (Purity: 97%).

Intermediate 5

2,6-difluoro-N-hydroxybenzenecarboximidamide

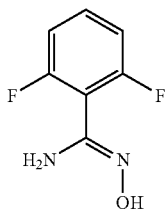

The title compound was prepared following procedure described for Intermediate 3, Step 2, but starting from 2,6-difluorobenzonitrile (1.0 g; 7.19 mmol), and isolated as a off white solid (1.036 g; 84%). $^1$H-NMR (DMSO-$d_6$, 300 MHz) δ 9.61 (s, 1H), 7.52 (tt, J=6.59 Hz, J=8.48 Hz, 1H), 7.17 (m, 2H), 6.00 (s, 2H). HPLC (Method B) Rt 2.09 min (Purity: 100%).

Intermediate 6

2-fluoro-N,4-dihydroxybenzenecarboximidamide

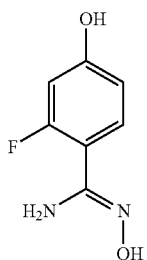

The title compound was prepared following procedure described for Intermediate 3, Step 2, but starting from 2-fluoro-4-hydroxybenzonitrile (500 mg; 3.65 mmol), and isolated as a off white solid (534.40 mg; 86%). $^1$H-NMR (DMSO-$d_6$, 300 MHz) δ 10.11 (s, 1H), 9.46 (s, 1H), 7.34 (t, J=8.67 Hz, 1H), 6.65-6.57 (m, 2H), 5.67 (s, 2H). HPLC (Method B) Rt 1.10 min (Purity: 100%).

Intermediate 7 tert-butyl 3-{4-[amino(hydroxyimino)methyl]-3-methoxyphenyl}propanoate

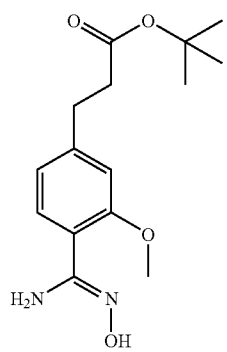

Step 1: tert-butyl 3-(4-cyano-3-methoxyphenyl)acrylate

A mixture of 4-bromo-2-methoxybenzonitirle (10 g, 0.047 mol), tert-butylacrylate (27.6 mL, 0.188 mol) and triethylamine (19.6 mL, 0.141 mol) in dry acetonitrile (100 mL) was purged with nitrogen for 10 min followed by the addition of palladium acetate (1.05 g, 0.0047 mol) and triphenyl phosphine (1.23 g, 0.0047 mol). The mixture was refluxed at 90° C. for 48 h and concentrated under vacuum. The residue purified by chromatography using silica gel (60-120 mesh) and pet ether/ethyl acetate as eluent to afford the title compound as a yellow solid. $^1$H-NMR (CDCl$_3$, 400 MHz) δ 7.50-7.56 (2H, m), 7.13-7.15 (1H, d), 7.05 (1H, s), 6.41-6.45 (1H, d), 3.95 (3H, s), 1.53 (9H, s).

Step 2: tert-butyl 3-(4-cyano-3-methoxyphenyl)propanoate

To a solution of tert-butyl 3-(4-cyano-3-methoxyphenyl) acrylate obtained in step 1 (3.5 g) in ethyl acetate (150 mL) was added palladium on carbon (500 mg) and the mixture was put under a pressure of 4 kg of hydrogen for 12 h at RT. The catalyst was removed by filtration and the solvents were removed under vacuum to afford the title compound as white solid (3.5 g, 97%). $^1$H-NMR (CDCl$_3$, 400 MHz) δ 7.41-7.43 (1H, s), 6.80-6.83 (2H, m), 3.88 (3H, s), 2.89-2.93 (2H, t), 2.51-2.55 (2H, t), 1.34 (9H, s). LC/MS: 279.1 (M+H)$^+$. HPLC (Method C) Rt 2.40 min (Purity: 99.7%).

Step 3: tert-butyl 3-{4-[amino(hydroxyimino)methyl]-3-methoxyphenyl}propanoate

To a mixture of sodium bicarbonate (1.92 g, 0.023 mol) in water (15 mL) and hydroxylamine hydrochloride (1.6 g, 0.023 mol), was added tert-butyl 3-(4-cyano-3-methoxyphenyl) propanoate, obtained in step 2 (6.0 g, 0.023 mol) in methanol (60 mL). The reaction mixture refluxed at 65° C. for 12 hours and concentrated under vacuum. The residue was slurred with ethanol (100 mL) and filtered. The filtrate was concentrated under vacuum and the residue purified by chromatography using silica gel (60-120 mesh) and chloroform/methanol as eluent. The white solid obtained was further recrystallised from pet ether/ethyl acetate to afford the title compound as a white solid. $^1$H-NMR (CDCl$_3$, 400 MHz) δ 9.33 (1H, s), 7.25-7.27 (1H, d), 6.91 (1H, s), 6.77 (1H, d), 5.54 (2H, bs), 3.76-3.78 (3H, s), 2.77-2.79 (2H, t), 2.52-2.54 (2H, t), 1.36 (9H, s). LC/MS: 295.1 (M+H)$^+$. HPLC (Method D) Rt 2.52 min (Purity: 93.5%).

Intermediate 8 tert-butyl 3-{4-[amino(hydroxyimino)methyl]-3-methylphenyl}propanoate

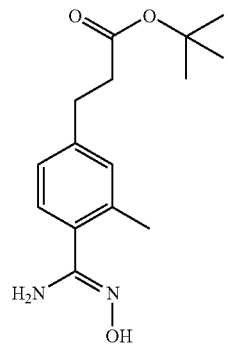

Step 1: tert-butyl 3-(4-cyano-3-methylphenyl)acrylate

A mixture of 4-bromo-2-methyl benzonitirle (5 g, 0.025 mol), tert-butylacrylate (15 mL, 0.102 mol), and triethylamine (10.6 mL, 0.076 mol) in dry acetonitrile (50 mL) was purged with nitrogen for 10 min. Palladium acetate (0.286 g, 0.0012 mol) and triphenyl phosphine (0.334 g, 0.0012 mol) were added to the reaction mixture and refluxed at 90° C. for 48 hrs. The reaction mixture was concentrated under vacuum. The residue was purified by column chromatography using silica gel (60-120 mesh) and pet ether/ethyl acetate as an eluent to afford the title compound as a white solid (5.3 g, 85%). $^1$H-NMR (DMSO d$_6$, 400 MHz) δ 7.84 (1H,s), 7.79-7.81 (1H, d), 7.69-7.71 (1H, d), 7.53-7.57 (1H, d), 6.67-6.71 (1H, d), 2.49 (3H, s), 1.49 (9H, s).

Step 2: tert-butyl 3-(4-cyano-3-methylphenyl)propanoate

To a solution of tert-butyl 3-(4-cyano-3-methylphenyl)acrylate obtained in step 1, (5.3 g) in ethyl acetate (50 mL) was added palladium on carbon (500 mg) and the mixture was placed under a pressure of 3 kg of hydrogen for 3 h at RT. The catalyst was removed by filtration and the filtrate was concentrated under vacuum to afford the title compound as white solid (5.2 g, 98%). $^1$H-NMR (CDCl$_3$, 400 MHz) δ 7.51-7.53 (1H, d), 7.16 (1H, s), 7.10-7.12 (1H, d), 2.91-2.94 (2H, t), 2.53-2.57 (2H, t), 2.52 (3H, s), 1.42 (9H, s). LC/MS: 246.0 (M+H)$^+$. HPLC (Method C) Rt 3.23 min (Purity: 96.2%).

Step 3: tert-butyl 3-{4-[amino(hydroxyimino)methyl]-3-methylphenyl}propanoate

The title compound was prepared following procedure described for Intermediate 3, Step 2, but starting from tert-butyl 3-(4-cyano-3-methylphenyl)propanoate (0.20 g; 0.82 mmol), and was isolated as a white solid (177.60 mg; 78%). $^1$H-NMR (DMSO-d$_6$, 300 MHz) δ 9.28 (s, 1H), 7.18 (d, J=7.71 Hz, 1H), 7.07 (s, 1H), 7.04 (d, J=7.77 Hz, 1H), 5.67 (s, 2H), 2.79 (t, J=7.47 Hz, 2H), 2.51 (m, 2H), 2.32 (s, 3H), 1.39 (s, 9H). LC/MS: 278.90 (M+H)$^+$. HPLC (Method B) Rt 2.62 min (Purity: 89%).

Intermediate 9

1-(2-Fluorophenyl)-5-methyl-1H-1,2,3-triazole-4-carboxylic acid

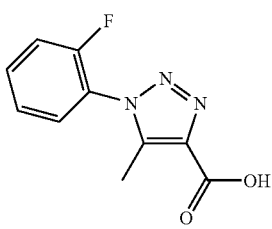

To a solution of 1-azido-2-fluorobenzene, prepared according to Platz, M. S. et al. J. Org. Chem. 1989, 54, 5938-5945 (9.166 g; 66.85 mmol; 1.5 eq.), and ethyl acetoacetate (5.69 mL; 44.57 mmol; 1 eq.) in absolute EtOH (60 mL) under N$_2$ at RT, sodium ethoxide (10.48 mL; 133.70 mmol; 3 eq.) was added and the mixture was heated at 70° C. for 5 days. During this reaction time, ethyl acetoacetate (2×2 mL; 2×13.37 mmol; 2×0.30 eq.) was added after 3 days and 4 days. After cooling to RT, a 5N NaOH solution (70 mL) was added to the mixture. The reaction was stirred for 1 h at RT. Water was added (70 mL), and the mixture was washed with Et$_2$O (3×70 mL). Then the aqueous layer was acidified to pH 2-3 with 1N HCl and extracted with EtOAc (3×80 mL). Combined organic phases were washed with brine (80 mL), dried over MgSO$_4$ and evaporated. The residue was triturated in DCM and filtrated, to afford Intermediate 9 as a white solid. $^1$H-NMR (DMSO-d$_6$, 300 MHz) δ 13.22 (s, 1H), 7.74-7.66 (m, 2H), 7.57 (t, J=9.50 Hz, 1H), 7.45 (t, J=7.73 Hz, 1H), 2.37 (s, 3H). LC/MS: 222.0 (M+H)$^+$. HPLC (Method A) Rt 2.24 min (Purity: 98%).

Intermediate 10

5-Ethyl-1-(2-fluorophenyl)-1H-1,2,3-triazole-4-carboxylic acid

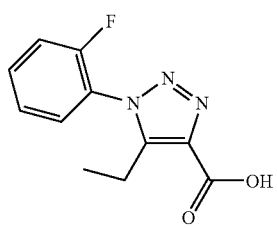

To a solution of 1-azido-2-fluorobenzene, prepared according to Platz, M. S. et al. J. Org. Chem. 1989, 54, 5938-5945 (4.22 g; 30.78 mmol; 1 eq.), and ethyl 3-oxovalerate (4.83 mL; 33.85 mmol; 1.10 eq.) in EtOH (75 mL) under argon was added portion wise sodium ethoxide (4.19 g; 61.55 mmol; 2 eq.). The resulting mixture was stirred for 30 min at RT, one hour at 65° C. and overnight at RT. The solvents were evaporated. EtOH (50 mL) and 5N NaOH solution (30 mL) were added and the resulting mixture was stirred at RT for 3 h. The mixture was diluted with water (75 mL), and washed with ether (2×50 mL). After cooling to 0° C., the aqueous layer was acidified with 5N HCl solution, and the product was extracted with EtOAc (3×50 mL). The combined organic layers were washed with brine and dried over MgSO$_4$. After concentration, a solid was obtained. It was triturated with ACN, filtrated and dried. Intermediate 10 was obtained as an off-white solid. $^1$H-NMR (DMSO-d$_6$, 300 MHz) δ 13.32 (s, 1H), 7.84-7.77 (m, 2H), 7.70-7.64 (m, 1H), 7.54 (t, J=7.54 Hz, 1H), 2.85 (q, J=7.51, 2H), 1.04 (t, J=7.50 Hz, 3H). LC/MS: 235.94 (M+1-1)$^+$. HPLC (Method A) Rt 2.61 min (Purity: 96%).

Intermediate 11

1-(2-Fluorophenyl)-5-(methoxymethyl)-1H-1,2,3-triazole-4-carboxylic acid.

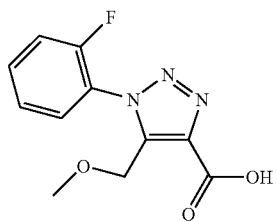

To a solution of 1-azido-2-fluorobenzene, prepared according to Platz, M. S. et al. J. Org. Chem. 1989, 54, 5938-5945 (500 mg; 3.65 mmol; 1 eq.), and methyl 4-methoxyacetoacetate (0.520 mL; 4.01 mmol; 1.10 eq.) in absolute EtOH (10 mL) under argon was added portion wise sodium ethoxide (496.30 mg; 7.29 mmol; 2 eq.) and the mixture was stirred for 5 h at 70° C., then overnight at RT. A 5N solution of NaOH (3.65 mL) was added and the mixture was stirred for 1 h at RT. Once no strating ester could be detected by LC/MS, the mixture was diluted with water (10 mL), and washed with ether (2×10 mL). After cooling to 0° C., the aqueous layer was acidified with 5N HCl solution, and the product was extracted with EtOAc (3×15 mL). The combined organic layers were washed with brine (15 mL) and dried over MgSO$_4$. After concentration, an oil was obtained, which was triturated with ACN. The resulting solid was filtrated and dried, affording Intermediate 11 as an off-white solid (3.90 g; 54%). $^1$H-NMR (DMSO-d$_6$, 300 MHz) δ 13.60 (s, 1H), 7.80-7.72 (m, 2H), 7.62 (t, J=9.23 Hz, 1H), 7.51 (t, J=7.54 Hz, 1H), 4.77 (s, 2H), 3.11 (s, 3H). LC/MS: 251.95 (M+H)$^+$. HPLC (Method A) Rt 2.20 min (Purity: 93%).

Intermediate 12

5-Butyl-1-(2-fluorophenyl)-1H-1,2,3-triazole-4-carboxylic acid

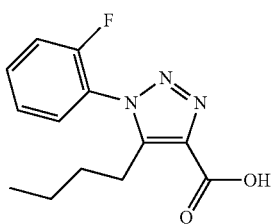

To a solution of 1-azido-2-fluorobenzene, prepared according to Platz, M. S. et al. *J. Org. Chem.* 1989, 54, 5938-5945 (548.47 mg; 4 mmol; 1 eq.), and methyl 3-oxo-heptanoate (0.635 mg; 4.01 mmol; 1.10 eq.) in absolute EtOH (10 mL) under argon was added portion wise sodium ethoxide (496.3 mg; 7.29 mmol; 2 eq.) and the mixture was stirred at 70° C. for 5 h, then overnight at RT. A 5N NaOH solution (3.65 mL) was added and the mixture was stirred for 1 h at RT. Once the saponification was complete, the mixture was diluted with water (10 mL), and washed with ether (2×10 mL). After cooling to 0° C., the aqueous layer was acidified with 5N solution of HCl, and the product was extracted with EtOAc (3×15 mL). The combined organic layers were washed with brine (15 mL) and dried over MgSO$_4$. After concentration, Intermediate 12 was isolated as an oil (700 mg; 73%) and was used without further purification. $^1$H-NMR (CDCl$_3$, 300 MHz) δ 9.18 (s, 1H), 7.66-7.59 (m, 1H), 7.50-7.32 (m, 3H), 2.93 (t, J=7.91 Hz, 2H), 1.53-1.17 (m, 4H), 0.78 (t, J=7.21 Hz, 3H). LC/MS: 263.96 (M+H)$^+$. HPLC (Method A) Rt 3.34 min (Purity: 72%).

Intermediate 13

5-phenyl-1-(2-fluorophenyl)-1H-1,2,3-triazole-4-carboxylic acid

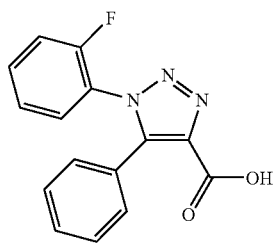

Sodium ethoxide (1.99 g; 29.17 mmol; 2 eq.) was dissolved in EtOH (50 mL) and the resulting solution was placed under N$_2$ atmosphere. 1-Azido-2-fluorobenzene, prepared according to Platz, M. S. et al. *J. Org. Chem.* 1989, 54, 5938-5945 (2 g; 14.59 mmol; 1 eq.), was dissolved in EtOH (15 mL) and ethyl benzoylacetate (3.08 g; 16.04 mmol; 1.10 eq.) was added. This solution was added portionwise to the sodium ethoxide solution at RT. The mixture was stirred for 5 h at 70° C. and overnight at RT. A 5N solution of NaOH (14.6 mL) was added and the mixture was stirred for 1 h at RT. The mixture was diluted with water (30 mL), and washed with ether (2×30 mL). After cooling to 0° C., the aqueous layer was acidified with 5N solution of HCl and the product was extracted with EtOAc (3×50 mL). The combined organic layers were washed with brine (25 mL) and dried over MgSO$_4$. The solvents were evaporated and the residue was triturated in ACN, filtrated and dried under vacuo to afford intermediate 13 as an off-white solid. $^1$H-NMR (DMSO-d$_6$, 300 MHz) δ 13.21 (s, 1H), 7.77 (dt, J=1.63 Hz, J=7.72 Hz, 1H), 7.67-7.60 (m, 1H), 7.45-7.36 (m, 7H). LC/MS: 283.87 (M+H)$^+$. HPLC (Method A) Rt 3.16 min (Purity: 92%).

Intermediate 14

1-(2-Fluorophenyl)-5-pyridin-3-yl-1H-1,2,3-triazole-4-carboxylic acid

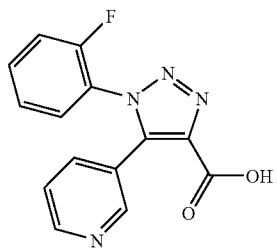

To a solution of methyl nicotinoylacetate (1.29 g; 7.22 mmol; 1.10 eq.) in EtOH (15 mL) was added 1-azido-2-fluorobenzene, prepared according to Platz, M. S. et al. *J. Org. Chem.* 1989, 54, 5938-5945 (0.90 g; 6.56 mmol; 1 eq.), followed by sodium ethoxide (0.89 g; 13.13 mmol; 2 eq.). The reaction mixture was heated to 70° C. for 4.5 h and stirred overnight at RT. A 5N NaOH solution (6.6 mL) was added together with EtOH (30 mL). The reaction mixture was stirred at RT for 2 h. Once the saponification was complete, the mixture was diluted with water (30 mL), and washed with ether (2×30 mL). After cooling to 0° C., the aqueous layer was adjusted to pH=6 with 5N HCl solution, and the product was extracted with EtOAc (3×50 mL). The combined organic layers were washed with brine (50 mL) and dried over MgSO$_4$. The solvents were evaporated and the residue was triturated with ACN, filtrated and dried, affording Intermediate 14 as an off-white solid. $^1$H-NMR (DMSO-d$_6$, 300 MHz) δ 13.39 (s, 1H), 8.62 (dd, J=4.88 Hz, J=1.52 Hz, 1H), 8.58 (d, J=1.59 Hz, 1H), 7.86-7.80 (m, 2H), 7.70-7.63 (m, 1H), 7.48-7.42 (m, 3H). LC/MS: 284.85 (M+H)$^+$. HPLC (Method A) Rt 1.69 min (Purity: 100%).

Intermediate 15

1-(2-Fluorophenyl)-5-pyridin-2-yl-1H-1,2,3-triazole-4-carboxylic acid

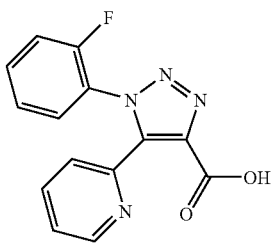

To a solution of ethyl picolinoylacetate (0.77 g; 4.01 mmol; 1.10 eq.) and 1-azido-2-fluorobenzene, prepared according to Platz, M. S. et al. J. Org. Chem. 1989, 54, 5938-5945 (0.50 g; 3.65 mmol; 1 eq.), in EtOH (25 mL) under argon was added sodium ethoxide (0.50 g; 7.29 mmol; 2 eq.). The reaction mixture was heated to 70° C. for 4.5 h and stirred for 3 days at RT. A 5 N solution of NaOH (3.65 mL) was added and the reaction mixture was stirred for 2 h at RT. Once the saponification was complete, the mixture was diluted with water (20 mL), and washed with ether (2×20 mL). After cooling to 0° C., the aqueous layer was adjusted to a pH=4 with HCl (5 N), and the product was extracted with EtOAc (3×30 mL). The combined organic layers were washed with brine (20 mL) and dried over MgSO$_4$. The solvents were evaporated and the product was dried to afford Intermediate 15 as an off-white solid. $^1$H-NMR (DMSO-d$_6$, 300 MHz) δ 13.45 (s, 1H), 8.47 (d, J=4.80 Hz, 1H), 7.96 (dt, J=7.96 Hz, J=1.71 Hz, 1H), 7.86 (d, J=7.86 Hz, 1H), 7.68-7.58 (m, 2H), 7.47-7.35 (m, 3H). LC/MS: 284.74 (M+1-1)$^+$. HPLC (Method A) Rt 2.30 min (Purity: 100%).

Intermediate 16

1-(2-Fluorophenyl)-5-pyridin-4-yl-1H-1,2,3-triazole-4-carboxylic acid

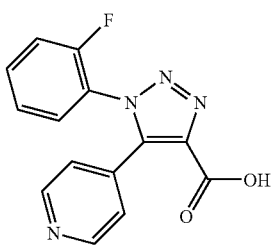

To a solution of ethyl isonicotinylacetate (0.77 g; 4.01 mmol; 1.10 eq.) and 1-azido-2-fluorobenzene, prepared according to Platz, M. S. et al. J. Org. Chem. 1989, 54, 5938-5945 (0.50 g; 3.65 mmol; 1 eq.), in EtOH (25 mL) under argon was added sodium ethoxide (0.50 g; 7.29 mmol; 2 eq.). The reaction mixture was heated for 5 h at 74° C. and stirred overnight at RT. A 5N solution of NaOH (3.65 mL) was added and the resulting reaction mixture was stirred for 2 h at RT. Once the saponification was complete, the mixture was diluted with water (20 mL), and washed with ether (2×20 mL). After cooling to 0° C., the aqueous layer was adjusted to a pH=3.5 with a 5N solution of HCl, and the product was extracted with EtOAc (3×30 mL). In the organic phase, a precipitate was formed. It was filtrated and triturated with ACN to afford Intermediate 16 (797.10 mg; 77%) as an off-white solid. $^1$H-NMR (DMSO-d$_6$, 300 MHz) δ 13.43 (s, 1H), 8.64 (d, J=6.00 Hz, 2H), 7.81 (t, J=7.55 Hz, 1H), 7.70-7.63 (m, 1H), 7.48-7.42 (m, 3H). LC/MS: 284.90 (M+H)$^+$. HPLC (Method A) Rt 1.52 min (Purity: 100%).

Intermediate 17

Ethyl 1-(2-fluorophenyl)-5-pyridin-4-yl-1H-1,2,3-triazole-4-carboxylate

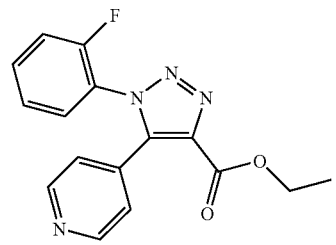

To a solution of 1-azido-2-fluorobenzene, prepared according to Platz, M. S. et al. J. Org. Chem. 1989, 54, 5938-5945 (25 g; 182.33 mmol; 1 eq.), and ethyl isonicotinoylacetate (38.04 g; 196.91 mmol; 1.08 eq.) in abs. EtOH (250 ml) under argon was added sodium ethylate (24.81 g; 364.65 mmol; 2 eq.). The reaction mixture was heated up to 70° C. for 21 h. MTBE (250 mL) was added and suspension was filtered. The resulting cake was washed with MTBE (2×100 mL) to give a pale orange solid, which was partitioned between ethyl acetate (250 mL) and 0.1 N NaOH solution (400 mL). The phases were separated and the aqueous phase was extracted with ethyl acetate (250 mL). Combined organic phases were washed with 1N NaOH solution, dried over MgSO$_4$, filtered and concentrated to give Intermediate 17 as off-white solid. $^1$H-NMR (DMSO-d$_6$, 300 MHz) δ 8.63-8.61 (m, 2H), 7.83-7.75 (m, 1H), 7.69-7.59 (m, 1H), 7.47-7.38 (m, 4H), 4.25 (q, J=7.1 Hz, 2H), 1.16 (t, J=7.1 Hz, 3H). LC/MS: 313.2 (M+H)$^+$. HPLC (Method A) Rt 1.98 min (Purity: 99.7%).

Intermediate 18

1-(2-fluorophenyl)-5-(2-methoxyethyl)-1H-1,2,3-triazole-4-carboxylic acid

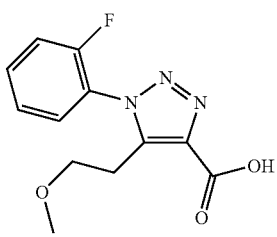

To a solution of 1-azido-2-fluorobenzene, prepared according to Platz, M. S. et al. *J. Org. Chem.* 1989, 54, 5938-5945 (500 mg; 3.65 mmol; 1 eq.) and methyl 5-methoxy-3-oxovalerate (642.46 mg; 4.01 mmol; 1.10 eq.) in absolute EtOH (10 ml) under $N_2$ was added portionwise sodium ethoxide (496.3 mg; 7.29 mmol; 2 eq.) and the mixture was stirred at 70° C. for 5 hours, then at RT overnight. A 5 N aqueous solution of NaOH (3.65 mL) was added and the mixture was stirred at RT for 1 hour. As the saponification was complete, the mixture was diluted with water, and washed with ether (2×15 mL). After cooling to 0° C., the aqueous layer was acidified with 5 N HCl aqueous solution, and the product was extracted with EtOAc (3×15 mL). The combined organic layer was washed with brine and dried over $MgSO_4$. After concentration, a dark oil was obtained. It was triturated in ACN, kept at 4° C. for 3 hours and filtrated to give Intermediate 18 as off-white solid. $^1$H-NMR (DMSO-$d_6$, 300 MHz) δ 13.38 (s, 1H), 7.82-7.72 (m, 2H), 7.67-7.61 (m, 1H), 7.55-7.50 (m, 1H), 3.45 (t, J=6 Hz, 2H), 3.11 (t, J=6 Hz, 2H), 3.04 (s, 3H). LC/MS: 266.2 $(M+H)^+$; 264.2 $(M-H)^-$. HPLC (Method A) Rt 2.51 min (Purity: 93.7%).

Intermediate 19

1-(2-fluorophenyl)-5-(morpholin-4-ylmethyl)-1H-1,2,3-triazole-4-carboxylic acid

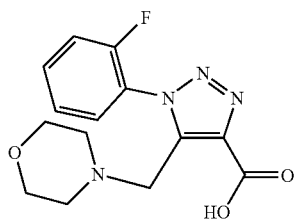

Step 1: Methyl 1-(2-fluorophenyl)-5-(morpholin-4-ylmethyl)-1H-1,2,3-triazole-4-carboxylate A solution of 1-azido-2-fluorobenzene, prepared according to Platz, M. S. et al. *J. Org. Chem.* 1989, 54, 5938-5945 (500 mg; 3.65 mmol; 1 eq.) and methyl 4-chloroacetoacetate (823 mg; 5.47 mmol; 1.5 eq.) in morpholine (10 ml) was stirred at 50° C. overnight. The reaction mixture was evaporated. Water was added (20 mL) and was extracted with EtOAc (2×20 mL). Combined organic phases were extracted with 3 portions of HCl 1 N. Combined aqueous phases were made alkaline with NaOH 5N and were extracted with EtOAc (3×20 mL). Organic layers were dried over magnesium sulfate and evaporated, affording the title product as a dark red oil. It was used in the next step without further purification. HPLC (Method A) Rt 1.81 min. (Purity: 82.5%).

Step 2: 1-(2-fluorophenyl)-5-(morpholin-4-ylmethyl)-1H-1,2,3-triazole-4-carboxylic acid Methyl 1-(2-fluorophenyl)-5-(morpholin-4-ylmethyl)-1H-1,2,3-triazole-4-carboxylate, obtained in Step 1 as described above (677 mg; 2.11 mmol; 1 eq.), was dissolved in MeOH (6 ml) and THF (6 ml). Sodium hydroxide (2.11 ml; 5 M; 10.57 mmol; 5 eq.) was added and the mixture was stirred at RT overnight. Sodium hydroxide (2.11 ml; 5 M; 10.57 mmol; 5 eq.) was added and the mixture was stirred further at RT. After 48 hours, the reaction was complete. HCl solution (4.22 ml; 5 M; 21.14 mmol; 10 eq.) was added and the solvents were evaporated. The resulting solid was purified by precipitation in ACN, affording Intermediate 19 as off-white solid. $^1$H-NMR (DMSO-$d_6$, 300 MHz) δ 7.85-7.72 (m, 2H), 7.65-7.57 (m, 1H), 7.52-7.46 (m, 1H), 4.22 (br s, 2H), 3.48 (br s, 4H), 2.60 (br s, 4H). LC/MS: 263.2 $(M+H)^+$; 261.2 $(M-H)^-$. HPLC (Method A) Rt 1.14 min (Purity: 100%).

Intermediate 20

N'-hydroxy-1H-indole-5-carboximidamide

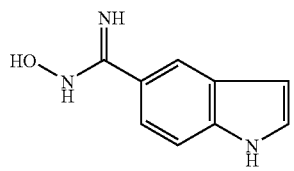

The title compound was prepared following procedure described for Intermediate 3, Step 2, but starting from 5-cyanoindole (2 g; 14.07 mmol; 1 eq.), and was isolated as a brown solid (2.4 g; 97%). $^1$H-NMR (DMSO-$d_6$, 300 MHz) δ 11.15 (s, 1H), 9.36 (s, 1H), 7.85 (m, 1H), 7.45 (dd, J=1.59 Hz, J=8.45 Hz, 1H), 7.36-7.33 (m, 2H), 6.44 (m, 1H), 5.69 (s, 2H). LC/MS: 176.1 $(M+H)^+$; 174.1 $(M-H)^-$ (Purity: 98.9%).

Intermediate 21

5-cyclopentyl-1-(2-fluorophenyl)-1H-1,2,3-triazole-4-carboxylic acid

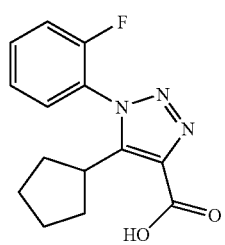

Step 1: Ethyl 5-cyclopentyl-1-(2-fluorophenyl)-1H-1,2,3-triazole-4-carboxylate

DBU (2.99 ml; 20.06 mmol; 1.10 eq.) was dissolved in DMF (25 ml) and put under nitrogen atmosphere. 3-Cyclopentyl-3-oxo-propionic acid ethyl ester (Pharmacore, 3.695 g; 20.06 mmol; 1.10 eq.) was added to the mixture and it was stirred for 15 min. Then a solution of 1-azido-2-fluorobenzene, prepared according to Platz, M. S. et al. J. Org. Chem. 1989, 54, 5938-5945, (2.5 g; 18.23 mmol; 1 eq.) in DMF (5 mL) was added dropwise to the solution at room temperature. The mixture was stirred at 90° C. for 2 hours. Water (50 mL) was added to the cooled reaction mixture and the aqueous layer was extracted with EtOAc (3×50 mL). Combined organics were washed with water and brine, dried over $MgSO_4$ and concentrated under vacuum affording the title compound as a yellow oil. It was used in the next step without further purification. LC/MS (Method B): 304.2 (M+H)+.

Step 2: 5-cyclopentyl-1-(2-fluorophenyl)-1H-1,2,3-triazole-4-carboxylic acid Ethyl 5-cyclopentyl-1-(2-fluorophenyl)-1H-1,2,3-triazole-4-carboxylate, obtained in Step 1 as described above, was dissolved in EtOH and NaOH (18 ml; 5 M; 91.16 mmol; 5 eq.) was added, the mixture was stirred overnight at room temperature. Water (50 mL) was added and the aqueous phase was washed with $Et_2O$ (2×50 mL). The aqueous layer was acidified to pH 2 with HCl 5 N and extracted with EtOAc (2×50 mL). The combined organics were washed with brine, dried over $MgSO_4$ and concentrated under vacuum giving the title compound as a brown solid. It was suspended in petroleum ether and the suspension was sonicated for a few minutes, then filtered off, washed with petroleum ether, dried under vacuum affording Intermediate 21 as a beige solid. $^1$H-NMR (DMSO-$d_6$, 300 MHz) δ 13.23 (br s, 1H), 7.82-7.74 (m, 2H), 7.67-7.49 (m, 2H), 3.20-3.08 (m, 1H), 2.01-1.42 (m, 8H). LC/MS (Method B): 276.1 (M+H)+. HPLC (Method A) Rt 3.92 min (Purity: 98.2%).

Intermediate 22

5-cyclopropyl-1-(2-fluorophenyl)-1H-1,2,3-triazole-4-carboxylic acid

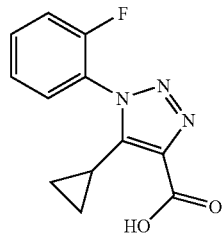

Step 1: Ethyl 5-cyclopropyl-1-(2-fluorophenyl)-1H-1,2,3-triazole-4-carboxylate

DBU (2.99 ml; 20.06 mmol; 1.10 eq.) was dissolved in DMF (37.5 ml) and put under nitrogen atmosphere. 3-Cyclopropyl-3-oxo-propionic acid ethyl ester (Betapharma, 3.132 g; 20.06 mmol; 1.10 eq.) was added to the mixture and it was stirred for 15 min. Then a solution of 1-azido-2-fluorobenzene prepared according to Platz, M. S. et al. *J. Org. Chem.* 1989, 54, 5938-5945, (2.5 g; 18.23 mmol; 1 eq.) in DMF (5 mL) was added dropwise to the solution at room temperature. Water (50 mL) was added to the cooled reaction mixture and the aqueous layer was extracted with EtOAc (3×50 mL). Combined organics were washed with water and brine, dried over $MgSO_4$ and concentrated under vacuum affording the title compound as a brown oil. It was used in the next step without further purification. LC/MS (Method B): 276.1 (M+H)+.

Step 2: 5-cyclopropyl-1-(2-fluorophenyl)-1H-1,2,3-triazole-4-carboxylic acid

Ethyl 5-cyclopropyl-1-(2-fluorophenyl)-1H-1,2,3-triazole-4-carboxylate, obtained in Step 1 as described above was dissolved in EtOH and NaOH (18 ml; 5 M; 91.16 mmol; 5 eq.) was added, the mixture was stirred overnight at room temperature. Water (50 mL) was added and the aqueous phase was washed with $Et_2O$ (2×50 mL). The aqueous layer was acidified to pH 2 with HCl 5 N and extracted with EtOAc (2×50 mL). The combined organics were washed with brine, dried over $MgSO_4$ and concentrated under vacuum affording Intermediate 22 as a beige solid. $^1$H-NMR (DMSO-$d_6$, 300 MHz) δ 13.19 (br s, 1H), 7.81-7.72 (m, 2H), 7.66-7.59 (m, 1H), 7.54-7.49 (m, 1H), 2.04-1.94 (m, 1H), 0.91-0.71 (m, 4H). LC/MS (Method B): 248.1 (M+H)+. HPLC (Method A) Rt 2.78 min (Purity: 93.6%).

Intermediate 23

1-(2-fluorophenyl)-5-(tetrahydrofuran-2-yl)-1H-1,2,3-triazole-4-carboxylic acid

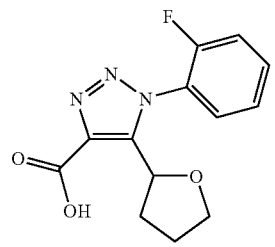

Step 1: Ethyl 1-(2-fluorophenyl)-5-(tetra hydrofuran-2-yl)-1H-1,2,3-triazole-4-carboxylate Potassium carbonate (2.419 g; 17.50 mmol; 2 eq.) was dissolved in DMSO (18 ml) and put under nitrogen atmosphere. 1-Azido-2-fluorobenzene, prepared according to Platz, M. S. et al. *J. Org. Chem.* 1989, 54, 5938-5945, (1.2 g; 8.75 mmol; 1 eq.) was dissolved in 10 mL of DMSO and ethyl 3-(tetrahydrofuran-2-yl)-3-oxopropanoate (Pharmacore, 1.793 mg; 9.63 mmol; 1.10 eq.) was added. This solution was added dropwise to the potassium carbonate solution at room temperature. The mixture was stirred at 70° C. for 3 hours. Water (30 mL) was added to the mixture and it was extracted with EtOAc (2×40 mL). Organics were washed with brine, dried over $MgSO_4$ and concentrated under vacuum affording the title compound as a brown oil. It was used in the next step without further purification. HPLC (Method A) Rt 4.14 min (Purity: 86.6%).

Step 2: 1-(2-fluorophenyl)-5-(tetrahydrofuran-2-yl)-1H-1,2,3-triazole-4-carboxylic acid Ethyl 1-(2-fluorophenyl)-5-(tetrahydrofuran-2-yl)-1H-1,2,3-triazole-4-carboxylate obtained in Step 1 as described above was dissolved in EtOH (150 mL) and NaOH (8.75 ml; 5 M; 43.76 mmol; 5 eq.) was added. The reaction mixture was stirred at room temperature for 1 hour. The mixture was diluted with water (30 mL), and washed with diethyl ether (2×40 mL). The aqueous layer was acidified to pH 2 with HCl 5 N, and the product was extracted with EtOAc (3×50 mL). Combined organic phases were washed with brine, dried over $MgSO_4$ and concentrated under vacuum affording Intermediate 23 as a brown oil. $^1$H-NMR (DMSO-d6, 300 MHz) δ 13.21 (br s, 1H), 7.76-7.68 (m, 2H), 7.52-7.42 (m, 2H), 5.56-5.51 (t, J=7.10 Hz, 1H), 3.58-3.48 (m, 1H), 3.02-2.91 (m, 1H), 2.45-2.26 (m, 1H), 1.91-1.62 (m, 3H). HPLC (Method A) Rt 3.10 min (Purity: 93.1%).

Intermediate 24

5-benzyl-1-(2-fluorophenyl)-1H-1,2,3-triazole-4-carboxylic acid

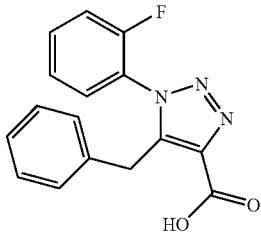

Step 1: Methyl 5-benzyl-1-(2-fluorophenyl)-1H-1,2,3-triazole-4-carboxylate

DBU (1.33 ml; 8.90 mmol; 1.10 eq.) was dissolved in DMF (17 ml) and put under nitrogen atmosphere. 3-Oxo-4-phenyl-butyric acid methyl ester (Chemcollect, 1.711 g; 8.90 mmol; 1.10 eq.) was added to the mixture and it was stirred for 15 min. Then a solution of 1-azido-2-fluorobenzene, prepared according to Platz, M. S. et al. *J. Org. Chem.* 1989, 54, 5938-5945, (1.11 g; 8.10 mmol; 1 eq.) in DMF (2 mL) was added dropwise to the solution at room temperature. The mixture was stirred at 90° C. for 2 hours. Water (30 mL) was added to the cooled reaction mixture and the aqueous layer was extracted with EtOAc (3×40 mL). Combined organics were washed with water and brine, dried over MgSO$_4$ and concentrated under vacuum giving the title compound as a yellow oil. It was used in the next step without further purification. LC/MS (Method B): 312.1 (M+H)$^+$.

Step 2: 5-benzyl-1-(2-fluorophenyl)-1H-1,2,3-triazole-4-carboxylic acid

Methyl 5-benzyl-1-(2-fluorophenyl)-1H-1,2,3-triazole-4-carboxylate obtained in Step 1 as described above was dissolved in EtOH and NaOH (8.10 ml; 5 M; 40.48 mmol; 5 eq.) was added, the mixture was stirred overnight at room temperature. Water (30 mL) was added and the aqueous phase was washed with Et$_2$O (2×30 mL). The aqueous layer was acidified to pH 2 with HCl 5 N and extracted with EtOAc (2×50 mL). The combined organics were washed with brine, dried over MgSO$_4$ and concentrated under vacuum affording the title compound as a yellow oil. It was taken up in petroleum ether and it was sonicated. The suspension was filtered off, affording Intermediate 24 as a beige solid. $^1$H-NMR (DMSO-d$_6$, 300 MHz) δ 13.43 (br s, 1H), 7.74-7.69 (m, 1H), 7.64-7.58 (m, 1H), 7.53-7.42 (m, 2H), 7.22-7.17 (m, 3H), 6.83-6.72 (m, 2H), 4.38 (s, 2H). LC/MS (Method B): 298.2 (M+H)$^+$. HPLC (Method A) Rt 3.60 min (Purity: 92.7%).

Intermediate 25

1-(2-fluorophenyl)-5-(tetrahydro-2H-pyran-4-yl)-1H-1,2,3-triazole-4-carboxylic acid

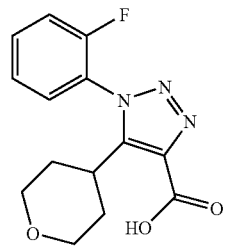

Step 1: Ethyl 1-(2-fluorophenyl)-5-(tetrahydro-2H-pyran-4-yl)-1H-1,2,3-triazole-4-carboxylate DBU (1.32 ml; 8.82 mmol; 1.10 eq.) was dissolved in DMF (16.5 ml) and put under nitrogen atmosphere. 3-Oxo-3-(tetrahydro-pyran-4-yl)-propionic acid ethyl ester (Pharmacore, 1.767 g; 8.82 mmol; 1.10 eq.) was added to the mixture and it was stirred for 15 min. Then a solution of 1-azido-2-fluorobenzene, prepared according to Platz, M. S. et al. *J. Org. Chem.* 1989, 54, 5938-5945, (1.1 g; 8.02 mmol; 1 eq.) in DMF (15 mL) was added dropwise to the solution at room temperature. The reaction mixture was stirred at 70° C. for 2 hours. Water (40 mL) was added to the reaction mixture. The aqueous layer was extracted with EtOAc (3×40 mL). Combined organic layers were washed with HCl 0.1N, brine, dried over MgSO$_4$ and concentrated under vacuum giving the title compound as a yellow oil. It was used in the next step without further purification. LC/MS (Method B): 320.2 (M+H)$^+$.

Step 2: 1-(2-fluorophenyl)-5-(tetrahydro-2H-pyran-4-yl)-1H-1,2,3-triazole-4-carboxylic acid Ethyl 1-(2-fluorophenyl)-5-(tetrahydro-2H-pyran-4-yl)-1H-1,2,3-triazole-4-carboxylate, obtained in Step 1 as described above was dissolved in EtOH and NaOH (8 ml; 5 M; 40.11 mmol; 5 eq.) was added to the solution. It was stirred at room temperature for 2 hours. Water (30 mL) was added to the mixture and it was washed with Et$_2$O (2×30 mL). The aqueous layer was acidified to pH 2 with HCl 5 N and extracted with EtOAc (3×40 mL). The combined organics were washed with brine, dried over MgSO$_4$ and concentrated under vacuum giving the title compound as a brown oil. It was taken up in petroleum ether and sonicated affording Intermediate 25 a beige solid. $^1$H-NMR (DMSO-d$_6$, 300 MHz) δ 13.38 (br s, 1H), 7.81-7.76 (m, 2H), 7.68-7.62 (m, 1H), 7.56-7.51 (m, 1H), 3.87-3.82 (m, 2H), 3.28-3.20 (m, 3H), 2.11-2.01 (m, 2H), 1.55-1.52 (m, 2H). LC/MS (Method B): 292.1 (M+H)$^+$. HPLC (Method A) Rt 2.66 min (Purity: 99.1%).

Intermediate 26

1-(2-fluorophenyl)-5-isopropyl-1H-1,2,3-triazole-4-carboxylic acid

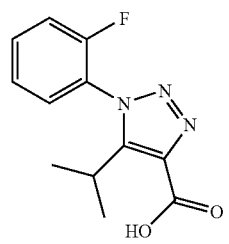

Step 1: Ethyl 1-(2-fluorophenyl)-5-isopropyl-1H-1,2,3-triazole-4-carboxylate

DBU (3.6 ml; 24.07 mmol; 1.10 eq.) was dissolved in DMF (45 ml) and put under nitrogen atmosphere. Ethyl isobutyrylacetate (Aldrich, 3.807 g; 24.07 mmol; 1.10 eq.) was added to the mixture and it was stirred for 15 min. Then a solution of 1-azido-2-fluorobenzene, prepared according to Platz, M. S. et al. *J. Org. Chem.* 1989, 54, 5938-5945, (3 g; 21.858 mmol; 1 eq.) in DMF (10 mL) was added dropwise to the solution at room temperature. The reaction mixture was stirred at 70° C. for 5 hours. Water (80 mL) was added to the reaction mixture. The aqueous layer was extracted with EtOAc (2×100 mL). Combined organics were washed with HCl 0.1N, brine, dried over MgSO$_4$ and concentrated under vacuum giving the title compound as a brown oil. It was used in the next step without further purification. LC/MS (Method B): 278.2 (M+H)$^+$.

Step 2: 1-(2-fluorophenyl)-5-isopropyl-1H-1,2,3-triazole-4-carboxylic acid

Ethyl 1-(2-fluorophenyl)-5-isopropyl-1H-1,2,3-triazole-4-carboxylate, obtained in Step 1 as described above was dissolved in EtOH and NaOH (22 ml; 5 M; 109.40 mmol; 5 eq.) was added to the solution. It was stirred at room temperature overnight. Water (100 mL) was added to the mixture and it was washed with Et$_2$O (2×100 mL). The aqueous layer was acidified to pH 2 with HCl 5 N and extracted with EtOAc (3×100 mL). The combined organics were washed with brine, dried over MgSO$_4$ and concentrated under vacuum giving the title compound as a brown oil. It was taken up in petroleum ether and sonicated affording Intermediate 26 a beige solid. $^1$H-NMR (DMSO-d$_6$, 300 MHz) δ 13.25 (br s, 1H), 7.80-7.75 (m, 2H), 7.68-7.61 (m, 1H), 7.56-7.49 (m, 1H), 3.29-3.19 (m, 1H), 1.25-1.23 (d, J=7.05 Hz, 6H). LC/MS (Method B): 250.1 (M+H)$^+$. HPLC (Method A) Rt 3.48 min (Purity: 97.0%).

Intermediate 27

4-[amino(hydroxyimino)methyl]benzaide

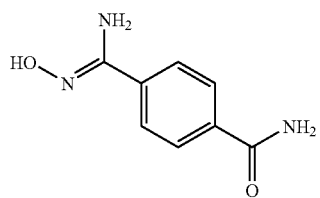

To a solution of 4-cyanobenzamide (512 mg; 3.93 mmol) in abs. EtOH (3 mL) was added hydroxylamine (0.8 mL; 12 mmol) (50% in water) and the mixture was heated to 78° C. for 18 hours. The mixture was poured into a crystallizing dish and the solvent was allowed to evaporate. The residue was washed with copious amounts of EtOAc, dry MeOH and dry MeCN which was filtered through a hydrophobic frit and the solvent removed in vacuo. Intermediate 27 was isolated as a yellow solid (513 mg; 79%). $^1$H NMR: (DMSO-d$_6$, 400 MHz) δ 9.81 (1H, s), 8.01 (1H, s), 7.89 (2H, d, J=8.2 Hz), 7.77 (2H, d, J=8.2 Hz), 7.40 (1H, s), 5.91 (2H, s).

Intermediate 28 tert-butyl {4-[amino(hydroxyimino)methyl]benzyl}carbamate

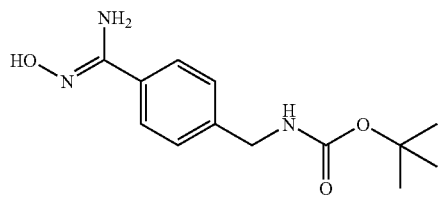

Step 1: tert-butyl 4-cyanobenzylcarbamate

To a solution of 4-cyanobenzylamine hydrochloride (1.05 g; 6.25 mmol) in water (10 mL) was added sodium hydroxide (0.75 g; 18.75 mmol) and di-tert-butyldicarbonate (1.49 g; 6.87 mmol) and the mixture was stirred for 16 hours. The solid was collected by filtration and dried in a vacuum oven at 40° C. for 48 hours. The title compound was isolated as a white solid (1.35 g; 80%). $^1$H NMR: (CDCl$_3$, 400 MHz) δ 7.62 (2H, d, J=8.1 Hz), 7.39 (2H, d, J=8.0 Hz), 4.97 (1H, s), 4.37 (2H, d, J=6.2 Hz), 1.46 (9H, s).

Step 2: tert-butyl {4-[amino(hydroxyimino)methyl]benzyl}carbamate

The title compound was prepared following the procedure described for Intermediate 27, but starting from tert-butyl 4-cyanobenzylcarbamate (1.87 g; 8.06 mmol), to give Intermediate 28 as a white solid. $^1$H NMR: (DMSO-d$_6$, 400 MHz) δ 9.59 (1H, s), 7.64 (2H, d, J=8.0 Hz), 7.42 (1H, t, J=6.2 Hz), 7.25 (2H, d, J=8.0 Hz), 5.79 (2H, s), 4.16 (2H, d, J=6.2 Hz), 1.43 (9H, s).

Intermediate 29

4-(aminosulfonyl)-N'-hydroxybenzenecarboximidamide

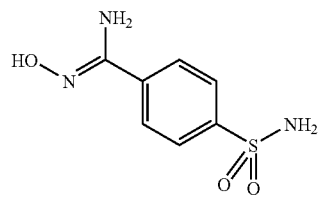

The title compound was prepared following the procedure described for Intermediate 27, but starting from 4-cyanobenzenesulfonamide (717 mg; 3.94 mmol), to give Intermediate 29 as a yellow solid. ¹H NMR: (DMSO-d₆, 400 MHz) δ 9.90 (1H, s), 7.89-7.81 (4H, m), 7.41 (2H, s), 5.97 (2H, s).

Intermediate 30

N'-hydroxy-1H-indazole-5-carboximidamide

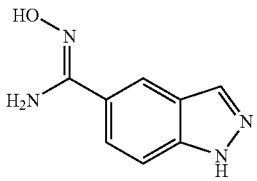

Step 1: 1H-indazole-5-carbonitrile 1H-5-bromoindazole (400 mg; 2.02 mmol), Pd₂(dba)₃ (79 mg; 009 mmol), S-Phos (89 mg; 0.2 mmol), Zn(CN)₂ (300 mg; 2.5 mmol) were dissolved in DMF/H₂O (10 mL, 99:1 v/v) in a microwave vial. The solution was degassed with N₂ for 10 min before being capped and heated in the microwave reactor for 30 min at 150° C. Once complete, the reaction was diluted with 1 N NaOH (40 mL) and EtOAc (100 mL). The EtOAc layer was removed, dried over MgSO₄, filtered, and the solvent removed in vacuo. The residue was purified by flash chromatography (silica, 20 g; 5-40% EtOAc/hexanes) to give the title compound as a white solid (251 mg; 86%). ¹H NMR: (CDCl₃, 400 MHz) δ 10.46 (1H, br s), 8.20 (2H, d, J=8.34 Hz), 7.61 (2H, s).

Step 2: N'-hydroxy-1H-indazole-5-carboximidamide

The title compound was prepared following the procedure described for Intermediate 27, but starting from 1H-indazole-5-carbonitrile (302 mg; 2.09 mmol), obtained in Step 1, to give Intermediate 30 as a pale brown solid. ¹H NMR: (DMSO-d₆, 400 MHz) δ 13.15 (1H, s), 9.57 (1H, s), 8.13 (1H, s), 8.08 (1H, s), 7.75 (1H, d, J=8.8 Hz), 7.53 (1H, d, J=8.8 Hz), 5.84 (2H, s). LC/MS (Method C): 177 (M+H)⁺. HPLC (Method H) Rt=3.24 min (Purity 90.6%).

Intermediate 31

N'-hydroxyfuran-2-carboximidamide

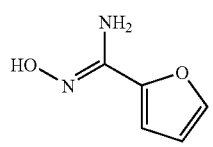

To a solution of 2-furonitrile (Avocado; 366 mg; 3.94 mmol), in abs. EtOH (7 mL) was added hydroxylamine (5 ml; 20 mmol) (50% in water) and the mixture was heated to 78° C. for 18 hours. Brine (30 mL) was added and the EtOH removed in vacuo. The solid formed was removed by filtration, washed with water and dried to give Intermediate 31 as a colourless oil (413 mg; 83%). ¹H NMR: (CDCl₃, 400 MHz) δ 8.24 (1H, s), 7.45 (1H, d, J=1.7 Hz), 6.75 (1H, d, J=3.5 Hz), 6.45 (1H, dd, J=3.5, 1.8 Hz), 4.97 (2H, s).

Intermediate 32

N'-hydroxy-4-(hydroxymethyl)benzenecarboximidamide

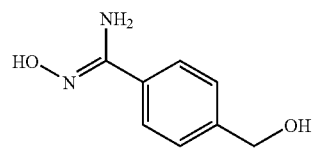

The title compound was prepared following the procedure described for Intermediate 27, but starting from 4-(hydroxymethyl)benzonitrile (1.03 g; 7.74 mmol), to give Intermediate 32 as a white solid (1.15 g; 89%). ¹H NMR: (DMSO-d₆, 400 MHz) δ 9.58 (1H, s), 7.70-7.62 (2H, m), 7.34 (2H, d, J=8.1 Hz), 5.79 (2H, s), 5.23 (1H, t, J=5.6 Hz), 4.54 (2H, d, J=5.6 Hz).

Intermediate 33

N'-hydroxy-3-(hydroxymethyl)benzenecarboximidamide

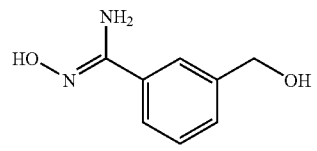

The title compound was prepared following the procedure described for Intermediate 27, but starting from 3-(hydroxymethyl)benzonitrile (8.43 g; 63.38 mmol), to give Intermediate 33 as a white solid (9.15 g; 86%). ¹H NMR: (DMSO-d₆, 400 MHz) δ 9.63 (1H, s), 7.67 (1H, s), 7.58-7.54 (1H, m), 7.35 (2H, d, J=4.7 Hz), 5.82 (2H, s), 5.27 (1H, t, J=5.7 Hz), 4.54 (2H, d, J=5.7 Hz).

Intermediate 34

N',3-dihydroxybenzenecarboximidamide

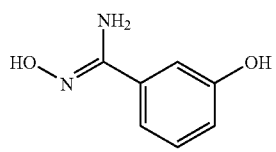

The title compound was prepared following the procedure described for Intermediate 27, but starting from 3-hydroxybenzonitrile (1.51 g; 12.68 mmol), to give Intermediate 34 as a white solid. $^1$H NMR: (DMSO-d$_6$, 400 MHz) δ 9.60 (1H, s), 9.49 (1H, s), 7.20-7.16 (1H, m), 7.19-7.10 (2H, m), 6.80-6.78 (1H, m), 5.74 (2H, s).

Intermediate 35

2-bromo-5-fluoro-N'-hydroxybenzenecarboximidamide

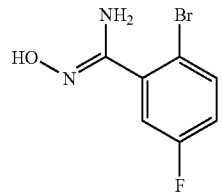

The title compound was prepared following the procedure described for Intermediate 31, but starting from 2-bromo-5-fluorobenzonitrile (1.03 g; 5.15 mmol), to give Intermediate 35 as a white solid (1.05 g; 88%). $^1$H NMR: (DMSO-d$_6$, 400 MHz) δ 9.57 (1H, s), 7.71 (1H, dd, J=8.4, 5.3 Hz), 7.34-7.22 (2H, m), 5.89 (2H, s).

Intermediate 36

1-acetyl-N'-hydroxyindoline-5-carboximidamide

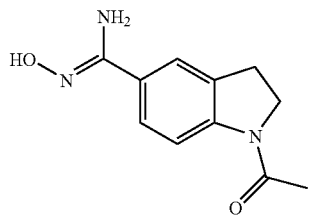

Step 1: 1-acetoylindoline-5-carbonitrile

A solution of 1-(5-aminoindolin-1-yl)ethanone (Aldrich, 865 mg; 4.91 mmol) in HCl (2.1 M, 2.95 mL) was treated with sodium nitrite (358 mg; 5.18 mmol) and the mixture was stirred at 0° C. for 3 hours. The solution was neutralized with sodium carbonate (3.12 g; 29.43 mmol) and the resulting mixture was added to a suspension of sodium cyanide (519 mg; 10.6 mmol) and copper cyanide (467 mg; 5.21 mmol) in water (4 mL) at 0° C. The resulting suspension was heated to 50° C., stirred for 30 minutes, cooled to 0° C. and the precipitated solid was collected by filtration. The collected solid was recrystallised from aqueous acetonitrile to give the title compound as a brown solid. $^1$H NMR: (DMSO-d$_6$, 400 MHz) δ 8.16 (1H, d, J=8.3 Hz), 7.72-7.62 (2H, m), 4.23-4.11 (2H, m), 2.54 (3H, t, J=2.1 Hz), 2.23 (3H, s).

Step 2: 1-acetyl-N'-hydroxyindoline-5-carboximidamide

The title compound was prepared following the procedure described for Intermediate 27, but starting from 1-acetoylindoline-5-carbonitrile, obtained in Step 1, (339 mg; 1.82 mmol) to give Intermediate 36 as a brown solid. $^1$H NMR: (DMSO-d$_6$, 400 MHz) δ 9.50 (1H, s), 8.02 (1H, d, J=8.5 Hz), 7.56 (1H, s), 7.50 (1H, d, J=8.5 Hz), 5.73 (2H, s), 4.15 (2H, q, J=9.6 Hz), 3.19 (2H, q, J=8.6 Hz), 2.20 (3H, s). LC/MS (Method C): 220 (M+H)$^+$. HPLC (Method I) Rt 10.34 min (Purity: 89.4%).

Intermediate 37

N'-hydroxy-1,2,3,4-tetrahydroisoquinoline-7-carboximidamide

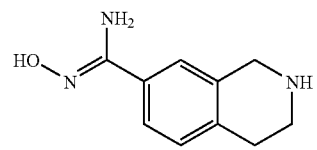

The title compound was prepared following the procedure described for Intermediate 27 but starting from 1,2,3,4-tetrahydroisoquinoline-7-carbonitrile (1.01 g; 6.39 mmol), to give Intermediate 37 as a brown solid (1.18 g; 96%). $^1$H NMR: (DMSO-d$_6$, 400 MHz) δ 9.50 (1H, s), 7.42 (1H, d, J=8.0 Hz), 7.34 (1H, s), 7.07 (1H, d, J=8.0 Hz), 5.72 (2H, s), 3.86 (2H, s), 2.96 (2H, t, J=5.8 Hz), 2.70 (2H, t, J=5.8 Hz). LC/MS (Method C): 192 (M+H)$^+$. HPLC (Method H) Rt 9.30 min (Purity: 88.3%).

Intermediate 38

2-ethyl-N'-hydroxy-1,2,3,4-tetrahydroisoquinoline-7-carboximidamide

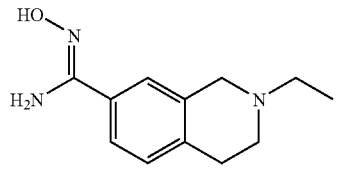

Step 1: 2-ethyl-1,2,3,4-tetrahydroisoquinoline-7-carbonitrile

To a solution of 1,2,3,4-tetrahydroisoquinoline-7-carbonitrile (ABCR; 500 mg; 3.16 mmol) in MeOH (5 mL) at 0° C. was added acetaldehyde (0.51 mL, 8.91 mmol) and acetic acid (5 µL) and the resulting mixture was stirred for 1 hour. Sodium cyanoborohydride (218 mg; 3.47 mmol) was added and the mixture was stirred for 5 hours and diluted with DCM (100 mL) and water (20 mL). The aqueous layer was extracted with DCM (3×20 mL), the combined organics were dried (MgSO$_4$) and the solvent was removed in vacuo. The residue was purified by flash chromatography on a Biotage 25+M column, eluting with petrol containing increasing amounts of EtOAc to give the title compound as a brown oil. $^1$H NMR: (CDCl$_3$, 400 MHz) δ 7.39 (1H, d, J=8.0 Hz), 7.33 (1H, s), 7.19 (1H, d, J=8.0 Hz), 3.62 (2H, s), 2.99-2.90 (2H, m), 2.77-2.70 (2H, m), 2.66-2.54 (2H, m), 1.19 (3H, t, J=7.2 Hz).

Step 2: 2-ethyl-N'-hydroxy-1,2,3,4-tetrahydroisoquinoline-7-carboximidamide

The title compound was prepared following the procedure described for Intermediate 27 but starting from 2-ethyl-1,2,3,4-tetrahydroisoquinoline-7-carbonitrile (351 mg; 1.87 mmol), obtained in Step 1, to give Intermediate 38 as a brown oil (309 mg; 75%). ¹H NMR: (DMSO-d₆, 400 MHz) δ 9.52 (1H, s), 7.49-7.39 (1H, m), 7.39 (1H, s), 7.13-7.06 (1H, m), 5.73 (2H, s), 3.56 (2H, s), 2.86-2.75 (2H, m), 2.73-2.60 (2H, m), 2.56-2.49 (2H, m), 1.16-1.07 (3H, m).

Intermediate 39

1-acetyl-N'-hydroxyindoline-6-carboximidamide

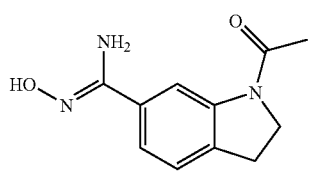

Step 1: 1-acetoylindoline-6-carbonitrile

The title compound was prepared following the procedure described for 1-acetoylindoline-5-carbonitrile but starting from 1-(5-aminoindolin-1-yl)ethanone (Aldrich, 844 mg; 4.79 mmol), to give 1-acetoylindoline-6-carbonitrile as an orange solid. ¹H NMR: (DMSO-d₆, 400 MHz) δ 8.31 (1H, s), 7.52-7.45 (2H, m), 4.18 (2H, t, J=8.6 Hz), 3.32-3.23 (2H, m), 2.23 (3H, s).

Step 2: 1-acetyl-N'-hydroxyindoline-6-carboximidamide

The title compound was prepared following the procedure described for Intermediate 36 Step 2, but starting from 1-acetoylindoline-6-carbonitrile, obtained in Step 1, (285 mg; 1.53 mmol), to give Intermediate 39 as an brown solid. ¹H NMR: (DMSO-d₆, 400 MHz) δ 9.58 (1H, s), 8.43 (1H, s), 7.32-7.21 (2H, m), 5.70 (2H, s), 4.14 (2H, q, J=8.4 Hz), 3.17 (2H, t, J=8.8 Hz), 2.20 (3H, d, J=5.4 Hz). LC/MS (Method C): 220 (M+H)⁺. HPLC (Method I) Rt 10.67 min (Purity: 63.2%).

Intermediate 40

N'-hydroxy-3-(methylsulfonyl)benzenecarboximidamide

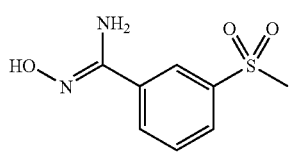

To a solution of 3-(methylsulfonyl)benzonitrile (Apollo; 2.7 g; 15 mmol) in abs. EtOH (20 mL) was added hydroxylamine (5 mL; 75 mmol) (50% in water) and the mixture was heated to 78° C. for 18 hours. Brine (100 mL) was added and the solid formed was removed by filtration, washed with water and dried to give Intermediate 40 as a white solid (2.67 g; 83%). ¹H NMR: (DMSO-d₆, 400 MHz) δ 9.91 (1H, s), 8.25 (1H, t, J=1.8 Hz), 8.04 (1H, dt, J=7.9, 1.4 Hz), 7.96-7.93 (1H, m), 7.70 (1H, t, J=7.9 Hz), 6.06 (2H, s), 3.27 (3H, s). LC/MS (Method C): 215 (M+H)⁺. HPLC (Method F) Rt 1.80 min (Purity: 99.2%).

Intermediate 41

N'-hydroxy-3-(1H-1,2,4-triazol-1-ylmethyl)benzenecarboximidamide

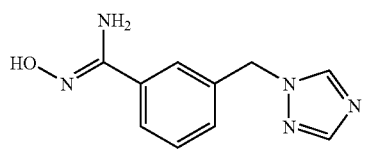

The title compound was prepared following the procedure described for Intermediate 31, but starting from 3-((1H-1,2,4-triazol-1-yl)methyl)benzonitrile (Maybridge; 488 mg; 2.65 mmol), to give Intermediate 41 as a white solid (470 mg; 82%). ¹H NMR: (DMSO-d₆, 400 MHz) δ 9.68 (1H, s), 8.70 (1H, s), 8.02 (1H, s), 7.67-7.58 (2H, m), 7.40 (1H, t, J=7.6 Hz), 7.31 (1H, d, J=7.6 Hz), 5.83 (2H, br s), 5.47 (2H, s). LC/MS (Method C): 218 (M+H)⁺. HPLC (Method F) Rt 1.77 min (Purity: 97.4%).

Intermediate 42

N'-hydroxyfuran-3-carboximidamide

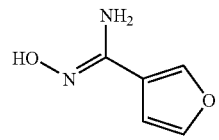

To a solution of furan-3-carbonitrile (Lancaster; 390 mg; 4.2 mmol) in abs. EtOH (5.6 mL) was added hydroxylamine (1.4 mL; 21 mmol) (50% in water) and the mixture was heated to 78° C. for 18 hours. Brine (25 mL) was added and the mixture was poured into a crystallizing dish and the solvent was allowed to evaporate. The residue was washed with copious amounts of EtOAc which was filtered through a hydrophobic frit and the solvent removed in vacuo. Intermediate 42 was isolated as a white solid (380 mg; 72%). ¹H NMR: (DMSO-d₆, 400 MHz)δ 9.41 (1H, s), 8.03 (1H, s), 7.66 (1H, t, J=1.8 Hz), 6.65 (1H, d, J=1.8 Hz), 5.70 (2H, br s).

Intermediate 43

N'-hydroxy-1H-indole-4-carboximidamide

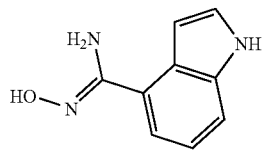

To a solution of 1H-indole-4-carbonitrile (1.2 g; 8.4 mmol) in abs. EtOH (11.2 mL) was added hydroxylamine (2.8 mL;

42 mmol) (50% in water) and the mixture was heated to 78° C. for 18 hours. The mixture was poured into a crystallizing dish and the solvent was allowed to evaporate. The residue was washed with copious amounts of EtOAc which was filtered through a hydrophobic frit and the solvent removed in vacuo. Intermediate 43 was isolated as a white solid (1.41 g; 96%). $^1$H NMR: (DMSO-$d_6$, 400 MHz) δ 11.17 (1H, s), 9.57 (1H, s), 7.44 (1H, d, J=8.0 Hz), 7.38-7.35 (1H, m), 7.28 (1H, d, J=7.3 Hz), 7.14-7.09 (1H, m), 6.86 (1H, t, J=2.4 Hz), 5.69 (2H, br s). LC/MS (Method C): 176 (M+H)$^+$. HPLC (Method F) Rt 1.82 min (Purity: 99.6%).

Intermediate 44

3-(aminosulfonyl)-N'-hydroxybenzenecarboximidamide

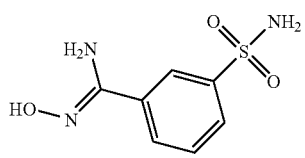

Step 1: 3-cyanobenzenesulfonamide

To a solution of ammonia in dioxane (0.5 M in dioxane; 50 mL; 25 mmol) was added a solution of 3-cyanobenzene-1-sulfonyl chloride (ABCR; 605 mg; 3 mmol) in dioxane (10 mL) and the mixture was allowed to stir at RT for 30 min. The solvent was removed in vacuo to give the title compound as a white solid (450 mg; 82%). $^1$H NMR: (DMSO-$d_6$, 400 MHz) δ 8.25 (1H, t, J=1.7 Hz), 8.18-8.12 (2H, m), 7.85 (1H, t, J=7.9 Hz), 7.63 (2H, br s). LC/MS (Method C): 181 (M+H)$^+$. HPLC (Method E) Rt 2.42 min (Purity: 99.3%).

Step 2: 3-(aminosulfonyl)-N'-hydroxybenzenecarboximidamide

To a solution of 3-cyanobenzenesulfonamide (420 mg; 2.3 mmol) in abs. EtOH (3 mL) was added hydroxylamine (0.8 mL; 12 mmol) (50% in water) and the mixture was heated to 78° C. for 18 hours. The mixture was poured into a crystallizing dish and the solvent was allowed to evaporate. The residue was washed with copious amounts of EtOAc, dry MeOH and dry MeCN which was filtered through a hydrophobic frit and the solvent removed in vacuo. Intermediate 44 was isolated as an off-white solid (357 mg; 72%). $^1$H NMR: (DMSO-$d_6$, 400 MHz) δ 9.84 (1H, s), 8.20 (1H, t, J=1.8 Hz), 7.91-7.81 (2H, m), 7.61 (1H, t, J=7.8 Hz), 7.40 (2H, br s), 5.96 (2H, br s). LC/MS (Method C): 216 (M+H)$^+$.

Intermediate 45

N'-hydroxy-2-oxoindoline-5-carboximidamide

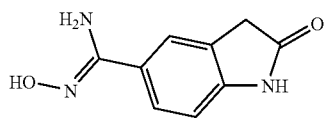

The title compound was prepared following the procedure described for Intermediate 31, but starting from 5-cyanooxindole (Combi-Blocks; 838 mg; 5.3 mmol), to give Intermediate 45 as an off-white solid (898 mg; 89%). $^1$H NMR: (DMSO-$d_6$, 400 MHz) δ 10.48 (1H, br s), 9.46 (1H, s), 7.57-7.49 (2H, m), 6.82 (1H, d, J=8.0 Hz), 5.71 (2H, br s), 3.52 (2H, s).

Intermediate 46

5-fluoro-N'-hydroxy-2-methoxybenzenecarboximidamide

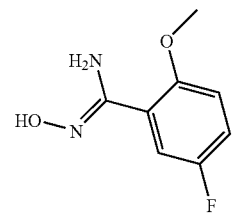

The title compound was prepared following the procedure described for Intermediate 31, but starting from 5-fluoro-2-methoxybenzonitrile (801 mg; 5.3 mmol), to give Intermediate 46 as a white solid (906 mg; 93%). $^1$H NMR: (DMSO-$d_6$, 400 MHz) δ 9.56 (1H, s), 7.27-7.19 (2H, m), 7.14-7.09 (1H, m), 5.71 (2H, br s), 3.83 (3H, s). LC/MS (Method C): 185 (M+H)$^+$. HPLC (Method H) Rt 10.19 min (Purity: 99.7%).

Intermediate 47

N'-hydroxy-4-(2-hydroxyethyl)benzenecarboximidamide

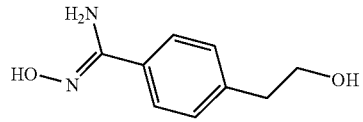

The title compound was prepared following the procedure described for Intermediate 31, but starting from 4-(2-hydroxyethyl)benzonitrile (Maybridge; 1.15 g; 7.8 mmol), to give Intermediate 47 as a white solid. $^1$H NMR: (DMSO-$d_6$, 400 MHz) δ 9.56 (1H, s), 7.60 (2H, d, J=8.0 Hz), 7.24 (2H, d, J=8.0 Hz), 5.76 (2H, s), 4.67 (1H, t, J=5.2 Hz), 3.67-3.61 (2H, m), 2.76 (2H, t, J=7.0 Hz). LC/MS (Method C): 181 (M+H)$^+$. HPLC (Method H) Rt 7.41 min (Purity: 98.3%).

Intermediate 48 tert-butyl {4-[amino(hydroxyimino)methyl]pyridin-2-yl}carbamate

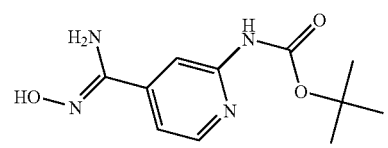

The title compound was prepared following the procedure described for Intermediate 31, but starting from tert-butyl 4-cyanopyridin-2-ylcarbamate (Lancaster; 2.19 g; 10 mmol), to give Intermediate 48 as an off-white solid (2.46 g; 98%). $^1$H NMR: (DMSO-$d_6$, 400 MHz) δ 10.00 (1H, s), 9.76 (1H, s), 8.27 (1H, d, J=5.2 Hz), 8.15 (1H, s), 7.29 (1H, dd, J=5.2, 1.5 Hz), 5.91 (2H, br s), 1.51 (9H, s).

Intermediate 49

N'-hydroxy-4-(1H-pyrazol-1-ylmethyl)benzenecarboximidamide

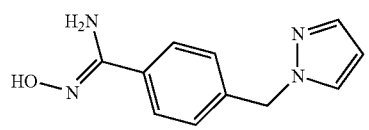

To a solution of 4-((1H-pyrazol-1-yl)methyl)benzonitrile (Maybridge; 1 g; 5.5 mmol) in abs. EtOH (7 mL) was added hydroxylamine (1.8 mL; 27 mmol) (50% in water) and the mixture was heated to 78° C. for 18 hours. Brine (10 mL) was added and the EtOH removed in vacuo. The mixture was extracted with EtOAc (3×20 mL) and the combined organic fractions passed through a hydrophobic frit and the solvent removed in vacuo to give Intermediate 49 as an orange oil (1.14 g; 96%). $^1$H NMR: (DMSO-$d_6$, 400 MHz) δ 9.64 (1H, s), 7.86 (1H, d, J=2.3 Hz), 7.65 (2H, d, J=8.1 Hz), 7.50 (1H, d, J=1.8 Hz), 7.22 (2H, d, J=8.1 Hz), 6.31 (1H, t, J=2.1 Hz), 5.81 (2H, br s), 5.38 (2H, s). LC/MS (Method C): 217 (M+H)$^+$. HPLC (Method H) Rt 10.63 min (Purity: 92.0%).

Intermediate 50

Ethyl 1-(2-fluorophenyl)-5-(morpholinomethyl)-1H-1,2,3-triazole-4-carboxylate

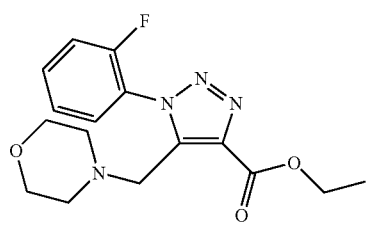

To a solution of ethyl 4-chloroacetoacetate (0.93 mL; 6.90 mmol) in morpholine (10 mL), was added 1-azido-2-fluorobenzene, prepared according to Platz, M. S. et al. *J. Org. Chem.* 1989, 54, 5938-5945 (630 mg; 4.60 mmol). The reaction mixture was heated at 80° C. for 65 hours. The mixture was cooled and EtOAc added (30 mL). The organic layer was washed with water (2×20 mL) before acidifying to pH 3 with HCl and the product extracted into water (3×20 mL). The aqueous layer was then basified with NaOH to pH 9 and the product extracted into EtOAc (3×20 mL). The residue was purified by flash chromatography on a Biotage 40+M column, eluting with petrol containing increasing amounts of EtOAc to give Intermediate 50 as a brown oil. $^1$H NMR (CDCl$_3$) δ 7.59-7.48 (2H, m), 7.34-7.28 (2H, m), 4.48 (2H, q, J=7.1 Hz), 3.95 (2H, s), 3.34-3.30 (4H, m), 2.26 (4H, t, J=4.8 Hz), 1.46 (3H, t, J=7.2 Hz).

Intermediate 51

N'-hydroxy-1H-benzimidazole-5-carboximidamide

Step 1: 1H-benzo[d]imidazole-5-carbonitrile 3,4-Diaminobenzonitrile (1.0 g; 7.5 mmol) was dissolved in formic acid (3 mL) and heated at 100° C. for 1.5 hours. The mixture was cooled, neutralised with 10% sodium hydroxide and the resulting precipitate isolated by filtration and dried in vacuo to yield the title compound as a brown solid (890 mg; 82%). $^1$H NMR (DMSO-$d_6$) δ 8.50 (1H, s), 8.19 (1H, s), 7.79 (1H, d, J=8.3 Hz), 7.62 (1H, dd, J=8.3, 1.54 Hz). LC/MS (Method C): 144 (M+H)'. HPLC (Method F) Rt=2.14 min (Purity: 99.4%).

Step 2: N'-hydroxy-1H-benzo[d]imidazole-5-carboximidamide Intermediate 51 was prepared following procedure described for Intermediate 3, Step 2, but starting from 1H-benzo[d]imidazole-5-carbonitrile (887 mg; 6.20 mmol) obtained in Step 1, and isolated as an off white solid (1.09 g; 99%) which was used directly without any purification. $^1$H NMR (DMSO-$d_6$) δ 12.55 (1H, s), 9.54 (1H, s), 8.26 (1H, s), 8.02-7.70 (1H, m), 7.59 (2H, s), 5.82 (2H, s). LC/MS (Method C): 177 (M+H)$^+$. HPLC (Method H) Rt=7.34 min (Purity: 99.3%).

Intermediate 52

Tert-butyl 4-[(hydroxyamino)(imino)methyl]-1-piperidinecarboxylate

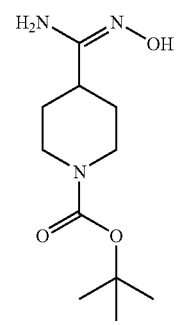

1-N-Boc-4-cyano-piperidine (2.103 g; 10 mmol; 1 eq.) was dissolved in EtOH (25 ml) and hydroxylamine 50% in water (2.95 ml; 50 mmol; 5 eq.) was added. The solution was heated at reflux overnight. The solvent was removed, the residue redissolved in ethyl acetate. After extraction with NaHCO$_3$ and brine, the organic extract was dried over MgSO$_4$, filtered and concentrated to give Intermediate 52 as off-white solid (2.25 g; 92%). $^1$H-NMR (CDCl$_3$, 300 MHz) δ 7.6 (br s, 1H), 4.6 (br s, 2H), 4.3-4.0 (m, 2H), 2.8-2.55 (m, 2H), 2.4-2.2 (m, 1H), 1.9-1.8 (m, 2H), 1.7-1.4 (m, 2H), 1.5 (s, 9H). LC/MS (Method A): 242.96 (M−H)$^−$.

Intermediate 53

Ethyl 1-(2-fluorophenyl)-5-pyridin-2-yl-1H-1,2,3-triazole-4-carboxylate

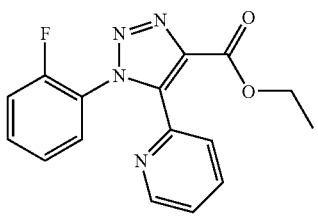

To a solution of 1-azido-2-fluorobenzene (25 g; 182 mmol; 1 eq.) and ethyl picolinoylacetate (38.04 g; 196.9 mmol; 1.08 eq.) in EtOH (250 ml) under argon was added portionwise sodium ethoxide (24.8 g; 365 mmol; 2 eq.) and the mixture was stirred at 70° C. for 24 h. The suspension was filtered and the resulting solid was washed with EtOH (2×100 mL). Combined filtrate was concentrated. NaOH 1N (400 mL) was added to the residue and was extracted with ethyl acetate (2×250 mL). Organic layers were dried over MgSO$_4$, affording Intermediate 53 as a brown solid. $^1$H-NMR (DMSO-d$_6$, 300 MHz) δ 8.47-8.43 (m, 1H), 7.93 (dt, J=1.76, 7.80 Hz, 1H), 7.84 (td, J=1.15, 7.80 Hz, 1H), 7.67-7.55 (m, 2H), 7.46-7.31 (m, 3H), 4.26 (q, J=7.11 Hz, 2H), 1.18 (t, J=7.11 Hz, 3H). LC/MS (Method B): 313.2 (M+H)$^+$; 309.2 (M−H)$^−$. HPLC (Method A) Rt 3.23 min (Purity: 94.8%).

Intermediate 54 tert-butyl {3-[amino(hydroxyimino)methyl]benzyl}carbamate

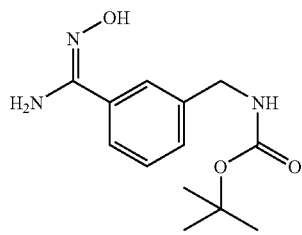

Step 1: tert-butyl (3-cyanobenzyl)carbamate

3-Cyanobenzylamine hydrochloride (1 g; 5.93 mmol; 1 eq.) and di-tert-butyl dicarbonate (1.42 g; 6.52 mmol; 1.1 eq.) were dissolved in DCM (10 ml) and triethylamine (1.64 ml; 11.86 mmol; 2 eq.) was added. The reaction mixture was stirred at RT overnight. The reaction mixture was diluted with DCM and the organic phase was washed with water, aqueous saturated solution of NH$_4$Cl and brine, dried over MgSO$_4$ and evaporated. The resulting crude product was purified by flash chromatography (SiO$_2$: 30 g; cyclohexane/EtOAc gradient from 95/5 till 30/70), affording the title compound as translucent oil (1.09 g; 79.13%). $^1$H NMR (DMSO-d$_6$, 300 MHz) δ 7.59-7.39 (m, 4H), 4.94 (br s, 1H), 3.39-4.31 (m, 2H), 1.46 (s, 9H). HPLC (Method A) Rt 3.77 min (Purity: 99%).

Step 2: tert-butyl {3-[amino(hydroxyimino)methyl]benzyl}carbamate

Tert-butyl (3-cyanobenzyl)carbamate, obtained in Step 1, (1.09 g; 4.69 mmol; 1 eq.) was dissolved in abs. EtOH (10 ml) and hydroxylamine (1.38 ml; 23.46 mmol; 5 eq.) (50% in water) was added. The mixture was stirred at 50° C. 3 hours. The solvents were evaporated and the residue was dissolved in ethylacetate. The organic phase was washed with brine (2×15 mL), dried over MgSO$_4$ and evaporated to give Intermediate 54 as white solid (1.09 g; 88%).

Give 1.09 g (88%) of the title compound as a white solid. $^1$H NMR (DMSO-d$_6$, 300 MHz) δ 9.62 (s, 1H), 7.65-7.51 (m, 2H), 7.46-7.23 (m, 3H), 5.79 (s, 2H), 4.21-4.98 (m, 2H), 1.43 (s, 9H). HPLC (Method A) Rt 2.08 min (Purity: 98.4%).

Example 1

3-[2-Fluorophenyl)-5-[1-(2-fluorophenyl)-5-methyl-1H-1,2,3-triazole-4-yl]-1,2,4-oxadiazole

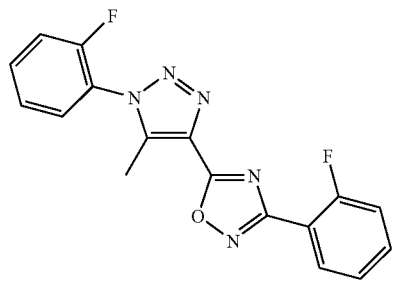

In a MW vial, a solution of Intermediate 9 (44.24 mg; 0.20 mmol) in anhydrous THF (2 mL) was prepared under N$_2$ atmosphere. Triphenylphosphine polymer bound (crosslinked with 2% dvb) (375.00 mg; 0.60 mmol; 3 eq.) and trichloroacetonitrile (30 μl; 0.30 mmol; 1.50 eq.) were added. The reaction vessel was sealed and heated to 100° C. for 5 min in a microwave reactor. After cooling, the reaction vessel was uncapped and Intermediate 4 (33.91 mg; 0.22 mmol) in anhydrous THF (2 mL) and N-ethyldiisopropylamine (DIEA) (69 μl; 0.40 mmol; 2 eq.) were added. The reaction vessel was sealed again and heated at 150° C. for 15 min in a microwave reactor. The reaction mixture was filtered through an NH$_2$ SPE column (1 g) and the solvents were evaporated. The residue was purified by flash chromatography (SiO$_2$: 10 g; cyclohexane/EtOAc gradient from 90/10 till 50/50), affording Example 1 as an off-white solid. $^1$H-NMR (DMSO-d$_6$, 300 MHz) δ 8.21 (dt, J=1.88 Hz, J=7.54 Hz, 1H), 7.90-7.68 (m, 4H), 7.62-7.49 (m, 3H), 2.68 (s, 3H). LC/MS: 340.32 (M+H)$^+$. HPLC (Method A) Rt 4.55 min (Purity: 99%).

Example 2

3-[2,5-Difluorophenyl]-5-[1-(2-fluorophenyl)-5-methyl-1H-1,2,3-triazole-4-yl]-1,2,4-oxadiazole

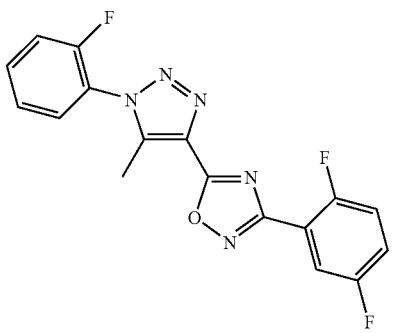

The title compound was prepared following procedure described for Example 1, but starting from Intermediate 9 (44.24 mg; 0.20 mmol) and 2,5-difluoro-N'-hydroxybenzenecarboximid amide (JRD-Fluoro, 37.87 mg; 0.22 mmol). The reaction mixture was filtered through an NH$_2$ SPE column (1 g) and was evaporated. The residue was purified by flash chromatography (SiO$_2$: 10 g; cyclohexane/EtOAc gradient from 90/10 till 50/50) and dried to afford Example 2 as a yellow solid. $^1$H NMR: (DMSO-d$_6$, 300 MHz) δ 7.86-7.80 (m, 1H) 7.75-7.65 (m, 2H), 7.60-7.41 (m, 4H), 2.53 (s, 3H). LC/MS: 357.69 (M+H)$^+$. HPLC (Method A) Rt 4.65 min (Purity: 100%).

Example 3

5-[1-(2-Bromophenyl)-5-methyl-1H-1,2,3-triazole-4-yl]-3-(2,5-difluorophenyl)-1,2,4-oxadiazole

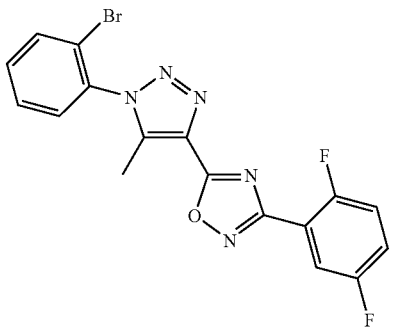

The title compound was prepared following procedure described for Example 1, but starting from 1-(2-bromophenyl)-5-methyl-1H-1,2,3-triazole-4-carboxylic acid, prepared according to Zhang, Z.-Y. et al. *Magn. Reson. Chem.* 1998, 36, 159-460 (56.42 mg; 0.20 mmol) and 2,5-difluoro-N'-hydroxybenzenecarboximid amide (JRD-Fluoro, 37.87 mg; 0.22 mmol). The reaction mixture was filtered through an NH$_2$ SPE column (1 g) and evaporated. The residue was taken up into pyridine and heated at 100° C. for 7 h, in order to complete oxadiazole formation. Pyridine was evaporated and the crude product was purified by flash chromatography (SiO$_2$: 10 g; cyclohexane/EtOAc gradient from 90/10 till 50/50) and dried to afford Example 3 as a yellow solid. $^1$H NMR: (DMSO-d$_6$, 300 MHz) δ 8.06 (dd, J=1.70 Hz, J=7.73 Hz, 1H), 8.02-7.97 (m, 1H), 7.86 (dd, J=1.89 Hz, J=7.53 Hz, 1H), 7.80-7.69 (m, 2H), 7.63 (dt, J=1.91 Hz, J=6.58 Hz, 2H), 2.61 (s, 3H). LC/MS: 419.93 (M+H)$^+$. HPLC (Method A) Rt 4.92 min (Purity: 96%).

Example 4

3-[2,6-Difluorophenyl]-5-[1-(2-fluorophenyl)-5-methyl-1H-1,2,3-triazole-4-yl]-1,2,4-oxadiazole

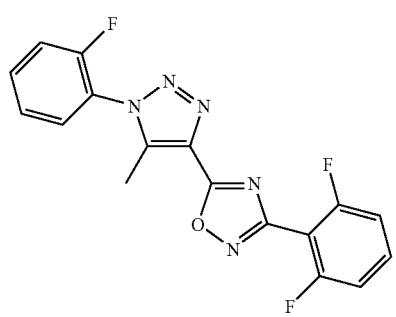

The title compound was prepared following procedure described for Example 1, but starting from Intermediate 9 (44.24 mg; 0.20 mmol) and Intermediate 5 (37.87 mg; 0.22 mmol). The reaction mixture was filtered through an NH$_2$ SPE column (1 g) and THF was evaporated. Reaction mixture was dissolved in toluene (3 mL) and pyridine (0.05 mL) was added. The mixture was heated in a microwave reactor for 45 min at 150° C. The solvents were evaporated and the residue was taken up into pyridine (4 mL) and heated at 100° C. for 4 h. Solvents were evaporated and the residue was purified by flash chromatography (SiO$_2$: 10 g; cyclohexane/EtOAc gradient from 90/10 till 50/50), affording Example 4 as a beige solid. $^1$H NMR: (DMSO-d$_6$, 300 MHz) δ 7.89-7.77 (m, 3H), 7.71 (t, J=9.42, 1H), 7.59 (t, J=7.72 Hz, 1H), 7.45 (t, J=8.48 Hz, 2H), 2.63 (s, 3H). LC/MS: 358.00 (M+H)$^+$. HPLC (Method A) Rt 4.56 min (Purity: 90%).

Example 5

5-[5-Ethyl-1-(2-fluorophenyl)-1H-1,2,3-triazole-4-yl]-3-phenyl-1,2,4-oxadiazole

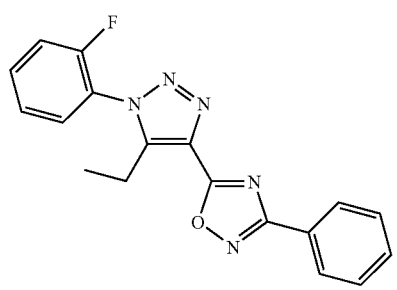

The title compound was prepared following procedure described for Example 1, but starting from Intermediate 10 (47.04 mg; 0.20 mmol) and N'-hydroxybenzenecarboximidamide (Apollo; 29.95 mg; 0.22 mmol). The reaction mixture was filtered through an NH$_2$ SPE column (1 g) and evaporated. The residue was purified by flash chromatography (SiO$_2$: 10 g; cyclohexane/EtOAc gradient from 90/10 till 50/50), affording Example 5 as a brown solid (52 mg; 76%). $^1$H NMR: (DMSO-d$_6$, 300 MHz) δ 8.18-8.15 (m, 2H), 7.92-7.82 (m, 2H), 7.75-7.57 (m, 5H), 3.09 (qua, J=7.54 Hz, 2H), 1.18 (t, J=7.54 Hz, 3H). LC/MS: 336.03 (M+H)$^+$. HPLC (Method A) Rt 4.98 min (Purity: 99%).

Example 6

5-[5-Ethyl-1-(2-fluorophenyl)-1H-1,2,3-triazole-4-yl]-3-(2-fluorophenyl)-1,2,4-oxadiazole

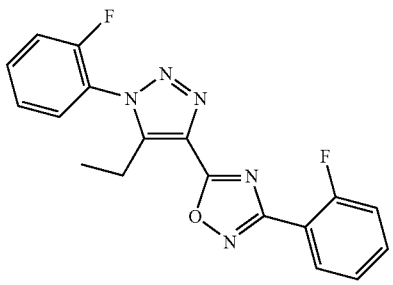

The title compound was prepared following procedure described for Example 1, but starting from Intermediate 10 (47.04 mg; 0.20 mmol) and Intermediate 4 (33.91 mg; 0.22 mmol). The reaction mixture was filtered through an NH$_2$ SPE column (1 g) and solvents were evaporated. The residue was purified by flash chromatography (SiO$_2$: 10 g; cyclohexane/EtOAc gradient from 90/10 till 50/50), affording Example 6 as an off-white solid. $^1$H NMR: (DMSO-d$_6$, 300 MHz) δ 8.19 (dt, J=1.63 Hz, J=7.63 Hz, 1H), 7.92-7.82 (m, 2H), 7.79-7.69 (m, 2H), 7.62-7.49 (m, 3H), 3.08 (qua, J=7.54 Hz, 2H), 1.18 (t, J=7.54 Hz, 3H). LC/MS: 354.02 (M+H)$^+$. HPLC (Method A) Rt 4.84 min (Purity: 100%).

Example 7

3-(2,5-Difluorophenyl)-5-[5-ethyl-1-(2-fluorophenyl)-1H-1,2,3-triazole-4-yl]-1,2,4-oxadiazole

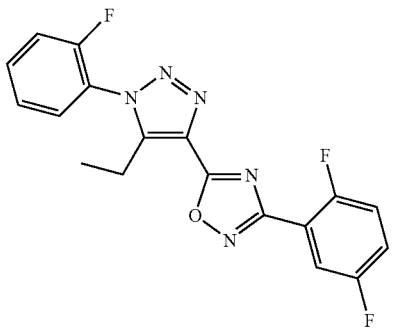

The title compound was prepared following procedure described for Example 1, but starting from Intermediate 10 (47.04 mg; 0.20 mmol) and 2,5-difluoro-N'-hydroxybenzenecarboximidamide (JRD-Fluoro, 37.87 mg; 0.22 mmol). The reaction mixture was filtered through an NH$_2$ SPE column (1 g) and solvents were evaporated. The resulting solid was dissolved in EtOAc and Cy was added. The resulting mixture was kept at 4° C. overnight. The formed solid was filtered and washed with cold Cy. It was then dissolved in EtOAc (15 mL) and washed with water (2×10 mL) and brine (10 mL), dried over MgSO$_4$ and concentrated, affording Example 7 as an off-white solid. $^1$H NMR: (DMSO-d$_6$, 300 MHz) δ 7.98-7.82 (m, 3H), 7.75-7.57 (m, 4H), 3.08 (qua, J=7.66 Hz, 2H), 1.17 (t, J=7.54 Hz, 3H). LC/MS: 372.00 (M+H)$^+$. HPLC (Method A) Rt 5.04 min (Purity: 95%).

Example 8

3-(2,4-Difluorophenyl)-5-[1-(2-fluorophenyl)-5-(methoxymethyl)-1H-1,2,3-triazole-4-yl]-1,2,4-oxadiazole

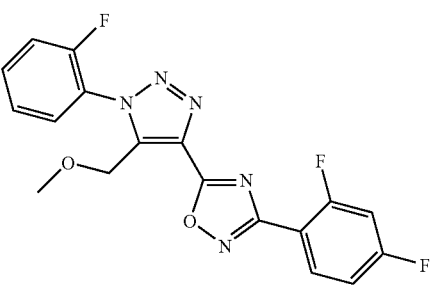

The title compound was prepared following procedure described for Example 1, but starting from Intermediate 11 (50.24 mg; 0.20 mmol) and 2,4-difluoro-N-hydroxybenzenecarboximidamide (JRD-Fluoro, 37.87 mg; 0.22 mmol). The reaction mixture was filtered through an NH$_2$ SPE column (1 g) and evaporated. The residue was purified by flash chromatography (SiO$_2$: 10 g; cyclohexane/EtOAc gradient from 90/10 till 50/50), affording Example 8 as a offwhite solid. $^1$H NMR: (DMSO-d$_6$, 300 MHz) δ 8.29 (dt, J=6.40, J=8.48, 1H), 7.90-7.78 (m, 2H), 7.71-7.54 (m, 3H), 7.43 (dt, J=2.64 Hz, J=8.48 Hz, 1H), 4.97 (s, 2H), 3.22 (s, 3H). LC/MS: 387.96 (M+H)$^+$. HPLC (Method A) Rt 4.78 min (Purity: 97%).

Example 9

3-(2-Fluorophenyl)-5-[1-(2-fluorophenyl)-5-(methoxymethyl)-1H-1,2,3-triazole-4-yl]-1,2,4-oxadiazole

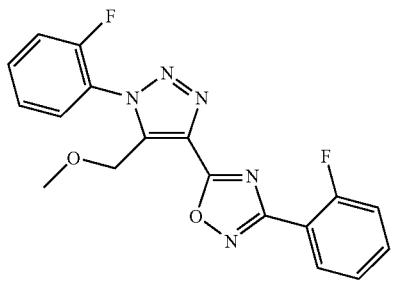

The title compound was prepared following procedure described for Example 1, but starting from Intermediate 11 (50.24 mg; 0.20 mmol) and Intermediate 4 (33.91 mg; 0.22 mmol). The reaction mixture was filtered through an NH$_2$ SPE column (1 g) and evaporated. The residue was purified by flash chromatography (SiO$_2$: 10 g; cyclohexane/EtOAc gradient from 95/5 till 60/40), affording Example 9 as a white solid. $^1$H NMR: (DMSO-d$_6$, 300 MHz) δ 8.23 (dt, J=1.63 Hz, J=7.63 Hz, 1H), 7.90-7.65 (m, 4H), 7.59-7.50 (m, 3H), 4.97 (s, 2H), 3.22 (s, 3H). LC/MS: 369.97 (M+H)$^+$. HPLC (Method A) Rt 4.62 min (Purity: 100%).

Example 10

3-(2,5-Difluorophenyl)-5-[1-(2-fluorophenyl)-5-(methoxymethyl)-1H-1,2,3-triazole-4-yl]-1,2,4-oxadiazole

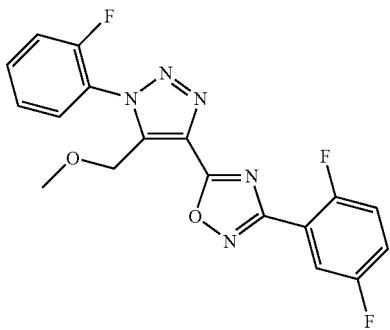

The title compound was prepared following procedure described for Example 1, but starting from Intermediate 11 (50.24 mg; 0.20 mmol) and 2,5-difluoro-N'-hydroxybenzenecarboximidamide (JRD-Fluoro, 37.87 mg; 0.22 mmol). The reaction mixture was filtered through an NH$_2$ SPE column (1 g) and evaporated. The residue was purified by flash chromatography (SiO$_2$: 10 g; cyclohexane/EtOAc gradient from 90/10 till 60/40). The product was taken up into EtOAc (15 mL) and washed with water (2×10 mL) and with brine (10 mL). The organic layer was dried over MgSO$_4$ and evaporated. The product was recrystallized from isopropanol, affording Example 10 as a white solid (58.07 mg; 78%). $^1$H NMR: (DMSO-d$_6$, 300 MHz) δ 8.04-7.99 (m, 1H) 7.90-7.78 (m, 2H), 7.79-7.54 (m, 4H), 4.98 (s, 2H), 3.22 (s, 3H). LC/MS: 388.01 (M+H)$^+$. HPLC (Method A) Rt 4.75 min (Purity: 98%).

Example 11

3-(2,4-Difluorophenyl)-5-[1-(2-fluorophenyl)-5-phenyl-1H-1,2,3-triazole-4-yl]-1,2,4-oxadiazole

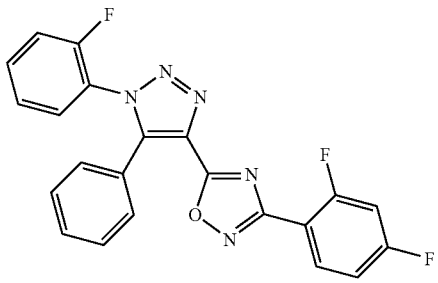

To a solution of Intermediate 13 (84.98 mg; 0.30 mmol; 1 eq.) in anhydrous ACN (4 mL) at RT was added 1-ethyl-3-(3-dimethylaminopropyl) carbodiimide hydrochloride (69.01 mg; 0.36 mmol; 1.20 eq.) followed by 2,4-difluoro-N-hydroxy-benzenecarboximid amide (JRD-Fluoro, 61.97 mg; 0.36 mmol; 1.20 eq.). The reaction mixture was stirred at 78° C. for 29 h. Anhydrous pyridine (2 mL) was added and the reaction mixture was stirred at 80° C. overnight. The solvents were evaporated and the residue was taken up into EtOAc (10 mL) washed with sat. aq. NaHCO$_3$ (2 mL) and dried over MgSO$_4$. The product was purified by flash chromatography (SiO$_2$: 10 g; cyclohexane/EtOAc gradient from 90/10 till 50/50) and dried to afford Example 11 as a white solid. $^1$H NMR: (DMSO-d$_6$, 300 MHz) δ 8.05 (dt, J=6.53 Hz, J=8.48 Hz, 1H), 7.89 (dt, J=1.38 Hz, J=7.63 Hz, 1H), 7.74-7.66 (m, 1H), 7.64-7.46 (m, 8H), 7.38 (dt, J=2.26 Hz, J=8.48 Hz, 1H). LC/MS: 420.09 (M+H)$^+$. HPLC (Method A) Rt 5.20 min (Purity: 97%).

Example 12

3-(2,5-Difluorophenyl)-5-[1-(2-fluorophenyl)-5-phenyl-1H-1,2,3-triazole-4-yl]-1,2,4-oxadiazole

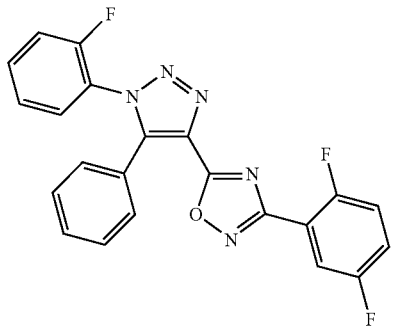

Step 1: 1-(2-fluorophenyl)-5-phenyl-1H-1,2,3-triazole-4-carbonyl chloride Intermediate 13 (0.47 g; 1.66 mmol; 1 eq.) was dissolved in anhydrous DCM (12 mL). Oxalyl chloride (0.15 mL; 1.74 mmol; 1.05 eq.) and one drop of anhydrous DMF were added under N$_2$. The mixture was stirred for 4 h at RT. The solvents were evaporated to give 1-(2-fluorophenyl)-5-phenyl-1H-1,2,3-triazole-4-carbonyl chloride as a solid and was used in the next step.

Step 2: 3-(2,5-Difluorophenyl)-5-[1-(2-fluorophenyl)-5-phenyl-1H-1,2,3-triazole-4-yl]-1,2,4-oxadiazole 1-(2-fluorophenyl)-5-phenyl-1H-1,2,3-triazole-4-carbonyl chloride, obtained in step 1 (60.34 mg; 0.20 mmol; 1 eq.), and 2,5-difluoro-N'-hydroxybenzenecarboximidamide (JRD-Fluoro, 37.87 mg; 0.22 mmol; 1.10 eq.) were dissolved in anhydrous pyridine (4 mL). The resulting mixture was stirred at RT for 2 h. Upon completion, the reaction mixture was heated at reflux for 1 h and was stirred at RT overnight. The solvents were evaporated and the residue was taken up into EtOAc (10 mL) and washed with water (2×10 mL), with brine (10 mL), dried over MgSO$_4$ and evaporated. The product was recrystallized from isopropanol and dried to afford Example 12 as a white solid. $^1$H NMR: (DMSO-d$_6$, 300 MHz) δ 7.89 (dt, J=7.81 Hz, J=1.49 Hz, 1H), 7.75-7.67 (m, 2H), 7.63-7.46 (m, 9H). LC/MS: 420.02 (M+H)+. HPLC (Method A) Rt 5.19 min (Purity: 97%).

Example 13

3-(2-Fluorophenyl)-5-[1-(2-fluorophenyl)-5-phenyl-1H-1,2,3-triazole-4-yl]-1,2,4-oxadiazole

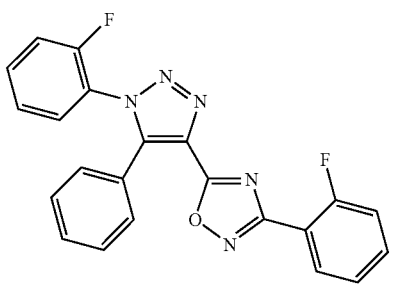

To a solution of Intermediate 13 (56.65 mg; 0.20 mmol; 1 eq.) in anhydrous ACN (2 mL) was added 1-ethyl-3-(3-dimethylaminopropyl)carbodiimide hydrochloride (EDC) (46 mg; 0.24 mmol; 1.20 eq.) followed by Intermediate 4 (36.99 mg; 0.24 mmol; 1.2 eq) in a MW vial under argon. The reaction mixture was stirred at RT for 30 min. Anhydrous pyridine (2 mL) was added. The reaction vessel was sealed and heated at 150° C. for 15 min in the MW. The solvents were evaporated and the residue was taken up into EtOAc (10 mL) and washed with sat. aq. NaHCO$_3$ (10 mL), dried over MgSO$_4$ and evaporated. The solid was recrystallized from isopropanol, affording Example 13 as a white solid. $^1$H NMR: (DMSO-d$_6$, 300 MHz) δ 8.00 (dt, J=1.63 Hz, J=7.44 Hz, 1H), 7.88 (t, J=7.72 Hz, 1H), 7.75-7.67 (m, 2H), 7.58-7.44 (m, 9H). LC/MS: 402.05 (M+H)+. HPLC (Method A) Rt 5.06 min (Purity: 99%).

Example 14

5-[1-(2-Fluorophenyl)-5-phenyl-1H-1,2,3-triazole-4-yl]-3-phenyl-1,2,4-oxadiazole

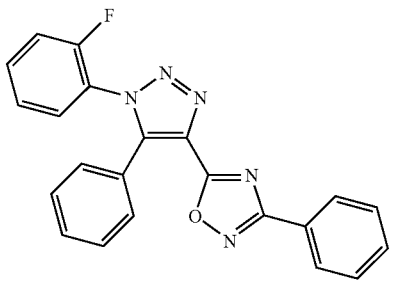

The title compound was prepared following procedure described for Example 13, but starting from Intermediate 13 (56.65 mg; 0.20 mmol) and N'-hydroxybenzenecarboximidamide (Apollo; 27.23 mg; 0.20 mmol). The solvents were evaporated and the residue was taken up into EtOAc (10 mL). The organic phase was washed with sat. aq. NaHCO$_3$ (10 mL), dried over MgSO$_4$ and evaporated. The solid was recrystallized from isopropanol and dried to afford Example 14 as an off-white solid. $^1$H NMR: (DMSO-d$_6$, 300 MHz) δ 8.02 (dd, J=1.88 Hz, J=7.54 Hz, 2H), 7.88 (t, J=7.54 Hz, 1H), 7.74-7.46 (m, 11H). LC/MS: 384.01 (M+H)+. HPLC (Method A) Rt 5.13 min (Purity: 99%).

Example 15

5-[1-(2-Fluorophenyl)-5-(methoxymethyl)-1H-1,2,3-triazole-4-yl]-3-phenyl-1,2,4-oxadiazole

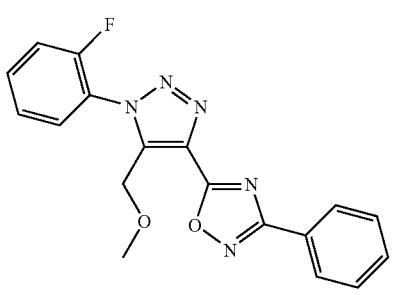

The title compound was prepared following procedure described for Example 13, but starting from Intermediate 11 (50.24 mg; 0.20 mmol) and N'-hydroxybenzenecarboximidamide (Apollo; 27.23 mg; 0.20 mmol). The solvents were evaporated and the residue was taken up into EtOAc (10 mL). The organic phase was washed with sat. aq. NaHCO$_3$ (10 mL), dried over MgSO$_4$ and evaporated. The solid was recrystallized from isopropanol, affording Example 15 as a white solid. $^1$H NMR: (DMSO-d$_6$, 300 MHz) δ 8.20-8.17 (m, 2H), 7.90-7.78 (m, 2H), 7.72-7.65 (m, 4H), 7.57 (t, J=7.72 Hz, 1H), 4.98 (s, 2H), 3.23 (s, 3H). LC/MS: 351.96 (M+H)+. HPLC (Method A) Rt 4.75 min (Purity: 100%).

Example 16

5-5-[5-Butyl-1-(2-fluorophenyl)-1H-1,2,3-triazole-4-yl]-3-(2-fluorophenyl)-1,2,4-oxadiazole

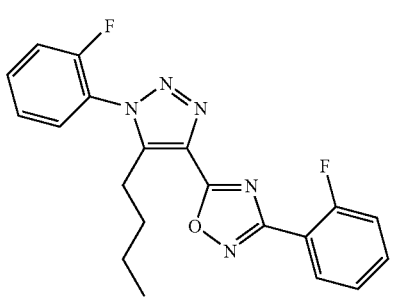

The title compound was prepared following procedure described for Example 13, but starting from Intermediate 12 (52.65 mg; 0.20 mmol) and Intermediate 4 (30.83 mg; 0.20 mmol). The solvents were evaporated and the residue was taken up into EtOAc (10 mL). The organic phase was washed with sat. aq. NaHCO$_3$ (10 mL), dried over MgSO$_4$ and evaporated. The residue was recrystallized from isopropanol, affording Example 16 as an off-white solid. $^1$H NMR: (DMSO-d$_6$, 300 MHz) δ 8.18 (t, J=7.44 Hz, 1H), 7.92-7.69 (m, 4H), 7.62-7.49 (m, 3H), 3.10 (t, J=7.72 Hz, 2H), 1.54

(quint., J=7.54 Hz, 2H), 1.25 (sext., J=7.41 Hz, 2H), 0.79 (t, J=7.35, 3H). LC/MS: 382.06 (M+H)+. HPLC (Method A) Rt 5.43 min (Purity: 99%).

Example 17

5-[5-Butyl-1-(2-fluorophenyl)-1H-1,2,3-triazole-4-yl]-3-phenyl-1,2,4-oxadiazole

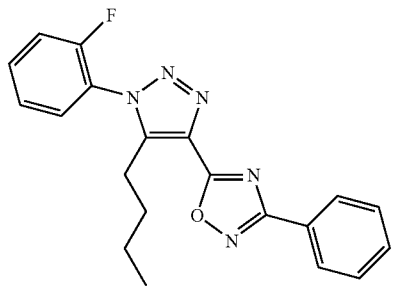

The title compound was prepared following procedure described for Example 13, but starting from Intermediate 12 (52.65 mg; 0.20 mmol) and N'-hydroxybenzenecarboximidamide (Apollo; 27.23 mg; 0.20 mmol). The solvents were evaporated and the residue was taken up into EtOAc (10 mL). The organic phase was washed with sat. aq. NaHCO₃ (10 mL), dried over MgSO₄ and evaporated. The residue was purified by flash chromatography (SiO₂: 10 g; cyclohexane/EtOAc gradient from 95/5 till 70/30), affording Example 17 as a yellow solid. ¹H NMR: (DMSO-d₆, 300 MHz) δ 8.18-8.14 (m, 2H), 7.93-7.87 (m, 2H), 7.81-7.57 (m, 5H), 3.11 (t, J=7.72 Hz, 2H), 1.54 (quint., J=7.35 Hz, 2H), 1.26 (sext., J=7.28, 2H), 0.80 (t, J=7.35 Hz). LC/MS: 364.08 (M+H)+. HPLC (Method A) Rt 5.55 min (Purity: 99%).

Example 18

3-Fluoro-4-{5-[1-(2-fluorophenyl)-5-phenyl-1H-1,2,3-triazole-4-yl]-1,2,4-oxadiazole-3-yl}phenol

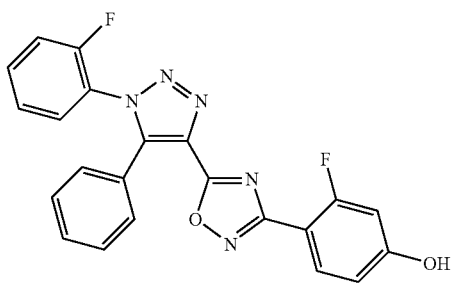

The title compound was prepared following procedure described for Example 13, but starting from Intermediate 13 (56.65 mg; 0.20 mmol) and Intermediate 6 (34.03 mg; 0.20 mmol). The solvents were evaporated and the residue was taken up into EtOAc (10 mL). The organic phase was washed with sat. aq. NaHCO₃ (10 mL), dried over MgSO₄ and evaporated. The residue was purified by flash chromatography (SiO₂: 10 g; cyclohexane/EtOAc gradient from 90/10 till 50/50). The resulting solid was triturated with ACN to afford Example 18 as a pale pink solid. ¹H NMR: (DMSO-d₆, 300 MHz) δ 10.77 (s, 1H), 7.91-7.78 (m, 2H), 7.73-7.66 (m, 1H), 7.56-7.46 (m, 7H), 6.85-6.78 (m, 2H). LC/MS: 417.98 (M+H)+. HPLC (Method A) Rt 4.47 min (Purity: 98%).

Example 19

Methyl 3-fluoro-4-{5-[1-(2-fluorophenyl)-5-phenyl-1H-1,2,3-triazole-4-yl]-1,2,4-oxadiazole-3-yl}benzoate

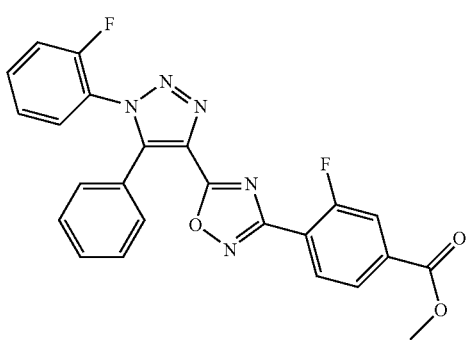

The title compound was prepared following procedure described for Example 13, but starting from Intermediate 13 (84.98 mg; 0.30 mmol) and Intermediate 2 (76.38 mg; 0.36 mmol; 1.20 eq). The solvents were evaporated and the residue was recrystallized from isopropanol, affording Example 19 as a yellow solid. ¹H NMR: (DMSO-d₆, 300 MHz) δ 8.18 (t, J=7.56 Hz, 1H), 8.02 (dd, J=8.09 Hz, J=1.45 Hz, 1H), 7.96 (dd, J=10.95 Hz, J=1.40 Hz 2H), 7.89 (t, J=7.64 Hz, 1H), 7.74-7.67 (m, 1H), 7.58-7.46 (m, 7H), 3.95 (s, 3H). LC/MS: 459.90 (M+H)+. HPLC (Method A) Rt 5.10 min (Purity: 93%).

Example 20

Methyl 3-{5-[1-(2-fluorophenyl)-5-phenyl-1H-1,2,3-triazole-4-yl]-1,2,4-oxadiazole-3-yl}benzoate

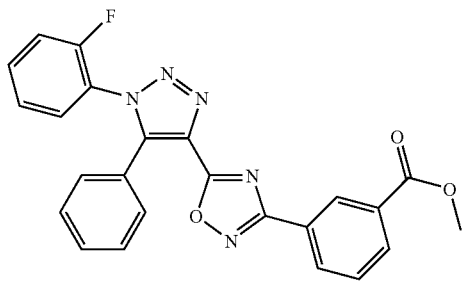

The title compound was prepared following procedure described for Example 13, but starting from Intermediate 13 (84.98 mg; 0.30 mmol) and Intermediate 3 (69.91 mg; 0.36 mmol). The solvents were evaporated and the residue was recrystallized from isopropanol affording Example 20 as a white solid. ¹H NMR: (DMSO-d₆, 300 MHz) δ 8.58 (t, J=1.51 Hz, 1H), 8.28 (dt, J=7.86 Hz, J=1.41 Hz, 1H), 8.21 (dt, J=7.98 Hz, J=1.41 Hz, 1H), 7.89 (t, J=7.63 Hz, 1H), 7.79 (t, J=7.83

Hz, 1H), 7.75-7.67 (m, 1H), 7.59-7.46 (m, 7H), 3.96 (s, 3H). LC/MS: 441.82 (M+H)+. HPLC (Method A) Rt 5.13 min (Purity: 95%).

Example 21

5-[1-(2-Fluorophenyl)-5-phenyl-1H-1,2,3-triazole-4-yl]-3-[3-(trifluoromethyl)phenyl]-1,2,4-oxadiazole

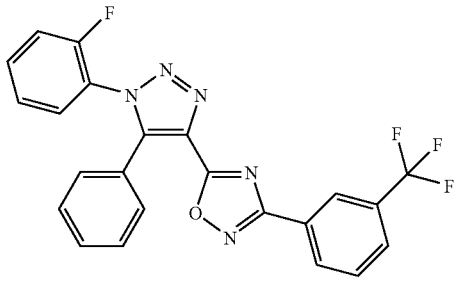

The title compound was prepared following procedure described for Example 13, but starting from Intermediate 13 (56.65 mg; 0.20 mmol) and 3-(trifluoromethyl)benzamidoxime (JRD-Fluoro, 49 mg; 0.24 mmol). The solvents were evaporated and the residue was recrystallized from isopropanol, affording Example 21 as a yellow solid. $^1$H NMR: (DMSO-d$_6$, 300 MHz) δ 8.32 (d, J=7.86 Hz, 1H), 8.25 (s, 1H), 8.05 (d, J=8.01 Hz, 1H), 7.89 (t, J=7.83 Hz, 2H), 7.74-7.67 (m, 1H), 7.59-7.46 (m, 7H). LC/MS: 451.92 (M+H)+. HPLC (Method A) Rt 5.66 min (Purity: 91%).

Example 22

5-[1-(2-Fluorophenyl)-5-phenyl-1H-1,2,3-triazole-4-yl]-3-(2-methoxyphenyl)-1,2,4-oxadiazole

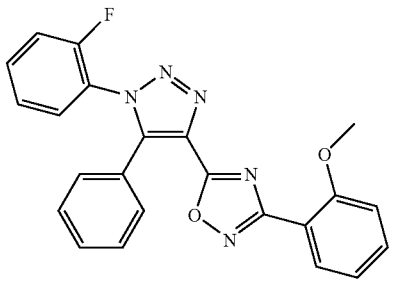

The title compound was prepared following procedure described for Example 13, but starting from Intermediate 13 (56.65 mg; 0.20 mmol) and N'-hydroxy-2-methoxybenzenecarboximidamide (Tyger; 39.88 mg; 0.24 mmol). The solvents were evaporated and the residue was dissolved in isopropanol. A precipitate was formed and filtered. It was then purified by flash chromatography (SiO$_2$: 10 g; cyclohexane/EtOAc gradient from 90/10 till 70/30), affording Example 22 as a white solid. $^1$H NMR: (DMSO-d$_6$, 300 MHz) δ 7.91-7.90 (m, 2H), 7.83-7.46 (m, 9H), 7.28 (d, J=8.40 Hz, 1H), 7.15 (dt, J=7.45 Hz, J=1.02 Hz, 1H), 3.91 (s, 3H). LC/MS: 413.91 (M+H)+. HPLC (Method A) Rt 4.75 min (Purity: 98%).

Example 23

2-Fluoro-4-{5-[1-(2-fluorophenyl)-5-phenyl-1H-1,2,3-triazole-4-yl]-1,2,4-oxadiazole-3-y}benzoic acid

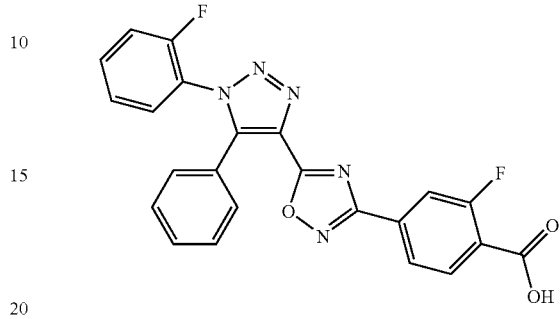

Step 1: Methyl 2-fluoro-4-{5-[1-(2-fluorophenyl)-5-phenyl-1H-1,2,3-triazole-4-yl]-1,2,4-oxadiazole-3-yl}benzoate The title compound was prepared following procedure described for Example 13, but starting from Intermediate 13 (84.98 mg; 0.30 mmol) and Intermediate 1 (76.38 mg; 0.36 mmol). The solvents were evaporated and the residue was recrystallized from isopropanol, affording the title compound as an off-white solid. $^1$H NMR: (DMSO-d$_6$, 300 MHz) δ 8.14 (t, J=7.77 Hz, 1H), 7.98 (dd, J=8.05 Hz, J=1.53 Hz, 1H), 7.91-7.86 (m, 2H), 7.74-7.67 (m, 1H), 7.58-7.46 (m, 7H) 3.94 (s, 3H). LC/MS: 459.89 (M+H)+. HPLC (Method A) Rt 5.18 min (Purity: 99%).

Step 2: 2-Fluoro-4-{5-[1-(2-fluorophenyl)-5-phenyl-1H-1,2,3-triazole-4-yl]-1,2,4-oxadiazole-3-yl}benzoic acid Methyl 2-fluoro-4-{5-[1-(2-fluorophenyl)-5-phenyl-1H-1,2,3-triazole-4-yl]-1,2,4-oxadiazole-3-yl}benzoate obtained in Step 1 (71.30 mg; 0.16 mmol; 1 eq.) was dissolved in MeOH (3 mL) and THF (3 mL). A 5N solution of sodium hydroxide was added (0.16 mL; 0.80 mmol; 5 eq). The mixture was stirred at RT overnight. The solvents were evaporated and the residue was taken up into EtOAc (10 mL) and washed with HCl (0.1N, 10 mL) and brine (2×10 mL), dried over MgSO$_4$ and evaporated, affording Example 23 as an off-white solid (57.20 mg; 83%). $^1$H NMR: (DMSO-d$_6$, 300 MHz) δ 13.64 (s, 1H), 8.11 (t, J=7.08 Hz, 2H), 7.96-7.81 (m, 3H), 7.74-7.67 (m, 1H), 7.58-7.46 (m, 7H). LC/MS: 445.92 (M+H)+. HPLC (Method A) Rt 4.43 min (Purity: 97%).

Example 24

4-{5-[1-(2-Fluorophenyl)-5-phenyl-1H-1,2,3-triazole-4-yl]-1,2,4-oxadiazole-3-yl}benzoic acid

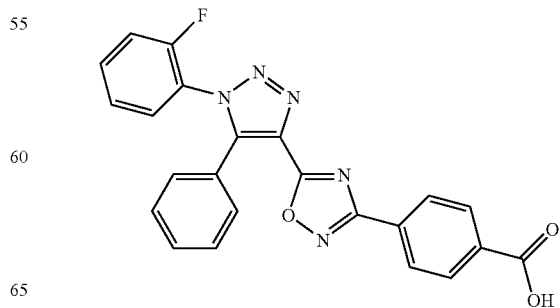

Step 1: Methyl 4-{5-[1-(2-fluorophenyl)-5-phenyl-1H-1,2,3-triazole-4-yl]-1,2,4-oxadiazole-3-yl}benzoate The title compound was prepared following procedure described for Example 13, but starting from Intermediate 13 (84.98 mg; 0.30 mmol) and methyl 4-[amino(hydroxyimino)methyl]benzoate (Maybridge; 69.91 mg; 0.36 mmol). The solvents were evaporated and the residue was recrystallized from isopropanol, affording the title compound as a white solid. $^1$H NMR: (DMSO-$d_6$, 300 MHz) δ 8.18 (m, 4H), 7.88 (t, J=7.62 Hz, 1H), 7.74-7.67 (m, 1H), 7.58-7.46 (m, 7H), 3.94 (s, 3H). LC/MS: 442.05 (M+H)$^+$. HPLC (Method A) Rt 5.16 min (Purity: 100%).

Step 2: 4-{5-[1-(2-Fluorophenyl)-5-phenyl-1H-1,2,3-triazole-4-yl]-1,2,4-oxadiazole-3-yl}benzoic acid Methyl 4-{5-[1-(2-fluorophenyl)-5-phenyl-1H-1,2,3-triazole-4-yl]-1,2,4-oxadiazole-3-yl}benzoate obtained in Step 1 (67.50 mg; 0.15 mmol; 1 eq.) was dissolved in MeOH (3 mL) and THF (3 mL). A 5N solution of sodium hydroxide was added (0.15 mL; 0.75 mmol; 5 eq). The mixture was stirred at RT overnight. The solvents were evaporated and the residue taken up into EtOAc (10 mL) and washed with HCl (0.1N, 10 mL), brine (2×10 mL), dried over MgSO$_4$ and evaporated, affording Example 24 as a white solid (60.70 mg; 93%). $^1$H NMR: (DMSO-$d_6$, 300 MHz) δ 13.34 (s, 1H), 8.15 (m, 4H), 7.89 (t, J=7.64 Hz, 1H), 7.74-7.67 (m, 1H), 7.58-7.46 (m, 7H). LC/MS: 427.93 (M+H)$^+$. HPLC (Method A) Rt 4.38 min (Purity: 96%).

Example 25

3-{1-(2-Fluorophenyl)-4-[3-(2-fluorophenyl)-1,2,4-oxadiazole-5-yl]-1H-1,2,3-triazole-5-yl}pyridine

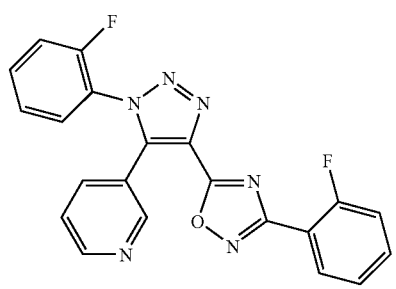

The title compound was prepared following procedure described for Example 13, but starting from Intermediate 14 (56.85 mg; 0.20 mmol) and Intermediate 4 (36.99 mg; 0.24 mmol). The solvents were evaporated and the residue was purified by flash chromatography (SiO$_2$: 10 g; cyclohexane/EtOAc gradient from 90/10 till 70/30), affording Example 25 as a white solid. $^1$H NMR: (DMSO-$d_6$, 300 MHz) δ 8.77 (d, J=1.59 Hz, 1H), 8.73 (dd, J=4.89 Hz, J=1.59 Hz, 1H), 8.05 (dt, J=7.95 Hz, J=1.94 Hz, 1H), 7.80-7.90 (m, 2H), 7.77-7.68 (m, 2H), 7.59-7.44 (m, 5H). LC/MS: 402.50 (M+H)$^+$. HPLC (Method A) Rt 3.97 min (Purity: 96%).

Example 26

3-[4-[3-(2,5-Difluorophenyl)-1,2,4-oxadiazole-5-yl]-1-(2-fluorophenyl)-1H-1,2,3-triazole-5-yl]pyridine

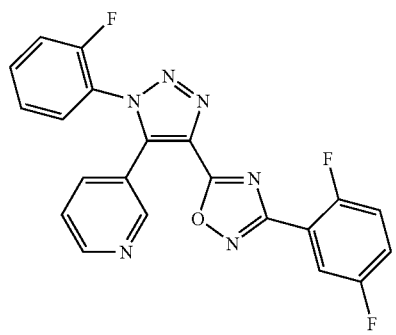

The title compound was prepared following procedure described for Example 13, but starting from Intermediate 14 (56.85 mg; 0.20 mmol) and 2,5-difluoro-N'-hydroxybenzenecarboximidamide (JRD-Fluoro, 41.31 mg; 0.24 mmol). The solvents were evaporated and the residue was purified by flash chromatography (SiO$_2$: 10 g; cyclohexane/EtOAc gradient from 90/10 till 70/30), affording Example 26 as a white solid. $^1$H NMR: (DMSO-$d_6$, 300 MHz) δ 8.77 (d, J=1.50 Hz, 1H), 8.74 (dd, J=4.88 Hz, J=1.64 Hz, 1H), 8.05 (dt, J=7.87 Hz, J=1.92 Hz, 1H), 7.93 (dt, J=7.80 Hz, J=1.59 Hz, 1H), 7.77-7.66 (m, 2H), 7.61-7.50 (m, 5H). LC/MS: 420.94 (M+H)$^+$. HPLC (Method A) Rt 4.16 min (Purity: 99%).

Example 27

2-{1-(2-Fluorophenyl)-4-[3-(2-fluorophenyl)-1,2,4-oxadiazole-5-yl]-1H-1,2,3-triazole-5-yl}pyridine

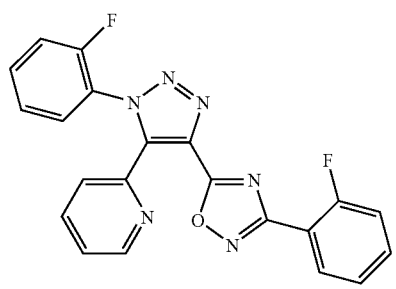

The title compound was prepared following procedure described for Example 13, but starting from Intermediate 15 (56.85 mg; 0.20 mmol) and Intermediate 4 (36.99 mg; 0.24 mmol). The solvents were evaporated and the residue was purified by flash chromatography (SiO$_2$: 10 g; cyclohexane/EtOAc gradient from 90/10 till 70/30), affording Example 27 as an off-white solid. $^1$H NMR: (DMSO-$d_6$, 300 MHz) δ 8.56 (d, J=5.04 Hz, 1H), 8.15-8.00 (m, 3H), 7.81-7.66 (m, 3H), 7.58-7.43 (m, 5H). LC/MS: 402.86 (M+H)$^+$. HPLC (Method A) Rt 4.53 min (Purity: 99%).

Example 28

2-[4-[3-(2,5-Difluorophenyl)-1,2,4-oxadiazole-5-yl]-1-(2-fluorophenyl)-1H-1,2,3-triazole-5-yl]pyridine

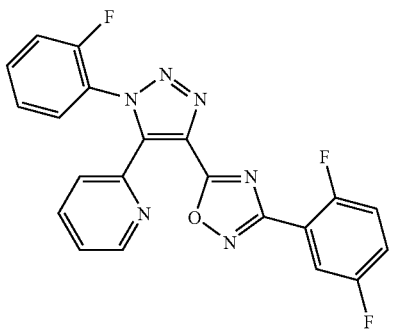

The title compound was prepared following procedure described for Example 13, but starting from Intermediate 15 (56.85 mg; 0.20 mmol) and 2,5-difluoro-N'-hydroxybenzenecarboximidamide (JRD-Fluoro, 41.31 mg; 0.24 mmol). The solvents were evaporated and the residue was purified by flash chromatography ($SiO_2$: 10 g; cyclohexane/EtOAc gradient from 90/10 till 70/30). The isolated product was recrystallized from ACN, affording Example 28 as an off-white solid. $^1$H NMR: (DMSO-$d_6$, 300 MHz) δ 8.56 (d, J=4.71 Hz, 1H), 8.15-8.04 (m, 2H), 7.81-7.43 (m, 8H). LC/MS: 420.86 (M+H)$^+$. HPLC (Method A) Rt 4.66 min (Purity: 100%).

Example 29

3-(4-{5-[1-(2-Fluorophenyl)-5-phenyl-1H-1,2,3-triazole-4-yl]-1,2,4-oxadiazole-3-yl}-3-methoxyphenyl)propanoic acid

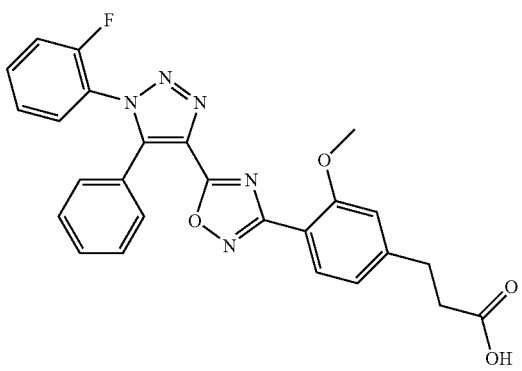

Step 1: Tert-butyl 3-(4-{5-[1-(2-fluorophenyl)-5-phenyl-1H-1,2,3-triazole-4-yl]-1,2,4-oxadiazole-3-yl}-3-methoxyphenyl)propanoate The title compound was prepared following procedure described for Example 13, but starting from Intermediate 13 (56.65 mg; 0.20 mmol) and Intermediate 7 (70.64 mg; 0.24 mmol). The solvents were evaporated and the residue was purified by flash chromatography ($SiO_2$: 10 g; cyclohexane/EtOAc gradient from 90/10 till 70/30), affording the title compound as an off-white solid. $^1$H NMR: (DMSO-$d_6$, 300 MHz) δ 7.88 (m, 1H), 7.75 (d, J=7.71 Hz, 1H), 7.72-7.66 (m, 1H), 7.55-7.45 (m, 7H), 7.15 (s, 1H), 7.01 (dd, J=7.90 Hz, J=1.33 Hz, 1H), 3.91 (s, 3H), 2.92 (t, J=7.53 Hz, 2H), 2.63 (t, J=7.55 Hz, 2H), 1.41 (s, 9H). LC/MS: 541.90 (M+H)$^+$. HPLC (Method A) Rt 5.57 min (Purity: 91%).

Step 2: 3-(4-{5-[1-(2-Fluorophenyl)-5-phenyl-1H-1,2,3-triazole-4-yl]-1,2,4-oxadiazole-3-yl}-3-methoxyphenyl)propanoic acid Tert-butyl 3-(4-{5-[1-(2-fluorophenyl)-5-phenyl-1H-1,2,3-triazole-4-yl]-1,2,4-oxadiazole-3-yl}-3-methoxy-phenyl)propanoate, obtained in step 1 (32 mg; 0.06 mmol; 1 eq.), was dissolved in DCM (0.40 mL). Trifluoroacetic acid (44 µl; 0.59 mmol; 10 eq.) was added at 0° C. The reaction mixture was then stirred overnight at RT. The solvents were evaporated, affording Example 29 as a white solid (27.40 mg; 96%). $^1$H NMR: (DMSO-$d_6$, 300 MHz) δ 7.90-7.85 (m, 1H), 7.77-7.66 (m, 2H), 7.56-7.45 (m, 7H), 7.16 (s, 1H), 7.01 (d, J=7.92 Hz, 1H), 2.93 (t, J=7.64 Hz, 2H), 2.64 (t, J=7.59 Hz, 2H). LC/MS: 485.79 (M+H)$^+$. HPLC (Method A) Rt 4.25 min (Purity: 93%).

Example 30

3-(4-{5-[1-(2-Fluorophenyl)-5-phenyl-1H-1,2,3-triazole-4-yl]-1,2,4-oxadiazole-3-yl}-3-methylphenyl)propanoic acid

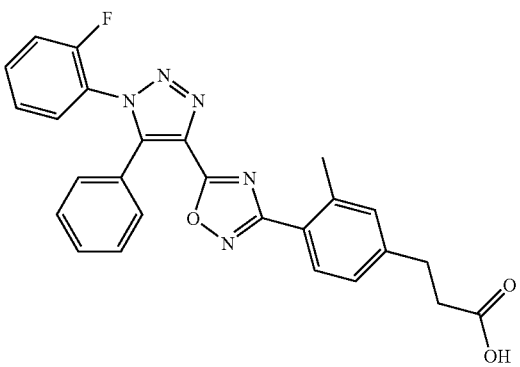

Step 1: Tert-butyl 3-(4-{5-[1-(2-fluorophenyl)-5-phenyl-1H-1,2,3-triazole-4-yl]-1,2,4-oxadiazole-3-yl}-3-methylphenyl)propanoate The title compound was prepared following procedure described for Example 13, but starting from Intermediate 13 (113.30 mg; 0.40 mmol) and Intermediate 8 (133.61 mg; 0.48 mmol). The solvents were evaporated and the residue purified by flash chromatography ($SiO_2$: 10 g; cyclohexane/EtOAc gradient from 90/10 till 70/30), affording the title compound as an off-white solid. $^1$H NMR: (DMSO-$d_6$, 300 MHz) δ 7.91-7.82 (m, 2H), 7.73-7.62 (m, 1H), 7.57-7.46 (m, 7H), 7.30-7.25 (m, 2H), 3.36 (s, 3H), 2.88 (t, J=7.56 Hz, 2H), 2.58 (m, 2H), 1.40 (s, 9H). LC/MS: 526.10 (M+H)$^+$. HPLC (Method A) Rt 6.12 min (Purity: 91%).

Step 2: 3-(4-{5-[1-(2-Fluorophenyl)-5-phenyl-1H-1,2,3-triazole-4-yl]-1,2,4-oxadiazole-3-yl}-3-methylphenyl)propanoic acid Tert-butyl 3-(4-{5-[1-(2-fluorophenyl)-5-phenyl-1H-1,2,3-triazole-4-yl]-1,2,4-oxadiazole-3-yl}-3-methyl-phenyl)propanoate obtained in step 1 (43.6 mg; 0.08 mmol; 1 eq.) was dissolved in DCM (0.60 mL). Trifluoroacetic acid (61.5 µl;

0.83 mmol; 10 eq.) was added at 0° C. and the reaction mixture was stirred overnight at RT. The solvents were evaporated and the residue was recrystallized from ACN, affording Example 30 as a white solid (32.7 mg; 85%). $^1$H NMR: (DMSO-d$_6$, 300 MHz) δ 12.16 (s, 1H), 7.85-7.77 (m, 2H), 7.69-7.63 (m, 1H), 7.54-7.43 (m, 7H), 7.29-7.23 (m, 2H), 2.86 (t, J=7.44 Hz, 2H), 2.60-2.57 (m, 2H). LC/MS: 469.95 (M+H)$^+$. HPLC (Method A) Rt 4.71 min (Purity: 97%).

Example 31

4-[4-[3-(2,5-Difluorophenyl)-1,2,4-oxadiazole-5-yl]-1-(2-fluorophenyl)-1H-1,2,3-triazole-5-yl]pyridine

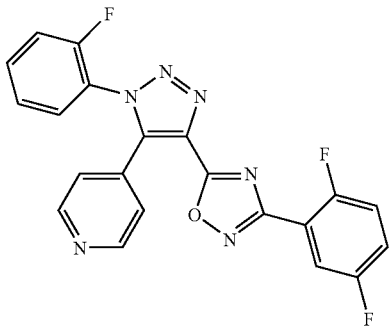

The title compound was prepared following procedure described for Example 13, but starting from Intermediate 16 (56.85 mg; 0.20 mmol) and 2,5-difluoro-N'-hydroxybenzenecarboximidamide (JRD-Fluoro, 41.31 mg; 0.24 mmol). The solvents were evaporated and the residue was purified by flash chromatography (SiO$_2$: 10 g; cyclohexane/EtOAc gradient from 90/10 till 70/30), affording Example 31 as a white solid. $^1$H NMR: (DMSO-d$_6$, 300 MHz) δ 8.75 (m, 2H), 7.92 (dt, J=7.50 Hz, J=1.57 Hz, 1H), 7.77-7.69 (m, 2H), 7.62-7.59 (m, 4H), 7.52 (t, J=8.67 Hz, 2H). LC/MS: 420.89 (M+H)$^+$. HPLC (Method A) Rt 4.00 min (Purity: 100%).

Example 32

4-{1-(2-Fluorophenyl)-4-[3-(2-fluorophenyl)-1,2,4-oxadiazole-5-yl]-1H-1,2,3-triazole-5-yl}pyridine

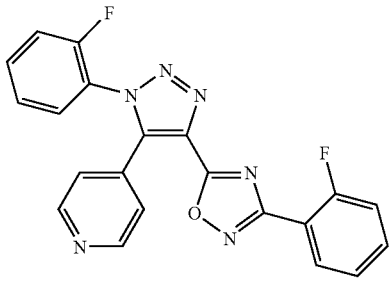

The title compound was prepared following procedure described for Example 13, but starting from Intermediate 16 (56.85 mg; 0.20 mmol) and Intermediate 4 (36.99 mg; 0.24 mmol). The solvents were evaporated and the residue was purified by flash chromatography (SiO$_2$: 10 g; cyclohexane/EtOAc gradient from 90/10 till 70/30), affording Example 32 as an off-white solid. $^1$H NMR: (DMSO-d$_6$, 300 MHz) δ 8.75 (m, 2H), 7.99 (dt, J=7.50 Hz, J=1.71 Hz, 1H), 7.92 (dt, J=7.63 Hz, J=1.64 Hz, 1H), 7.78-7.68 (m, 2H), 7.62 (m, 2H), 7.55-7.45 (m, 4H). LC/MS: 402.84 (M+H)$^+$. HPLC (Method A) Rt 3.84 min (Purity: 96%).

Example 33

3-Fluoro-4-{5-[1-(2-fluorophenyl)-5-phenyl-1H-1,2,3-triazole-4-yl]-1,2,4-oxadiazole-3-yl}benzoic acid

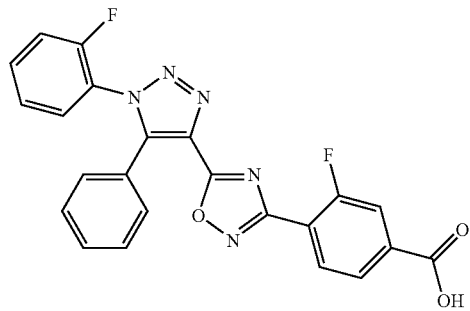

Step 1: Methyl 3-fluoro-4-{5-[1-(2-fluorophenyl)-5-phenyl-1H-1,2,3-triazole-4-yl]-1,2,4-oxadiazole-3-yl}benzoate The title compound was prepared following procedure described for Example 13, but starting from Intermediate 13 (84.98 mg; 0.30 mmol) and Intermediate 2 (76.38 mg; 0.36 mmol; 1.20 eq). The solvents were evaporated and the residue was recrystallized from isopropanol, affording the title compound as a yellow solid. $^1$H NMR: (DMSO-d$_6$, 300 MHz) δ 8.18 (t, J=7.56 Hz, 1H), 8.02 (dd, J=8.09 Hz, J=1.45 Hz, 1H), 7.96 (dd, J=10.95 Hz, J=1.40 Hz 2H), 7.89 (t, J=7.64 Hz, 1H), 7.74-7.67 (m, 1H), 7.58-7.46 (m, 7H), 3.95 (s, 3H). LC/MS: 459.90 (M+H)$^+$. HPLC (Method A) Rt 5.10 min (Purity: 93%).

Step 2: 3-Fluoro-4-{5-[1-(2-fluorophenyl)-5-phenyl-1H-1,2,3-triazole-4-yl]-1,2,4-oxadiazole-3-yl}benzoic acid Methyl 3-fluoro-4-{5-[1-(2-fluorophenyl)-5-phenyl-1H-1,2,3-triazole-4-yl]-1,2,4-oxadiazole-3-yl}benzoate, obtained in step 1 (57.90 mg; 0.13 mmol; 1 eq.), was dissolved in MeOH (3 mL) and THF (3 mL). A 5N solution of sodium hydroxide was added (0.13 mL; 0.65 mmol; 5 eq). The mixture was stirred at RT overnight. The solvents were evaporated and the residue taken up into EtOAc (10 mL) and washed with HCl (0.1N, 10 mL) and brine (2×10 mL), dried over MgSO$_4$ and evaporated, affording Example 33 as an off-white solid (49.30 mg; 88%). $^1$H NMR: (DMSO-d$_6$, 300 MHz) δ 13.66 (s, 1H), 8.15 (t, J=7.55 Hz, 1H), 8.00 (d, J=8.10 Hz, 1H), 7.94-7.86 (m, 2H), 7.74-7.67 (m, 1H), 7.59-7.46 (m, 7H). LC/MS: 402.50 (M+H)$^+$. HPLC (Method A) Rt 3.97 min (Purity: 99%).

Example 34

5-[1-(2-fluorophenyl)-5-methyl-1H-1,2,3-triazol-4-yl]-3-phenyl-1,2,4-oxadiazole

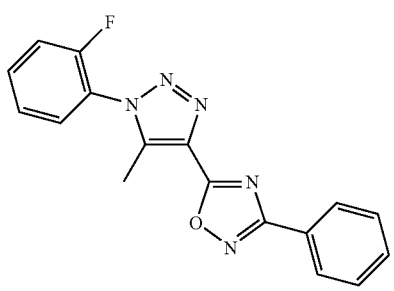

To a solution of Intermediate 9 (100 mg; 0.45 mmol; 1.00 eq.) in dry ACN at RT was added 1-ethyl-3-(3-dimethylaminopropyl)carbodiimide hydrochloride (104 mg; 0.54 mmol; 1.20 eq.), followed by N'-hydroxybenzenecarboximidamide (Apollo; 73.87 mg; 0.54 mmol; 1.20 eq.). The mixture was stirred at RT for 30 min. The mixture was heated at 120° C. overnight. After cooling to RT, the solvents were evaporated. The residue was taken up into EtOAc (20 mL), washed with sat. aq. NaHCO$_3$ (2 mL) and dried over MgSO$_4$. After concentration, the residue was purified by recrystallisation from isopropanol, affording Example 34 as a white solid. $^1$H NMR: (CDCl$_3$, 300 MHz) δ 8.23-8.20 (m, 2H), 7.66-7.35 (m, 7H), 2.71 (s, 3H). LC/MS: 322.06 (M+H)$^+$. HPLC (Method A) Rt 4.70 min (Purity: 93%).

Example 35

5-[1-(2-Bromophenyl)-5-methyl-1H-1,2,3-triazole-4-yl]-3-(2-fluorophenyl)-1,2,4-oxadiazole

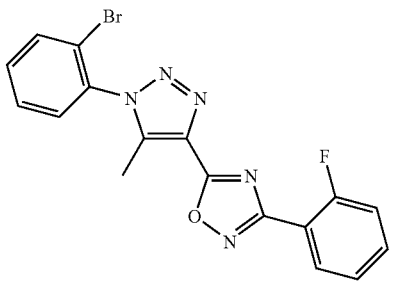

The title compound was prepared following procedure described for Example 1, but starting from 1-(2-bromophenyl)-5-methyl-1H-1,2,3-triazole-4-carboxylic acid, prepared according to Zhang, Z.-Y. et al. *Magn. Reson. Chem.* 1998, 36, 159-460 (50 mg; 0.18 mmol) and Intermediate 4 (30.05 mg; 0.19 mmol). The reaction mixture was filtrated and evaporated. The residue was purified by flash chromatography (SiO$_2$: 25 g; cyclohexane/EtOAc gradient from 90/10 till 50/50), affording Example 35 as a white solid. $^1$H NMR: (DMSO-d$_6$, 300 MHz) δ 8.21 (dt, J=1.88 Hz, J=7.54 Hz, 1H), 8.06 (dd, J=1.88 Hz, J=7.54 Hz, 1H), 7.86 (dd, J=1.88 Hz, J=8.54 Hz, 1H), 7.87-7.69 (m, 3H), 7.58-7.49 (m, 2H). LC/MS: 401.14 (M+H)$^+$. HPLC (Method A) Rt 4.77 min (Purity: 100%).

Example 36

5-[5-ethyl-1-(2-fluorophenyl)-1H-1,2,3-triazol-4-yl]-3-[3-(trifluoromethyl)penyl]-1,2,4-oxadiazole

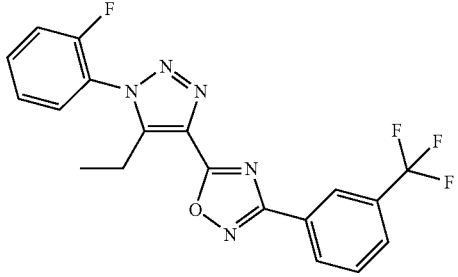

To a solution of Intermediate 10 (47.04 mg; 0.20 mmol) in anhydrous THF (2 mL) and anhydrous ACN (2 mL), was added 1-ethyl-3-(3-dimethylaminopropyl) carbodiimide hydrochloride (42.17 mg; 0.22 mmol; 1.10 eq.) followed by 3-(trifluoromethyl)benzamidoxime (JRD-Fluoro, 40.83 mg; 0.20 mmol; 1 eq.) under argon. The mixture was stirred at RT for 7 h and heated to 60° C. overnight. N-ethyldiisopropylamine (75 μl; 0.44 mmol; 2.20 eq.) was added and the mixture was heated for 20 min at 150° C. in the MW. The reaction mixture was filtered through a NH$_2$ SPE column (1 g) and rinsed with ACN. The filtrate was passed through a SCX SPE column (1 g) and rinsed with ACN. Combined filtrates were evaporated. The residue was purified by flash chromatography (SiO$_2$: 10 g; cyclohexane/EtOAc gradient from 95/5 till 70/30) and dried. The resulting solid was triturated in ACN (1 mL) and filtrated to afford Example 36 as a white solid. $^1$H NMR: (DMSO-d$_6$, 300 MHz) δ 8.47 (d, J=7.91 Hz, 1H), 8.39 (s, 1H), 8.09 (d, J=7.91 Hz, 1H), 7.97-7.82 (m, 3H), 7.73 (t, J=8.85 Hz, 1H), 7.60 (t, J=7.72 Hz, 1H), 3.09 (q, J=7.54 Hz, 2H), 1.19 (t, J=7.54 Hz, 3H). LC/MS: 404.03 (M+H)$^+$. HPLC (Method A) Rt 5.52 min (Purity: 99%).

Example 37

5-[5-Ethyl-1-(2-fluorophenyl)-1H-1,2,3-triazole-4-yl]-3-(2-methoxyphenyl)-1,2,4-oxadiazole

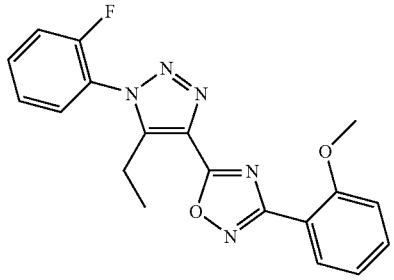

To a solution of Intermediate 10 (47.04 mg; 0.20 mmol; 1 eq.) in anhydrous THF (2 mL) and anhydrous ACN (2 mL), was added 1-ethyl-3-(3-dimethylamino-propyl)carbodiimide hydrochloride (42.17 mg; 0.22 mmol; 1.10 eq.) followed by N'-hydroxy-2-methoxybenzenecarboximidamide (Tyger; 33.24 mg; 0.20 mmol; 1 eq) under argon. The mixture was stirred for 7 h at RT and overnight at 60° C. N-ethyldiisopropylamine (75 μl; 0.44 mmol; 2.20 eq.) was added and the solution was heated at 150° C. for 20 min. in the MW. The reaction mixture was filtered through a NH$_2$ SPE column (1 g) and rinsed with ACN. The filtrate was passed through a SCX SPE column (1 g) and rinsed with ACN. The filtrates were evaporated and the residue was purified by flash chromatography (SiO$_2$: 10 g; cyclohexane/EtOAc gradient from 95/5 till 70/30). The resulting oil was taken up into ACN (1 mL) and water was added. The precipitate was filtered to afford Example 37 as an off-white solid. $^1$H NMR: (DMSO-d$_6$, 300 MHz) δ 8.02 (dd, J=1.32 Hz, J=7.72 Hz, 1H), 7.91-7.82 (m, 2H), 7.75-7.57 (m, 3H), 7.32 (d, J=8.29 Hz, 1H), 7.21 (t, J=7.54 Hz, 1H), 3.96 (s, 3H), 3.06 (q, J=7.54 Hz, 2H), 1.17 (t, J=7.54 Hz, 3H). LC/MS: 366.01 (M+H)+. HPLC (Method A) Rt 4.63 min (Purity: 97%).

Example 38

5-[1-(2-bromophenyl)-5-methyl-1H-1,2,3-triazol-4-yl]-3-pentyl-1,2,4-oxadiazole

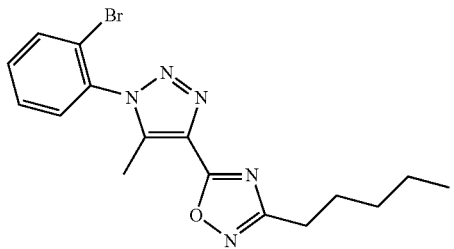

A solution of oxalyl chloride (355 µl; 2.00 M; 0.71 mmol; 2.00 eq.) was added dropwise to a solution of 1-(2-bromophenyl)-5-methyl-1H-1,2,3-triazole-4-carboxylic acid, prepared according to Zhang, Z.-Y. et al. *Magn. Reson. Chem.* 1998, 36, 159-460 (100 mg; 0.35 mmol; 1.00 eq.) in dry DCM (1 mL), followed by 2 drops of dry DMF. After 30 min at RT, the mixture was concentrated under vacuum. The residue under argon was dissolved in dry Toluene (3.00 mL). N-Hydroxy-hexanimidamide (Tyger, 55.4 mg; 0.43 mmol; 1.20 eq.) was added, followed by dry Py (500 µl), and the mixture was heated at 140° C. for 7 h, and cooled to RT. The mixture was partitioned between HCl 1M (20 mL) and EtOAc (20 mL). The organic layer was washed with HCl 1M (3×15 mL), sat. eq. NaHCO₃ (5 mL), brine (5 mL) and dried (MgSO₄). The product was purified by preparative HPLC, affording Example 38 as colorless oil. LC/MS: 376.02 (M+H)+. HPLC (Method A) Rt 5.25 min (Purity: 98%).

Example 39

4-{[4-[3-(2,5-difluorophenyl)-1,2,4-oxadiazol-5-yl]-1-(2-fluorophenyl)-1H-1,2,3-triazol-5-yl]methyl}morpholine

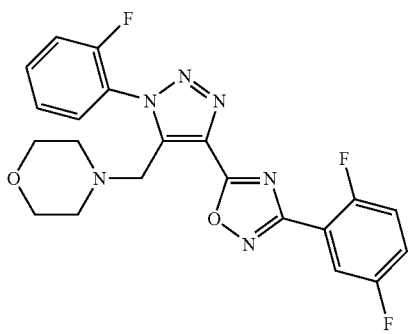

The title compound was prepared following procedure described for Example 13, but starting from Intermediate 19 (61.26 mg; 0.2 mmol; 1 eq) and 2,5-difluoro-N'-hydroxybenzenecarboximidamide (JRD-Fluoro, 41.31 mg; 0.24 mmol; 1.2 eq). The solvents were evaporated and the residue was dissolved in DCM and washed with brine. Aqueous phase was extracted with DCM. Combined organic phases were dried over MgSO₄, affording the crude product as a yellow oil. It was purified by flash chromatography (SiO₂: 10 g; cyclohexane/EtOAc gradient from 90/10 till 50/50), affording Example 39 as light pink solid. ¹H NMR (DMSO-d₆) δ 7.86-7.80 (m, 1H), 7.60-7.53 (m, 2H), 7.36-7.26 (m, 2H), 7.20-7.15 (m, 2H), 4.13 (br s, 2H), 3.38 (br s, 4H), 2.36 (br s, 4H). LC/MS: 443.2 (M+H)+. HPLC (Method A) Rt 3.82 min (Purity: 98.4%).

Example 40

4-{1-(2-fluorophenyl)-4-[3-(2-methoxyphenyl)-1,2,4-oxadiazol-5-yl]-1H-1,2,3-triazol-5-yl}pyridine

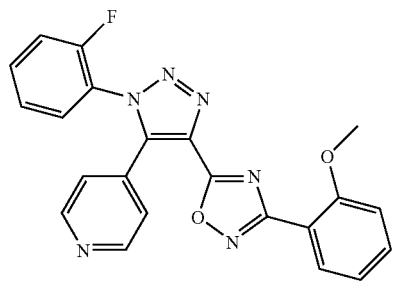

In a MW vial, Intermediate 17 (418.5 mg; 1.34 mmol; 1 eq.) was suspended in Toluene (4 ml) and N'-hydroxy-2-methoxybenzenecarboximidamide (Tyger; 245 mg; 1.47 mmol; 1.1 eq.) was added followed by potassium carbonate (203.7 mg; 1.47 mmol; 1.1 eq.). The MW vial was sealed and the suspension was heated to 180° C. for 10 min in the MW. The reaction mixture was cooled down to room temperature, diluted with DCM and washed with water and brine. The organic phase was dried over MgSO₄, filtrated and evaporated affording a dark oil, which was triturated in isopropanol. The resulting solid was filtered, affording Example 40 as a white solid (416.2 mg; 75%). ¹H NMR (DMSO-d₆) δ 8.75 (dd, J=4.3; 1.7 Hz, 2H), 7.92 (dt, J=7.7; 1.5 Hz, 1H), 7.84 (dd, J=7.7; 1.7 Hz, 1H), 7.78-7.68 (m, 1H), 7.65-7.43 (m, 5H), 7.31-7.25 (m, 1H), 7.15 (dt, J=7.5; 0.9 Hz, 1H), 3.91 (s, 3H). LC/MS: 415.3 (M+H)+. HPLC (Method A) Rt 3.53 min (Purity: 98.4%).

Example 41

4-[1-(2-fluorophenyl)-4-(3-pyridin-4-yl-1,2,4-oxadiazol-5-yl)-1H-1,2,3-triazol-5-yl]pyridine

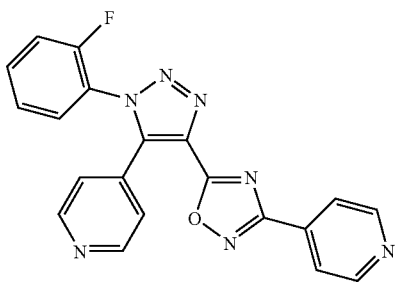

The title compound was prepared following procedure described for Example 40, but starting from Intermediate 17 (200 mg; 0.64 mmol; 1 eq.) and N'-hydroxypyridine-4-carboximidamide (96.6 mg; 0.70 mmol; 1.1 eq.). The resulting crude product was recrystallized in iPr$_2$O/ACN/MeOH mixture 10/1/1, affording Example 41 as white solid. $^1$H NMR: (DMSO-d$_6$, 300 MHz) δ 8.87 (dd, J=4.6; 1.6 Hz, 2H), 8.77 (dd, J=4.6; 1.5 Hz, 2H), 7.97-7.89 (m, 3H), 7.79-7.69 (m, 1H), 7.63 (dd, J=4.5; 1.6 Hz, 2H), 7.57-7.47 (m, 2H). LC/MS: 386.3 (M+H)$^+$. HPLC (Method A) Rt 2.39 min (Purity. 99.2%)

Example 42

3-{5-[1-(2-fluorophenyl)-5-pyridin-4-yl-1H-1,2,3-triazol-4-yl]-1,2,4-oxadiazol-3-yl}pyridine

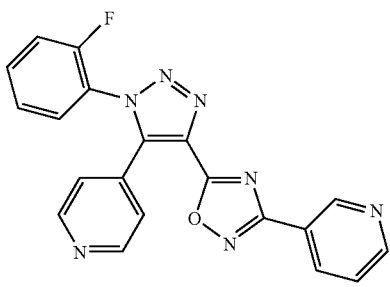

Isobutyl chloroformate (41 μl; 0.32 mmol; 1.05 eq.) was dissolved in ACN (0.5 mL) and was added dropwise into the suspension. The reaction mixture was stirred at −40° C. for 1.5 hours. Pyrid-3-yl-amidoxime (Tyger, 49.4 mg; 0.36 mmol; 1.2 eq.) was dissolved in ACN (4 mL) and THF (1 mL) and was added to the reaction mixture. The reaction was slowly allowed to warm up. After 2 hours the solvents were evaporated and the residue was taken into anhydrous ACN (2 ml) and Py (2 ml). The suspension was heated in MW at 150° C. for 15 min. The solvents were evaporated and the residue was taken in water (20 mL). The product was extracted with DCM (3×20 mL). The combined organic layers were washed with brine, dried over MgSO$_4$ and evaporated. The resulting crude product was purified by flash chromatography (SiO$_2$: 10 g; cyclohexane/EtOAc gradient from 90/10 till 20/80). It was then recrystallized in isopropanol, affording Example 42 as a white solid. $^1$H NMR: (DMSO-d$_6$, 300 MHz) δ 9.17 (dd, J=2.3; 0.8 Hz, 1H), 8.85 (dd, J=4.9; 1.7 Hz, 1H), 8.76 (dd, J=4.3; 1.7 Hz, 2H), 8.40-8.34 (m, 1H), 7.93 (dt, J=7.6; 1.5 Hz, 1H), 7.79-7.60 (m, 4H), 7.57-7.48 (m, 2H). LC/MS: 386.3 (M+H)$^+$. HPLC (Method A) Rt 2.54 min (Purity: 97.1%).

Example 43

5-{5-[1-(2-fluorophenyl)-5-pyridin-4-yl-1H-1,2,3-triazol-4-yl]-1,2,4-oxadiazol-3-yl}-1H-indole

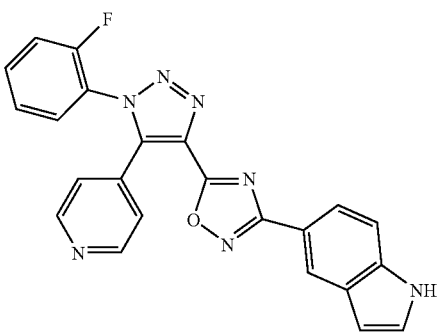

The title compound was prepared following procedure described for Example 40, but starting from Intermediate 17 (200 mg; 0.64 mmol; 1 eq.) and Intermediate 20 (123.41 mg; 0.70 mmol; 1.10 eq.). The resulting crude product was purified by flash chromatography (SiO$_2$: 10 g; cyclohexane/EtOAc gradient from 90/10 till 30/70). It was then recrystallized from isopropanol, affording Example 43 as an off-white solid. $^1$H NMR (DMSO-d$_6$) δ 11.50 (s, 1H), 8.77 (dd, J=4.5; 1.7 Hz, 2H), 8.27-8.23 (m, 1H), 7.92 (dt, J=7.7; 1.6 Hz, 1H), 7.79-7.69 (m, 2H), 7.66-7.47 (m, 6H), 6.66-6.61 (m, 1H). LC/MS: 424.3 (M+H)$^+$; 422.3 (M−H)$^−$. HPLC (Method A) Rt 3.72 min (Purity: 99.3%).

Example 44

3-(2,5-difluorophenyl)-5-[1-(2-fluorophenyl)-5-(2-methoxyethyl)-1H-1,2,3-triazol-4-yl]-1,2,4-oxadiazole

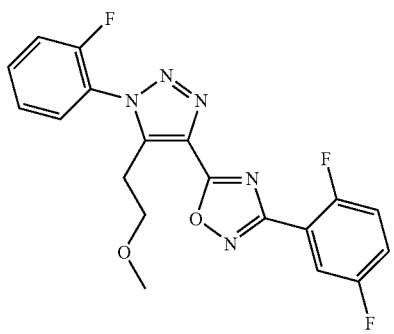

The title compound was prepared following procedure described for Example 13, but starting from Intermediate 18 (79.6 mg; 0.3 mmol; 1 eq) and 2,5-difluoro-N'-hydroxybenzenecarboximidamide (JRD-Fluoro, 62 mg; 0.36 mmol; 1.2 eq.). The solvents were evaporated and the residue was dissolved in DCM and washed with brine. Aqueous phase was extracted with DCM. Combined organic phases were dried over MgSO$_4$, affording the crude product, which was purified by flash chromatography (SiO$_2$: 10 g; cyclohexane/EtOAc gradient from 90/10 to 30/70). The resulting solid was recrystallized from iPrOH and dried under vacuum, affording Example 44 as a white solid. $^1$H NMR (DMSO-d$_6$) δ 8.00-7.92 (m, 1H), 7.89-7.78 (m, 2H), 7.74-7.53 (m, 4H), 3.60 (t, J=6.2 Hz, 2H), 3.39-3.31 (m, 2H), 3.06 (s, 3H). LC/MS: 402.2 (M+H)$^+$. HPLC (Method A) Rt 4.90 min (Purity: 99.2%).

Example 45

2-{5-[1-(2-fluorophenyl)-5-pyridin-4-yl-1H-1,2,3-triazol-4-yl]-1,2,4-oxadiazol-3-yl}pyridine

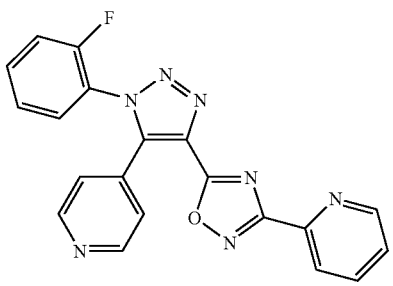

The title compound was prepared following procedure described for Example 40, but starting from Intermediate 17 (200 mg; 0.64 mmol; 1 eq.) and N'-hydroxypyridine-2-carboximidamide (96.6 mg; 0.70 mmol; 1.1 eq.). The resulting crude product was taken into DCM and washed with water and brine. The organic phase was dried over MgSO$_4$, filtrated and evaporated. The crude product was then recrystallized from isopropanol, affording Example 45 as a white solid. $^1$H NMR: (DMSO-d$_6$, 300 MHz) δ 8.84-8.79 (m, 1H), 8.76 (dd, J=4.5; 1.6 Hz, 2H), 8.13-8.01 (m, 2H), 7.97-7.88 (m, 1H), 7.79-7.59 (m, 4H), 7.57-7.46 (m, 2H). LC/MS: 386.3 (M+H)$^+$. HPLC (Method A) Rt 2.84 min (Purity: 97.3%).

Example 46

3-{5-[1-(2-fluorophenyl)-5-(2-methoxyethyl)-1H-1,2,3-triazol-4-yl]-1,2,4-oxadiazol-3-yl}pyridine

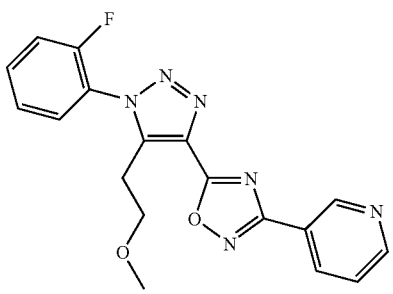

To a solution of Intermediate 18 (80 mg; 0.3 mmol) in anhydrous ACN (2 mL) was added 1-ethyl-3-(3-dimethylaminopropyl)carbodiimide hydrochloride (EDC) (80.5 mg; 0.42 mmol) followed by N'-hydroxynicotinimidamide (Tyger, 49 mg; 0.36 mmol) in a MW vial. The mixture stirred at RT for 18 h. Anhydrous pyridine (2 mL) was added. The reaction vessel was sealed and heated at 150° C. for 15 min in a microwave reactor. This reaction was repeated and the two reactions were combined for workup. The solvents were evaporated and H$_2$O (10 mL) added. The solid was removed by filtration, washed with water, triturated with isopropanol and dried to give Example 46 as an off-white solid. $^1$H NMR: (CDCl$_3$, 400 MHz) δ 9.42 (1H, d, J=1.5 Hz), 8.79 (1H, dd, J=5.1, 1.5 Hz), 8.48 (1H, dt, 8.1, 2.0 Hz), 7.67-7.55 (2H, m), 7.47 (1H, dd, J=8.1, 5.1 Hz), 7.43-7.33 (2H, m), 3.65 (2H, t, J=6.1 Hz), 3.37 (2H, t, J=6.1 Hz), 3.16 (3H, s). LC/MS (Method C): 367 (M+H)$^+$. HPLC (Method F) Rt 3.19 min (Purity: 94.0%).

Example 47

3-{5-[1-(2-fluorophenyl)-5-(methoxymethyl)-1H-1,2,3-triazol-4-yl]-1,2,4-oxadiazol-3-yl}pyridine

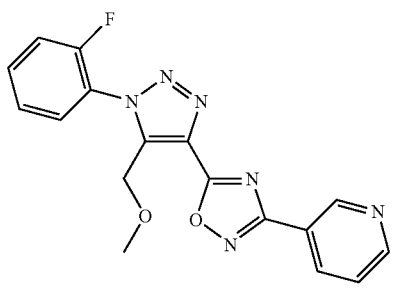

To a solution of Intermediate 11 (75 mg; 0.3 mmol) in anhydrous ACN (2 mL) was added 1-ethyl-3-(3-dimethylaminopropyl)carbodiimide hydrochloride (EDC) (81 mg; 0.42 mmol) followed by N'-hydroxynicotinimidamide (Tyger, 49 mg; 0.36 mmol) in a MW vial. The mixture stirred at RT for 18 h. Anhydrous pyridine (2 mL) was added. The reaction vessel was sealed and heated at 150° C. for 15 min in the microwave. The solvents were evaporated and the residue was dissolved in DCM and washed with water and brine. The organic phase was passed through a hydrophobic frit and evaporated affording a solid which was triturated with isopropanol and dried to give Example 47 as a white solid. $^1$H NMR: (CDCl$_3$, 400 MHz) δ 9.43 (1H, s), 8.79 (1H, d, J=4.8 Hz), 8.49 (1H, d, J=7.9 Hz), 7.62 (2H, t, J=7.1 Hz), 7.48 (1H, dd, J=8.0, 4.9 Hz), 7.42-7.33 (2H, m), 4.98 (2H, s), 3.31 (3H, s). LC/MS (Method C): 353 (M+H)$^+$. HPLC (Method F) Rt 3.32 min (Purity: 99.0%).

Example 48

4-{1-(2-fluorophenyl)-4-[3-(4-methoxyphenyl)-1,2,4-oxadiazol-5-yl]-1H-1,2,3-triazol-5-yl}pyridine

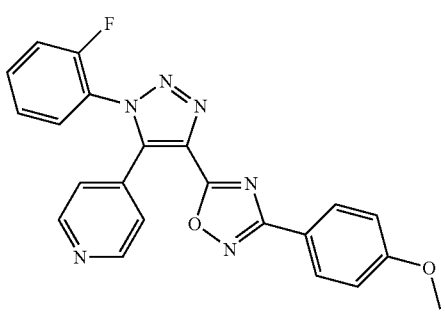

In a microwave vial, Intermediate 17 (209 mg; 0.67 mmol) was suspended in toluene (2 mL) and N'-hydroxy-4-methoxybenzimidamide (Acros; 102 mg; 0.74 mmol) was added followed by potassium carbonate (123 mg; 0.74 mmol). The MW vial was sealed and the suspension was heated to 180° C. for 15 min in a microwave reactor. The reaction mixture was cooled down to room temperature, diluted with DCM and washed with water and brine. The organic phase was passed through a hydrophobic frit and evaporated affording a solid which was triturated with methanol. The solid was dried to give Example 48 as an off-white solid (218 mg; 79%). $^1$H NMR: (CDCl$_3$, 400 MHz) δ 8.73-8.70 (2H, m), 8.06-8.01 (2H, m), 7.65-7.51 (2H, m), 7.40-7.34 (3H, m), 7.21-7.15 (1H, m), 7.01-6.97 (2H, m), 3.88 (3H, s); LC/MS (Method C): 415 (M+H)$^+$. HPLC (Method E) Rt 3.84 min (Purity: 97.8%).

Example 49

3-(2-fluorophenyl)-5-[1-(2-fluorophenyl)-5-(2-methoxyethyl)-1H-1,2,3-triazol-4-yl]-1,2,4-oxadiazole

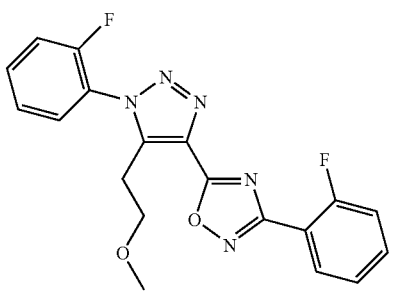

To a solution of Intermediate 18 (80 mg; 0.3 mmol) in anhydrous ACN (2 mL) was added 1-ethyl-3-(3-dimethylaminopropyl)carbodiimide hydrochloride (EDC) (80.5 mg; 0.42 mmol) followed by Intermediate 4 (55.5 mg; 0.36 mmol) in a MW vial. The mixture stirred at RT for 18 h. Anhydrous pyridine (2 mL) was added. The reaction vessel was sealed and heated at 150° C. for 15 min in the microwave. This reaction was repeated and the two reactions were combined for workup. The solvents were evaporated and the solid was triturated with water and isopropanol and dried to give Example 49 as an off-white solid. $^1$H NMR: (CDCl$_3$, 400 MHz) δ 8.20 (1H, app td, J=7.6, 1.5 Hz), 7.66-7.50 (3H, m), 7.42-7.24 (4H, m), 3.65 (2H, t, J=6.1 Hz), 3.36 (2H, t, J=6.1 Hz), 3.15 (3H, s); LC/MS (Method C): 384 (M+H)$^+$. HPLC (Method F) Rt 3.84 min (Purity: 96.7%).

Example 50

5-[1-(2-fluorophenyl)-5-(methoxymethyl)-1H-1,2,3-triazol-4-yl]-3-(2-methoxyphenyl)-1,2,4-oxadiazole

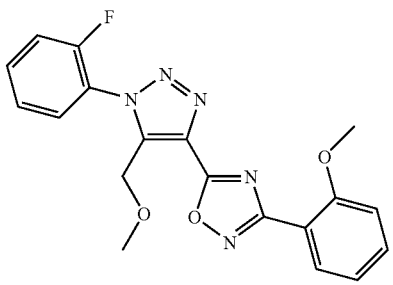

The title compound was prepared following the procedure described for Example 49, but starting from Intermediate 11 (75 mg; 0.3 mmol) and N'-hydroxy-2-methoxybenzimidamide (Enamine, 60 mg; 0.36 mmol), to give Example 50 as an off-white solid. $^1$H NMR: (CDCl$_3$, 400 MHz) δ 8.19 (1H, dd, J=7.6, 1.5 Hz), 7.65-7.58 (2H, m), 7.55-7.49 (1H, m), 7.42-7.32 (2H, m), 7.15-7.08 (2H, m), 4.98 (2H, s), 4.03 (3H, s), 3.29 (3H, s); LC/MS (Method C): 382 (M+H)$^+$. HPLC (Method F) Rt 3.68 min (Purity: 98.9%).

Example 51

4-{1-(2-fluorophenyl)-4-[3-(3-methoxyphenyl)-1,2,4-oxadiazol-5-yl]-1H-1,2,3-triazol-5-yl}pyridine

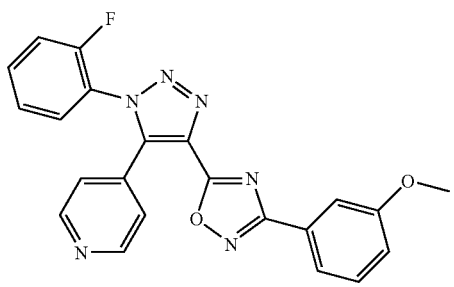

In a microwave vial, Intermediate 17 (209 mg; 0.67 mmol) was suspended in toluene (2 mL) and N'-hydroxy-3-methoxybenzimidamide (Aurora, 111 mg; 0.67 mmol) was added followed by potassium carbonate (102 mg; 0.74 mmol). The MW vial was sealed and the suspension was heated to 180° C. for 15 min. The reaction mixture was cooled down to room temperature, diluted with DCM and washed with water and brine. The organic phase was passed through a hydrophobic frit and evaporated affording a solid which was triturated with isopropanol. The solid was dried to give Example 51 as an off-white solid. $^1$H NMR: (CDCl$_3$, 400 MHz) δ 8.72 (2H, dd, J=4.8, 1.5 Hz), 7.71-7.66 (1H, m), 7.64-7.51 (3H, m), 7.42-7.33 (4H, m), 7.23-7.14 (1H, m), 7.07 (1H, dd, J=8.3, 2.6 Hz), 3.87 (3H, s). LC/MS (Method C): 415 (M+H)$^+$. HPLC (Method F) Rt 3.69 min (Purity: 97.8%).

Example 52

4-(1-(2-fluorophenyl)-4-{3-[3-(methylsulfonyl)phenyl]-1,2,4-oxadiazol-5-yl}-1H-1,2,3-triazol-5-yl)pyridine

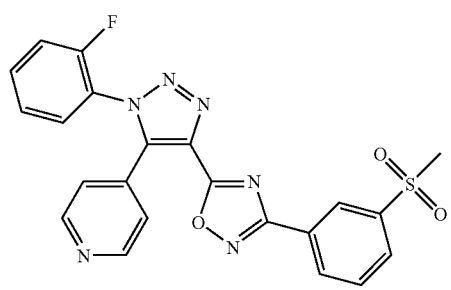

In a microwave vial, Intermediate 17 (209 mg; 0.67 mmol) was suspended in toluene (2 mL) and Intermediate 40 (144 mg; 0.74 mmol) was added followed by potassium carbonate (123 mg; 0.74 mmol). The MW vial was sealed and the suspension was heated to 180° C. for 25 min in a microwave reactor. The reaction mixture was cooled down to room temperature, diluted with DCM and washed with water. The organic phase was passed through a hydrophobic frit and evaporated affording a solid which was triturated with isopropanol. The solid was dried to give Example 52 as an off-white solid. $^1$H NMR: (CDCl$_3$, 400 MHz) δ 8.76-8.73 (2H, m, 2), 8.70 (1H, t, J=1.5 Hz), 8.38 (1H, dt, J=7.6, 1.5 Hz), 8.12 (1H, dt, J=8.1, 1.5 Hz), 7.73 (1H, t, J=8.1 Hz), 7.66-7.55 (2H, m), 7.42-7.35 (3H, m), 7.23-7.17 (1H, m), 3.12 (3H, s); LC/MS (Method C): 463 (M+H)$^+$. HPLC (Method F) Rt 3.25 min (Purity: 96.5%).

Example 53

3-(2-fluorophenyl)-5-[1-(2-fluorophenyl)-5-(tetrahydrofuran-2-yl)-1H-1,2,3-triazol-4-yl]-1,2,4-oxadiazole

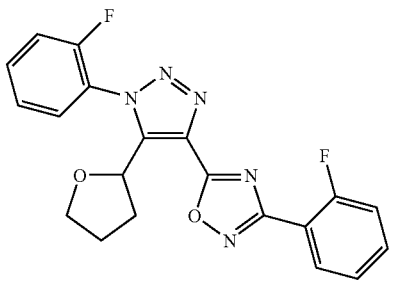

The title compound was prepared following the procedure described for Example 47, but starting from Intermediate 23 (166 mg; 0.6 mmol) and Intermediate 4 (111 mg; 0.72 mmol), to give Example 53 as an off-white solid. $^1$H NMR: (CDCl$_3$, 400 MHz) δ 8.17 (1H, td, J=7.4, 1.8 Hz), 7.60-7.47 (3H, m), 7.37-7.20 (4H, m), 5.54 (1H, t, J=7.9 Hz), 3.73 (1H, td, J=7.7, 5.5 Hz), 3.52-3.42 (1H, m), 2.57-2.46 (1H, m), 2.16-2.03 (1H, m), 2.02-1.88 (2H, m); LC/MS (Method C): 396 (M+H)$^+$. HPLC (Method F) Rt 3.94 min (Purity: 95.9%).

Example 54

3-{5-[1-(2-fluorophenyl)-5-(tetrahydrofuran-2-yl-1H-1,2,3-triazol-4-yl]-1,2,4-oxadiazol-3-yl}pyridine

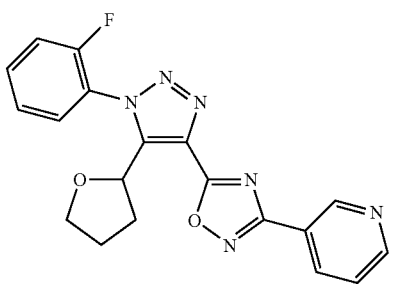

The title compound was prepared following the procedure described for Example 47, but starting from Intermediate 23 (166 mg; 0.6 mmol) and N'-hydroxynicotinimidamide (Tyger, 98 mg; 0.72 mmol), to give Example 54 as an off-white solid. $^1$H NMR: (CDCl$_3$, 400 MHz) δ 9.41 (1H, dd, J=2.2, 0.9 Hz), 8.78 (1H, dd, J=4.9, 1.7 Hz), 8.47 (1H, dt, J=7.9, 1.9 Hz), 7.64-7.52 (2H, m), 7.48 (1H, ddd, J=7.9, 4.8, 0.8 Hz), 7.41-7.28 (2H, m), 5.59 (1H, t, J=7.8 Hz), 3.77 (1H, td, J=7.8, 5.3 Hz), 3.50 (1H, q, J=7.5 Hz), 2.60-2.49 (1H, m), 2.19-1.91 (3H, m). LC/MS (Method C): 379 (M+H)$^+$. HPLC (Method F) Rt 3.43 min (Purity: 98.1%).

Example 55

4-[4-[3-(1-acetylpiperidin-4-yl)-1,2,4-oxadiazol-5-yl]-1-(2-fluorophenyl)-1H-1,2,3-triazol-5-yl]pyridine

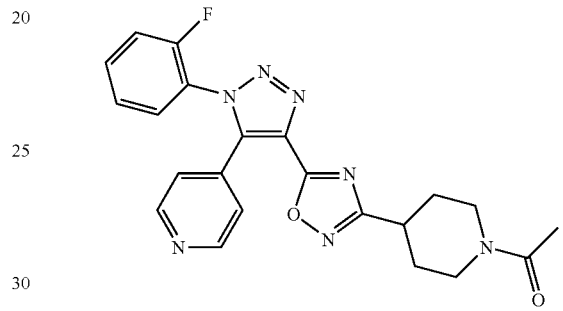

Step 1: tert-butyl 4-{5-[1-(2-fluorophenyl)-5-pyridin-4-yl-1H-1,2,3-triazol-4-yl]-1,2,4-oxadiazol-3-yl}piperidine-1-carboxylate The title compound was prepared following the procedure described for Example 51, but starting from Intermediate 52 (179 mg; 0.737 mmol). This reaction was performed four times, and the reaction mixtures were combined for workup, to give the title compound as a white solid. $^1$H NMR: (CDCl$_3$, 400 MHz) δ 8.68 (2H, dd, J=4.5, 1.7 Hz), 7.60-7.51 (2H, m), 7.36 (1H, t, J=7.8 Hz), 7.26 (3H, m), 7.20-7.14 (1H, m), 4.11 (2H, m), 3.07-2.89 (3H, m), 2.02 (2H, d, J=13.3 Hz), 1.85-1.73 (2H, m), 1.47 (9H, s). LC/MS (Method C): 492 (M+H)$^+$. HPLC (Method F) Rt 3.67 min (Purity: 95.3%).

Step 2: 4-[1-(2-fluorophenyl)-4-(3-piperidin-4-yl-1,2,4-oxadiazol-5-yl)-1H-1,2,3-triazol-5-yl]pyridine hydrochloride To a suspension of tert-butyl 4-(5-(1-(2-fluorophenyl)-5-(pyridin-4-yl)-1H-1,2,3-triazol-4-yl)-1,2,4-oxadiazol-3-yl) piperidine-1-carboxylate, obtained in Step 1, (601 mg; 1.22 mmol) in MeOH (30 mL) was added HCl (3 M, 30 mL) and the mixture was heated at 50° C. for 5 hours. The solvent was removed in vacuo affording the title compound as a white solid (462 mg; 96%). $^1$H NMR: (DMSO-d$_6$, 400 MHz) δ 9.38-9.36 (1H, m), 9.26-9.24 (1H, m), 8.88 (2H, d, J=5.4 Hz), 7.94-7.84 (3H, m), 7.76-7.69 (1H, m), 7.55-7.46 (2H, m), 3.34-3.24 (3H, m), 3.06 (2H, q, J=11.1 Hz), 2.14 (2H, d, J=13.8 Hz), 2.04-1.90 (2H, m). LC/MS (Method C): 392 (M+H)$^+$. HPLC (Method E) Rt 2.14 min (Purity: 97.5%).

Step 3: 4-[4-[3-(1-acetylpiperidin-4-yl)-1,2,4-oxadiazol-5-yl]-1-(2-fluorophenyl)-1H-1,2,3-triazol-5-yl]pyridine To a suspension of 5-(1-(2-fluorophenyl)-5-(pyridin-4-yl)-1H-1,2,3-triazol-4-yl)-3-(piperidin-4-yl)-1,2,4-oxadiazole hydrochloride, obtained in Step 2, (100 mg; 0.23 mmol) in DCM (1 mL) was added diisopropylethylamine (122 μL, 0.7 mmol) and acetyl chloride (18 μL, 0.26 mmol) at 0° C. and the mixture was stirred for 20 minutes. The mixture was diluted with DCM (10 mL) and treated with saturated sodium hydrogen carbonate (10 mL). The aqueous layer was extracted with DCM (3×20 mL), the combined organics were dried (MgSO$_4$) and the solvent removed in vacuo. The residue was purified by flash chromatography on a Biotage 25+S column, eluting with petrol containing increasing amounts of EtOAc to give Example 55 as a yellow oil. $^1$H NMR: (CDCl$_3$, 400 MHz) δ 8.69 (2H, d, J=4.9 Hz), 7.62-7.52 (2H, m), 7.41-7.25 (3H, m), 7.17 (1H, t, J=9.0 Hz), 4.52 (1H, d, J=13.5 Hz), 3.87 (1H, d, J=13.4 Hz), 3.31-3.19 (1H, m), 3.12 (1H, tt, J=10.8, 3.9 Hz), 2.98-2.82 (1H, m), 2.16-2.04 (4H, m), 1.93-1.69 (3H, m). LC/MS (Method C): 434 (M+H)$^+$. HPLC (Method F) Rt 2.79 min (Purity: 92.5%).

Example 56

4-{5-[1-(2-fluorophenyl)-5-(tetrahydrofuran-2-yl)-1H-1,2,3-triazol-4-yl]-1,2,4-oxadiazol-3-yl}pyridine

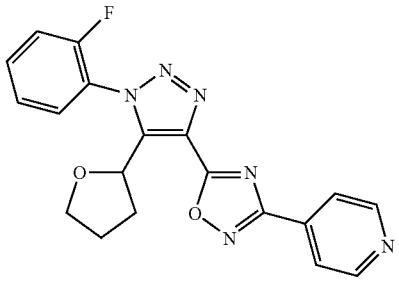

The title compound was prepared following the procedure described for Example 47, but starting from Intermediate 23 (166 mg; 0.6 mmol) and N'-hydroxyisonicotinimidamide (Fl-rochem, 98 mg; 0.72 mmol), to give Example 56 as an off-white solid. $^1$H NMR: (CDCl$_3$, 400 MHz) δ 8.82 (2H, dd, J=4.5, 1.6 Hz), 8.05 (2H, dd, J=4.5, 1.6 Hz), 7.65-7.53 (2H, m), 7.39-7.30 (2H, m), 5.58 (1H, t, J=7.8 Hz), 3.77 (1H, td, J=7.8, 5.3 Hz), 3.56-3.46 (3H, m), 2.62-2.49 (1H, m), 2.18-1.91 (3H, m), 1.53-1.37 (1H, m). LC/MS (Method C): 379 (M+H)$^+$. HPLC (Method F) Rt 3.43 min (Purity: 95.8%).

Example 57

2-{1-(2-fluorophenyl)-4-[3-(4-methoxyphenyl)-1,2,4-oxadiazol-5-yl]-1H-1,2,3-triazol-5-yl}pyridine

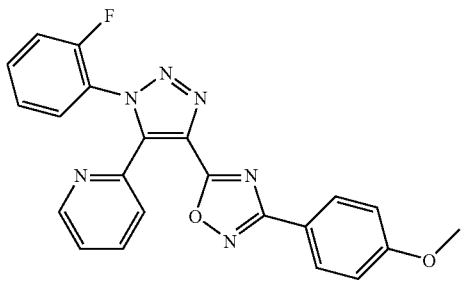

The title compound was prepared following the procedure described for Example 51, but starting from Intermediate 53 (209 mg; 0.67 mmol) and N'-hydroxy-4-methoxybenzimida-mide (Acros; 122 mg; 0.74 mmol), to give Example 57 as a light brown solid. $^1$H NMR: (CDCl$_3$, 400 MHz) δ 8.49 (1H, ddd, J=4.8, 1.7, 1.0 Hz), 8.10-8.05 (2H, m), 7.99 (1H, dt, J=7.9, 1.0 Hz), 7.89-7.81 (1H, m), 7.70 (1H, td, J=7.6, 1.7 Hz), 7.52-7.45 (1H, m), 7.37-7.32 (2H, m), 7.13-7.05 (1H, m), 7.02-6.97 (2H, m), 3.88 (3H, s). LC/MS (Method C): 415 (M+H)$^+$. HPLC (Method F) Rt 3.81 min (Purity: 90.7%).

Example 58

5-[5-benzyl-1-(2-fluorophenyl)-1H-1,2,3-triazol-4-yl]-3-(2-fluorophenyl)-1,2,4-oxadiazole

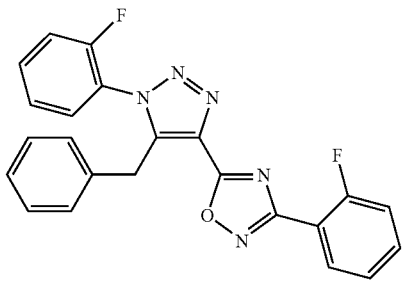

The title compound was prepared following the procedure described for Example 47, but starting from Intermediate 24 (178 mg; 0.6 mmol) and Intermediate 4 (110 mg; 0.72 mmol), to give Example 58 as an off-white solid. $^1$H NMR: (CDCl$_3$, 400 MHz) δ 8.20 (1H, td, J=7.4, 1.8 Hz), 7.60-7.49 (2H, m), 7.33-7.17 (5H, m), 7.15-7.09 (3H, m), 6.90-6.86 (2H, m), 4.55 (2H, s). LC/MS (Method C): 416 (M+H)$^+$. HPLC (Method F) Rt 4.15 min (Purity: 94.6%).

Example 59

3-(2-fluorophenyl)-5-[1-(2-fluorophenyl)-5-(tetrahydro-2H-pyran-4-yl)-1H-1,2,3-triazol-4-yl]-1,2,4-oxadiazole

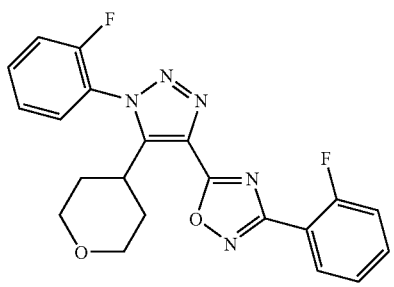

The title compound was prepared following the procedure described for Example 47, but starting from Intermediate 25 (174 mg; 0.6 mmol) and Intermediate 4 (111 mg; 0.72 mmol), to give Example 59 as a white solid. $^1$H NMR: (CDCl$_3$, 400 MHz) δ 8.26-8.18 (1H, m), 7.71-7.64 (1H, m), 7.58-7.50 (2H, m), 7.49-7.26 (4H, m), 4.04 (2H, dd, J=11.6, 4.2 Hz), 3.42

(3H, t, J=11.9 Hz), 2.44-2.31 (2H, m), 1.66 (2H, d, J=12.8 Hz). LC/MS (Method C): 410 (M+H)+. HPLC (Method F) Rt 3.68 min (Purity: 99.3%).

Example 60

4-(3-{5-[1-(2-fluorophenyl)-5-pyridin-4-yl-1H-1,2,3-triazol-4-yl]-1,2,4-oxadiazol-3-yl}benzyl)morpholine

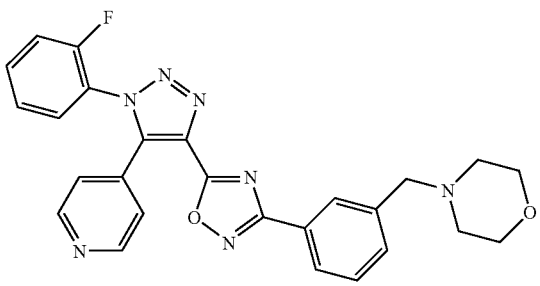

The title compound was prepared following the procedure described for Example 52, but starting from Intermediate 17 (209 mg; 0.67 mmol) and N'-hydroxy-3-(morpholinomethyl)benzimidamide (Aurora, 174 mg; 0.74 mmol) to give Example 60 as an off-white solid. $^1$H NMR: (CDCl$_3$, 400 MHz) δ 8.74-8.70 (2H, m), 8.09 (1H, s), 7.98 (1H, d, J=7.6 Hz), 7.65-7.49 (3H, m), 7.45 (1H, t, J=7.6 Hz), 7.40-7.35 (3H, m), 7.19 (1H, t, J=9.6 Hz), 3.72 (4H, t, J=4.5 Hz), 3.56 (2H, s), 2.47 (4H, t, J=4.5 Hz); LC/MS (Method C): 484 (M+H)+. HPLC (Method F) Rt 3.44 min (Purity: 98.1%)

Example 61

4-(1-(2-fluorophenyl)-4-{3-[3-(1H-1,2,4-triazol-1-ylmethyl)phenyl]-1,2,4-oxadiazol-5-yl}-1H-1,2,3-triazol-5-yl)pyridine

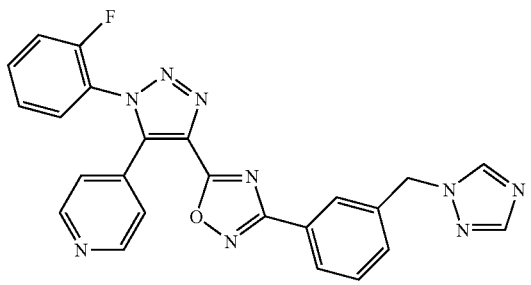

The title compound was prepared following the procedure described for Example 52, but starting from Intermediate 17 (209 mg; 0.67 mmol) and Intermediate 41 (161 mg; 0.74 mmol) to give Example 61 as an off-white solid (221 mg; 71%). $^1$H NMR: (CDCl$_3$, 400 MHz) δ 8.74-8.71 (2H, m), 8.13 (1H, s), 8.08 (1H, d, J=7.6 Hz), 8.05 (1H, s), 8.00 (1H, s), 7.64-7.53 (2H, m), 7.51 (1H, t, J=8.1 Hz), 7.43-7.36 (2H, m), 7.36-7.33 (2H, m), 7.19 (1H, t, J=9.6 Hz), 5.42 (2H, s); LC/MS (Method C): 466 (M+H)+. HPLC (Method F) Rt 3.09 min (Purity: 97.6%).

Example 62

3-(2,5-difluorophenyl)-5-[1-(2-fluorophenyl)-5-(tetrahydro-2H-pyran-4-yl-1H-1,2,3-triazol-4-yl]-1,2,4-oxadiazole

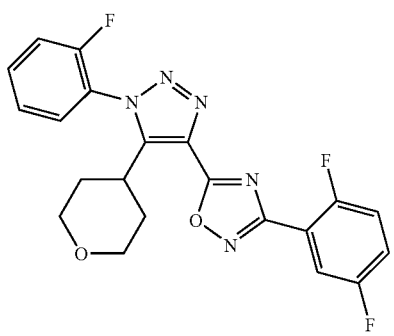

The title compound was prepared following the procedure described for Example 47, but starting from Intermediate 25 (174 mg; 0.6 mmol) and 2,5-difluoro-N'-hydroxybenzimidamide (JRD-Fluorochemical, 123 mg; 0.72 mmol), to give Example 62 as a white solid. $^1$H NMR: (CDCl3, 400 MHz) δ 7.94-7.89 (1H, m), 7.71-7.64 (1H, m), 7.52 (1H, td, J=7.5, 1.8 Hz), 7.46-7.36 (2H, m), 7.27-7.20 (2H, m), 4.04 (2H, dd, J=11.7, 4.3 Hz), 3.47-3.36 (3H, m), 2.32 (2H, qd, J=12.5, 4.4 Hz), 1.70-1.62 (2H, m). LC/MS (Method C): 428 (M+H)+. HPLC (Method F) Rt 3.78 min (Purity: 99.4%).

Example 63

3-(2,5-difluorophenyl)-5-[1-(2-fluorophenyl)-5-isopropyl-1H-1,2,3-triazol-4-yl]-1,2,4-oxadiazole

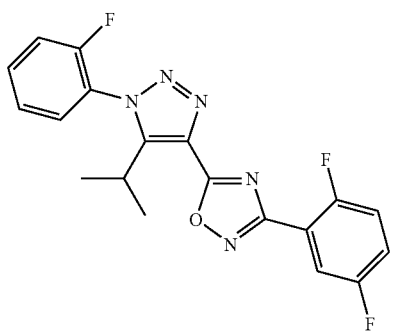

The title compound was prepared following the procedure described for Example 47, but starting from Intermediate 26 (149 mg; 0.6 mmol) and 2,5-difluoro-N'-hydroxybenzimidamide (JRD-Fluorochemical, 123 mg; 0.72 mmol), to give Example 63 as a white solid. $^1$H NMR: (CDCl3, 400 MHz) δ 7.95-7.89 (1H, m), 7.68-7.61 (1H, m), 7.52 (1H, td, J=7.5, 1.8 Hz), 7.43-7.32 (2H, m), 7.26-7.20 (2H, m), 3.41-3.32 (1H, m), 1.45 (6H, d, J=7.1 Hz). LC/MS (Method C): 386 (M+H)+. HPLC (Method F) Rt 4.10 min (Purity: 99.4%).

Example 64

4-{5-[1-(2-fluorophenyl)-5-pyridin-4-yl-1H-1,2,3-triazol-4-yl]-1,2,4-oxadiazol-3-yl}phenol

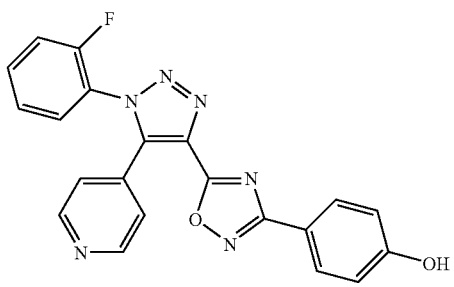

To a solution of Example 48 (120 mg; 0.29 mmol) in toluene (9 mL) was added AlCl₃ (280 mg; 2.1 mmol) and the mixture heated to 60° C. for 5 hours. The reaction was quenched by the addition of aqueous 2M HCl until a significant precipitate was observed. The mixture was allowed to stir for 1 hour and stand for 18 hours and the solid removed by filtration and dried to give Example 64 as a white solid. ¹H NMR: (CDCl₃, 400 MHz) δ 10.19 (1H, s), 8.72-8.69 (2H, m), 7.87 (1H, td, J=7.6, 1.5 Hz), 7.82-7.77 (2H, m), 7.72-7.65 (1H, m), 7.58-7.54 (2H, m), 7.47 (2H, t, J=8.6 Hz), 6.95-6.90 (2H, m); LC/MS (Method C): 401 (M+H)+. HPLC (Method F) Rt 3.05 min (Purity: 97.1%).

Example 65

5-{5-[1-(2-fluorophenyl)-5-(methoxymethyl)-1H-1,2,3-triazol-4-yl]-1,2,4-oxadiazol-3-yl}-1H-indole

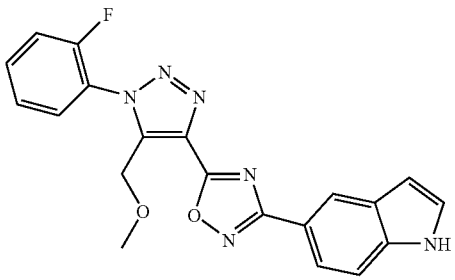

To a solution of Intermediate 11 (75 mg; 0.3 mmol) in anhydrous ACN (2 mL) was added 1-ethyl-3-(3-dimethylaminopropyl)carbodiimide hydrochloride (EDC) (80.5 mg; 0.42 mmol) followed by Intermediate 20 (63 mg; 0.36 mmol) in a MW vial. The mixture stirred at RT for 18 h. Anhydrous pyridine (2 mL) was added. The reaction vessel was sealed and heated at 150° C. for 15 min in a microwave reactor. This reaction was performed two times. Combined reaction mixtures were evaporated and H₂O (10 mL) and DCM (10 mL) added. The mixture was passed through a hydrophobic frit and the solvent removed in vacuo. The residue was purified by flash chromatography on a Biotage 25+S column, eluting with petrol containing increasing amounts of EtOAc to give Example 65 as an off-white solid. ¹H NMR: (CDCl₃, 400 MHz) δ 8.55 (1H, s), 8.35 (1H, br s), 8.06 (1H, dd, J=8.5, 1.4 Hz), 7.65-7.59 (2H, m), 7.52 (1H, d, J=8.5 Hz), 7.42-7.34 (2H, m), 7.30 (1H, t, J=2.8 Hz), 6.71-6.68 (1H, m), 5.04 (2H, s), 3.32 (3H, s). LC/MS (Method C): 391 (M+H)+. HPLC (Method F) Rt 3.67 min (Purity: 97.9%).

Example 66

2-[1-(2-fluorophenyl)-4-(3-pyridin-4-yl-1,2,4-oxadiazol-5-yl)-1H-1,2,3-triazol-5-yl]pyridine

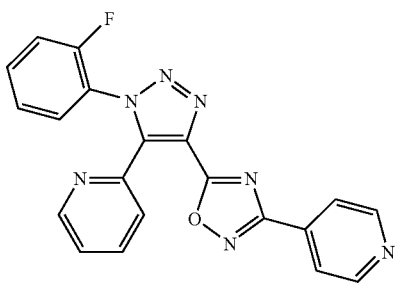

The title compound was prepared following the procedure described for Example 51, but starting from Intermediate 53 (187 mg; 0.67 mmol) and N'-hydroxyisonicotinimidamide (Flrochem, 98.7 mg; 0.72 mmol), to give Example 66 as a light brown solid. ¹H NMR: (CDCl3, 400 MHz) δ 8.82-8.78 (2H, m), 8.52 (1H, d, J=4.8 Hz), 7.99-7.85 (4H, m), 7.72-7.66 (1H, m), 7.54-7.46 (1H, m), 7.42-7.32 (2H, m), 7.12 (1H, t, J=9.2 Hz). LC/MS (Method C): 386 (M+H)+. HPLC (Method F) Rt 3.27 min (Purity: 95.2%).

Example 67

2-{1-(2-fluorophenyl)-4-[3-(2-methoxyphenyl)-1,2,4-oxadiazol-5-yl]-1H-1,2,3-triazol-5-yl}pyridine

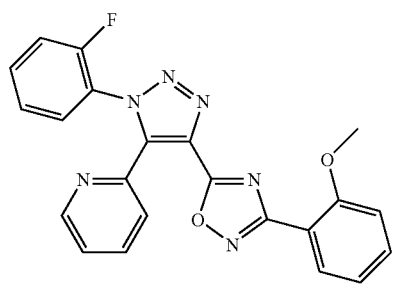

The title compound was prepared following the procedure described for Example 51, but starting from Intermediate 53 (187 mg; 0.67 mmol) and N'-hydroxy-2-methoxybenzimidamide (Enamine, 119 mg; 0.72 mmol), to give Example 67 as a brown solid. ¹H NMR: (CDCl3, 400 MHz) δ 8.48 (1H, ddd, J=4.8, 1.8, 1.0 Hz), 8.14 (1H, dd, J=7.7, 1.8 Hz), 8.00 (1H, dt, J=7.9, 1.1 Hz), 7.85 (1H, td, J=7.8, 1.8 Hz), 7.70 (1H, td, J=7.6, 1.7 Hz), 7.52-7.44 (2H, m), 7.36-7.29 (2H, m), 7.13-

7.05 (3H, m), 3.99 (3H, s). LC/MS (Method C): 415 (M+H)+. HPLC (Method F) Rt 3.62 min (Purity: 97.3%).

Example 68

5-[1-(2-fluorophenyl)-5-(methoxymethyl)-1H-1,2,3-triazol-4-yl]-3-[3-(methylsulfonyl)phenyl]-1,2,4-oxadiazole

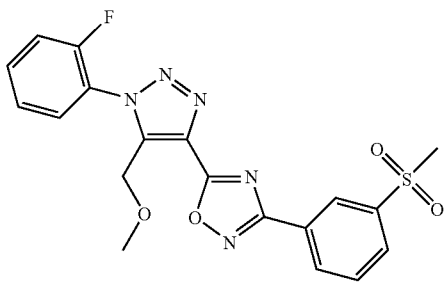

The title compound was prepared following the procedure described for Example 65, with two identical reactions combined for workup, but starting from Intermediate 11 (75 mg; 0.3 mmol) and Intermediate 40 (77 mg; 0.36 mmol). Purification by preparative HPLC gave Example 68 as a white solid. ¹H NMR: (CDCl₃, 400 MHz) δ 8.78-8.76 (1H, m), 8.53-8.48 (1H, m), 8.16-8.12 (1H, m), 7.77 (1H, t, J=7.6 Hz), 7.66-7.59 (2H, m), 7.43-7.34 (2H, m), 4.99 (2H, s), 3.31 (3H, s), 3.14 (3H, s); LC/MS (Method C): 430 (M+H)+. HPLC (Method F) Rt 3.29 min (Purity: 99.7%).

Example 69

5-[5-cyclopropyl-1-(2-fluorophenyl)-1H-1,2,3-triazol-4-yl]-3-(2,5-difluorophenyl)-1,2,4-oxadiazole

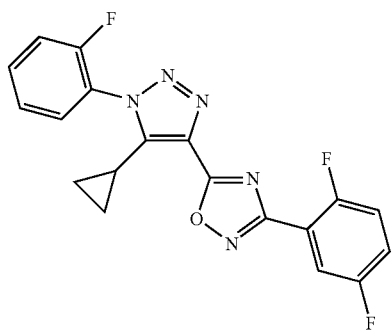

The title compound was prepared following the procedure described for Example 47, but starting from Intermediate 22 (149 mg; 0.6 mmol) and 2,5-difluoro-N'-hydroxybenzimidamide (JRD-Fluorochemical, 123 mg; 0.72 mmol), to give Example 69 as a white solid. ¹H NMR: (CDCl₃, 400 MHz) δ 7.98-7.92 (1H, m), 7.66-7.56 (2H, m), 7.43-7.33 (2H, m), 7.26-7.20 (2H, m), 2.13-2.05 (1H, m), 1.12-1.02 (2H, m), 0.91-0.84 (2H, m). LC/MS (Method C): 384 (M+H)+. HPLC (Method E) Rt 4.24 min (Purity: 99.5%).

Example 70

2-{1-(2-fluorophenyl)-4-[3-(3-methoxyphenyl)-1,2,4-oxadiazol-5-yl]-1H-1,2,3-triazol-5-yl}pyridine

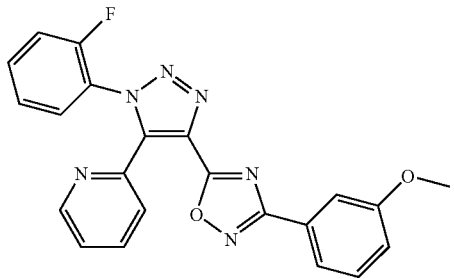

The title compound was prepared following the procedure described for Example 51, but starting from Intermediate 53 (187 mg; 0.67 mmol) and N'-hydroxy-3-methoxybenzimidamide (Aurora, 119 mg; 0.72 mmol), to give Example 70 as a white solid. ¹H NMR: (CDCl₃, 400 MHz) δ 8.51-8.48 (1H, m), 7.99 (1H, d, J=7.9 Hz), 7.87 (1H, td, J=7.8, 1.8 Hz), 7.74-7.66 (3H, m), 7.52-7.45 (1H, m), 7.42-7.29 (3H, m), 7.14-7.02 (2H, m), 3.88 (3H, s). LC/MS (Method C): 415 (M+H)+. HPLC (Method E) Rt 4.10 min (Purity: 99.3%).

Example 71

3-(2,5-difluorophenyl)-5-[1-(2-fluorophenyl)-5-(tetrahydrofuran-2-yl)-1H-1,2,3-triazol-4-yl]-1,2,4-oxadiazole

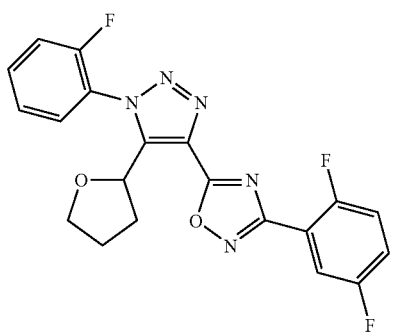

The title compound was prepared following the procedure described for Example 47, but starting from Intermediate 23 (166 mg; 0.6 mmol) and 2,5-difluoro-N'-hydroxybenzimidamide (JRD-Fluorochemical, 123 mg; 0.72 mmol), to give Example 71 as an off-white solid. ¹H NMR: (CDCl₃, 400 MHz) δ 7.93-7.87 (1H, m), 7.64-7.52 (2H, m), 7.39-7.28 (2H, m), 7.27-7.19 (2H, m), 5.56 (1H, t, J=7.9 Hz), 3.76 (1H, td, J=7.8, 5.4 Hz), 3.49 (1H, q, J=7.5 Hz), 2.58-2.49 (1H, m), 2.17-1.92 (3H, m). LC/MS (Method C): 414 (M+H)⁺. HPLC (Method E) Rt 4.19 min (Purity: 99.9%).

Example 72

4-{5-[5-cyclopentyl-1-(2-fluorophenyl)-1H-1,2,3-triazol-4-yl]-1,2,4-oxadiazol-3-yl}pyridine

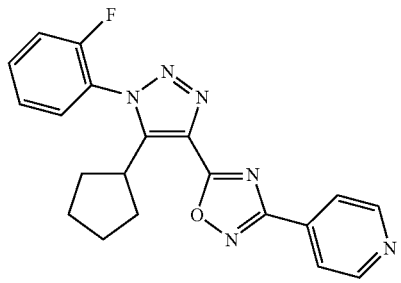

The title compound was prepared following the procedure described for Example 49, with two identical reactions combined for workup, but starting from Intermediate 21 (83 mg; 0.3 mmol) and N'-hydroxyisonicotinimidamide (Flrochem, 41 mg; 0.36 mmol) to give Example 72 as an off-white solid. ¹H NMR: (CDCl₃, 400 MHz) δ 8.83 (2H, d, J=5.2 Hz), 8.07-8.02 (2H, m), 7.68-7.61 (1H, m), 7.57-7.50 (1H, m), 7.45-7.33 (2H, m), 3.21 (1H, quintet, J=9.1 Hz), 2.22-2.09 (2H, m), 2.06-1.92 (4H, m), 1.73-1.65 (2H, m). LC/MS (Method C): 377 (M+H)⁺. HPLC (Method E) Rt 3.93 min (Purity: 97.7%).

Example 73

4-{5-[1-(2-fluorophenyl)-5-pyridin-4-yl-1H-1,2,3-triazol-4-yl]-1,2,4-oxadiazol-3-yl}benzamide

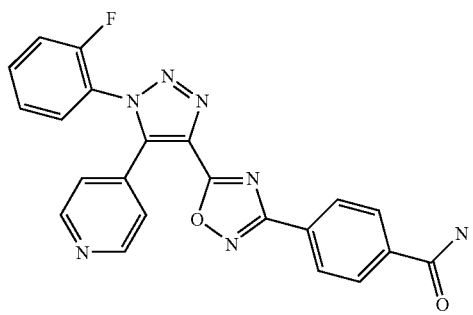

The title compound was prepared following the procedure described for Example 51, but starting from Intermediate 17 (209 mg; 0.67 mmol) and Intermediate 27 (132 mg; 0.72 mmol), to give Example 73 as an off-white solid. ¹H NMR: (DMSO-d₆, 400 MHz) δ 8.76 (2H, d, J=5.3 Hz), 8.16 (1H, s), 8.14-8.01 (3H, m), 7.92 (1H, t, J=7.7 Hz), 7.77-7.69 (1H, m), 7.66-7.45 (5H, m). LC/MS (Method C): 428 (M+H)⁺. HPLC (Method E) Rt 3.02 min (Purity: 94.6%).

Example 74 tert-butyl (4-{5-[1-(2-fluorophenyl)-5-pyridin-4-yl-1H-1,2,3-triazol-4-yl]-1,2,4-oxadiazol-3-yl}benzyl)carbamte

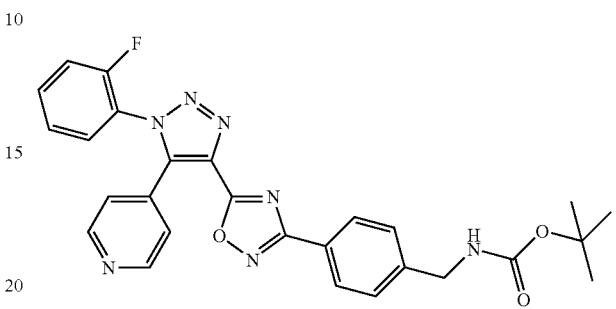

The title compound was prepared following the procedure described for Example 51, but starting from Intermediate 17 (209 mg; 0.67 mmol) and Intermediate 28 (195 mg; 0.72 mmol), to give Example 74 as an off-white solid (316 mg; 92%). ¹H NMR: (DMSO-d₆, 400 MHz) δ 8.72 (2H, dd, J=4.5, 1.7 Hz), 8.06 (2H, d, J=8.1 Hz), 7.63-7.52 (2H, m), 7.41-7.33 (4H, m), 7.22-7.15 (1H, m), 4.92 (1H, s), 4.39 (2H, d, J=6.1 Hz), 1.47 (9H, s). LC/MS (Method C): 514 (M+H)⁺. HPLC (Method F) Rt 3.63 min (Purity: 97.6%).

Example 75

3-{5-[5-benzyl-1-(2-fluorophenyl)-1H-1,2,3-triazol-4-yl]-1,2,4-oxadiazol-3-yl}pyridine

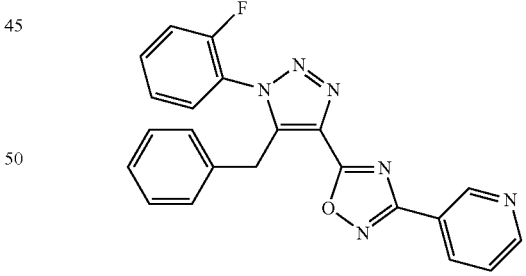

The title compound was prepared following the procedure described for Example 47, but starting from Intermediate 24 (178 mg; 0.6 mmol) and N'-hydroxynicotinimidamide (Tyger, 98 mg; 0.72 mmol), to give Example 75 as an off-white solid. ¹H NMR: (CDCl₃, 400 MHz) δ 9.41 (1H, d, J=2.1 Hz), 8.78 (1H, dd, J=4.9, 1.7 Hz), 8.46 (1H, dt, J=8.0, 2.0 Hz), 7.61-7.54 (1H, m), 7.48-7.44 (1H, m), 7.33-7.26 (1H, m), 7.28-7.19 (2H, m), 7.15-7.09 (3H, m), 6.90-6.85 (2H, m), 4.56 (2H, s). LC/MS (Method C): 399 (M+H)⁺. HPLC (Method F) Rt 3.67 min (Purity: 97.6%).

Example 76

4-{5-[1-(2-fluorophenyl)-5-(methoxymethyl)-1H-1,2,3-triazol-4-yl]-1,2,4-oxadiazol-3-yl}benzenesulfonamide

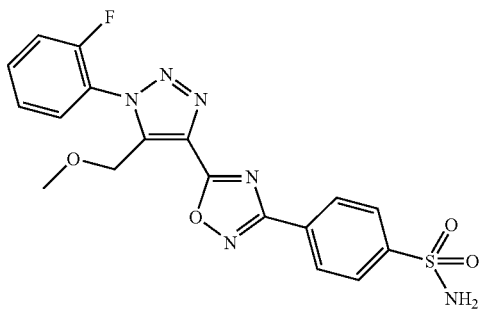

The title compound was prepared following the procedure described for Example 47, but starting from Intermediate 11 (150 mg; 0.6 mmol) and Intermediate 29 (155 mg; 0.72 mmol), to give Example 76 as an off-white solid. $^1$H NMR: (DMSO-d$_6$, 400 MHz) δ 8.41-8.35 (2H, m), 8.12-8.08 (2H, m), 7.89-7.78 (2H, m), 7.71-7.65 (1H, m), 7.62 (2H, s), 7.56 (1H, t, J=7.8 Hz), 4.99 (2H, s), 3.23 (3H, s). LC/MS (Method C): 431 (M+H)$^+$. HPLC (Method F) Rt 3.14 min (Purity: 94.1%).

Example 77

5-[5-cyclopentyl-1-(2-fluorophenyl)-1H-1,2,3-triazol-4-yl]-3-(2,5-difluorophenyl)-1,2,4-oxadiazole

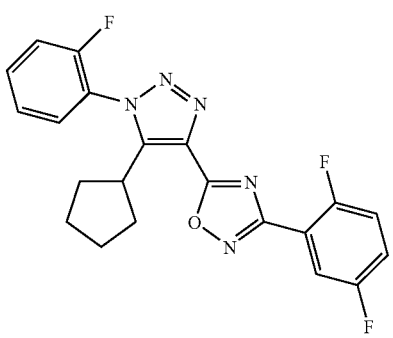

The title compound was prepared following the procedure described for Example 49, with two identical reactions combined for workup, but starting from Intermediate 21 (83 mg; 0.3 mmol) and 2,5-difluoro-N'-hydroxybenzimidamide (JRD-Fluorochemical, 62 mg; 0.36 mmol). The residue was purified by flash chromatography on a Biotage 12+M column, eluting with petrol containing increasing amounts of EtOAc. The residue was triturated with isopropanol and dried to give Example 77 as a white solid. $^1$H NMR: (CDCl$_3$, 400 MHz) δ 7.93-7.87 (1H, m), 7.67-7.61 (1H, m), 7.56-7.51 (1H, m), 7.43-7.33 (2H, m), 7.27-7.18 (2H, m), 3.19 (1H, quintet, J=9.3 Hz), 2.25-2.07 (2H, m), 2.06-1.89 (4H, m), 1.73-1.58 (2H, m). LC/MS (Method C): 412 (M+H)$^+$. HPLC (Method E) Rt 4.57 min (Purity: 97.1%).

Example 78

5-[5-cyclopentyl-1-(2-fluorophenyl)-1H-1,2,3-triazol-4-yl]-3-(2-fluorophenyl)-1,2,4-oxadiazole

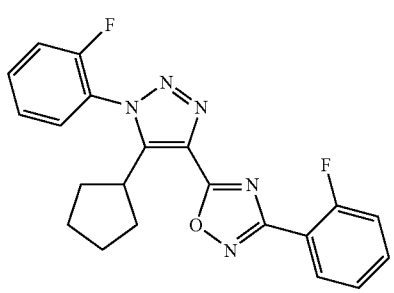

The title compound was prepared following the procedure described for Example 49, with two identical reactions combined for workup, but starting from Intermediate 21 (83 mg; 0.3 mmol) and Intermediate 4 (46 mg; 0.36 mmol) to give Example 78 as an off-white solid. $^1$H NMR: (CDCl$_3$, 400 MHz) δ 8.20 (1H, t, J=7.3 Hz), 7.67-7.59 (1H, m), 7.57-7.49 (2H, m), 7.44-7.23 (4H, m), 3.18 (1H, quintet, J=8.8 Hz), 2.2.5-2.10 (2H, m), 2.09-1.88 (4H, m), 1.71-1.59 (2H, m). LC/MS (Method C): 394 (M+H)$^+$. HPLC (Method E) Rt 4.53 min (Purity: 99.1%).

Example 79

3-{5-[5-cyclopentyl-1-(2-fluorophenyl)-1H-1,2,3-triazol-4-yl]-1,2,4-oxadiazol-3-yl}pyridine

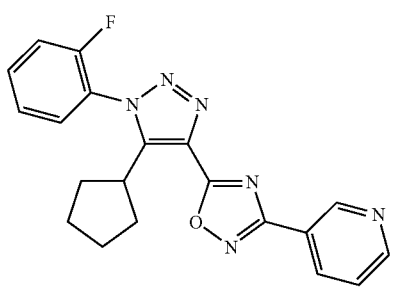

The title compound was prepared following the procedure described for Example 49, with two identical reactions combined for workup, but starting from Intermediate 21 (83 mg; 0.3 mmol) and N'-hydroxynicotinimidamide (Tyger, 41 mg; 0.36 mmol) to give Example 79 as an off-white solid. $^1$H NMR: (CDCl$_3$, 400 MHz) δ 9.41 (1H, d, J=2.0 Hz), 8.78 (1H, dd, J=4.9, 1.7 Hz), 8.47 (1H, dt, J=8.0, 2.0 Hz), 7.68-7.61 (1H, m), 7.56-7.51 (1H, m), 7.48 (1H, dd, J=8.0, 4.9 Hz), 7.45-7.32 (2H, m), 3.21 (1H, quintet, J=9.2 Hz), 2.28-2.10 (2H, m), 2.09-1.87 (4H, m), 1.74-1.60 (2H, m). LC/MS (Method C): 377 (M+H)$^+$. HPLC (Method E) Rt 4.10 min (Purity: 96.9%).

Example 80

1-(4-{5-[1-(2-fluorophenyl)-5-pyridin-4-yl-1H-1,2,3-triazol-4-yl]-1,2,4-oxadiazol-3-yl}phenyl)methanamine hydrochloride

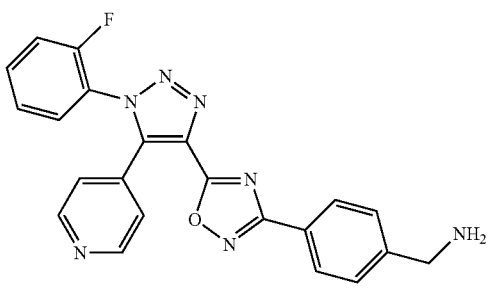

The title compound was prepared following the procedure described for Example 55, Step 2, but starting from Example 74 (128 mg; 0.245 mmol), to give Example 80 as an off-white solid (95.2 mg; 84%). $^1$H NMR: (DMSO-$d_6$, 400 MHz) δ 8.82 (2H, d, J=5.4 Hz), 8.70 (3H, br s), 8.04 (2H, d, J=8.0 Hz), 7.95-7.88 (1H, m), 7.78-7.70 (5H, m), 7.56-7.48 (2H, m), 4.14 (2H, d, J=6.3 Hz). LC/MS (Method C): 414 (M+H)$^+$. HPLC (Method E) Rt 2.30 min (Purity: 97.4%).

Example 81

1-(4-{5-[1-(2-fluorophenyl)-5-(methoxymethyl)-1H-1,2,3-triazol-4-yl]-1,2,4-oxadiazol-3-yl}phenyl)methanamine

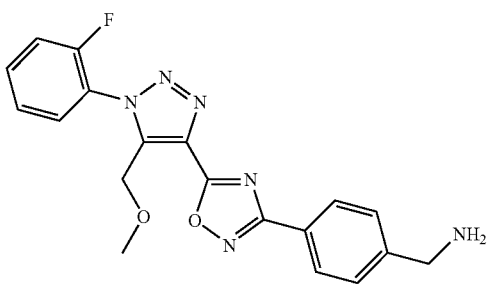

Step 1: tert-butyl 4-(5-(1-(2-fluorophenyl)-5-(methoxymethyl)-1H-1,2,3-triazol-4-yl)-1,2,4-oxadiazol-3-yl)benzylcarbamate The title compound was prepared following the procedure described for Example 47, but starting from Intermediate 11 (150 mg; 0.597 mmol) and Intermediate 28, to give the title compound as a white solid. $^1$H NMR: (CDCl$_3$, 400 MHz) δ 8.17 (2H, d, J=8.1 Hz), 7.66-7.58 (2H, m), 7.46-7.30 (4H, m), 4.99 (2H, s), 4.94 (1H, s), 4.41 (2H, d, J=6.1 Hz), 3.30 (3H, s), 1.48 (9H, s). LC/MS (Method C): 481 (M+H)$^+$. HPLC (Method F) Rt 3.85 min (Purity: 99.1%).

Step 2: 1-(4-{5-[1-(2-fluorophenyl)-5-(methoxymethyl)-1H-1,2,3-triazol-4-yl]-1,2,4-oxadiazol-3-yl}phenyl)methanamine The title compound was prepared following the procedure described for Example 55, Step 2, but starting from tert-butyl fluorophenyl)-5-(methoxymethyl)-1H-1,2,3-triazol-4-yl)-1,2,4-oxadiazol-3-yl)benzylcarbamate (103 mg; 0.214 mmol), obtained in Step 1, to give Example 81 as a white solid (73 mg; 81%). $^1$H NMR: (CDCl$_3$, 400 MHz) δ 8.18 (2H, d, J=8.0 Hz), 7.66-7.58 (2H, m), 7.47 (2H, t, J=8.0 Hz), 7.44-7.32 (2H, m), 5.03-4.94 (2H, m), 3.97 (2H, s), 3.30 (3H, s). LC/MS (Method C): 381 (M+H)$^+$. HPLC (Method E) Rt 2.34 min (Purity: 95.5%).

Example 82

4-(1-(2-fluorophenyl)-4-{3-[3-(1H-imidazol-1-ylmethyl)phenyl]-1,2,4-oxadiazol-5-yl}-1H-1,2,3-triazol-5-yl)pyridine

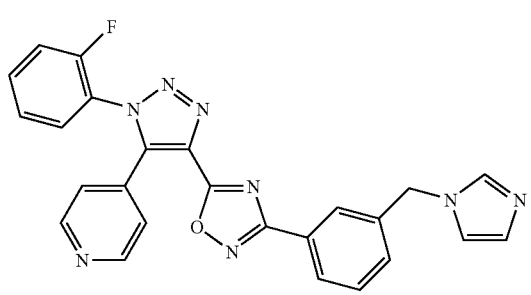

The title compound was prepared following the procedure described for Example 52, but starting from Intermediate 17 (209 mg; 0.67 mmol) and 3-((1H-imidazol-1-yl)methyl)-N'-hydroxybenzimidamide (Aurora, 160 mg; 0.74 mmol) to give Example 82 as an off-white solid. $^1$H NMR: (CDCl$_3$, 400 MHz) δ 8.74-8.71 (2H, m), 8.06 (1H, d, J=7.8 Hz), 7.97 (1H, s), 7.64-7.53 (3H, m), 7.49 (1H, t, J=7.8 Hz), 7.40-7.32 (3H, m), 7.30-7.23 (1H, m), 7.19 (1H, t, J=9.1 Hz), 7.12 (1H, s), 6.93 (1H, s), 5.19 (2H, s). LC/MS (Method C): 465 (M+H)$^+$. HPLC (Method E) Rt 2.40 min (Purity: 98.6%).

Example 83

4-{1-(2-fluorophenyl)-4-[3-(3-fluorophenyl)-1,2,4-oxadiazol-5-yl]-1H-1,2,3-triazol-5-yl}pyridine

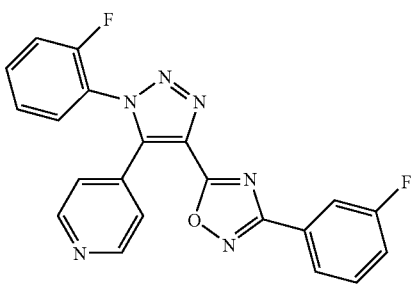

The title compound was prepared following the procedure described for Example 52, but starting from Intermediate 17 (209 mg; 0.67 mmol) and 3-fluoro-N'-hydroxybenzimidamide (Tyger, 114 mg; 0.74 mmol) to give Example 83 as a white solid (211 mg; 78%). $^1$H NMR: (CDCl$_3$, 400 MHz) δ 8.74-8.72 (2H, m), 7.89 (1H, d, J=7.8 Hz), 7.79 (1H, dt, J=9.5, 2.0 Hz), 7.64-7.53 (2H, m), 7.50-7.43 (1H, m), 7.40-7.34 (3H, m), 7.28-7.16 (2H, m). LC/MS (Method C): 403 (M+H)+. HPLC (Method E) Rt 3.92 min (Purity: 98.8%).

Example 84

2-(1-(2-fluorophenyl)-4-{3-[3-(methylsulfonyl)phenyl]-1,2,4-oxadiazol-5-yl}-1H-1,2,3-triazol-5-yl)pyridine

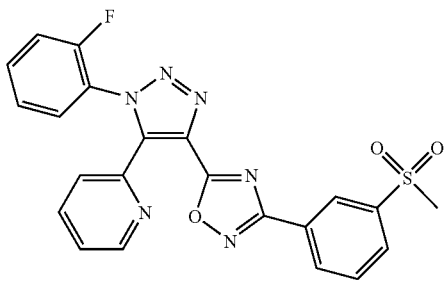

The title compound was prepared following the procedure described for Example 51, but starting from Intermediate 53 (209 mg; 0.67 mmol) and Intermediate 40 (157 mg; 0.74 mmol), to give Example 84 as a green solid. $^1$H NMR: (DMSO-d$_6$, 400 MHz) δ 8.59-8.55 (1H, m), 8.55-8.49 (1H, m), 8.39-8.34 (1H, m), 8.24-8.19 (1H, m), 8.15-8.11 (1H, m), 8.09-8.02 (1H, m), 7.98-7.90 (1H, m), 7.83-7.75 (1H, m), 7.73-7.65 (1H, m), 7.60-7.53 (1H, m), 7.53-7.43 (2H, m), 3.36 (3H, s). LC/MS (Method C): 463 (M+H)+. HPLC (Method E) Rt 3.64 min (Purity: 99.5%).

Example 85

5-[5-cyclopropyl-1-(2-fluorophenyl)-1H-1,2,3-triazol-4-yl]-3-(2-fluorophenyl)-1,2,4-oxadiazole

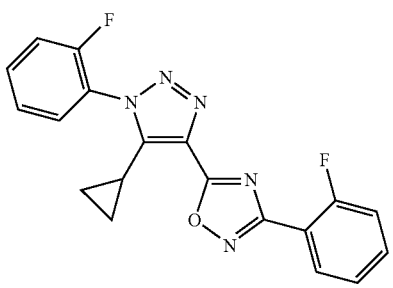

The title compound was prepared following the procedure described for Example 49, with two identical reactions combined for workup, but starting from Intermediate 22 (74 mg; 0.3 mmol) and Intermediate 4 (46 mg; 0.36 mmol). The residue was purified by preparative HPLC to give Example 85 as a white solid. $^1$H NMR: (CDCl$_3$, 400 MHz) δ 8.27-8.20 (1H, m), 7.66-7.50 (3H, m), 7.43-7.22 (4H, m), 2.12-2.04 (1H, m), 1.11-1.01 (2H, m), 0.94-0.86 (2H, m). LC/MS (Method C): 366 (M+H)+. HPLC (Method E) Rt 4.16 min (Purity: 99.7%).

Example 86

2-(1-(2-fluorophenyl)-4-{3-[3-(1H-1,2,4-triazol-1-ylmethyl)phenyl]-1,2,4-oxadiazol-5-yl}-1H-1,2,3-triazol-5-yl)pyridine

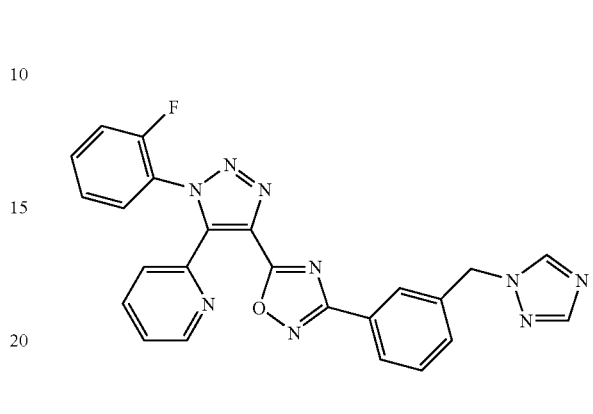

The title compound was prepared following the procedure described for Example 51, but starting from Intermediate 53 (209 mg; 0.67 mmol) and Intermediate 41 (160 mg; 0.74 mmol), to give Example 86 as an off-white solid. $^1$H NMR: (DMSO-d$_6$, 400 MHz) δ 8.76 (1H, s), 8.56 (1H, d, J=4.8 Hz), 8.12-8.04 (3H, m), 7.98 (1H, d, J=7.6 Hz), 7.91 (1H, s), 7.80-7.53 (5H, m), 7.53-7.41 (2H, m), 5.59 (2H, s). LC/MS (Method C): 466 (M+H)+. HPLC (Method E) Rt 3.44 min (Purity: 98.5%).

Example 87

5-{5-[1-(2-fluorophenyl)-5-(methoxymethyl)-1H-1,2,3-triazol-4-yl]-1,2,4-oxadiazol-3-yl}-1H-indazole

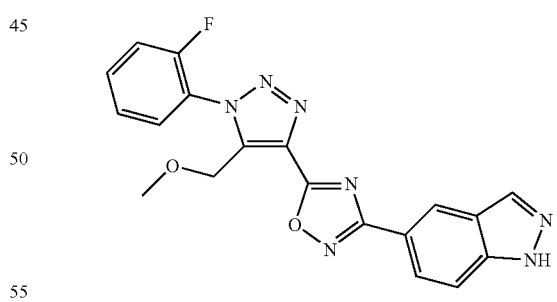

The title compound was prepared following the procedure described for Example 47, but starting from Intermediate 11 (178 mg; 0.71 mmol) and Intermediate 30 (123 mg; 0.71 mmol), to give Example 87 as a red solid. $^1$H NMR: (DMSO-d$_6$, 400 MHz) δ 13.46 (1H, s), 8.67 (1H, s), 8.34 (1H, s), 8.13 (1H, d, J=8.8 Hz), 7.91-7.76 (3H, m), 7.68 (1H, t, J=9.4 Hz), 7.57 (1H, t, J=7.7 Hz), 5.02 (2H, s), 3.37-3.08 (3H, m). LC/MS (Method C): 392 (M+H)+. HPLC (Method E) Rt 3.55 min (Purity: 92.3%).

Example 88

4-{1-(2-fluorophenyl)-4-[3-(3-furyl)-1,2,4-oxadiazol-5-yl]-1H-1,2,3-triazol--yl}pyridine

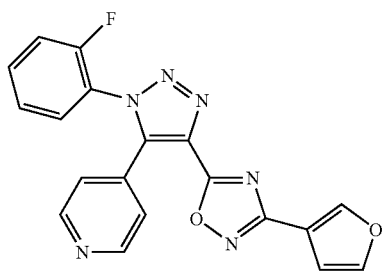

The title compound was prepared following the procedure described for Example 52, but starting from Intermediate 17 (209 mg; 0.67 mmol) and Intermediate 42 (93 mg; 0.74 mmol) to give Example 88 as a white solid. $^1$H NMR: (CDCl$_3$, 400 MHz) δ 8.72-8.69 (2H, m), 8.12-8.11 (1H, m), 7.64-7.52 (3H, m), 7.37 (1H, t, J=7.8 Hz), 7.34-7.31 (2H, m), 7.21-7.14 (1H, m), 6.92-6.89 (1H, m). LC/MS (Method C): 375 (M+H)$^+$. HPLC (Method E) Rt 3.55 min (Purity: 99.3%).

Example 89

4-{1-(2-fluorophenyl)-4-[3-(2-furyl)-1,2,4-oxadiazol-5-yl]-1H-1,2,3-triazol-5-yl}pyridine

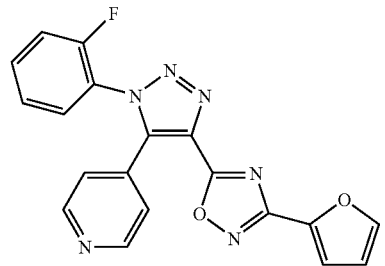

The title compound was prepared following the procedure described for Example 52, but starting from Intermediate 17 (209 mg; 0.67 mmol) and N-hydroxy-furan-2-carboxamidine (Tyger, 93 mg; 0.74 mmol). The residue was purified by flash chromatography on a Biotage 25+S column, eluting with petrol containing increasing amounts of EtOAc, to give Example 89 as a white solid. $^1$H NMR: (CDCl$_3$, 400 MHz) δ 8.72-8.69 (2H, m), 7.63-7.53 (3H, m), 7.37 (1H, t, J=7.8 Hz), 7.34-7.32 (2H, m), 7.20-7.15 (2H, m), 6.58 (1H, dd, J=3.5, 1.8 Hz). LC/MS (Method C): 375 (M+H)$^+$. HPLC (Method E) Rt 3.51 min (Purity: 99.2%).

Example 90

4-{5-[1-(2-fluorophenyl)-5-(methoxymethyl)-1H-1,2,3-triazol-4-yl]-1,2,4-oxadiazol-3-yl}-1H-indole

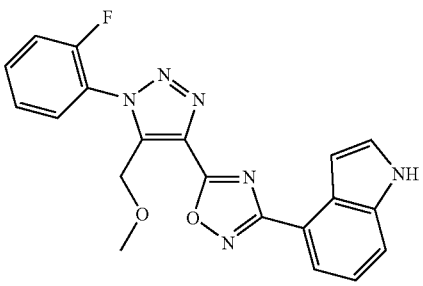

The title compound was prepared following the procedure described for Example 49, but starting from Intermediate 11 (75 mg; 0.3 mmol) and Intermediate 43 (63 mg; 0.36 mmol), to give Example 90 as an off-white solid. $^1$H NMR: (DMSO-d$_6$, 400 MHz) δ 11.59 (1H, br s), 8.00 (1H, d, J=7.4 Hz), 7.88 (1H, td, J=7.7, 1.7 Hz), 7.85-7.78 (1H, m), 7.75-7.64 (2H, m), 7.64 (1H, t, J=2.8 Hz), 7.57 (1H, t, J=7.7 Hz), 7.36 (1H, t, J=7.7 Hz), 7.16-7.13 (1H, m), 5.02 (2H, s, 2H, s), 3.25 (3H, s). LC/MS (Method C): 391 (M+H)$^+$. HPLC (Method F) Rt 3.57 min (Purity: 95.8%).

Example 91

1-[4-[3-(2,5-difluorophenyl)-1,2,4-oxadiazol-5-yl]-1-(2-fluorophenyl)-1H-1,2,3-triazol-5-yl]-N,N-dimethylmethanamine

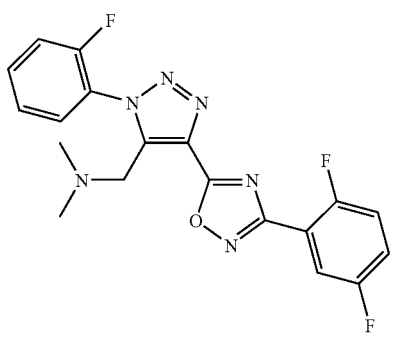

Step 1: 5-(5-(bromomethyl)-1-(2-fluorophenyl)-1H-1,2,3-triazol-4-yl)-3-(2,5-difluorophenyl)-1,2,4-oxadiazole To a solution of Example 2 (314 mg; 0.879 mmol) in carbon tetrachloride (15 mL) was added benzoyl peroxide (21 mg; 0.088 mmol) and N-bromosuccinamide (343 mg; 1.93 mmol). The resulting mixture was refluxed for 6 hours, the solvent was removed in vacuo and the residue was purified by flash chromatography on a Biotage 25+M column, eluting with petrol containing increasing amounts of EtOAc to give the title compound as a white solid (352 mg; 91%). $^1$H NMR: (CDCl$_3$, 400 MHz) δ 7.95-7.88 (1H, m), 7.72-7.63 (2H, m), 7.49-7.36 (2H, m), 7.28-7.21 (2H, m), 4.90 (2H, s).

Step 2: 1-(4-(3-(2,5-difluorophenyl)-1,2,4-oxadiazol-5-yl)-1-(2-fluorophenyl)-1H-1,2,3-triazol-5-yl)-N,N-dimethylmethanamine To a solution of 5-(5-(bromomethyl)-1-(2-fluorophenyl)-1H-1,2,3-triazol-4-yl)-3-(2,5-difluorophenyl)-1,2,4-oxadiazole, obtained in Step 1, (100 mg; 0.23 mmol) in THF (3 mL) was added dimethylamine hydrochloride (37 mg; 0.459 mmol) and potassium carbonate (76.2 mg; 0.76 mmol) and the mixture was heated in a sealed tube at 60° C. for 16 hours. The mixture was diluted with water (10 mL) and extracted with DCM (3×20 mL), the combined organics were dried ($MgSO_4$) and the solvent removed in vacuo. The residue was purified by preparative HPLC to give Example 91 as a white solid. $^1$H NMR: ($CDCl_3$, 400 MHz) δ 7.96-7.90 (1H, m), 7.64-7.55 (2H, m), 7.40-7.29 (2H, m), 7.28-7.20 (2H, m), 3.98 (2H, s), 2.11 (6H, s). LC/MS (Method C): 401 (M+H)$^+$. HPLC (Method E) Rt 2.61 min (Purity: 99.8%).

Example 92

3-(2,5-difluorophenyl)-5-[1-(2-fluorophenyl)-5-(pyrrolidin-1-ylmethyl)-1H-1,2,3-triazol-4-yl]-1,2,4-oxadiazle

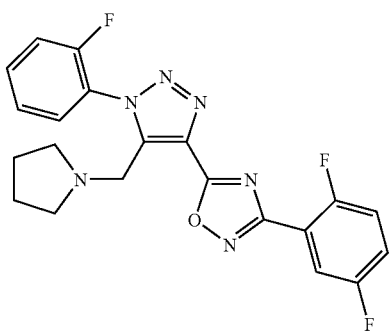

The title compound was prepared following the procedure described for Example 91, but using pyrrolidine in Step 2 (32.7 mg; 0.46 mmol), to give Example 92 as a white solid. $^1$H NMR: ($CDCl_3$, 400 MHz) δ 7.96-7.91 (1H, m), 7.62-7.53 (2H, m), 7.38-7.30 (2H, m), 7.27-7.21 (2H, m), 4.21 (2H, s), 2.43-2.31 (4H, m), 1.58-1.53 (4H, m). LC/MS (Method C): 427 (M+H)$^+$. HPLC (Method E) Rt 2.59 min (Purity: 97.4%).

Example 93

3-{5-[1-(2-fluorophenyl)-5-(methoxymethyl)-1H-1,2,3-triazol-4-yl]-1,2,4-oxadiazol-3-yl}benzenesulfonamide

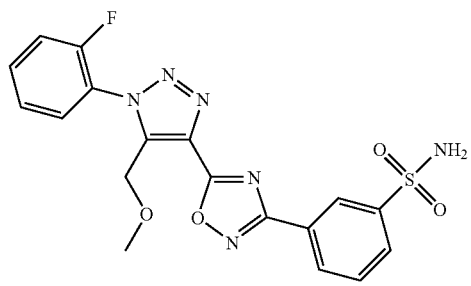

The title compound was prepared following the procedure described for Example 49, but starting from Intermediate 11 (75 mg; 0.3 mmol) and Intermediate 44 (77 mg; 0.36 mmol), to give Example 93 as an off-white solid. $^1$H NMR: (DMSO-$d_6$, 400 MHz) δ 8.61 (1H, s), 8.39 (1H, d, J=7.8 Hz), 8.12 (1H, d, J=7.8 Hz), 7.92-7.77 (3H, m), 7.73-7.62 (3H, m), 7.57 (1H, t, J=7.8 Hz), 4.99 (2H, s), 3.23 (3H, s). LC/MS (Method C): 431 (M+H)$^+$. HPLC (Method E) Rt 3.45 min (Purity: 99.3%).

Example 94

1-(3-{5-[1-(2-fluorophenyl)-5-pyridin-4-yl-1H-1,2,3-triazol-4-yl]-1,2,4-oxadiazol-3-yl}phenyl)-N,N-dimethylmethanamine

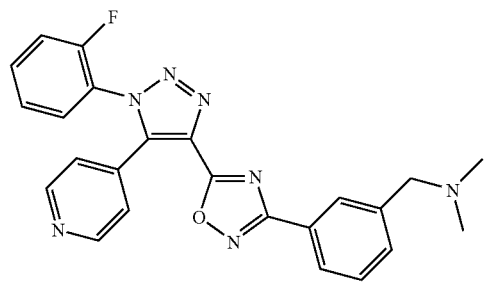

Step 1: 3-(5-(1-(2-fluorophenyl)-5-(pyridin-4-yl)-1H-1,2,3-triazol-4-yl)-1,2,4-oxadiazol-3-yl)benzaldehyde To a solution of oxalyl chloride (1.83 mL, 3.67 mmol, 2 M in DCM) in DCM (75 mL), at −78° C., was added DMSO (780 μL, 11 mmol) and the mixture was stirred for 30 minutes. To this mixture was added by syringe a suspension of Example 111 (1.52 g; 3.67 mmol) in DCM (30 mL) and the resulting mixture was stirred for 30 minutes. Triethylamine (2.224 g; 22 mmol) was added and the resulting mixture was stirred for 2 hours at −78° C. The mixture was allowed to warm to room temperature and a saturated solution of ammonium chloride (150 mL) was added. The aqueous layer was extracted with DCM (3×150 mL) and the combined organics were dried ($MgSO_4$), the solvent was removed in vacuo and the residue was purified by flash chromatography on a Biotage 25+M column, eluting with petrol containing increasing amounts of EtOAc to give the title compound as a white solid (1.34 g; 88%). $^1$H NMR: (DMSO-$d_6$, 400 MHz) δ 10.17 (1H, s), 8.77 (2H, dd, J=4.5, 1.6 Hz), 8.54-8.50 (1H, m), 8.31 (1H, dt, J=7.7, 1.44 Hz), 8.18 (1H, dt, J=7.7, 1.4 Hz), 7.96-7.82 (2H, m), 7.77-7.70 (1H, m), 7.63 (2H, dd, J=4.6, 1.6 Hz), 7.59-7.48 (2H, m).

Step 2: 1-(3-(5-(1-(2-fluorophenyl)-5-(pyridin-4-yl)-1H-1,2,3-triazol-4-yl)-1,2,4-oxadiazol-3-yl)phenyl)-N,N-dimethylmethanamine To a solution of 3-(5-(1-(2-fluorophenyl)-5-(pyridin-4-yl)-1H-1,2,3-triazol-4-yl)-1,2,4-oxadiazol-3-yl)benzaldehyde, obtained in Step 1, (100 mg; 0.24 mmol), in MeOH (3.0 mL) and DCM (1.0 mL) was added dimethylamine hydrochloride (39.5 mg; 0.48 mmol) and acetic acid (75 μL) and the mixture was stirred for 1 hour. The mixture was treated with sodium cyanoborohydride (17 mg; 0.27 mmol), stirred for 16 hours and the solvent was removed in vacuo. The residue was purified by preparative HPLC to give Example 94 as a white solid. $^1$H NMR: (DMSO-$d_6$, 400 MHz) δ 8.75 (2H, dd, J=4.5, 1.6 Hz), 7.97 (1H, s), 7.93-7.84 (2H, m), 7.76-7.69 (1H, m), 7.61 (2H, dd, J=4.5, 1.6 Hz), 7.58-7.47 (4H, m), 3.51 (2H, s), 2.21 (6H, s). LC/MS (Method C): 442 (M+H)$^+$. HPLC (Method E) Rt 2.16 min (Purity: 99.7%).

Example 95

4-[1-(2-fluorophenyl)-4-(3-phenyl-1,2,4-oxadiazol-5-yl)-1H-1,2,3-triazol-5-yl]pyridine

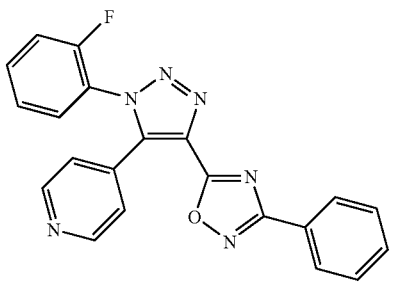

The title compound was prepared following the procedure described for Example 52, but starting from Intermediate 17 (209 mg; 0.67 mmol) and N'-hydroxybenzimidamide (Apollo, 101 mg; 0.74 mmol) to give Example 95 as a white solid. $^1$H NMR: (CDCl$_3$, 400 MHz) δ 8.74-8.70 (2H, m), 8.11-8.08 (2H, m), 7.63-7.45 (5H, m), 7.39-7.34 (3H, m), 7.22-7.15 (1H, m). LC/MS (Method C): 385 (M+H)$^+$. HPLC (Method E) Rt 3.69 min (Purity: 98.8%).

Example 96

4-{1-(2-fluorophenyl)-4-[3-(4-fluorophenyl)-1,2,4-oxadiazol-5-yl]-1H-1,2,3-triazol-5-yl}pyridine

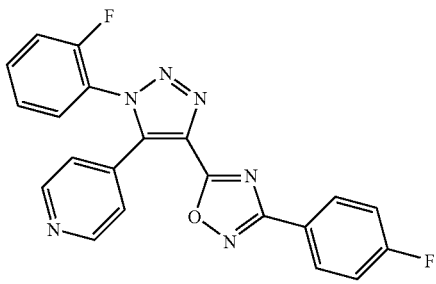

The title compound was prepared following the procedure described for Example 52, but starting from Intermediate 17 (209 mg; 0.67 mmol) and 4-fluoro-N'-hydroxybenzimidamide (Apollo, 114 mg; 0.74 mmol) to give Example 96 as a white solid. $^1$H NMR: (CDCl$_3$, 400 MHz) δ 8.74-8.70 (2H, m), 8.12-8.06 (2H, m), 7.65-7.51 (2H, m), 7.40-7.33 (3H, m), 7.22-7.14 (3H, m). LC/MS (Method C): 403 (M+H)$^+$. HPLC (Method E) Rt 3.73 min (Purity: 99.0%).

Example 97

4-[4-[3-(3,4-difluorophenyl)-1,2,4-oxadiazol-5-yl]-1-(2-fluorophenyl)-1H-1,2,3-triazol--yl]pyridine

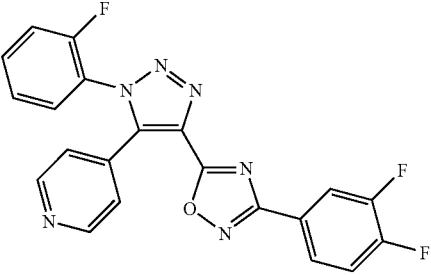

The title compound was prepared following the procedure described for Example 52, but starting from Intermediate 17 (209 mg; 0.67 mmol) and 3,4-difluoro-N'-hydroxybenzimidamide (JRD-Fluorochemical, 127 mg; 0.74 mmol) to give Example 97 as a white solid. $^1$H NMR: (CDCl$_3$, 400 MHz) δ 8.75-8.71 (2H, m), 7.95-7.83 (2H, m), 7.64-7.51 (2H, m), 7.40-7.23 (4H, m), 7.23-7.14 (1H, m). LC/MS (Method C): 421 (M+H)$^+$. HPLC (Method E) Rt 3.81 min (Purity: 99.2%).

Example 98

4-(4-{5-[1-(2-fluorophenyl)-5-pyridin-4-yl-1H-1,2,3-triazol-4-yl]-1,2,4-oxadiazol-3-yl}benzyl)morpholine

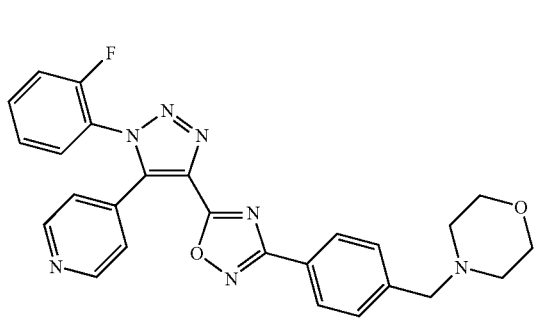

The title compound was prepared following the procedure described for Example 52, but starting from Intermediate 17 (209 mg; 0.67 mmol) and N'-hydroxy-4-(morpholinomethyl)benzimidamide (Aurora, 174 mg; 0.74 mmol) to give Example 98 as a white solid. $^1$H NMR: (CDCl$_3$, 400 MHz) δ 8.74-8.69 (2H, m), 8.05 (2H, d, J=8.1 Hz), 7.64-7.51 (2H, m), 7.46 (2H, d, J=8.1 Hz), 7.40-7.34 (3H, m), 7.23-7.15 (1H, m), 3.72 (4H, t, J=4.5 Hz), 3.56 (2H, s), 2.47 (4H, t, J=4.5 Hz). LC/MS (Method C): 484 (M+H)+. HPLC (Method E) Rt 2.19 min (Purity: =99.4%).

Example 99

4-[4-[3-(2,6-difluorophenyl)-1,2,4-oxadiazol-5-yl]-1-(2-fluorophenyl)-1H-1,2,3-triazol-5-yl]pyridine

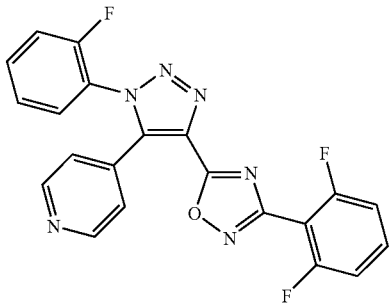

The title compound was prepared following the procedure described for Example 52, but starting from Intermediate 17 (209 mg; 0.67 mmol) and Intermediate 5 (127 mg; 0.74 mmol) to give Example 99 as a white solid. ¹H NMR: (CDCl₃, 400 MHz) δ 8.70-8.67 (2H, m), 7.63-7.45 (3H, m), 7.40-7.34 (3H, m), 7.23-7.15 (1H, m), 7.11-7.01 (2H, m). LC/MS (Method C): 421 (M+H)+. HPLC (Method E) Rt 3.55 min (Purity: 98.2%).

Example 100

4-[4-[3-(3-bromophenyl)-1,2,4-oxadiazol-5-yl]-1-(2-fluorophenyl)-1H-1,2,3-triazol-5-yl]pyridine

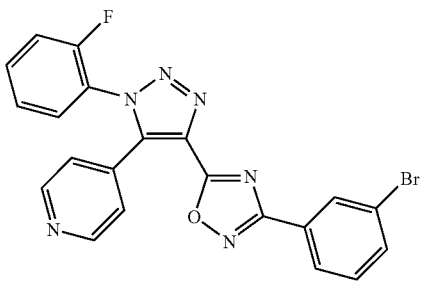

The title compound was prepared following the procedure described for Example 51, but starting from Intermediate 17 (209 mg; 0.67 mmol) and 3-bromo-N'-hydroxybenzimidamide (Enamine, 158 mg; 0.74 mmol), to give Example 100 as an off-white solid. ¹H NMR: (CDCl₃, 400 MHz) δ 8.73 (2H, dd, J=4.6, 1.6 Hz), 8.27 (1H, t, J=1.8 Hz), 8.02 (1H, dt, J=7.8, 1.3 Hz), 7.67-7.52 (3H, m), 7.40-7.34 (4H, m), 7.23-7.14 (1H, m). LC/MS (Method C): 463 (M+H)+. HPLC (Method E) Rt 4.02 min (Purity: 98.4%).

Example 101

4-[4-[3-(2,3-difluorophenyl)-1,2,4-oxadiazol-5-yl]-1-(2-fluorophenyl)-1H-1,2,3-triazol-5-yl]pyridine

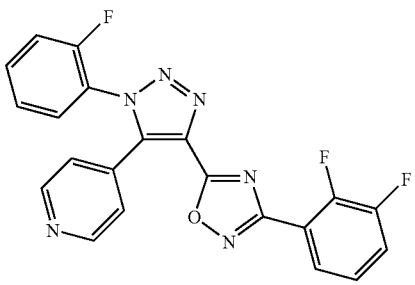

The title compound was prepared following the procedure described for Example 52, but starting from Intermediate 17 (209 mg; 0.67 mmol) and 2,3-difluoro-N'-hydroxybenzimidamide (JRD-Fluorochemical, 127 mg; 0.74 mmol) to give Example 101 as a white solid. ¹H NMR: (CDCl₃, 400 MHz) δ 8.73-8.71 (2H, m), 7.87-7.82 (1H, m), 7.64-7.53 (2H, m), 7.39-7.30 (4H, m), 7.27-7.16 (2H, m). LC/MS (Method C): 421 (M+H)+. HPLC (Method F) Rt 3.60 min (Purity: 98.3%).

Example 102

4-[4-[3-(3,5-difluorophenyl)-1,2,4-oxadiazol-5-yl]-1-(2-fluorophenyl)-1H-1,2,3-triazol-5-yl]pyridine

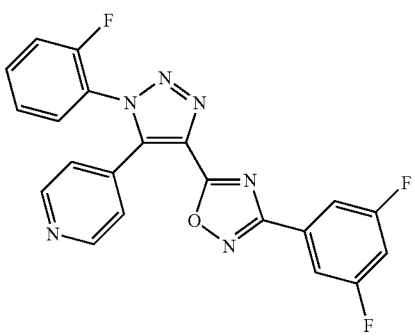

The title compound was prepared following the procedure described for Example 52, but starting from Intermediate 17 (209 mg; 0.67 mmol) and 3,5-difluoro-N'-hydroxybenzimidamide (JRD-Fluorochemical, 127 mg; 0.74 mmol) to give Example 102 as a white solid. ¹H NMR: (CDCl₃, 400 MHz) δ 8.75-8.72 (2H, m), 7.66-7.54 (4H, m), 7.40-7.32 (3H, m), 7.22-7.15 (1H, m), 6.97 (1H, tt, J=8.7, 2.4 Hz). LC/MS (Method C): 421 (M+H)[30]. HPLC (Method F) Rt 3.74 min (Purity: 98.5%).

Example 103

4-(1-(2-fluorophenyl)-4-{3-[3-(trifluoromethyl)phenyl]-1,2,4-oxadiazol-5-yl}-1H-1,2,3-triazol-5-yl)pyridine

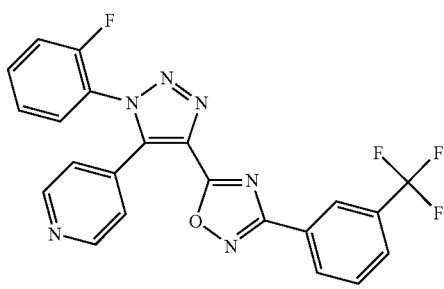

The title compound was prepared following the procedure described for Example 52, but starting from Intermediate 17 (209 mg; 0.67 mmol) and N'-hydroxy-3-(trifluoromethyl)benzimidamide (JRD-Fluorchemical, 151 mg; 0.74 mmol) to give Example 103 as a white solid (246 mg; 81%). $^1$H NMR: (CDCl$_3$, 400 MHz) δ 8.75-8.72 (2H, m), 8.40 (1H, s), 8.28 (1H, d, J=7.9 Hz), 7.79 (1H, d, J=7.9 Hz), 7.66-7.53 (3H, m), 7.40-7.33 (3H, m), 7.22-7.15 (1H, m). LC/MS (Method C): 453 (M+H)$^+$. HPLC (Method F) Rt 3.88 min (Purity: 97.8%).

Example 104

4-{1-(2-fluorophenyl)-4-[3-(3-methylphenyl)-1,2,4-oxadiazol-5-yl]-1H-1,2,3-triazol-5-yl}pyridine

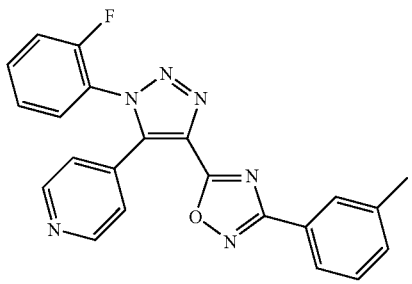

The title compound was prepared following the procedure described for Example 51, but starting from Intermediate 17 (209 mg; 0.67 mmol) and N'-hydroxy-3-methylbenzimidamide (110 mg; 0.74 mmol), to give Example 104 as a white solid (249 mg; 93%). $^1$H NMR: (CDCl$_3$, 400 MHz) δ 8.72 (2H, dd, J=4.5, 1.7 Hz), 7.95 (1H, s), 7.89 (1H, d, J=7.5 Hz), 7.64-7.53 (2H, m), 7.40-7.31 (5H, m), 7.21-7.14 (1H, m), 2.43 (3H, s). LC/MS (Method C): 399 (M+H)$^+$. HPLC (Method E) Rt 3.99 min (Purity: 99.8%).

Example 105

7-{5-[1-(2-fluorophenyl)-5-pyridin-4-yl-1H-1,2,3-triazol-4-yl]-1,2,4-oxadiazol-3-yl}-1,2,3,4-tetrahydroisoquinoline

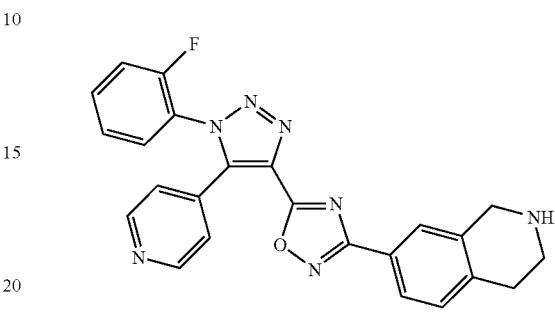

The title compound was prepared following the procedure described for Example 108, but starting from Intermediate 37 (140 mg; 0.74 mmol), to give Example 105 as a brown solid. $^1$H NMR: (CDCl$_3$, 400 MHz) δ 8.74-8.69 (2H, m), 7.87-7.81 (1H, m), 7.79 (1H, s), 7.63-7.52 (2H, m), 7.39-7.33 (3H, m), 7.23-7.15 (2H, m), 4.08 (2H, s), 3.17 (2H, t, J=5.9 Hz), 2.86 (2H, t, J=5.9 Hz). LC/MS (Method C): 440 (M+H)$^+$. HPLC (Method E) Rt 2.13 min (Purity: 99.10%).

Example 106

5-{5-[1-(2-fluorophenyl)-5-pyridin-4-yl-1H-1,2,3-triazol-4-yl]-1,2,4-oxadiazol-3-yl}-1,3-dihydro-2H-indol-2-one

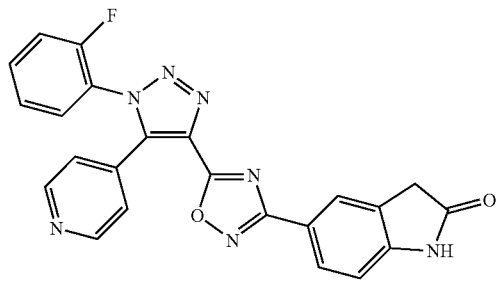

In a microwave vial, Intermediate 17 (209 mg; 0.67 mmol) was suspended in toluene (2 mL) and DMF (2 mL) and Intermediate 45 (141 mg; 0.74 mmol) was added followed by potassium carbonate (123 mg; 0.74 mmol). The MW vial was sealed and the suspension was heated to 180° C. for 20 min in a microwave reactor. The toluene was removed in vacuo and the residue purified by preparative HPLC to give Example 106 as an off-white solid. $^1$H NMR: (CDCl$_3$, 400 MHz) δ 8.74-8.71 (2H, m), 8.00 (1H, d, J=8.2 Hz), 7.97 (1H, s), 7.64-7.55 (3H, m), 7.39-7.33 (3H, m), 7.21-7.15 (1H, m), 6.96 (1H, d, J=8.2 Hz), 3.61 (2H, s). LC/MS (Method C): 440 (M+H)$^+$. HPLC (Method F) Rt 2.90 min (Purity: 98.9%).

Example 107

4-{1-(2-fluorophenyl)-4-[3-(4-methylphenyl)-1,2,4-oxadiazol-5-yl]-1H-1,2,3-triazol-5-yl}pyridine

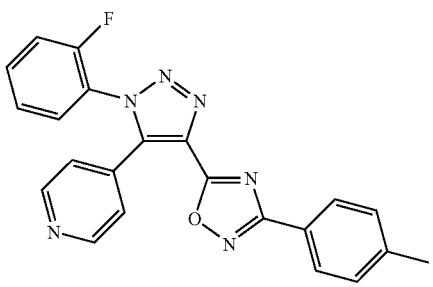

The title compound was prepared following the procedure described for Example 51, but starting from Intermediate 17 (450 mg; 1.442 mmol), N'-hydroxy-4-methylbenzimidamide (Aldrich, 237 mg; 1.58 mmol) and potassium carbonate (218 mg; 1.58 mmol) to give Example 107 as a white solid. $^1$H NMR: (CDCl$_3$, 400 MHz) δ 8.71 (2H, dd, J=4.5, 1.7 Hz), 7.98 (2H, d, J=8.1 Hz), 7.64-7.49 (2H, m), 7.39-7.34 (3H, m), 7.33-7.26 (2H, m), 7.25-7.15 (1H, m), 2.42 (2H, s). LC/MS (Method C): 399 (M+H)$^+$. HPLC (Method E) Rt 3.83 min (Purity: 98.4%).

Example 108

(4-{5-[1-(2-fluorophenyl)-5-pyridin-4-yl-1H-1,2,3-triazol-4-yl]-1,2,4-oxadiazol-3-yl}phenyl)methanol

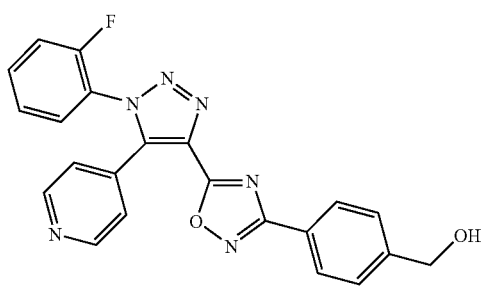

In a microwave vial, Intermediate 17 (661 mg; 2.12 mmol) was suspended in toluene (3 mL) and DMF (2 mL), Intermediate 32 (352 mg; 2.12 mmol) was added followed by potassium carbonate (321 mg; 2.33 mmol). The MW vial was sealed and the suspension was heated to 180° C. for 15 min. The reaction mixture was cooled down to room temperature and poured into isopropanol (5 mL) and water (5 mL). The volume was reduced by removing solvent in vacuo until precipitation occurred and the solid was collected by filtration and washed with isopropanol (3×10 mL). Afforded Example 108 as a white solid. $^1$H NMR: (CDCl$_3$, 400 MHz) δ 8.72 (2H, dd, J=4.5, 1.7 Hz), 8.12-8.06 (2H, m), 7.63-7.52 (2H, m), 7.52-7.48 (2H, m), 7.38-7.35 (3H, m), 7.19 (1H, ddd, J=9.7, 8.4, 1.3 Hz), 4.79 (2H, s). LC/MS (Method C): 415 (M+H)$^+$. HPLC (Method E) Rt 3.03 min (Purity: 95.8%).

Example 109

4-(1-(2-fluorophenyl)-4-{3-[4-(trifluoromethyl)phenyl]-1,2,4-oxadiazol-5-yl}-1H-1,2,3-triazol-5-yl)pyridine

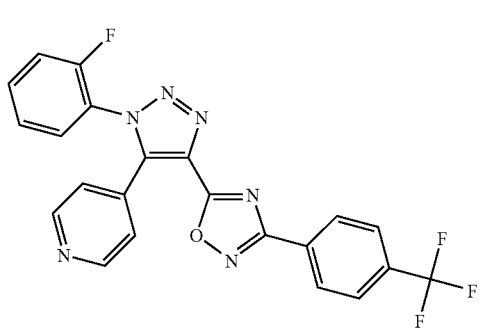

The title compound was prepared following the procedure described for Example 52, but starting from Intermediate 17 (209 mg; 0.67 mmol) and N'-hydroxy-4-(trifluoromethyl)benzimidamide (Apollo; 151 mg; 0.74 mmol) to give Example 109 as a white solid (252 mg; 83%). $^1$H NMR: (CDCl$_3$, 400 MHz) δ 8.75-8.71 (2H, m), 8.23 (2H, d, J=8.08 Hz), 7.76 (2H, d, J=8.10 Hz), 7.64-7.53 (2H, m), 7.40-7.33 (3H, m), 7.19 (1H, t, J=9.08 Hz); LC/MS (Method C): 453 (M+H)$^+$. HPLC (Method E) Rt 3.98 min (Purity: 99.7%).

Example 110

4-[4-{3-[4-(1,3-dioxolan-2-yl)phenyl]-1,2,4-oxadiazol-5-yl}-1-(2-fluorophenyl)-1H-1,2,3-triazol-5-yl]pyridine

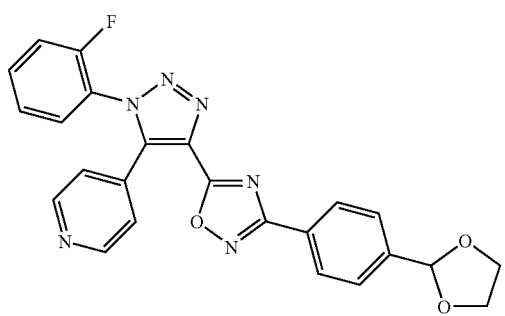

The title compound was prepared following the procedure described for Example 52, but starting from Intermediate 17 (209 mg; 0.67 mmol) and 4-(1,3-dioxolan-2-yl)-N'-hydroxybenzimidamide (ASDI; 154 mg; 0.74 mmol) to give Example 110 as a white solid (232 mg; 76%). $^1$H NMR: (CDCl$_3$, 400 MHz) δ 8.73-8.70 (2H, m), 8.12 (2H, d, J=8.12 Hz), 7.64-7.51 (4H, m), 7.40-7.33 (3H, m), 7.19 (1H, t, J=9.10 Hz), 5.88 (1H, s), 4.17-4.04 (4H, m); LC/MS (Method C): 457 (M+H)$^+$. HPLC (Method E) Rt=3.51 min (Purity: 99.3%).

Example 111

(3-{5-[1-(2-fluorophenyl)-5-pyridin-4-yl-1H-1,2,3-triazol-4-yl]-1,2,4-oxadiazol-3-yl}phenyl)methanol

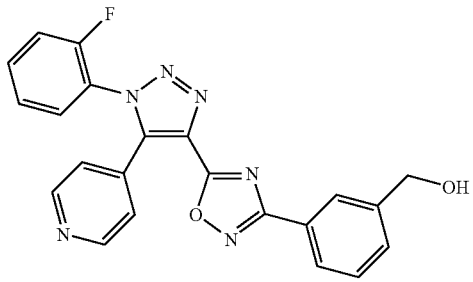

The title compound was prepared following the procedure described for Example 108, but starting from Intermediate 33 (352 mg; 2.12 mmol), to give Example 111 as a white solid. $^1$H NMR: (CDCl$_3$, 400 MHz) δ 8.74-8.70 (2H, m), 8.12 (1H, s), 8.05-7.95 (1H, m), 7.65-7.44 (4H, m), 7.42-7.31 (3H, m), 7.18 (1H, t, J=9.1 Hz), 4.78 (2H, s). LC/MS (Method C): 415 (M+H)$^+$. HPLC (Method E) Rt 3.07 min (Purity: 95.9%).

Example 112

1-cyclopropyl-N-{[4-[3-(2,5-difluorophenyl)-1,2,4-oxadiazol-5-yl]-1-(2-fluorophenyl)-1H-1,2,3-triazol-5-yl]methyl}methanamine

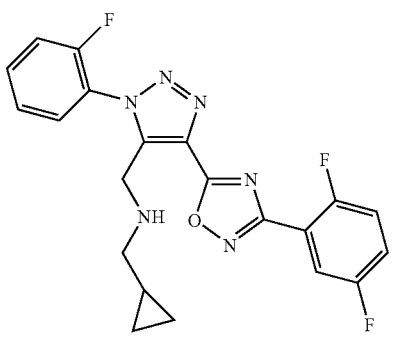

The title compound was prepared following the procedure described for Example 91, but using cyclopropylmethylamine in Step 2, (134 mg; 1.71 mmol), to give Example 112 as a white solid. $^1$H NMR: (CDCl$_3$, 400 MHz) δ 7.91-7.85 (1H, m), 7.69-7.61 (2H, m), 7.45-7.34 (2H, m), 7.28-7.25 (2H, m), 4.23 (2H, s), 2.33 (2H, d, J=6.8 Hz), 0.82-0.73 (1H, m), 0.42-0.36 (2H, m), 0.00-minus 0.06 (2H, m). LC/MS (Method C): 427 (M+H)$^+$. HPLC (Method E) Rt 2.37 min (Purity: 96.2%).

Example 113

1-(4-{5-[1-(2-fluorophenyl)-5-pyridin-4-yl-1H-1,2,3-triazol-4-yl]-1,2,4-oxadiazol-3-yl}benzyl)azetidine-3-carboxylic acid

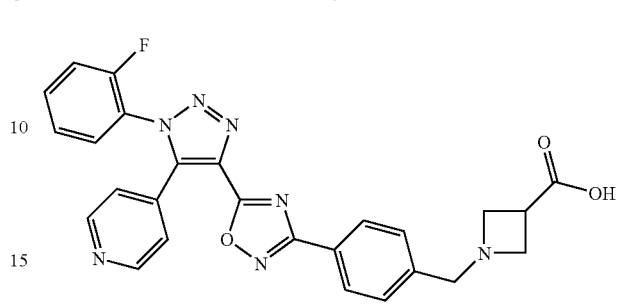

Step 1: 4-(5-(1-(2-fluorophenyl)-5-(pyridin-4-yl)-1H-1,2,3-triazol-4-yl)-1,2,4-oxadiazol-3-yl)benzaldehyde To a solution of oxalyl chloride (0.121 mL, 0.241 mmol, 2 M in DCM) in DCM (5 mL), at −78° C., was added DMSO (51 µL, 0.724 mmol) and the mixture was stirred for 30 minutes. To this mixture was added by syringe a suspension of Example 108 (100 mg; 0.241 mmol) in DCM (2 mL) and the resulting mixture was stirred for 30 minutes. Triethylamine (146 mg; 1.45 mmol) was added and the resulting mixture was stirred for 2 hours at −78° C. The mixture was allowed to warm to room temperature and a saturated solution of ammonium chloride (10 mL) was added. The aqueous layer was extracted with DCM (3×10 mL) and the combined organics were dried (MgSO$_4$), the solvent was removed in vacuo and the residue was purified by flash chromatography on a Biotage 25+S column, eluting with petrol containing increasing amounts of EtOAc to give the title compound as a white solid (97 mg; 96%). $^1$H NMR: (CDCl$_3$, 400 MHz) δ 10.10 (1H, s), 8.74 (2H, dd, J=4.5, 1.7 Hz), 8.28 (2H, d, J=8.1 Hz), 8.03-7.98 (2H, m), 7.64-7.53 (2H, m), 7.40-7.34 (3H, m), 7.22-7.16 (1H, m).

Step 2: 1-(4-{5-[1-(2-fluorophenyl)-5-pyridin-4-yl-1H-1,2,3-triazol-4-yl]-1,2,4-oxadiazol-3-yl}benzyl)azetidine-3-carboxylic acid The title compound was prepared following the procedure described for Example 94, Step 2, but starting from 4-(5-(1-(2-fluorophenyl)-5-(pyridin-4-yl)-1H-1,2,3-triazol-4-yl)-1,2,4-oxadiazol-3-yl)benzaldehyde, obtained in Step 1, (100 mg; 0.24 mmol) and azetidine-3-carboxylic acid (49 mg; 0.48 mmol) to give Example 113 as a white solid. $^1$H NMR: (DMSO-d$_6$, 400 MHz) δ 8.76 (2H, d, J=4.9 Hz), 8.00 (2H, d, J=7.8 Hz), 7.91 (1H, t, J=7.7 Hz), 7.82-7.64 (1H, m), 7.67-7.53 (4H, m), 7.52 (2H, t, J=8.5 Hz), 4.01 (3H, s), 3.76 (2H, s), 3.65 (2H, s). LC/MS (Method C): 498 (M+H)$^+$. HPLC (Method E) Rt 2.19 min (Purity: 95.0%).

Example 114

N-(4-{5-[1-(2-fluorophenyl)-5-pyridin-4-yl-1H-1,2,3-triazol-4-yl]-1,2,4-oxadiazol-3-yl}benzyl)-2-methoxyethanamine

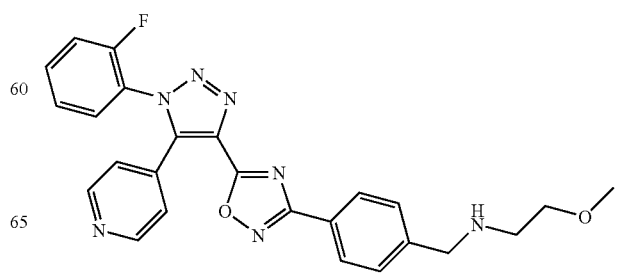

The title compound was prepared following the procedure described for Example 94, but starting from 4-(5-(1-(2-fluorophenyl)-5-(pyridin-4-yl)-1H-1,2,3-triazol-4-yl)-1,2,4-oxadiazol-3-yl)benzaldehyde, obtained as described in Example 113, Step 1, (100 mg; 0.24 mmol) and 2-methoxyethanamine (36.4 mg; 0.48 mmol) to give Example 114 as a white solid. $^1$H NMR: (CDCl$_3$, 400 MHz) δ 8.73-8.69 (2H, m), 8.05 (2H, d, J=8.0 Hz), 7.66-7.52 (2H, m), 7.46 (2H, d, J=8.0 Hz), 7.40-7.33 (3H, m), 7.18 (1H, t, J=9.1 Hz), 3.88 (2H, s), 3.53 (2H, t, J=5.1 Hz), 3.36 (3H, s), 2.82 (2H, t, J=5.1 Hz). LC/MS (Method C): 472 (M+H)$^+$. HPLC (Method F) Rt 3.07 min (Purity: 96.5%).

Example 115

11-(4-{5-[1-(2-fluorophenyl)-5-pyridin-4-yl-1H-1,2,3-triazol-4-yl]-1,2,4-oxadiazol-3-yl}benzyl)piperidine-4-carboxamide

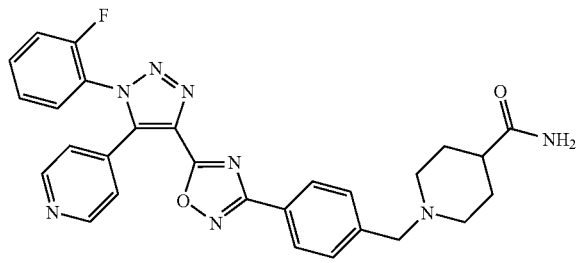

The title compound was prepared following the procedure described for Example 94, but starting from 4-(5-(1-(2-fluorophenyl)-5-(pyridin-4-yl)-1H-1,2,3-triazol-4-yl)-1,2,4-oxadiazol-3-yl)benzaldehyde, obtained as described in Example 113, Step 1, (100 mg; 0.24 mmol) and piperidine-4-carboxamide (62.2 mg; 0.48 mmol) to give Example 115 as an off-white solid. $^1$H NMR: (DMSO-d$_6$, 400 MHz) δ 8.78-8.71 (2H, m), 7.99-7.87 (3H, m), 7.77-7.69 (1H, m), 7.64-7.57 (2H, m), 7.56-7.47 (4H, m), 7.22 (1H, s), 6.73 (1H, s), 3.55 (2H, s), 2.84 (2H, d, J=10.8 Hz), 2.09 (1H, t, J=11.2 Hz), 1.98 (2H, t, J=11.4 Hz), 1.73-1.53 (4H, m). LC/MS (Method C): 525 (M+H)$^+$. HPLC (Method E) Rt 2.12 min (Purity: 98.1%).

Example 116

5-{5-[1-(2-fluorophenyl)-5-pyridin-4-yl-1H-1,2,3-triazol-4-yl]-1,2,4-oxadiazol-3-yl}-1H-indazole

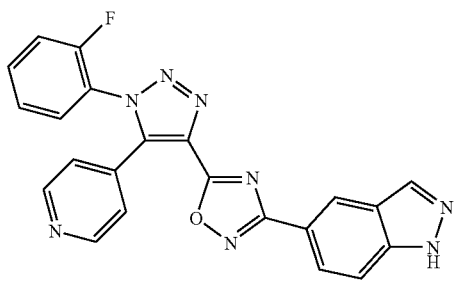

The title compound was prepared following the procedure described for Example 51, but starting from Intermediate 17 (209 mg; 0.67 mmol) and Intermediate 30 (129 mg; 0.74 mmol). The residue was purified by flash chromatography on a Biotage 25+S column, eluting with petrol containing increasing amounts of EtOAc to give Example 116 as an off-white solid. $^1$H NMR: (DMSO-d$_6$, 400 MHz) δ 13.37 (1H, s), 8.73 (2H, dd, J=4.56, 1.62 Hz), 8.43 (1H, s), 8.25 (1H, s), 7.95 (1H, dd, J=8.74, 1.55 Hz), 7.87 (1H, td, J=7.68, 1.70 Hz), 7.72-7.65 (2H, m), 7.58 (2H, dd, J=4.55, 1.63 Hz), 7.51-7.43 (2H, m). LC/MS (Method C): 425 (M+H)$^+$. HPLC (Method E) Rt 3.09 min (Purity: 93.5%).

Example 117

2,6-dichloro-4-{5-[1-(2-fluorophenyl)-5-pyridin-4-yl-1H-1,2,3-triazol-4-yl]-1,2,4-oxadiazol-3-yl}aniline

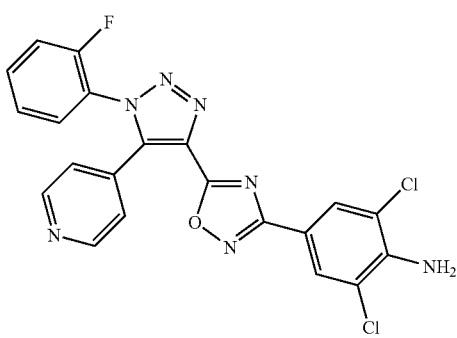

The title compound was prepared following the procedure described for Example 52, but starting from Intermediate 17 (209 mg; 0.67 mmol) and 4-amino-3,5-dichloro-N'-hydroxybenzimidamide (Apollo; 163 mg; 0.74 mmol) to give Example 117 as an off-white solid (230 mg; 73%). $^1$H NMR: (CDCl$_3$, 400 MHz) δ 8.74-8.71 (2H, m), 7.96 (2H, s), 7.63-7.51 (2H, m), 7.40-7.32 (3H, m), 7.21-7.15 (1H, m), 4.81 (2H, br s). LC/MS (Method C): 468 (M+H)$^+$. HPLC (Method E) Rt=3.80 min (Purity: 99.7%).

Example 118

5-{5-[1-(2-fluorophenyl)-5-pyridin-4-yl-1H-1,2,3-triazol-4-yl]-1,2,4-oxadiazol-3-yl}pyridin-2-amine

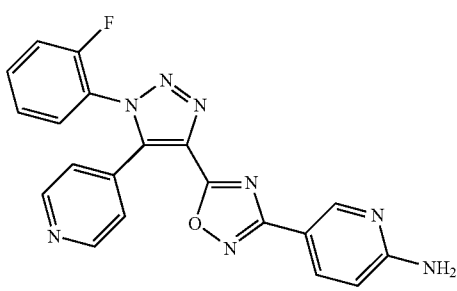

In a microwave vial, Intermediate 17 (209 mg; 0.67 mmol) was suspended in toluene (2 mL) and ACN (1 mL) and 6-amino-N'-hydroxypyridine-3-carboximidamide (J. Med. Chem., 2007, 3442-3456; 113 mg; 0.74 mmol) was added followed by potassium carbonate (123 mg; 0.74 mmol). The MW vial was sealed and the suspension was heated to 180° C. for 30 min in a microwave reactor. The reaction mixture was cooled down to room temperature and diluted with DCM and water. The solid was removed by filtration and redissolved in 2M HCl aqueous solution. The solution was neutralized with sat NaHCO$_3$ solution and the precipitate removed by filtration, washed with H$_2$O and dried to give Example 118 as an off-white solid. $^1$H NMR: (DMSO-d$_6$, 400 MHz) δ 8.74 (2H, app d, J=5.2 Hz), 8.51 (1H, d, J=2.4 Hz), 7.93-7.86 (2H, m), 7.77-7.68 (1H, m), 7.59 (2H, app d, J=5.2 Hz), 7.51 (2H, app t, J=8.5 Hz), 6.72 (2H, br s), 6.60 (1H, d, J=8.8 Hz). LC/MS (Method C): 401 (M+H)$^+$. HPLC (Method E) Rt=2.14 min (Purity: 97.6%).

Example 119

2-{5-[1-(2-fluorophenyl)-5-pyridin-4-yl-1H-1,2,3-triazol-4-yl]-1,2,4-oxadiazol-3-yl}pyrazine

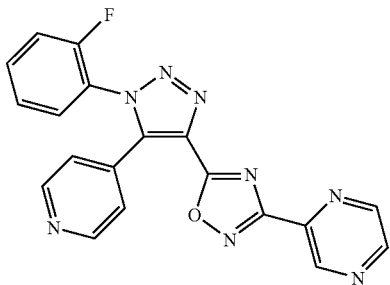

The title compound was prepared following the procedure described for Example 52, but starting from Intermediate 17 (105 mg; 0.34 mmol) and N'-hydroxypyrazine-2-carboximidamide (Fluorochem; 51 mg; 0.37 mmol) to give Example 119 as an off-white solid (96 mg; 73%). $^1$H NMR: (CDCl$_3$, 400 MHz) δ 9.33 (1H, d, J=1.4 Hz), 8.78-8.72 (4H, m), 7.65-7.54 (2H, m), 7.40-7.33 (3H, m), 7.23-7.17 (1H, m). LC/MS (Method C): 387 (M+H)$^+$. HPLC (Method E) Rt=2.83 min (Purity: 95.2%).

Example 120

5-{5-[1-(2-fluorophenyl)-5-pyridin-4-yl-1H-1,2,3-triazol-4-yl]-1,2,4-oxadiazol-3-yl}-2-(trifluoromethyl)pyridine

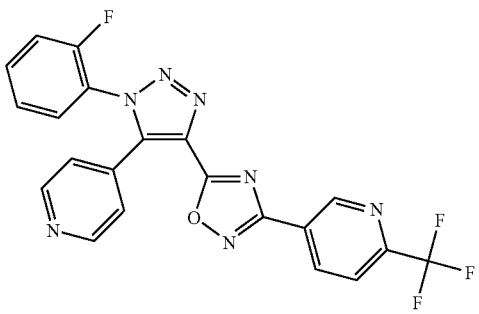

The title compound was prepared following the procedure described for Example 52, but starting from Intermediate 17 (105 mg; 0.34 mmol) and N'-hydroxy-6-(trifluoromethyl) nicotinimidamide (Fluorochem; 76 mg; 0.37 mmol) to give Example 120 as a white solid (134 mg; 87%). $^1$H NMR: (CDCl$_3$, 400 MHz) δ 9.42 (1H, s), 8.75-8.72 (2H, m), 8.57 (1H, dd, J=8.2, 2.0 Hz), 7.84 (1H, d, J=8.2 Hz), 7.64-7.54 (2H, m), 7.42-7.32 (3H, m), 7.23-7.16 (1H, m). LC/MS (Method C): 454 (M+H)$^+$. HPLC (Method E) Rt=3.69 min (Purity: 99.4%).

Example 121

4-{1-(2-fluorophenyl)-4-[3-(2-methylphenyl)-1,2,4-oxadiazol-5-yl]-1H-1,2,3-triazol-5-yl}pyridine

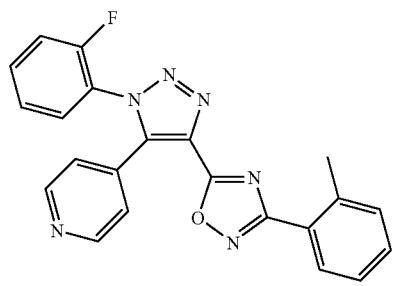

The title compound was prepared following the procedure described for Example 52, but starting from Intermediate 17 (209 mg; 0.67 mmol) and N'-hydroxy-2-methylbenzimidamide (Enamine, 111 mg; 0.74 mmol) to give Example 121 as a white solid (213 mg; 80%). $^1$H NMR: (CDCl$_3$, 400 MHz) δ 8.73-8.67 (2H, m), 8.01 (1H, d, J=7.7 Hz), 7.63-7.52 (2H, m), 7.44-7.28 (6H, m), 7.23-7.12 (1H, m), 2.62 (3H, s). LC/MS (Method C): 399 (M+H)$^+$. HPLC (Method E) Rt=3.81 min (Purity: 99.1%).

Example 122

4-[4-[3-(5-fluoro-2-methoxyphenyl)-1,2,4-oxadiazol-5-yl]-1-(2-fluorophenyl)-1H-1,2,3-triazol-5-yl]pyridine

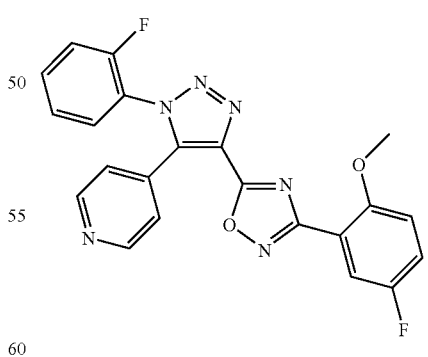

The title compound was prepared following the procedure described for Example 52, but starting from Intermediate 17 (209 mg; 0.67 mmol) and Intermediate 46 (111 mg; 0.74 mmol) to give Example 122 as a white solid. $^1$H NMR: (CDCl$_3$, 400 MHz) δ 8.73-8.68 (2H, m), 7.81 (1H, dd, J=9.0, 3.2 Hz), 7.63-7.51 (2H, m), 7.39-7.33 (3H, m), 7.22-7.15 (2H, m), 7.00 (1H, dd, J=9.1, 4.2 Hz), 3.96 (3H, s). LC/MS (Method C): 433 (M+H)⁺. HPLC (Method E) Rt=3.50 min (Purity: 98.9%).

Example 123

5-{5-[1-(2-fluorophenyl)-5-(methoxymethyl)-1H-1,2,3-triazol-4-yl]-1,2,4-oxadiazol-3-yl}pyridin-2-amine

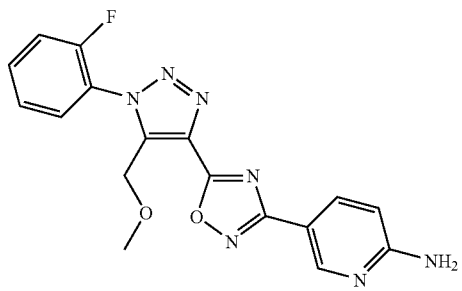

To a solution of Intermediate 11 (75 mg; 0.3 mmol) in anhydrous ACN (2 mL) was added 1-ethyl-3-(3-dimethylaminopropyl)carbodiimide hydrochloride (EDC) (81 mg; 0.42 mmol) followed by 6-amino-N'-hydroxypyridine-3-carboximidamide (J. Med. Chem., 2007, 3442-3456; 50 mg; 0.33 mmol) in a MW vial. The mixture stirred at RT for 18 h. Anhydrous pyridine (2 mL) was added. The reaction vessel was sealed and heated at 150° C. for 15 min in the microwave. The reaction mixture was cooled down to room temperature and poured into isopropanol (5 mL) and water (5 mL). The volume was reduced by removing solvent in vacuo until precipitation occurred and the solid was collected by filtration and washed with isopropanol (3×10 mL) to give Example 123 as a brown solid. ¹H NMR: (DMSO-d₆, 400 MHz) δ 8.70 (1H, d, J=2.4 Hz), 8.05 (1H, dd, J=8.7, 2.4 Hz), 7.88-7.77 (2H, m), 7.71-7.64 (1H, m), 7.56 (1H, t, J=7.7 Hz), 6.75 (2H, s), 6.64 (1H, d, J=8.7 Hz), 4.96 (2H, s), 3.21 (3H, s). LC/MS (Method C): 368 (M+H)⁺. HPLC (Method E) Rt 2.23 min (Purity: 97.4%).

Example 124

3-{5-[1-(2-fluorophenyl)-5-pyridin-4-yl-1H-1,2,3-triazol-4-yl]-1,2,4-oxadiazol-3-yl}phenol

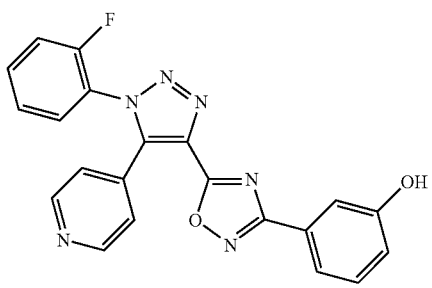

The title compound was prepared following the procedure described for Example 108, but starting from Intermediate 17 (209 mg; 0.67 mmol) and Intermediate 34 (118 mg; 0.74 mmol), to give Example 124 as an off-white solid. ¹H NMR: (DMSO-d₆, 400 MHz) δ 9.98 (1H, br s), 8.77-8.73 (2H, m), 7.94-7.86 (1H, m), 7.76-7.69 (1H, m), 7.63-7.59 (2H, m), 7.51 (2H, t, J=8.5 Hz), 7.47-7.36 (3H, m), 7.04-7.00 (1H, m). LC/MS (Method C): 399 (M+H)⁺. HPLC (Method E) Rt 3.19 min (Purity: 98.6%).

Example 125

1-(3-{5-[1-(2-fluorophenyl)-5-pyridin-4-yl-1H-1,2,3-triazol-4-yl]-1,2,4-oxadiazol-3-yl}phenyl)methanamine hydrochloride

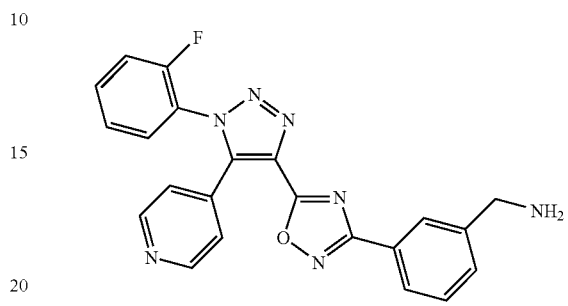

Step 1: tert-butyl (3-(5-(1-(2-fluorophenyl)-5-(pyridin-4-yl)-1H-1,2,3-triazol-4-yl)-1,2,4-oxadiazol-3-yl)benzylcarbamate The title compound was prepared following the procedure described for Example 116, but starting from Intermediate 17 (209 mg; 0.67 mmol) and Intermediate 54 (196 mg; 0.72 mmol), and was isolated as a white solid. ¹H NMR: (CDCl₃, 400 MHz) δ 8.75-8.71 (2H, m), 8.04 (1H, s), 8.01-7.96 (1H, m), 7.65-7.52 (2H, m), 7.48-7.42 (2H, m), 7.41-7.34 (3H, m), 7.19 (1H, app t, J=9.1 Hz), 4.91 (1H, br s), 4.40 (2H, br d, J=6.0 Hz), 1.48 (9H, s). LC/MS (Method C): 514 (M+H)⁺. HPLC (Method E) Rt 3.74 min (Purity: 99.7%).

Step 2: 1-(3-{5-[1-(2-fluorophenyl)-5-pyridin-4-yl-1H-1,2,3-triazol-4-yl]-1,2,4-oxadiazol-3-yl}phenyl)methanamine hydrochloride The title compound was prepared following the procedure described for Example 55, Step 2, but starting from tert-butyl (3-(5-(1-(2-fluorophenyl)-5-(pyridin-4-yl-1H-1,2,3-triazol-4-yl-1,2,4-oxadiazol-3-yl)benzylcarbamate, obtained in Step 1, (190 mg; 0.361 mmol), to give Example 125 as a white solid (147 mg; 90%). ¹H NMR: (DMSO-d₆, 400 MHz) δ 8.85-8.81 (2H, m), 8.53 (3H, s), 8.21 (1H, s), 8.00 (1H, d, J=7.7 Hz), 7.92 (1H, t, J=7.6 Hz), 7.81-7.69 (4H, m), 7.68 (1H, t, J=7.7 Hz), 7.56-7.48 (2H, m), 4.18 (2H, q, J=5.9 Hz). LC/MS (Method C): 414 (M+H)⁺. HPLC (Method F) Rt 2.82 min (Purity: 99.0%).

Example 126

5-{5-[1-(2-fluorophenyl)-5-pyridin-4-yl-1H-1,2,3-triazol-4-yl]-1,2,4-oxadiazol-3-yl}-2-methoxypyridine

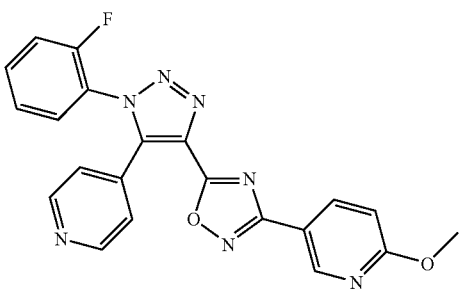

The title compound was prepared following the procedure described for Example 108, but starting from Intermediate 17 (209 mg; 0.67 mmol) and N'-hydroxy-6-methoxynicotinimidamide (Aurora, 123 mg; 0.74 mmol), to give Example 126 as an off-white solid. $^{1}$H NMR: (DMSO-$d_6$, 400 MHz) δ 8.78 (1H, d, J=2.4 Hz), 8.77-8.74 (2H, m), 8.25 (1H, dd, J=8.7, 2.4 Hz), 7.91 (1H, td, J=7.6, 1.7 Hz), 7.76-7.69 (1H, m), 7.61 (2H, dd, J=4.6, 1.6 Hz), 7.52 (2H, t, J=8.5 Hz), 7.07 (1H, d, J=8.7 Hz), 3.98 (3H, s). LC/MS (Method C): 416 (M+H)$^+$. HPLC (Method F) Rt 3.49 min (Purity: 95.4%).

Example 127

N-(4-{5-[1-(2-fluorophenyl)-5-pyridin-4-yl-1H-1,2,3-triazol-4-yl]-1,2,4-oxadiazol-3-yl}benzyl)-beta-alanine

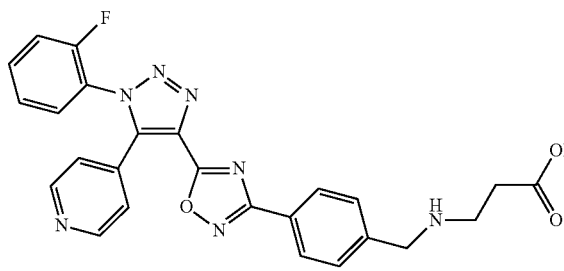

The title compound was prepared following the procedure described for Example 94, but starting from 4-(5-(1-(2-fluorophenyl)-5-(pyridin-4-yl)-1H-1,2,3-triazol-4-yl)-1,2,4-oxadiazol-3-yl)benzaldehyde, obtained as described in Example 113, Step 1, (100 mg; 0.24 mmol) and β-alanine (43.2 mg; 0.48 mmol) to give Example 127 as a white solid. $^{1}$H NMR: (DMSO-$d_6$, 400 MHz) δ 8.75 (2H, dd, J=4.5, 1.6 Hz), 7.97 (2H, d, J=8.1 Hz), 7.91 (1H, td, J=7.6, 1.7 Hz), 7.76-7.69 (1H, m), 7.61 (2H, dd, J=4.5, 1.7 Hz), 7.58 (2H, d, J=8.1 Hz), 7.55-7.45 (2H, m), 3.87 (2H, s), 2.81-2.68 (2H, m), 2.39 (2H, t, J=6.7 Hz). LC/MS (Method C): 484 (M+H)$^+$. HPLC (Method F) Rt 2.83 min (Purity: 99.2%).

Example 128

1-(4-{5-[1-(2-fluorophenyl)-5-pyridin-4-yl-1H-1,2,3-triazol-4-yl]-1,2,4-oxadiazol-3-yl}benzyl)piperidine-4-carboxylic acid

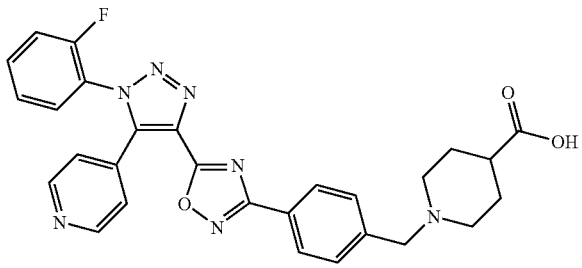

The title compound was prepared following the procedure described for Example 94, but starting from 4-(5-(1-(2-fluorophenyl)-5-(pyridin-4-yl)-1H-1,2,3-triazol-4-yl)-1,2,4-oxadiazol-3-yl)benzaldehyde, obtained as described in Example 113, Step 1, (100 mg; 0.24 mmol) and piperidine-4-carboxylic acid (62.6 mg; 0.48 mmol) to give Example 128 as a white solid. $^{1}$H NMR: (DMSO-$d_6$, 400 MHz) δ 8.75 (2H, d, J=5.3 Hz), 7.97-7.88 (3H, m), 7.73 (1H, q, J=6.9 Hz), 7.61 (2H, d, J=5.4 Hz), 7.55-7.48 (4H, m), 3.56 (2H, s), 2.78 (2H, d, J=10.9 Hz), 2.27-2.18 (1H, m), 2.05 (2H, m), 1.81 (2H, m), 1.61 (2H, m). LC/MS (Method C): 526 (M+H)$^+$. HPLC (Method E) Rt 2.20 min (Purity: 97.7%).

Example 129

1-(4-{5-[1-(2-fluorophenyl)-5-pyridin-4-yl-1H-1,2,3-triazol-4-yl]-1,2,4-oxadiazol-3-yl}phenyl)-N-methylmethanamine

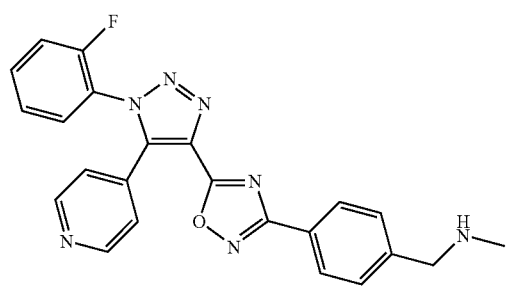

The title compound was prepared following the procedure described for Example 94, but starting from 4-(5-(1-(2-fluorophenyl)-5-(pyridin-4-yl)-1H-1,2,3-triazol-4-yl)-1,2,4-oxadiazol-3-yl)benzaldehyde, obtained as described in Example 113, Step 1, (100 mg; 0.24 mmol) and methylamine hydrochloride (32.7 mg; 0.48 mmol) to give Example 129 as a white solid. $^{1}$H NMR: (DMSO-$d_6$, 400 MHz) δ 8.76-8.73 (2H, m), 7.97-7.87 (3H, m), 7.76-7.69 (1H, m), 7.64-7.49 (6H, m), 3.76 (2H, s), 2.31 (3H, s). LC/MS (Method C): 428 (M+H)$^+$. HPLC (Method E) Rt 2.14 min (Purity: 98.9%).

Example 130

N-(4-{5-[1-(2-fluorophenyl)-5-pyridin-4-yl-1H-1,2,3-triazol-4-yl]-1,2,4-oxadiazol-3-yl}benzyl)-N-methylglycine

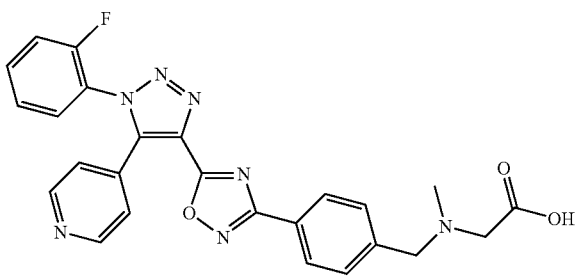

The title compound was prepared following the procedure described for Example 94, but starting from 4-(5-(1-(2-fluorophenyl)-5-(pyridin-4-yl)-1H-1,2,3-triazol-4-yl)-1,2,4-oxadiazol-3-yl)benzaldehyde, obtained as described in Example 113, Step 1, (100 mg; 0.24 mmol) and 2-(methylamino)acetic acid (43.2 mg; 0.48 mmol) to give Example 130 as a white solid. $^{1}$H NMR: (DMSO-$d_6$, 400 MHz) δ

8.76-8.73 (2H, m), 7.97 (2H, d, J=8.0 Hz), 7.93-7.88 (1H, m), 7.76-7.69 (1H, m), 7.63-7.58 (2H, m), 7.61-7.47 (4H, m), 3.78 (2H, s), 3.26 (2H, s), 2.32 (3H, s). LC/MS (Method C): 484 (M+H)⁺. HPLC (Method E) Rt 2.36 min (Purity: 98.9%).

Example 131

1-(4-{5-[1-(2-fluorophenyl)-5-pyridin-4-yl-1H-1,2,3-triazol-4-yl]-1,2,4-oxadiazol-3-yl}phenyl)-N,N-dimethylmethanamine

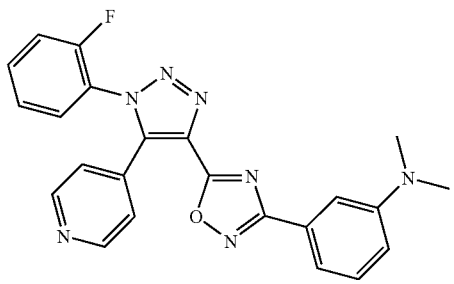

The title compound was prepared following the procedure described for Example 94, but starting from 4-(5-(1-(2-fluorophenyl)-5-(pyridin-4-yl)-1H-1,2,3-triazol-4-yl)-1,2,4-oxadiazol-3-yl)benzaldehyde, obtained as described in Example 113, Step 1, (100 mg; 0.24 mmol) and dimethylamine hydrochloride (39.5 mg; 0.48 mmol) to give Example 131 as a white solid. ¹H NMR: (DMSO-d₆, 400 MHz) δ 8.62 (2H, dd, J=4.5, 1.7 Hz), 7.84 (2H, d, J=8.1 Hz), 7.78 (1H, td, J=7.6, 1.7 Hz), 7.63-7.56 (1H, m), 7.48 (2H, dd, J=4.5, 1.7 Hz), 7.42-7.35 (4H, m), 3.38 (2H, s), 2.08 (6H, s). LC/MS (Method C): 442 (M+H)⁺. HPLC (Method E) Rt 2.14 min (Purity: 94.2%).

Example 132

2-[(3-{5-[1(2-fluorophenyl)-5-pyridin-4-yl-1H-1,2,3-triazol-4-yl]-1,2,4-oxadiazol-3-yl}benzyl)amino]ethanol formate

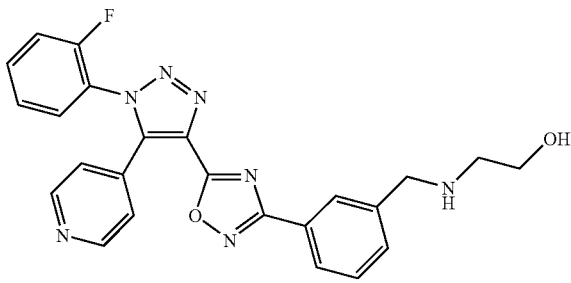

The title compound was prepared following the procedure described for Example 94, starting from 3-(5-(1-(2-fluorophenyl)-5-(pyridin-4-yl)-1H-1,2,3-triazol-4-yl)-1,2,4-oxadiazol-3-yl)benzaldehyde (100 mg; 0.24 mmol) and 2-aminoethanol (29.6 mg; 0.48 mmol) to give Example 132 as a white solid. ¹H NMR: (DMSO-d₆, 400 MHz) δ 8.63-8.60 (2H, m), 8.13 (1H, s), 7.93 (1H, s), 7.82-7.73 (2H, m), 7.63-7.56 (1H, m), 7.54-7.36 (6H, m), 3.78 (2H, s), 3.42 (2H, t, J=5.8 Hz), 2.56 (2H, t, J=5.8 Hz). LC/MS (Method C): 458 (M+H)⁺. HPLC (Method E) Rt 2.11 min (Purity: 97.9%).

Example 133

1-(3-{5-[1-(2-fluorophenyl)-5-pyridin-4-yl-1H-1,2,3-triazol-4-yl]-1,2,4-oxadiazol-3-yl}phenyl)-N-methylmethanamine formate

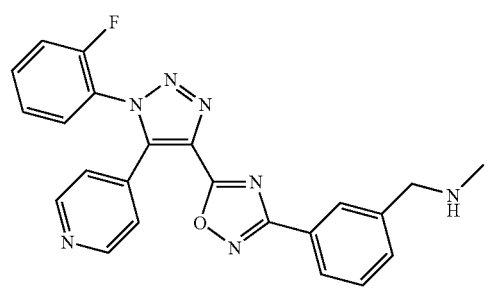

The title compound was prepared following the procedure described for Example 94, starting from 3-(5-(1-(2-fluorophenyl)-5-(pyridin-4-yl)-1H-1,2,3-triazol-4-yl)-1,2,4-oxadiazol-3-yl)benzaldehyde (100 mg; 0.24 mmol) and methylamine hydrochloride (32.7 mg; 0.48 mmol) to give Example 133 as a white solid. ¹H NMR: (DMSO-d₆, 400 MHz) δ 8.74 (2H, dd, J=4.49, 1.64 Hz), 8.28 (1H, s), 8.07 (1H, s), 7.92-7.86 (2H, m), 7.75-7.68 (1H, m), 7.65-7.55 (3H, m), 7.50 (2H, t, J=8.4 Hz), 3.93 (2H, s), 2.40 (3H, s). LC/MS (Method C): 428 (M+H)⁺. HPLC (Method E) Rt 2.13 min (Purity: 99.4%).

Example 134

1-(3-{5-[1-(2-fluorophenyl)-5-pyridin-4-yl-1H-1,2,3-triazol-4-yl]-1,2,4-oxadiazol-3-yl}benzyl)pyrrolidin-3-ol

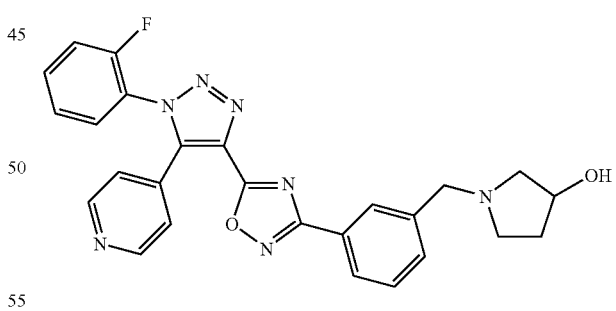

The title compound was prepared following the procedure described for Example 94, starting from 3-(5-(1-(2-fluorophenyl)-5-(pyridin-4-yl)-1H-1,2,3-triazol-4-yl)-1,2,4-oxadiazol-3-yl)benzaldehyde (100 mg; 0.24 mmol) and 3-pyrrolidinol (32.7 mg; 0.48 mmol) to give Example 134 as an off-white solid. ¹H NMR: (DMSO-d₆, 400 MHz) δ 8.76-8.73 (2H, m), 7.97 (1H, s), 7.96-7.84 (2H, m), 7.76-7.69 (1H, m), 7.61 (2H, dd, J=4.5, 1.6 Hz), 7.59-7.49 (4H, m), 4.74 (1H, d, J=4.4 Hz), 4.29-4.21 (1H, m), 3.75-3.63 (2H, m), 2.75 (1H, dd, J=9.6, 6.2 Hz), 2.63 (1H, q, J=7.8 Hz), 2.51-2.45 (1H, m), 2.36 (1H, dd, J=9.6, 3.8 Hz), 2.10-1.99 (1H, m), 1.64-1.55

(1H, m). LC/MS (Method C): 484 (M+H)+. HPLC (Method E) Rt 2.13 min (Purity: 97.8%).

Example 135

1-(4-{5-[1-(2-fluorophenyl)-5-pyridin-4-yl-1H-1,2,3-triazol-4-yl]-1,2,4-oxadiazol-3-yl}benzyl)azetidin-3-ol

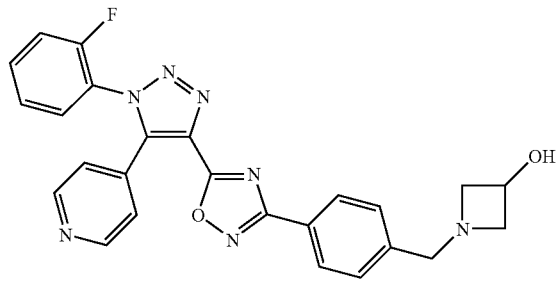

The title compound was prepared following the procedure described for Example 94, but starting from 4-(5-(1-(2-fluorophenyl)-5-(pyridin-4-yl)-1H-1,2,3-triazol-4-yl)-1,2,4-oxadiazol-3-yl)benzaldehyde, obtained as described in Example 113, Step 1, (100 mg; 0.24 mmol) and 3-azetidinol (35.4 mg; 0.48 mmol) to give Example 135 as a white solid. $^1$H NMR: (DMSO-$d_6$, 400 MHz) δ 8.75 (2H, dd, J=4.7, 1.5 Hz), 7.97-7.87 (3H, m), 7.76-7.69 (1H, m), 7.61 (2H, dd, J=4.7, 1.6 Hz), 7.57-7.47 (4H, m), 5.35 (1H, d, J=6.4 Hz), 4.27-4.19 (1H, m), 3.67 (2H, s), 3.55 (2H, dd, J=7.4, 5.8 Hz), 2.83 (2H, t, J=6.6 Hz). LC/MS (Method C): 470 (M+H)+. HPLC (Method E) Rt 2.13 min (Purity: 98.2%).

Example 136

2-[(4-{5-[1-(2-fluorophenyl)-5-pyridin-4-yl-1H-1,2,3-triazol-4-yl]-1,2,4-oxadiazol-3-yl}benzyl)amino]ethanol

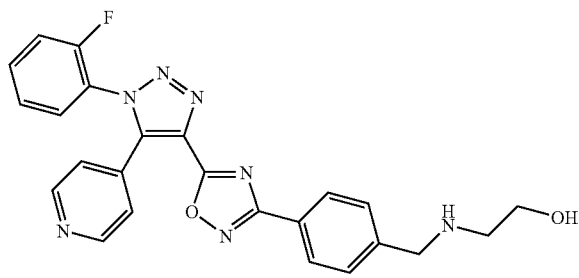

The title compound was prepared following the procedure described for Example 94, but starting from 4-(5-(1-(2-fluorophenyl)-5-(pyridin-4-yl)-1H-1,2,3-triazol-4-yl)-1,2,4-oxadiazol-3-yl)benzaldehyde, obtained as described in Example 113, Step 1, (100 mg; 0.24 mmol) and 2-aminoethanol (29.6 mg; 0.48 mmol) to give Example 136 as a white solid. $^1$H NMR: (DMSO-$d_6$, 400 MHz) δ 8.75 (2H, dd, J=4.6, 1.6 Hz), 7.96-7.87 (3H, m), 7.76-7.69 (1H, m), 7.61 (2H, dd, J=4.6, 1.6 Hz), 7.57 (2H, d, J=8.0 Hz), 7.51 (2H, t, J=8.5 Hz), 4.52 (1H, s), 3.83 (2H, s), 3.51 (2H, q, J=5.1 Hz), 2.62 (2H, t, J=5.8 Hz). LC/MS (Method C): 458 (M+H)+. HPLC (Method E) Rt 2.10 min (Purity: 99.9%).

Example 137

N-[1-(4-{5-[1-(2-fluorophenyl)-5-pyridin-4-yl-1H-1,2,3-triazol-4-yl]-1,2,4-oxadiazol-3-yl}benzyl)piperidin-4-yl]acetamide

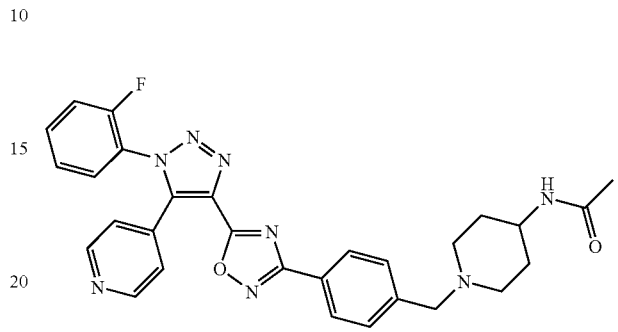

The title compound was prepared following the procedure described for Example 94, but starting from 4-(5-(1-(2-fluorophenyl)-5-(pyridin-4-yl)-1H-1,2,3-triazol-4-yl)-1,2,4-oxadiazol-3-yl)benzaldehyde, obtained as described in Example 113, Step 1, (100 mg; 0.24 mmol) and N-(piperidin-4-yl)acetamide (69 mg; 0.48 mmol) to give Example 137 as a white solid. $^1$H NMR: (DMSO-$d_6$, 400 MHz) δ 8.76-8.73 (2H, m), 7.96 (2H, d, J=8.0 Hz), 7.94-7.88 (1H, m), 7.78-7.68 (2H, m), 7.61 (2H, dd, J=4.5, 1.6 Hz), 7.56-7.48 (4H, m), 3.56 (3H, m), 2.78 (2H, d, J=11.1 Hz), 2.06 (2H, t, J=11.3 Hz), 1.81 (3H, s), 1.73 (2H, d, J=12.3 Hz), 1.43 (2H, t, J=11.6 Hz). LC/MS (Method C): 539 (M+H)+. HPLC (Method E) Rt 2.13 min (Purity: 99.9%).

Example 138

4-[4-{3-[4-(azetidin-1-ylmethyl)phenyl]-1,2,4-oxadiazol-5-yl}-1-(2-fluorophenyl)-1H-1,2,3-triazol-5-yl]pyridine

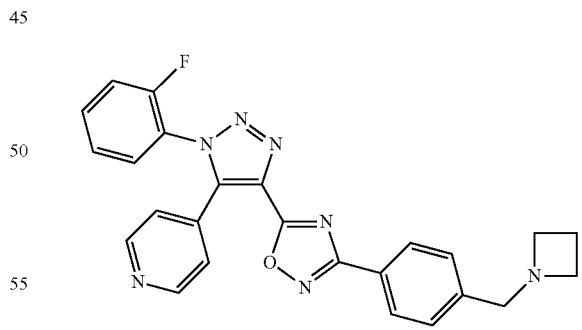

The title compound was prepared following the procedure described for Example 94, but starting from 4-(5-(1-(2-fluorophenyl)-5-(pyridin-4-yl)-1H-1,2,3-triazol-4-yl)-1,2,4-oxadiazol-3-yl)benzaldehyde, obtained as described in Example 113, Step 1, (100 mg; 0.24 mmol) and azetidine hydrochloride (45.4 mg; 0.48 mmol) to give Example 138 as a white solid. $^1$H NMR: (DMSO-$d_6$, 400 MHz) δ 8.75 (2H, dd, J=4.6, 1.6 Hz), 7.96-7.87 (3H, m), 7.76-7.69 (1H, m), 7.61 (2H, dd, J=4.6, 1.6 Hz), 7.51 (4H, t, J=8.1 Hz), 3.67 (2H, s), 3.22 (4H, t, J=6.9 Hz), 2.04 (2H, m). LC/MS (Method C): 454 (M+H)⁺. HPLC (Method E) Rt 2.19 min (Purity: 96.2%).

Example 139

[1-(4-{5-[1(2-fluorophenyl)-5-pyridin-4-yl-1H-1,2,3-triazol-4-yl]-1,2,4-oxadiazol-3-yl}benzyl)piperidin-4-yl]methanol

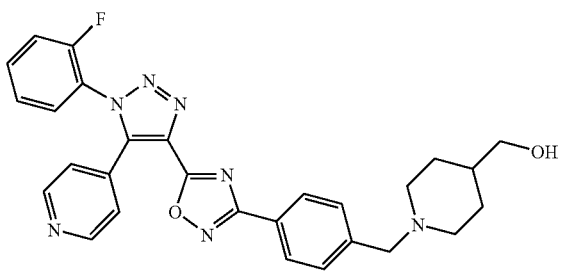

The title compound was prepared following the procedure described for Example 94, but starting from 4-(5-(1-(2-fluorophenyl)-5-(pyridin-4-yl)-1H-1,2,3-triazol-4-yl)-1,2,4-oxadiazol-3-yl)benzaldehyde, obtained as described in Example 113, Step 1, (100 mg; 0.24 mmol) and 4-hydroxymethylpiperidine (55.9 mg; 0.48 mmol) to give Example 139 as a white solid. $^1$H NMR: (DMSO-$d_6$, 400 MHz) δ 8.75 (2H, dd, J=4.48, 1.64 Hz), 7.97-7.86 (3H, m), 7.76-7.69 (1H, m), 7.61 (2H, dd, J=4.5, 1.7 Hz), 7.55-7.48 (4H, m), 4.43 (1H, t, J=5.3 Hz), 3.55 (2H, s), 3.28 (2H, t, J=5.8 Hz), 2.84 (2H, d, J=10.8 Hz), 1.96 (2H, t, J=11.3 Hz), 1.66 (2H, d, J=12.6 Hz), 1.37 (1H, d, J=10.8 Hz), 1.25-1.12 (2H, m). LC/MS (Method C): 512 (M+H)⁺. HPLC (Method E) Rt 2.16 min (Purity: 99.2%).

Example 140

[1-(4-{5-[1-(2-fluorophenyl)-5-pyridin-4-yl-1H-1,2,3-triazol-4-yl]-1,2,4-oxadiazol-3-yl}benzyl)piperidin-3-yl]methanol

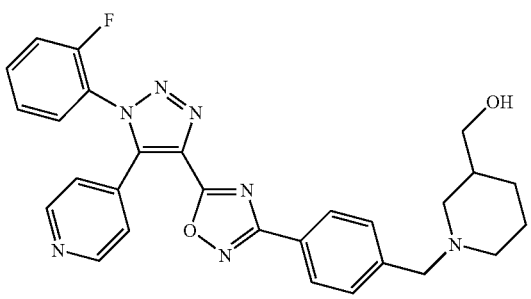

The title compound was prepared following the procedure described for Example 94, but starting from 4-(5-(1-(2-fluorophenyl)-5-(pyridin-4-yl)-1H-1,2,3-triazol-4-yl)-1,2,4-oxadiazol-3-yl)benzaldehyde, obtained as described in Example 113, Step 1, (100 mg; 0.24 mmol) and 3-hydroxymethylpiperidine (55.9 mg; 0.48 mmol) to give Example 140 as a white solid. $^1$H NMR: (DMSO-$d_6$, 400 MHz) δ 8.75 (2H, dd, J=4.5, 1.6 Hz), 7.97-7.87 (3H, m), 7.76-7.69 (1H, m), 7.61 (2H, dd, J=4.5, 1.7 Hz), 7.55-7.48 (4H, m), 4.40 (1H, t, J=5.2 Hz), 3.61-3.48 (2H, m), 3.34-3.27 (1H, m), 3.25-3.17 (1H, m), 2.87 (1H, d, J=9.3 Hz), 2.74 (1H, d, J=10.9 Hz), 1.96 (1H, t, J=11.0 Hz), 1.76-1.62 (4H, m), 1.50 (1H, d, J=12.6 Hz), 0.92 (1H, d, J=12.3 Hz). LC/MS (Method C): 512 (M+H)⁺. HPLC (Method E) Rt 2.16 min (Purity: 99.3%).

Example 141

1-(4-{5-[1-(2-fluorophenyl)-5-pyridin-4-yl-1H-1,2,3-triazol-4-yl]-1,2,4-oxadiazol-3-yl}benzyl)piperidin-4-ol

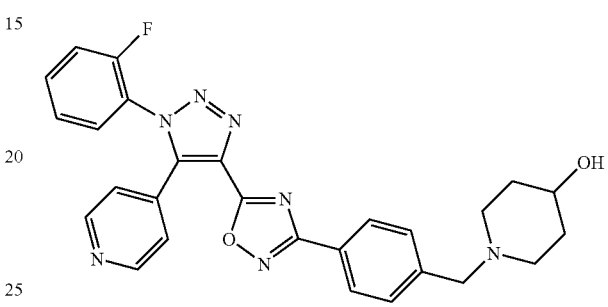

The title compound was prepared following the procedure described for Example 94, but starting from 4-(5-(1-(2-fluorophenyl)-5-(pyridin-4-yl)-1H-1,2,3-triazol-4-yl)-1,2,4-oxadiazol-3-yl)benzaldehyde, obtained as described in Example 113, Step 1, (100 mg; 0.24 mmol) and 4-hydroxypiperidine (49.1 mg; 0.48 mmol) to give Example 141 as a white solid. $^1$H NMR: (DMSO-$d_6$, 400 MHz) δ 8.76-8.73 (2H, m), 7.97-7.87 (3H, m), 7.76-7.69 (1H, m), 7.61 (2H, dd, J=4.5, 1.6 Hz), 7.52 (4H, t, J=8.4 Hz), 4.57 (1H, d, J=4.1 Hz), 3.56-3.43 (3H, m), 2.70 (2H, d, J=10.5 Hz), 2.13-2.04 (2H, m), 1.74 (2H, d, J=12.0 Hz), 1.48-1.37 (2H, m). LC/MS (Method C): 498 (M+H)⁺. HPLC (Method E) Rt 2.13 min (Purity: 99.9%).

Example 142

1-(4-{5-[1-(2-fluorophenyl)-5-pyridin-4-yl-1H-1,2,3-triazol-4-yl]-1,2,4-oxadiazol-3-yl}benzyl)pyrrolidin-3-ol

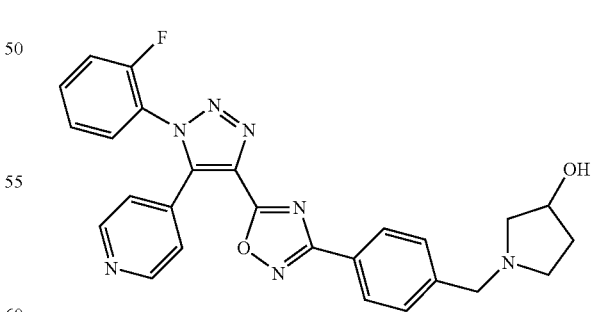

The title compound was prepared following the procedure described for Example 94, but starting from 4-(5-(1-(2-fluorophenyl)-5-(pyridin-4-yl)-1H-1,2,3-triazol-4-yl)-1,2,4-oxadiazol-3-yl)benzaldehyde, obtained as described in Example 113, Step 1, (100 mg; 0.24 mmol) and 3-pyrrolidinol (42.3 mg; 0.48 mmol) to give Example 142 as a white solid. $^1$H NMR: (DMSO-$d_6$, 400 MHz) δ 8.76-8.73 (2H, m), 7.97-7.87 (3H, m), 7.76-7.69 (1H, m), 7.62-7.59 (2H, m), 7.56-7.47 (4H, m), 4.73 (1H, d, J=4.5 Hz), 4.26-4.20 (1H, m), 3.72-3.61 (2H, m), 2.73 (1H, dd, J=9.7, 6.2 Hz), 2.63 (1H, q, J=7.8 Hz), 2.49-2.46 (1H, m), 2.36 (1H, dd, J=9.5, 3.7 Hz), 2.09-1.99 (1H, m), 1.63-1.55 (1H, m). LC/MS (Method C): 484 (M+H)$^+$. HPLC (Method E) Rt 2.13 min (Purity: 99.9%).

Example 143

[4-(4-{5-[1-(2-fluorophenyl)-5-pyridin-4-yl-1H-1,2,3-triazol-4-yl]-1,2,4-oxadiazol-3-yl}benzyl)morpholin-2-yl]methanol

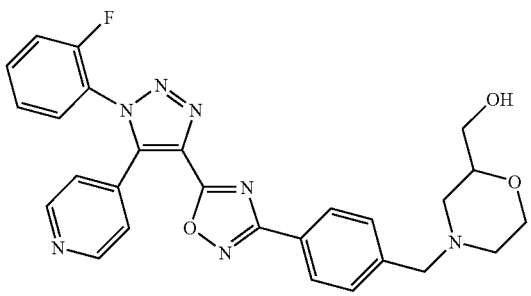

The title compound was prepared following the procedure described for Example 94, but starting from 4-(5-(1-(2-fluorophenyl)-5-(pyridin-4-yl)-1H-1,2,3-triazol-4-yl)-1,2,4-oxadiazol-3-yl)benzaldehyde, obtained as described in Example 113, Step 1, (100 mg; 0.24 mmol) and morpholin-2-ylmethanol (56.8 mg; 0.48 mmol) to give Example 143 as a white solid. $^1$H NMR: (DMSO-$d_6$, 400 MHz) δ 8.75 (2H, dd, J=4.7, 1.6 Hz), 7.97 (2H, d, J=7.9 Hz), 7.94-7.87 (1H, m), 7.76-7.69 (1H, m), 7.61 (2H, dd, J=4.7, 1.6 Hz), 7.58-7.48 (4H, m), 4.65 (1H, t, J=5.6 Hz), 3.80 (1H, d, J=11.2 Hz), 3.62-3.50 (3H, m), 3.46-3.39 (2H, m), 3.34-3.28 (1H, m), 2.79 (1H, d, J=11.1 Hz), 2.66 (1H, d, J=11.4 Hz), 2.12 (1H, td, J=11.3, 3.3 Hz), 1.84 (1H, t, J=10.4 Hz). LC/MS (Method C): 514 (M+H)$^+$. HPLC (Method E) Rt 2.12 min (Purity: 99.9%).

Example 144

2-[(4-{5-[1-(2-fluorophenyl)-5-pyridin-4-yl-1H-1,2,3-triazol-4-yl]-1,2,4-oxadiazol-3-yl}benzyl)(methyl)amino]ethanol

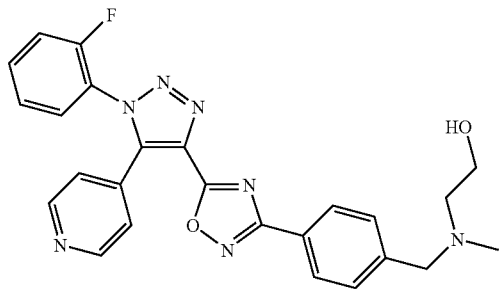

The title compound was prepared following the procedure described for Example 94, but starting from 4-(5-(1-(2-fluorophenyl)-5-(pyridin-4-yl)-1H-1,2,3-triazol-4-yl)-1,2,4-oxadiazol-3-yl)benzaldehyde, obtained as described in Example 113, Step 1, (100 mg; 0.24 mmol) and N-methylaminoethanol (36.4 mg; 0.48 mmol) to give Example 144 as a white solid. $^1$H NMR: (DMSO-$d_6$, 400 MHz) δ 8.77-8.72 (2H, m), 7.99-7.87 (3H, m), 7.76-7.69 (1H, m), 7.64-7.58 (2H, m), 7.58-7.48 (4H, m), 4.44 (1H, t, J=5.4 Hz), 3.62 (2H, s), 3.56 (2H, q, J=5.9 Hz), 2.49 (2H, t, J=6.4 Hz), 2.21 (3H, s). LC/MS (Method C): 472 (M+H)$^+$. HPLC (Method E) Rt 2.13 min (Purity: 99.5%).

Example 145

N-(5-{5-[1-(2-fluorophenyl)-5-pyridin-4-yl-1H-1,2,3-triazol-4-yl]-1,2,4-oxadiazol-3-yl}pyridin-2-yl)acetamide

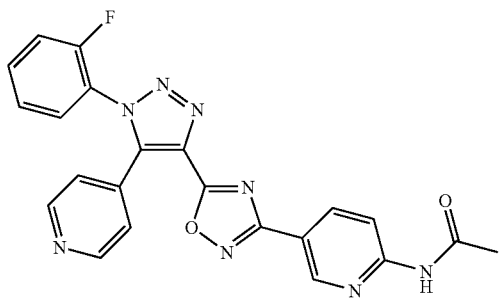

The title compound was prepared following the procedure described for Example 55, Step 3, but starting from Example 118 (82 mg; 0.21 mmol) to give Example 145 as a white solid. $^1$H NMR: (CDCl$_3$, 400 MHz) δ 8.99-8.95 (1H, m), 8.73 (2H, dd, J=4.7, 1.6 Hz), 8.40-8.31 (2H, m), 8.09 (1H, br s), 7.64-7.51 (2H, m), 7.39-7.32 (3H, m), 7.23-7.15 (1H, m), 2.25 (3H, s). LC/MS (Method C): 443 (M+H)$^+$. HPLC (Method E) Rt 3.00 min (Purity: 99.0%).

Example 146

N-[1-(4-{5-[1-(2-fluorophenyl)-5-pyridin-4-yl-1H-1,2,3-triazol-4-yl]-1,2,4-oxadiazol-3-yl}benzyl)piperidin-4-yl]methanesulfonamide

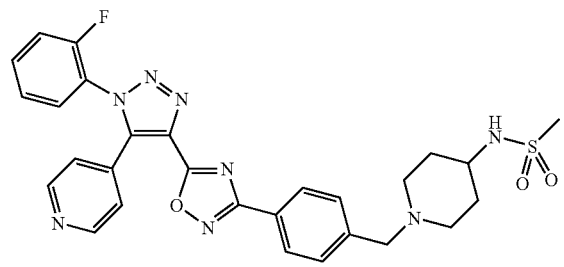

The title compound was prepared following the procedure described for Example 94, but starting from 4-(5-(1-(2-fluorophenyl)-5-(pyridin-4-yl)-1H-1,2,3-triazol-4-yl)-1,2,4-oxadiazol-3-yl)benzaldehyde, obtained as described in Example 113, Step 1, (100 mg; 0.24 mmol) and N-(piperidin-4-yl)methanesulfonamide (86.5 mg; 0.48 mmol) to give Example 146 as a white solid. $^1$H NMR: (CDCl$_3$, 400 MHz) δ 8.72 (2H, dd, J=4.5, 1.6 Hz), 8.04 (2H, d, J=8.1 Hz), 7.63-

7.52 (2H, m), 7.44-7.33 (5H, m), 7.22-7.15 (1H, m), 4.20 (1H, d, J=7.7 Hz), 3.55 (2H, s), 3.40-3.31 (1H, m), 2.98 (3H, s), 2.82 (2H, d, J=11.4 Hz), 2.16 (2H, t, J=11.3 Hz), 1.99 (2H, d, J=12.5 Hz), 1.66-1.50 (2H, m). LC/MS (Method C): 573 (M+H)⁺. HPLC (Method F) Rt 3.33 min (Purity: 99.2%).

Example 147

N-(3-{5-[1-(2-fluorophenyl)-5-pyridin-4-yl-1H-1,2,3-triazol-4-yl]-1,2,4-oxadiazol-3-yl}benzyl)-2-methoxyethanamine

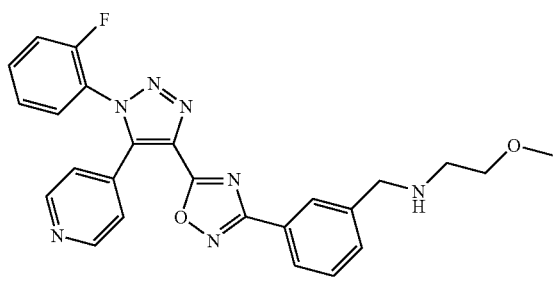

The title compound was prepared following the procedure described for Example 94, starting from 3-(5-(1-(2-fluorophenyl)-5-(pyridin-4-yl)-1H-1,2,3-triazol-4-yl)-1,2,4-oxadiazol-3-yl)benzaldehyde (100 mg; 0.24 mmol) and 2-methoxyethanamine (36.4 mg; 0.48 mmol) to give Example 147 as a yellow solid. ¹H NMR: (DMSO-d₆, 400 MHz) δ 8.75 (2H, dd, J=4.62, 1.58 Hz), 8.05 (1H, s), 7.95-7.85 (2H, m), 7.76-7.69 (1H, m), 7.64-7.49 (6H, m), 3.90 (2H, s), 3.47 (2H, t, J=5.6 Hz), 3.29 (3H, s), 2.76 (2H, t, J=5.6 Hz). LC/MS (Method C): 472 (M+H)⁺. HPLC (Method E) Rt 2.18 min (Purity: 94.9%).

Example 148

4-[4-{3-[3-(azetidin-1-ylmethyl)phenyl]-1,2,4-oxadiazol-5-yl}-1-(2-fluorophenyl)-1H-1,2,3-triazol-5-yl]pyridine formate

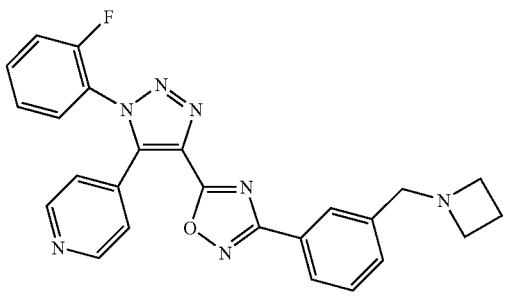

The title compound was prepared following the procedure described for Example 94, starting from 3-(5-(1-(2-fluorophenyl)-5-(pyridin-4-yl)-1H-1,2,3-triazol-4-yl)-1,2,4-oxadiazol-3-yl)benzaldehyde (100 mg; 0.24 mmol) and azetidine hydrochloride (45.4 mg; 0.48 mmol) to give Example 148 as a white solid. ¹H NMR: (DMSO-d₆, 400 MHz) δ 8.73 (2H, dd, J=4.7, 1.7 Hz), 8.47 (1H, s), 8.07 (2H, dd, J=4.9, 2.3 Hz), 7.65-7.50 (4H, m), 7.39-7.34 (3H, m), 7.19 (1H, t, J=9.1 Hz), 4.01 (2H, s), 3.71 (2H, t, J=7.7 Hz), 2.35 (2H, m). LC/MS (Method C): 454 (M+H)⁺. HPLC (Method E) Rt 2.16 min (Purity: 95.1%).

Example 149

4-[4-[3-(2-bromo-5-fluorophenyl)-1,2,4-oxadiazol-5-yl]-1-(2-fluorophenyl)-1H-1,2,3-triazol-5-yl]pyridine

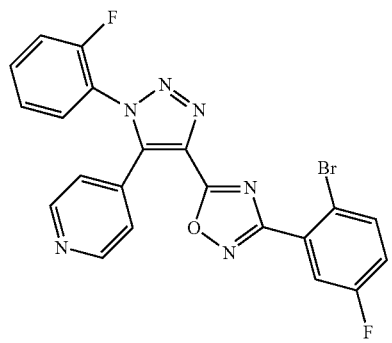

The title compound was prepared following the procedure described for Example 52, but starting from Intermediate 17 (209 mg; 0.67 mmol) and Intermediate 35 (172 mg; 0.74 mmol) to give Example 149 as an off-white solid. ¹H NMR: (CDCl₃, 400 MHz) δ 8.72-8.67 (2H, m), 7.72-7.52 (4H, m), 7.40-7.34 (3H, m), 7.21-7.14 (1H, m), 7.13-7.06 (1H, m). LC/MS (Method C): 481 (M+H)⁺. HPLC (Method F) Rt=3.29 min (Purity: 98.0%).

Example 150

2-(4-{5-[1(2-fluorophenyl)-5-pyridin-4-yl-1H-1,2,3-triazol-4-yl]-1,2,4-oxadiazol-3-yl}phenyl)ethanol The title compound was prepared following the procedure described for Example 52, but starting from Intermediate 17 (209 mg; 0.67 mmol) and Intermediate 47 (172 mg; 0.74 mmol). The residue was purified by flash chromatography on a Biotage 25+S column, eluting with petrol containing increasing amounts of EtOAc to give Example 150 as a white solid. ¹H NMR: (CDCl₃, 400 MHz) δ 8.73-8.69 (2H, m), 8.05 (2H, d, J=7.9 Hz), 7.65-7.52 (2H, m), 7.40-7.33 (5H, m), 7.21-7.14 (1H, m), 3.92 (2H, app q, J=6.2 Hz), 2.95 (2H, t, J=6.5 Hz), 1.43 (1H, t, J=5.8 Hz). LC/MS (Method C): 429 (M+H)⁺. HPLC (Method E) Rt=3.17 min (Purity: 95.6%).

Example 151

4-[(1-(2-fluorophenyl)-4-{3-[3-(trifluoromethyl)phenyl]-1,2,4-oxadiazol-5-yl}-1H-1,2,3-triazol-5-yl)methyl]morpholine

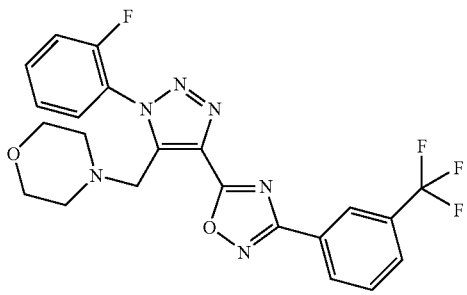

N'-hydroxy-3-(trifluoromethyl)benzimidamide (JRD-Fluorochemical, 45.0 mg; 0.221 mmol) and potassium carbonate (31.9 mg; 0.231 mmol) were added to a solution of Intermediate 50 (70.2 mg; 0.210 mmol) in toluene (2 mL) and heated at 180° C. for 1 hour in the microwave. Water (5 mL) was added followed by DCM with vigorous stirring until all material was in solution. The organic layer was separated, passed through a hydrophobic and the solvent removed in vacuo. The residue was purified by flash chromatography on a Biotage 12+M column, eluting with petrol containing increasing amounts of EtOAc, and then by preparative HPLC to give Example 151 as a lilac solid. ¹H NMR (CDCl₃) δ 8.48 (1H, s), 8.40 (1H, d, J=7.9 Hz), 7.82 (1H, d, J=7.9 Hz), 7.70-7.55 (3H, m), 7.41-7.31 (2H, m), 4.12 (2H, s), 3.37 (4H, t, J=4.0 Hz), 2.35 (4H, t, J=4.6 Hz). LC/MS (Method C): 475 (M+H)⁺. HPLC (Method E) Rt=4.25 min (Purity: 99.82%).

Example 152

4-{5-[1-(2-fluorophenyl)-5-pyridin-4-yl-1H-1,2,3-triazol-4-yl]-1,2,4-oxadiazol-3-yl}pyridin-2-amine

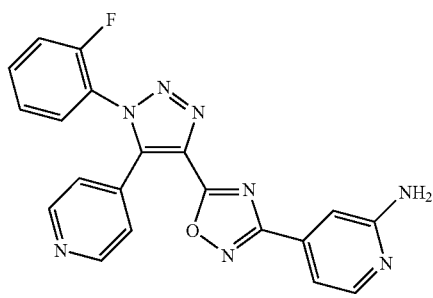

In a microwave vial, Intermediate 17 (209 mg; 0.67 mmol) was suspended in toluene (2 mL) and ACN (1 mL) and Intermediate 48 (187 mg; 0.74 mmol) was added followed by potassium carbonate (123 mg; 0.74 mmol). The MW vial was sealed and the suspension was heated to 180° C. for 30 min in a microwave reactor. The reaction mixture was cooled down to room temperature and diluted with DCM and water. The mixture was passed through a hydrophobic frit and the solvent removed in vacuo. The residue was purified by flash chromatography on a Biotage 12+M column, eluting with petrol containing increasing amounts of EtOAc to give Example 152 as an off-white solid. ¹H NMR: (CDCl₃, 400 MHz) δ 8.74-8.71 (2H, m), 8.22 (1H, d, J=5.3 Hz), 7.64-7.54 (2H, m), 7.39 (1H, d, J=7.8 Hz), 7.38-7.31 (2H, m), 7.28 (1H, dd, J=5.3, 1.4 Hz), 7.23-7.16 (2H, m), 4.62 (2H, br s). LC/MS (Method C): 401 (M+H)⁺. HPLC (Method E) Rt=2.08 min (Purity: 98.2%).

Example 153

1-acetyl-5-{5-[1-(2-fluorophenyl)-5-pyridin-4-yl-1H-1,2,3-triazol-4-yl]-1,2,4-oxadiazol-3-yl}indoline

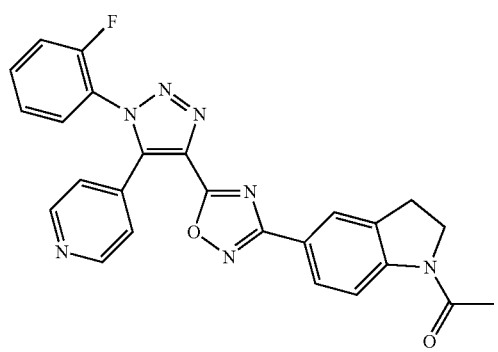

The title compound was prepared following the procedure described for Example 51, but starting from Intermediate 36 (235 mg; 1.07 mmol), to give Example 153 as a yellow solid. ¹H NMR: (CDCl₃, 400 MHz) δ 8.72 (2H, dd, J=4.5, 1.7 Hz), 8.29 (1H, d, J=8.5 Hz), 7.98-7.89 (2H, m), 7.64-7.51 (2H, m), 7.39-7.33 (3H, m), 7.21-7.14 (1H, m), 4.13 (2H, t, J=8.5 Hz), 3.27 (2H, t, J=8.5 Hz), 2.26 (3H, s). LC/MS (Method C): 468 (M+H)⁺. HPLC (Method E) Rt 3.28 min (Purity: 98.5%).

Example 154

2-ethyl-7-{5-[1-(2-fluorophenyl)-5-pyridin-4-yl-1H-1,2,3-triazol-4-yl]-1,2,4-oxadiazol-3-yl}-1,2,3,4-tetrahydroisoquinoline

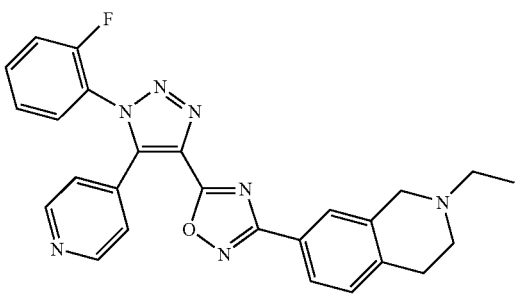

The title compound was prepared following the procedure described for Example 51, but using Intermediate 17 (398 mg; 1.27 mmol) and Intermediate 38 (309 mg; 1.40 mmol), to give Example 154 as a brown solid. ¹H NMR (CDCl₃, 400 MHz) δ 8.71 (2H, dd, J=5.1, 1.3 Hz), 7.87-7.79 (2H, m), 7.63-7.52 (2H, m), 7.39-7.32 (3H, m), 7.24-7.13 (2H, m), 3.69 (2H, s), 2.98 (2H, t, J=5.9 Hz), 2.77 (2H, t, J=5.9 Hz), 2.62 (2H, q, J=7.2 Hz), 1.21 (3H, t, J=7.2 Hz). LC/MS (Method C): 468 (M+H)+. HPLC (Method H) Rt 22.61 min (Purity: 93.9%).

Example 155

5-{5-[1-(2-fluorophenyl)-5-pyridin-4-yl-1H-1,2,3-triazol-4-yl]-1,2,4-oxadiazol-3-yl}-1H-benzimidazole

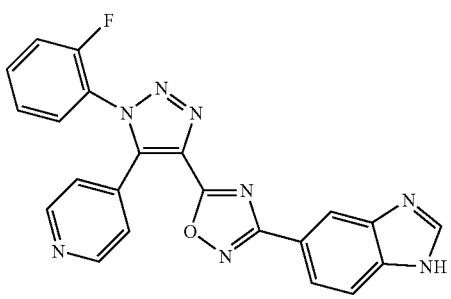

Intermediate 17 (93.7 mg; 0.30 mmol), Intermediate 51 (55.5 mg; 0.315 mmol) and potassium carbonate (45.6 mg; 0.330 mmol) were suspended in a 1:1 mixture of toluene:MeCN (4 mL) and heated at 180° C. for 30 minutes in the microwave. The solvent was removed in vacuo and the residue was purified by preparative HPLC to give Example 155 as a pale brown solid. 1H NMR (DMSO-d6) δ 12.81 (1H, s), 8.77 (2H, dd, J=4.8, 1.6 Hz), 8.41 (1H, s), 8.20 (1H, s), 7.97-7.85 (2H, m), 7.85-7.67 (2H, m), 7.64 (2H, dd, J=4.8, 1.6 Hz), 7.52 (2H, t, J=8.4 Hz). LC/MS (Method C): 425 (M+H)+. HPLC (Method E) Rt=2.30 min (Purity: 97.55%).

Example 156

5-{5-[1-(2-fluorophenyl)-5-pyridin-4-yl-1H-1,2,3-triazol-4-yl]-1,2,4-oxadiazol--yl}indoline hydrochloride

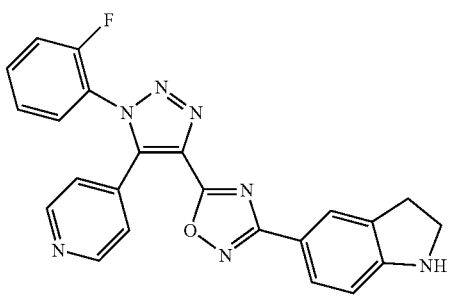

To a solution of Example 153 (135 mg; 0.289 mmol) in MeOH (10 mL) was added HCl (2 M, 1 mL) and the mixture was heated at 60° C. for 5 hours. The solvent was removed in vacuo to afford Example 156 as a purple oil. 1H NMR: (DMSO-d6, 400 MHz) δ 8.85 (2H, d, J=5.3 Hz), 7.97-7.86 (1H, m), 7.81-7.69 (5H, m), 7.54-7.47 (2H, m), 6.95 (1H, d, J=8.2 Hz), 3.65 (2H, t, J=8.4 Hz), 3.13 (2H, t, J=8.4 Hz). LC/MS (Method C): 426 (M+H)+. HPLC (Method I) Rt 16.12 min (Purity: 96.8%).

Example 157

6-{5-[1-(2-fluorophenyl)-5-pyridin-4-yl-1H-1,2,3-triazol-4-yl]-1,2,4-oxadiazol-3-yl}indoline

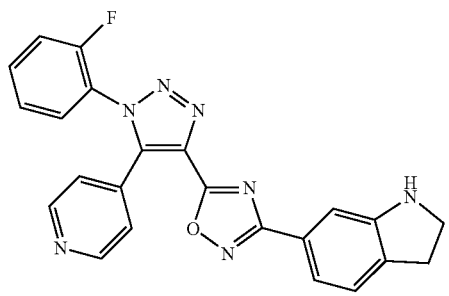

Step 1: 6-{5-[1-(2-fluorophenyl)-5-pyridin-4-yl-1H-1,2,3-triazol-4-yl]-1,2,4-oxadiazol-3-yl}indoline The title compound was prepared following the procedure described for Example 51, but starting from Intermediate 39 (171 mg; 0.78 mmol), and was isolated as an orange solid. 1H NMR: (CDCl3, 400 MHz) δ 8.92 (1H, s), 8.74 (2H, s), 7.77 (1H, d, J=7.7 Hz), 7.64-7.53 (2H, m), 7.43-7.33 (3H, m), 7.18 (2H, m), 4.12 (2H, s), 3.25 (2H, s), 2.26 (3H, s). LC/MS (Method C): 468 (M+H)+. HPLC (Method E) Rt 3.37 min (Purity: 82.2%).

Step 2: 6-{5-[1-(2-fluorophenyl)-5-pyridin-4-yl-1H-1,2,3-triazol-4-yl]-1,2,4-oxadiazol-3-yl}indoline The title compound was prepared following the procedure described for Example 156, but using 1-(6-(5-(1-(2-fluorophenyl)-5-(pyridin-4-yl)-1H-1,2,3-triazol-4-yl)-1,2,4-oxadiazol-3-yl)indolin-1-yl)ethanone, obtained in Step 1, (101 mg; 0.22 mmol). The solvent was removed in vacuo to afford a purple oil which was dissolved in HCl (1 M, 1 mL) and MeOH (1 mL). The solution was passed through an SCX column eluting with MeOH (50 mL) followed by NH3 (1 M in MeOH, 50 mL). The solvent was removed in vacuo from the fractions containing product to afford Example 157 as a yellow solid. 1H NMR: (DMSO-d5, 400 MHz) δ 8.74 (2H, d, J=5.2 Hz), 7.90 (1H, t, J=7.7 Hz), 7.77-7.68 (1H, m), 7.60 (2H, d, J=5.2 Hz), 7.55-7.41 (2H, m), 7.24-7.15 (2H, m), 7.10-6.95 (1H, m), 5.89 (1H, s), 3.56-3.44 (2H, m), 3.01 (2H, t, J=8.6 Hz). LC/MS (Method C): 426 (M+H)+. HPLC (Method I) Rt 14.83 min (Purity: 95.2%).

Example 158

1-(4-{5-[1-(2-fluorophenyl)-5-pyridin-4-yl-1H-1,2,3-triazol-4-yl]-1,2,4-oxadiazol-3-yl}benzyl)piperidine-3-carboxylic acid

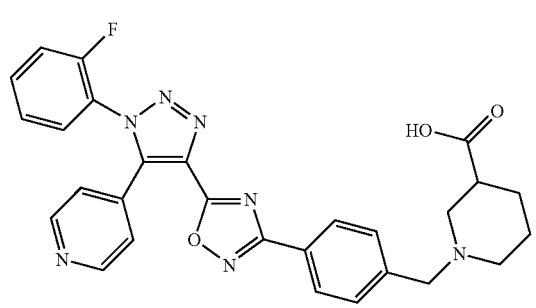

The title compound was prepared following the procedure described for Example 94, but starting from 4-(5-(1-(2-fluorophenyl)-5-(pyridin-4-yl)-1H-1,2,3-triazol-4-yl)-1,2,4-oxadiazol-3-yl) benzaldehyde, obtained as described in Example 113, Step 1, (200 mg; 0.48 mmol) and piperidine-3-carboxylic acid (125 mg; 0.97 mmol) to give Example 158 as a yellow solid. $^1$H NMR: (DMSO-$d_6$, 400 MHz) δ 12.25 (1H, br s), 8.75 (2H, dd, J=4.5, 1.6 Hz), 7.97-7.88 (3H, m), 7.76-7.69 (1H, m), 7.61 (2H, dd, J=4.5, 1.7 Hz), 7.57-7.47 (4H, m), 3.59 (2H, t, J=14.7 Hz), 2.85 (1H, d, J=11.0 Hz), 2.68 (1H, d, J=11.2 Hz), 2.50-2.42 (1H, m), 2.28-1.95 (2H, m), 1.84 (1H, d, J=12.1 Hz), 1.68 (1H, dd, J=12.2, 4.7 Hz), 1.58-1.31 (2H, m). LC/MS (Method C): 526 (M+H)$^+$. HPLC (Method F) Rt 2.83 min (Purity: 98.7%).

Example 159

1-(4-{5-[1(2-fluorophenyl)-5-pyridin-4-yl-1H-1,2,3-triazol-4-yl]-1,2,4-oxadiazol-3-yl}benzyl)-L-proline

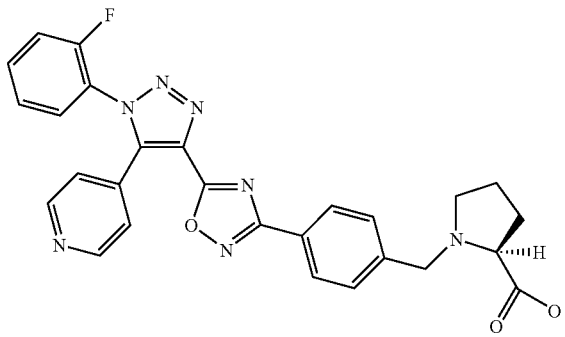

The title compound was prepared following the procedure described for Example 94, but starting from 4-(5-(1-(2-fluorophenyl)-5-(pyridin-4-yl)-1H-1,2,3-triazol-4-yl)-1,2,4-oxadiazol-3-yl)benzaldehyde, obtained as described in Example 113, Step 1, (200 mg; 0.48 mmol) and (S)-pyrrolidine-2-carboxylic acid (111 mg; 0.97 mmol) to give Example 159 as an off-white solid. $^1$H NMR: (DMSO-$d_6$, 400 MHz) δ 8.77-8.74 (2H, m), 7.98-7.87 (3H, m), 7.76-7.69 (1H, m), 7.64-7.57 (4H, m), 7.52 (2H, t, J=8.5 Hz), 4.11 (1H, d, J=13.5 Hz), 3.72 (1H, d, J=13.5 Hz), 3.31 (1H, dd, J=8.9, 5.9 Hz), 3.04-2.96 (1H, m), 2.50 (1H, d, J=8.5 Hz), 2.16-2.07 (1H, m), 1.94-1.84 (1H, m), 1.84-1.73 (2H, m). LC/MS (Method C): 412 (M+H)$^+$. HPLC (Method I) Rt 15.21 min (Purity: 95.3%).

Example 160

4-{1-(2-fluorophenyl)-4-[3-(4-{[(3R)-3-fluoropyrrolidin-1-yl]methyl}phenyl)-1,2,4-oxadiazol-5-yl]-1H-1,2,3-triazol-5-yl}pyridine

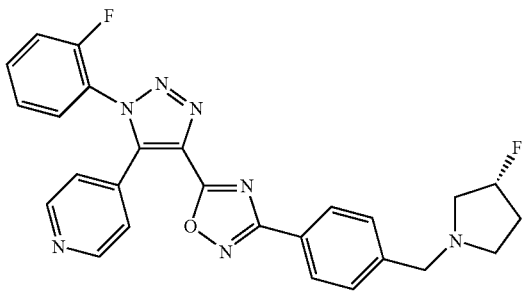

The title compound was prepared following the procedure described for Example 94, but starting from 4-(5-(1-(2-fluorophenyl)-5-(pyridin-4-yl)-1H-1,2,3-triazol-4-yl)-1,2,4-oxadiazol-3-yl)benzaldehyde, obtained as described in Example 113, Step 1, (200 mg; 0.48 mmol) and (S)-3-fluoropyrrolidine (121 mg; 0.97 mmol) to give Example 160 as a white solid. $^1$H NMR: (CDCl$_3$, 400 MHz) δ 8.73-8.70 (2H, m), 8.05 (2H, d, J=8.03 Hz), 7.63-7.52 (2H, m), 7.47 (2H, d, J=8.0 Hz), 7.39-7.34 (3H, m), 7.18 (1H, t, J=9.1 Hz), 5.27-5.08 (1H, m), 3.72 (2H, s), 2.92-2.70 (3H, m), 2.49 (1H, q, J=7.4 Hz), 2.22-2.02 (2H, m). LC/MS (Method C): 486 (M+H)$^+$. HPLC (Method F) Rt 3.99 min (Purity: 99.5%).

Example 161

4-{1-(2-fluorophenyl)-4-[3-(4-{[(3R)-3-fluoropyrrolidin-1-yl]methyl}phenyl)-1,2,4-oxadiazol-5-yl]-1H-1,2,3-triazol-5-yl}pyridine

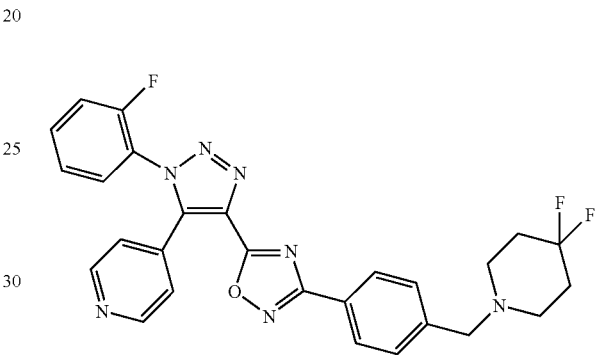

The title compound was prepared following the procedure described for Example 94, but starting from 4-(5-(1-(2-fluorophenyl)-5-(pyridin-4-yl)-1H-1,2,3-triazol-4-yl)-1,2,4-oxadiazol-3-yl)benzaldehyde, obtained as described in Example 113, Step 1, (200 mg; 0.48 mmol) and 4,4-difluoropiperidine (168 mg; 0.97 mmol) to give Example 161 as a white solid. $^1$H NMR: (CDCl$_3$, 400 MHz) δ 8.72 (2H, dd, J=4.5, 1.7 Hz), 8.05 (2H, d, J=8.1 Hz), 7.63-7.52 (2H, m), 7.45 (2H, d, J=8.0 Hz), 7.40-7.34 (2H, m), 7.22-7.15 (1H, m), 3.61 (2H, s), 2.57 (4H, t, J=5.4 Hz), 2.07-1.94 (4H, m). LC/MS (Method C): 518 (M+H)$^+$. HPLC (Method I) Rt 15.55 min (Purity: 97.6%).

Example 162

1-(4-(5-(1-(2-fluorophenyl)-5-(pyridin-4-yl)-1H-1,2,3-triazol-4-yl)-1,2,4-oxadiazol-3-yl)benzylamino)cyclopropanecarboxylic acid

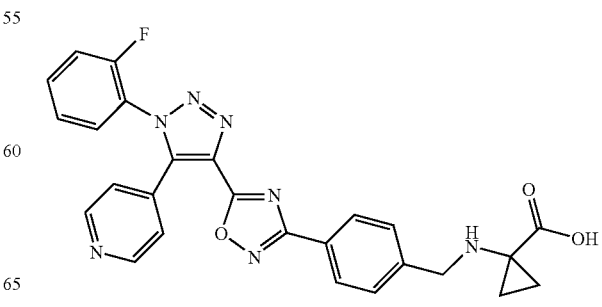

The title compound was prepared following the procedure described for Example 94, but starting from 4-(5-(1-(2-fluorophenyl)-5-(pyridin-4-yl)-1H-1,2,3-triazol-4-yl)-1,2,4-oxadiazol-3-yl)benzaldehyde, obtained as described in Example 113, Step 1, (200 mg; 0.48 mmol) and 1-aminocyclopropanecarboxylic acid (98.1 mg; 0.97 mmol) to give Example 162 as a white solid. ¹H NMR: (DMSO-d₆, 400 MHz) δ 8.75 (2H, dd, J=4.5, 1.6 Hz), 7.95-7.87 (3H, m), 7.76-7.69 (1H, m), 7.61 (2H, dd, J=4.5, 1.7 Hz), 7.56-7.47 (4H, m), 3.95 (2H, s), 1.18-1.14 (2H, m), 0.96-0.92 (2H, m). LC/MS (Method C): 498 (M+H)⁺. HPLC (Method F) Rt 2.70 min (Purity: 98.6%).

Example 163

(cis)-4-(4-(5-(1-(2-fluorophenyl)-5-(pyridin-4-yl)-1H-1,2,3-triazol-4-yl)-1,2,4-oxadiazol-3-yl)benzylamino)cyclohexanecarboxylic acid

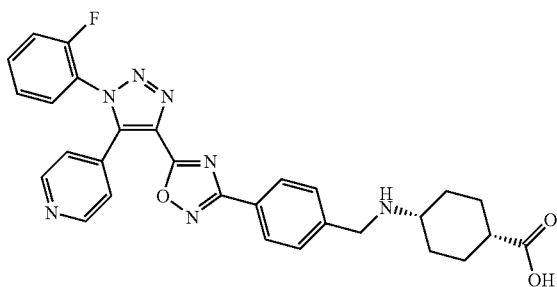

The title compound was prepared following the procedure described for Example 94, but starting from 4-(5-(1-(2-fluorophenyl)-5-(pyridin-4-yl)-1H-1,2,3-triazol-4-yl)-1,2,4-oxadiazol-3-yl)benzaldehyde, obtained as described in Example 113, Step 1, (200 mg; 0.48 mmol) and 4-aminocyclohexanecarboxylic acid (138 mg; 0.97 mmol) to give Example 163 as a white solid. ¹H NMR: (DMSO-d₆, 400 MHz) δ 8.77-8.72 (2H, m), 7.97-7.86 (3H, m), 7.77-7.69 (1H, m), 7.65-7.48 (6H, m), 3.84 (2H, s), 2.41-2.33 (1H, m), 2.20-2.10 (1H, m), 2.03-1.85 (4H, m), 1.36-1.24 (2H, m), 1.17-1.01 (2H, m). LC/MS (Method C): 540 (M+H)⁺. HPLC (Method I) Rt 11.38 min (Purity: 85.6%).

Example 164

N-(4-{5-[1-2-fluorophenyl)-5-pyridin-4-yl-1H-1,2,3-triazol-4-yl]-1,2,4-oxadiazol-3-yl}benzyl)cyclopropanamine formate

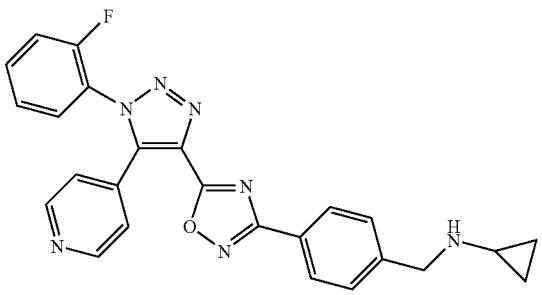

The title compound was prepared following the procedure described for Example 94, but starting from 4-(5-(1-(2-fluorophenyl)-5-(pyridin-4-yl)-1H-1,2,3-triazol-4-yl)-1,2,4-oxadiazol-3-yl)benzaldehyde, obtained as described in Example 113, Step 1, (200 mg; 0.48 mmol) and cyclopropylamine (56.4 mg; 0.97 mmol) to give Example 164 as a yellow solid. ¹H NMR: (CDCl₃, 400 MHz) δ 8.72 (2H, dd, J=4.6, 1.7 Hz), 8.27 (1H, s), 8.04 (2H, d, J=8.0 Hz), 7.65-7.52 (2H, m), 7.46-7.33 (4H, m), 7.22-7.13 (1H, m), 3.95 (2H, s), 2.25-2.18 (1H, m), 0.58-0.48 (4H, m). LC/MS (Method C): 454 (M+H)⁺. HPLC (Method F) Rt 3.79 min (Purity: 93.0%).

Example 165

N-(4-{5-[1-(2-fluorophenyl)-5-pyridin-4-yl-1H-1,2,3-triazol-4-yl]-1,2,4-oxadiazol-3-yl}benzyl)propan-2-amine

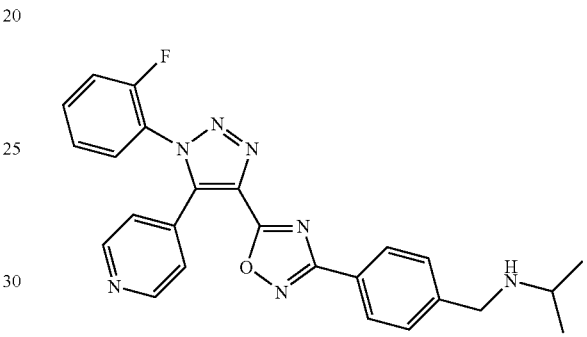

The title compound was prepared following the procedure described for Example 94, but starting from 4-(5-(1-(2-fluorophenyl)-5-(pyridin-4-yl)-1H-1,2,3-triazol-4-yl)-1,2,4-oxadiazol-3-yl)benzaldehyde, obtained as described in Example 113, Step 1, (200 mg; 0.48 mmol) and iso-propylamine (57.3 mg; 0.97 mmol) to give Example 165 as a yellow solid. ¹H NMR: (CDCl₃, 400 MHz) δ 8.72 (2H, dd, J=4.6, 1.6 Hz), 8.05 (2H, d, J=8.1 Hz), 7.64-7.53 (2H, m), 7.46 (2H, d, J=8.0 Hz), 7.39-7.34 (3H, m), 7.22-7.16 (1H, m), 3.86 (2H, s), 2.92-2.85 (1H, m), 1.12 (6H, d, J=6.3 Hz). LC/MS (Method C): 456 (M+H)⁺. HPLC (Method I) Rt 11.31 min (Purity: 91.3%).

Example 166

N-(4-(5-(1-(2-fluorophenyl)-5-(pyridin-4-yl)-1H-1,2,3-triazol-4-yl)-1,2,4-oxadiazol-3-yl)benzyl)-2-methoxy-N-methylethanamine

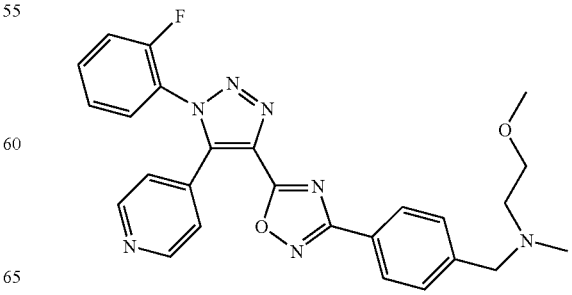

The title compound was prepared following the procedure described for Example 94, but starting from 4-(5-(1-(2-fluorophenyl)-5-(pyridin-4-yl)-1H-1,2,3-triazol-4-yl)-1,2,4-oxadiazol-3-yl) benzaldehyde, obtained as described in Example 113, Step 1, (200 mg; 0.48 mmol) and 2-methoxy-N-methylethanamine (86.3 mg; 0.97 mmol) to give Example 166 as an off-white solid. $^1$H NMR: (CDCl$_3$, 400 MHz) δ 8.74-8.69 (2H, m), 8.04 (2H, d, J=7.9 Hz), 7.65-7.52 (2H, m), 7.46 (2H, d, J=7.9 Hz), 7.37 (3H, t, J=5.5 Hz), 7.18 (1H, t, J=9.1 Hz), 3.62 (2H, s), 3.53 (2H, t, J=5.7 Hz), 3.35 (3H, s), 2.63 (2H, t, J=5.7 Hz), 2.29 (3H, s). LC/MS (Method C): 486 (M+H)$^+$. HPLC (Method I) Rt 15.20 min (Purity: 96.4%).

Example 167

4-{1-(2-fluorophenyl)-4-[3-(4-{[(3S)-3-fluoropyrrolidin-1-yl]methyl}phenyl)-1,2,4-oxadiazol-5-yl]-1H-1,2,3-triazol-5-yl}pyridine

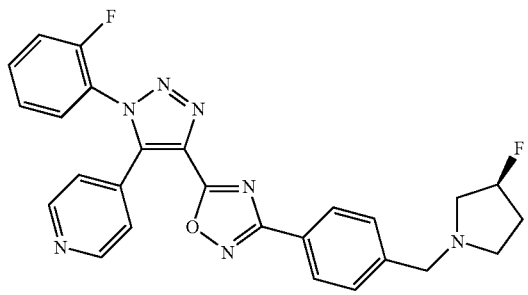

The title compound was prepared following the procedure described for Example 94, but starting from 4-(5-(1-(2-fluorophenyl)-5-(pyridin-4-yl)-1H-1,2,3-triazol-4-yl)-1,2,4-oxadiazol-3-yl)benzaldehyde, obtained as described in Example 113, Step 1, (200 mg; 0.48 mmol) and (R)-3-fluoropyrrolidine (121 mg; 0.97 mmol) to give Example 167 as a white solid. $^1$H NMR: (CDCl$_3$, 400 MHz) 8.72 (2H, dd, J=4.6, 1.6 Hz), 8.05 (2H, d, J=8.0 Hz), 7.63-7.52 (2H, m), 7.47 (2H, d, J=8.0 Hz), 7.40-7.33 (3H, m), 7.19 (1H, t, J=9.1 Hz), 5.25-5.11 (1H, m), 3.72 (2H, s), 2.92-2.69 (3H, m), 2.53-2.45 (1H, m), 2.24-1.99 (2H, m). LC/MS (Method C): 486 (M+HPLC (Method I) Rt 14.98 min (Purity: 95.7%).

Example 168

(trans)-4-(4-(5-(1-(2-fluorophenyl)-5-(pyridin-4-yl)-1H-1,2,3-triazol-4-yl)-1,2,4-oxadiazol-3-yl)benzylamino)cyclohexanecarboxylic acid

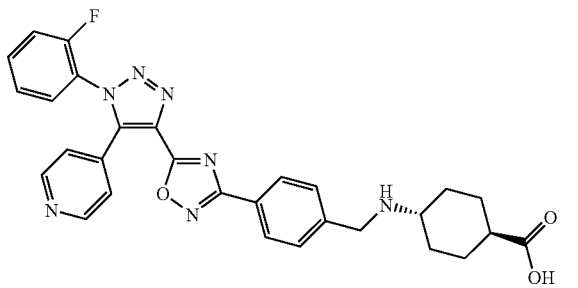

The title compound was prepared following the procedure described for Example 94, but starting from 4-(5-(1-(2-fluorophenyl)-5-(pyridin-4-yl)-1H-1,2,3-triazol-4-yl)-1,2,4-oxadiazol-3-yl)benzaldehyde, obtained as described in Example 113, Step 1, (200 mg; 0.48 mmol) and 4-aminocyclohexanecarboxylic acid (138 mg; 0.97 mmol), to give Example 168 as a white solid. $^1$H NMR: (DMSO-d$_6$, 400 MHz) δ 8.76-8.73 (2H, m), 7.95-7.88 (3H, m), 7.76-7.69 (1H, m), 7.64-7.49 (6H, m), 3.81 (2H, s), 2.58 (1H, d, J=5.6 Hz), 2.35 (1H, d, J=6.4 Hz), 1.96-1.85 (2H, m), 1.60 (2H, t, J=10.0 Hz), 1.53-1.44 (4H, m). LC/MS (Method C): 540 (M+H)$^+$. HPLC (Method I) Rt 11.49 min (Purity: 93.8%).

Example 169

(1S, 3R)-3-(4-(5-(1-(2-fluorophenyl)-5-(pyridin-4-yl)-1H-1,2,3-triazol-4-yl)-1,2,4-oxadiazol-3-yl)benzylamino)cyclopentanecarboxylic acid

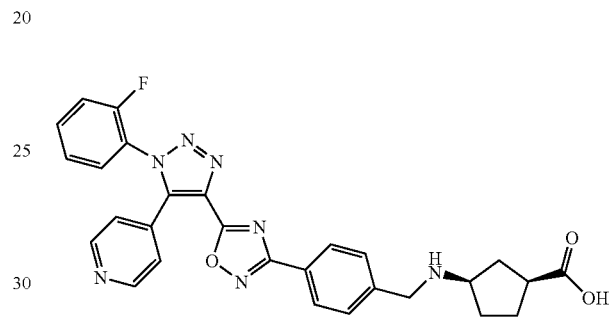

The title compound was prepared following the procedure described for Example 94, but starting from 4-(5-(1-(2-fluorophenyl)-5-(pyridin-4-yl)-1H-1,2,3-triazol-4-yl)-1,2,4-oxadiazol-3-yl)benzaldehyde, obtained as described in Example 113, Step 1, (200 mg; 0.48 mmol) and (1R,3S)-3-aminocyclopentanecarboxylic acid (125 mg; 0.97 mmol), to give Example 169 as a white solid. $^1$H NMR: (DMSO-d$_6$, 400 MHz) δ 8.76-8.71 (2H, m), 7.98 (2H, d, J=8.0 Hz), 7.93-7.85 (1H, m), 7.76-7.68 (1H, m), 7.64-7.58 (4H, m), 7.53-7.46 (2H, m), 3.97 (1H, d, J=13.8 Hz), 3.89 (1H, d, J=13.8 Hz), 3.27 (1H, t, J=4.8 Hz), 2.76-2.67 (1H, m), 1.94-1.73 (6H, m). LC/MS (Method C): 524 (M+H)$^+$. HPLC (Method F) Rt 2.86 min (Purity: 96.2%).

Example 170

4-(1-(2-fluorophenyl)-4-{3-[4-(1H-imidazol-1-ylmethyl)phenyl]-1,2,4-oxadiazol-5-yl}-1H-1,2,3-triazol-5-yl)pyridine

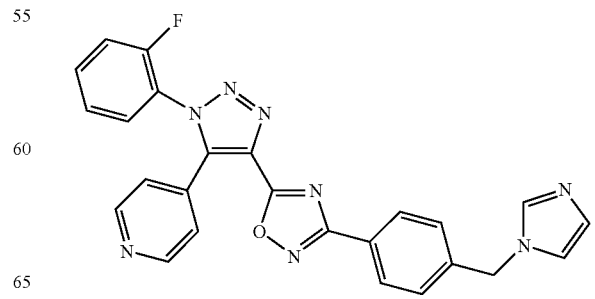

In a microwave vial, Intermediate 17 (209 mg; 0.67 mmol) was suspended in toluene (2 mL) and DMF (2 mL) and 4-((1H-imidazol-1-yl)methyl)-N'-hydroxybenzimidamide (Aurora, 160 mg; 0.74 mmol) was added followed by potassium carbonate (123 mg; 0.74 mmol). The MW vial was sealed and the suspension was heated to 180° C. for 45 min in a microwave reactor. The reaction mixture was cooled down to room temperature and diluted with DCM and water. The mixture was passed through a hydrophobic frit and the solvent evaporated affording a solid which was triturated with isopropanol. The solid was dried to give Example 170 as a white solid. $^1$H NMR: (CDCl$_3$, 400 MHz) δ 8.72-8.69 (2H, m), 8.09 (2H, d, J=8.2 Hz), 7.64-7.52 (3H, m), 7.40-7.32 (3H, m), 7.29-7.23 (2H, m), 7.22-7.15 (1H, m), 7.12 (1H, s), 6.93 (1H, t, J=1.3 Hz), 5.20 (2H, s). LC/MS (Method C): 465 (M+H)$^+$. HPLC (Method F) Rt=2.90 min (Purity: 98.0%).

Example 171

4-(1-(2-fluorophenyl)-4-{3-[4-(1H-pyrazol-1-ylmethyl)phenyl]-1,2,4-oxadiazol-5-yl}-1H-1,2,3-triazol-5-yl)pyridine

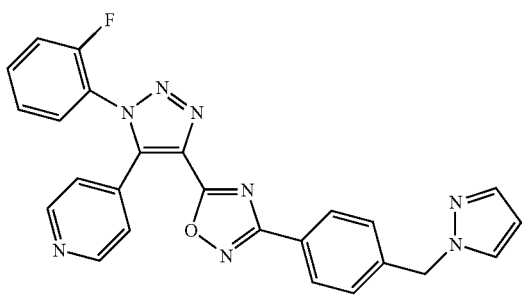

The title compound was prepared following the procedure described for Example 52, but starting from Intermediate 17 (209 mg; 0.67 mmol) and Intermediate 49 (160 mg; 0.74 mmol) to give Example 171 as a white solid. $^1$H NMR: (CDCl$_3$, 400 MHz) δ 8.73-8.69 (2H, m), 8.07 (2H, d, J=8.1 Hz), 7.63-7.52 (3H, m), 7.44 (1H, d, J=2.3 Hz), 7.39-7.32 (3H, m), 7.29 (2H, d, J=8.1 Hz), 7.18 (1H, t, J=9.1 Hz), 6.32 (1H, t, J=2.1 Hz), 5.40 (2H, s). LC/MS (Method C): 465 (M+H)$^+$. HPLC (Method F) Rt=3.15 min (Purity: 99.4%).

Example 172

4-(1-(2-fluorophenyl)-4-{3-[4-(1H-1,2,4-triazol-1-ylmethyl)phenyl]-1,2,4-oxadiazol-5-yl}-1H-1,2,3-triazol-5-yl)pyridine

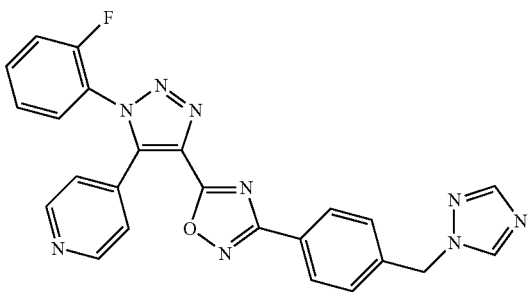

The title compound was prepared following the procedure described for Example 52, but starting from Intermediate 17 (209 mg; 0.67 mmol) and 4-(1H-1,2,4-triazol-1-yl)methyl)-N'-hydroxybenzimidamide (Aurora, 161 mg; 0.74 mmol) to give Example 172 as a white solid. $^1$H NMR: (CDCl$_3$, 400 MHz) δ 8.72-8.69 (2H, m), 8.13-8.08 (3H, m), 8.00 (1H, s), 7.63-7.52 (2H, m), 7.39-7.33 (5H, m), 7.22-7.16 (1H, m), 5.42 (2H, s). LC/MS (Method C): 466 (M+H)$^+$. HPLC (Method F) Rt=2.81 min (Purity: 99.2%).

Example 173

5-[1-(2-fluorophenyl)-5-(methoxymethyl)-1H-1,2,3-triazol-4-yl]-3-[4-(1H-pyrazol-1-ylmethyl)phenyl]-1,2,4-oxadiazole

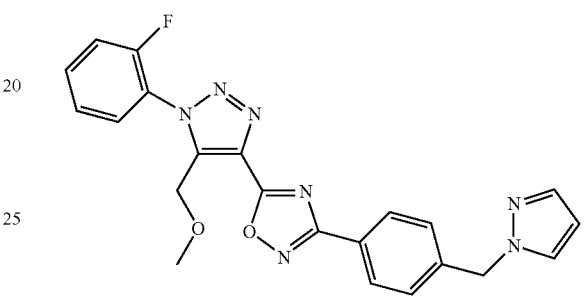

To a solution of Intermediate 11 (75 mg; 0.3 mmol) in anhydrous ACN (2 mL) was added 1-ethyl-3-(3-dimethylaminopropyl)carbodiimide hydrochloride (EDC) (80.5 mg; 0.42 mmol) followed by Intermediate 49 (78 mg; 0.36 mmol) in a MW vial. The mixture stirred at RT for 18 h. Anhydrous pyridine (2 mL) was added. The reaction vessel was sealed and heated at 150° C. for 45 min in a microwave reactor. This reaction was performed twice and the reaction mixtures were combined for workup. The solvents were evaporated and the residue partitioned between DCM and H$_2$O. The mixture was passed through a hydrophobic frit and the solvent evaporated affording a solid which was triturated with isopropanol to give Example 173 as an off-white solid. $^1$H NMR: (CDCl$_3$, 400 MHz) δ 8.18 (2H, d, J=8.1 Hz), 7.65-7.58 (3H, m), 7.45 (1H, d, J=2.3 Hz), 7.42-7.31 (4H, m), 6.33 (1H, t, J=2.1 Hz), 5.42 (2H, s), 4.97 (2H, s), 3.29 (3H, s). LC/MS (Method C): 432 (M+H)$^+$. HPLC (Method F) Rt=3.34 min (Purity: 99.6%).

Example 174

N-(4-{5-[1-(2-fluorophenyl)-5-pyridin-4-yl-1H-1,2,3-triazol-4-yl]-1,2,4-oxadiazol-3-yl}benzyl)-2-methylalanine

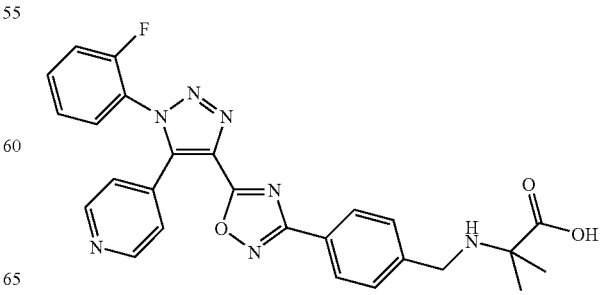

The title compound was prepared following the procedure described for Example 94, but starting from 4-(5-(1-(2-fluorophenyl)-5-(pyridin-4-yl)-1H-1,2,3-triazol-4-yl)-1,2,4-oxadiazol-3-yl)benzaldehyde, obtained as described in Example 113, Step 1, (200 mg; 0.48 mmol) and 2-amino-2-methylpropanoic acid (100 mg; 0.97 mmol), to give Example 174 as a white solid. $^1$H NMR: (DMSO-$d_6$, 400 MHz) δ 8.76-8.73 (2H, m), 8.00 (2H, d, J=8.1 Hz), 7.94-7.87 (1H, m), 7.77-7.60 (5H, m), 7.55-7.47 (2H, m), 3.96 (2H, s), 1.36 (6H, s). LC/MS (Method C): 498 (M+H)$^+$. HPLC (Method E) Rt 2.35 min (Purity: 98.9%).

Example 175

5-[1-(2-fluorophenyl)-5-(methoxymethyl)-1H-1,2,3-triazol-4-yl]-3-[4-(1H-imidazol-1-ylmethyl)phenyl]-1,2,4-oxadiazole

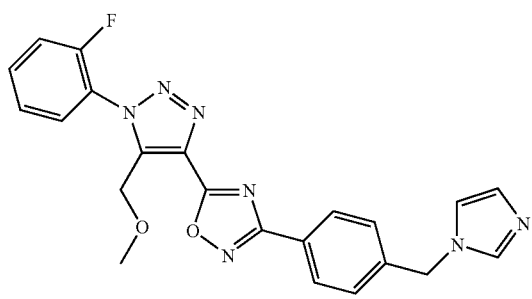

To a solution of Intermediate 11 (75 mg; 0.3 mmol) in anhydrous ACN (2 mL) was added 1-ethyl-3-(3-dimethylaminopropyl)carbodiimide hydrochloride (EDC) (80.5 mg; 0.42 mmol) followed by 4-(1H-imidazol-1-yl)methyl)-N'-hydroxybenzimidamide (Aurora, 78 mg; 0.36 mmol) in a MW vial. The mixture stirred at RT for 18 h. Anhydrous pyridine (2 mL) was added. The reaction vessel was sealed and heated at 150° C. for 45 min in a microwave reactor. This reaction was performed twice and the reaction mixtures were combined for workup. The solvents were evaporated and the residue partitioned between DCM and H$_2$O. The mixture was passed through a hydrophobic frit and the solvent evaporated. The residue was purified by flash chromatography on a Biotage 12+M column, eluting with petrol containing increasing amounts of EtOAc to give Example 175 as an off-white solid. $^1$H NMR: (CDCl$_3$, 400 MHz) δ 8.20 (2H, d, J=8.1 Hz), 7.65-7.59 (3H, m), 7.43-7.32 (2H, m), 7.30 (2H, d, J=8.1 Hz), 7.14 (1H, s), 6.94 (1H, s), 5.22 (2H, s), 4.97 (2H, s), 3.30 (3H, s). LC/MS (Method C): 432 (M+H)$^+$. HPLC (Method E) Rt=2.27 min (Purity: 99.1%).

Example 176

5-[1-(2-fluorophenyl)-5-(methoxymethyl)-1H-1,2,3-triazol-4-yl]-3-[4-(1H-1,2,4-triazol-1-ylmethyl)phenyl]-1,2,4-oxadiazole

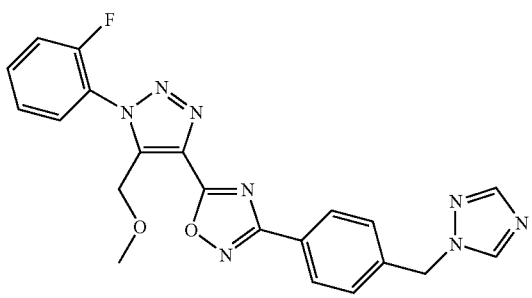

The title compound was prepared following the procedure described for Example 173, but starting from Intermediate 11 (75 mg; 0.3 mmol) and 4-(1H-1,2,4-triazol-1-yl)methyl)-N'-hydroxybenzimidamide (Aurora, 78 mg; 0.36 mmol) to give Example 176 as an off-white solid. $^1$H NMR: (CDCl$_3$, 400 MHz) δ 8.23 (2H, d, J=8.1 Hz), 8.14 (1H, s), 8.02 (1H, s), 7.67-7.59 (2H, m), 7.43-7.32 (4H, m), 5.45 (2H, s), 4.97 (2H, s), 3.30 (3H, s). LC/MS (Method C): 433 (M+H)$^+$. HPLC (Method F) Rt=3.20 min (Purity: 99.1%).

Example 177

(1S,2R)-2-[(4-{5-[1-(2-fluorophenyl)-5-pyridin-4-yl-1H-1,2,3-triazol-4-yl]-1,2,4-oxadiazol-3-yl}benzyl)amino]cyclopentanecarboxylic acid

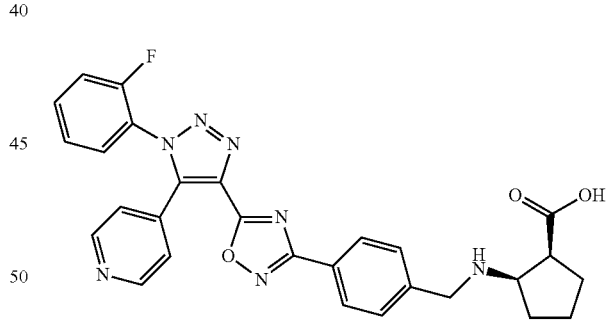

The title compound was prepared following the procedure described for Example 94, but starting from 4-(5-(1-(2-fluorophenyl)-5-(pyridin-4-yl)-1H-1,2,3-triazol-4-yl)-1,2,4-oxadiazol-3-yl)benzaldehyde, obtained as described in Example 113, Step 1, (200 mg; 0.48 mmol) and (1R,2S)-2-aminocyclopentanecarboxylic acid (125 mg; 0.97 mmol), to give Example 177 as a white solid. $^1$H NMR: (TFA-d, 400 MHz) δ 10.08 (2H, d, J=6.0 Hz), 9.40 (2H, d, J=5.9 Hz), 9.18 (2H, d, J=7.9 Hz), 8.87 (1H, t, J=7.5 Hz), 8.79-8.66 (3H, m), 8.55 (1H, t, J=7.9 Hz), 8.28 (1H, t, J=9.3 Hz), 5.62 (1H, d, J=13.2 Hz), 5.48 (1H, d, J=13.3 Hz), 5.01-4.88 (1H, m), 4.49-4.37 (1H, m), 3.46-3.37 (1H, m), 3.36-3.25 (2H, m), 3.20-3.00 (2H, m), 2.97-2.89 (1H, m). LC/MS (Method C): 524 (M+H)$^+$. HPLC (Method I) Rt 13.12 min (Purity: 96.4%).

Example 178

In vitro Assays

Receptor binding assay: Membranes were prepared from CHO cells expressing S1P1 or S1P3 for use in ligand and 35S-GTPTS binding studies. Cells were suspended in 50 mM TRIS, pH 7.4, 2 mM EDTA, 250 mM Sucrose (buffer A) and 1× Complete protease inhibitor cocktail (Roche), and disrupted at 4° C. by nitrogen decompression using a cell disruption bomb (Parr Instrument). Following centrifugation at 1000 RPM for 10 min at 4° C., the supernatant was suspended in buffer A and centrifuged again at 19000 RPM for 60 min at 4° C. The pellet was then suspended in 10 mM HEPES, pH 7.4, 1 mM EDTA, 250 mM Sucrose (Buffer B), and 1× Complete EDTA-free protease inhibitor cocktail and homogenized using a potter. Membranes were flash frozen in liquid nitrogen and stored at −80° C. [33P]sphingosine 1-phosphate (3000 Ci/mmol; American Radiolabeled Chemicals, Inc.) was added to test compounds in DMSO. Membranes and WGA SPA beads (GE Healthcare) were added to give a final volume of 100 µl in 96-well plates with assay concentrations of 25 µM or 10 µM [33P]sphingosine 1-phosphate (respectively for S1P1 or S1P3), 50 mM HEPES, pH 7.5, 5 mM MgCl$_2$, 100 mM NaCl, 0.4% fatty acid-free BSA, 1-5 µg/well of proteins and 100 µg/well of WGA SPA beads. Binding was performed for 60 min at room temperature on a shaker and bound radioactivity was measured on a PerkinElmer 1450 MicroBeta counter. Specific binding was calculated by subtracting remaining radioactivity in the presence of 1000-fold excess of unlabeled S1P. Binding data were analyzed using the GraphPad Prism program.

Measurements of $^{35}$S-GTPγS Binding: Membranes (1 to 10 µg protein) prepared as described above, were incubated in 96-well Scintiplates (PerkinElmer) with test compounds diluted in DMSO, in 180 µl of 20 mM HEPES, pH 7.4, 10 mM MgCl$_2$, 2 µg/well Saponin, 0.2% fatty acid free BSA (Assay buffer), 140 mM NaCl and 1.7 µM GDP. The assay was initiated with the addition of 20 µl of 1.5 nM [35S]-GTPγS (1100 Ci/mmol; GE Healthcare) in assay buffer. After 60 min incubation at 30° C. on a shaker, plates were centrifuged for 10 min at 2000 RPM. Supernatant was discarded and membrane bound radioactivity was measured on a PerkinElmer 1450 MicroBeta counter. Triplicate samples were averaged and expressed as response relative to S1P activation in absence of compound (n=2).

The examples disclosed herein have utility as immunoregulatory agents as demonstrated by their activity as potent and selective agonists of the S1P1 receptor over the S1P3 receptor as measured in the assays described above. In particular, the examples disclosed herein possess a selectivity for the S1P1 receptor over the S1P3 receptor as measured by the ratio of EC50 for the S1P1 receptor to the EC50 for the S1P3 receptor as evaluated in the $^{35}$S-GTPTS binding assay described above in Table I.

TABLE I

| Example No | Compound | S1P1 EC$_{50}$ µM | S1P3 EC$_{50}$ µM |
|---|---|---|---|
| 2 | 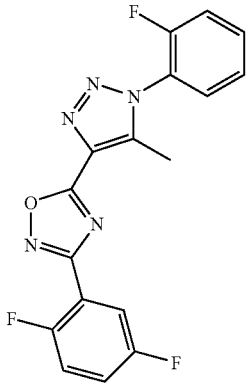 | 1.130 | — |
| 3 | 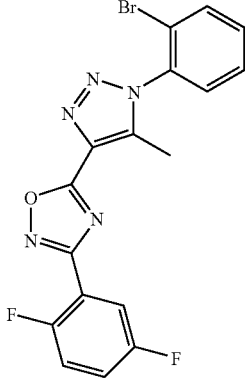 | 2.720 | — |

TABLE I-continued
| Example No | Compound | S1P1 EC$_{50}$ μM | S1P3 EC$_{50}$ μM |
|---|---|---|---|
| 5 | 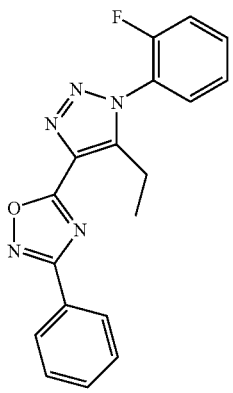 | 0.862 | >30 |
| 6 | 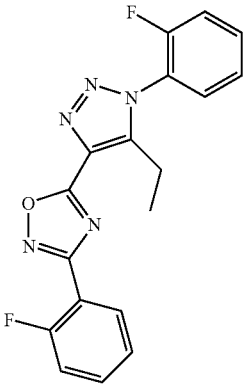 | 0.561 | >30 |
| 7 | 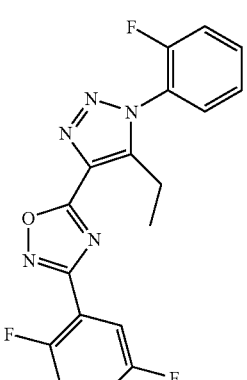 |  | >30 |

TABLE I-continued

| Example No | Compound | S1P1 EC$_{50}$ μM | S1P3 EC$_{50}$ μM |
|---|---|---|---|
| 8 | | 0.744 | >10 |
| 9 | | 0.211 | >30 |
| 10 | | 0.045 | >30 |
| 11 | | 0.053 | >30 |

TABLE I-continued

| Example No | Compound | S1P1 EC$_{50}$ μM | S1P3 EC$_{50}$ μM |
|---|---|---|---|
| 12 | | 0.007 | 14 |
| 13 | | 0.029 | 0.486 |
| 14 | | 0.038 | 0.399 |
| 15 | | 0.391 | >30 |
| 16 | | 0.158 | 7.360 |

TABLE I-continued

| Example No | Compound | S1P1 EC$_{50}$ μM | S1P3 EC$_{50}$ μM |
|---|---|---|---|
| 17 | | 0.144 | 4.900 |
| 18 | | 0.022 | 0.221 |
| 20 | | 0.084 | 8.550 |
| 21 | | 0.041 | >30 |

TABLE I-continued

| Example No | Compound | S1P1 EC$_{50}$ μM | S1P3 EC$_{50}$ μM |
|---|---|---|---|
| 22 | | 0.140 | 6.860 |
| 23 | | 0.646 | — |
| 24 | | 1.840 | — |

TABLE I-continued

| Example No | Compound | S1P1 EC$_{50}$ μM | S1P3 EC$_{50}$ μM |
|---|---|---|---|
| 25 | | 0.272 | >20 |
| 26 | | 0.095 | >20 |
| 27 | | 0.188 | 2.890 |
| 28 | | 0.044 | 7.250 |

TABLE I-continued

| Example No | Compound | S1P1 EC$_{50}$ μM | S1P3 EC$_{50}$ μM |
|---|---|---|---|
| 29 | (structure) | 1.272 | — |
| 30 | (structure) | 0.709 | — |
| 31 | (structure) | 0.007 | 1.785 |

TABLE I-continued

| Example No | Compound | S1P1 EC$_{50}$ μM | S1P3 EC$_{50}$ μM |
|---|---|---|---|
| 32 | (structure) | 0.020 | 1.2 |
| 33 | (structure) | 0.501 | >20 |
| 34 | (structure) | 1.100 | >30 |
| 39 | (structure) | 0.092 | 0.741 |

TABLE I-continued

| Example No | Compound | S1P1 EC$_{50}$ μM | S1P3 EC$_{50}$ μM |
|---|---|---|---|
| 40 | (structure) | 0.12 | >20 |
| 41 | (structure) | 0.16 | >20 |
| 42 | (structure) | 0.042 | — |
| 43 | (structure) | 0.019 | — |
| 44 | (structure) | 0.053 | — |

TABLE I-continued

| Example No | Compound | S1P1 EC$_{50}$ μM | S1P3 EC$_{50}$ μM |
|---|---|---|---|
| 45 | | 2.17 | — |
| 46 | | 0.516 | >20 |
| 47 | | 0.672 | >20 |
| 48 | | 0.127 | 10.37 |
| 49 | | 0.119 | 13.335 |

TABLE I-continued

| Example No | Compound | S1P1 EC$_{50}$ μM | S1P3 EC$_{50}$ μM |
|---|---|---|---|
| 50 | | 0.443 | — |
| 51 | | 0.01 | 0.741 |
| 52 | | 0.033 | >20 |
| 53 | | 0.211 | — |
| 54 | | 0.953 | — |

TABLE I-continued

| Example No | Compound | S1P1 EC$_{50}$ μM | S1P3 EC$_{50}$ μM |
|---|---|---|---|
| 55 | | 1.42 | — |
| 56 | | 1.85 | — |
| 57 | | 0.959 | — |
| 58 | | 1.156 | — |
| 59 | | 0.154 | >20 |

TABLE I-continued

| Example No | Compound | S1P1 EC$_{50}$ μM | S1P3 EC$_{50}$ μM |
|---|---|---|---|
| 60 | | 0.62 | — |
| 61 | | 0.182 | >20 |
| 62 | | 0.046 | >20 |
| 63 | | 0.31 | — |
| 64 | | 0.008 | — |

TABLE I-continued

| Example No | Compound | S1P1 EC$_{50}$ μM | S1P3 EC$_{50}$ μM |
|---|---|---|---|
| 65 | | 0.119 | >20 |
| 66 | | 0.026 | — |
| 67 | | 0.873 | — |
| 68 | | 0.594 | >20 |
| 69 | | 0.116 | >20 |

TABLE I-continued

| Example No | Compound | S1P1 EC₅₀ μM | S1P3 EC₅₀ μM |
|---|---|---|---|
| 70 | | 0.284 | — |
| 71 | | 0.176 | — |
| 72 | | 0.98 | — |
| 73 | | 0.049 | — |
| 74 | | 1.1 | — |

TABLE I-continued

| Example No | Compound | S1P1 EC$_{50}$ μM | S1P3 EC$_{50}$ μM |
|---|---|---|---|
| 75 | | 0.665 | — |
| 76 | | 0.583 | — |
| 77 | | 0.206 | 0.033 |
| 78 | | 0.397 | — |
| 79 | | 0.23 | — |

TABLE I-continued

| Example No | Compound | S1P1 EC$_{50}$ μM | S1P3 EC$_{50}$ μM |
|---|---|---|---|
| 80 | | 0.038 | 2.27 |
| 81 | | 0.236 | — |
| 82 | | 0.176 | — |
| 83 | | 0.017 | 0.242 |
| 84 | | 0.418 | — |

TABLE I-continued
| Example No | Compound | S1P1 EC50 μM | S1P3 EC50 μM |
|---|---|---|---|
| 85 | 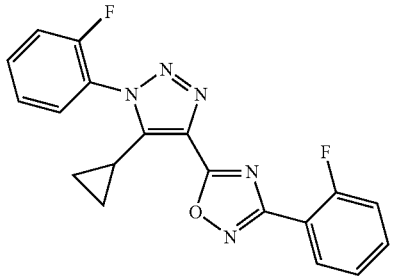 | 0.451 | — |
| 86 | 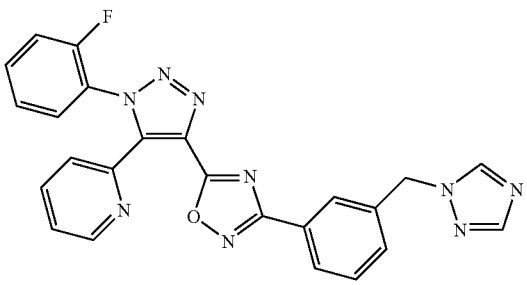 | 0.751 | — |
| 87 | 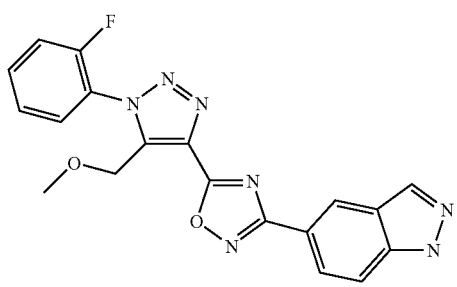 | 0.098 | >20 |
| 88 | 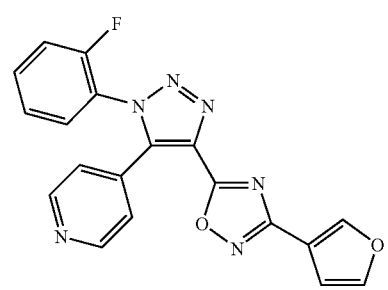 | 0.945 | — |
| 89 | 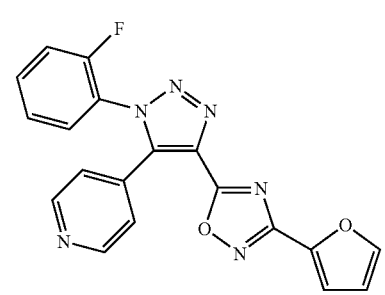 | 1.033 | — |

TABLE I-continued

| Example No | Compound | S1P1 EC$_{50}$ μM | S1P3 EC$_{50}$ μM |
|---|---|---|---|
| 90 | | 0.204 | — |
| 91 | | 0.443 | — |
| 92 | | 0.092 | >20 |
| 93 | | 0.754 | — |
| 94 | | 0.226 | — |

TABLE I-continued

| Example No | Compound | S1P1 EC$_{50}$ μM | S1P3 EC$_{50}$ μM |
|---|---|---|---|
| 95 | | 0.013 | — |
| 96 | | 0.138 | — |
| 97 | | 0.06 | >20 |
| 98 | | 0.439 | — |
| 99 | | 0.106 | — |

TABLE I-continued

| Example No | Compound | S1P1 EC$_{50}$ μM | S1P3 EC$_{50}$ μM |
|---|---|---|---|
| 100 | | 0.018 | — |
| 101 | | 0.009 | 0.214 |
| 102 | | 0.006 | 0.149 |
| 103 | | 0.017 | — |
| 104 | | 0.014 | 0.66 |

TABLE I-continued

| Example No | Compound | S1P1 EC$_{50}$ μM | S1P3 EC$_{50}$ μM |
|---|---|---|---|
| 105 | | 0.026 | — |
| 106 | | 0.018 | — |
| 107 | | 0.049 | — |
| 108 | | 0.021 | — |
| 109 | | 0.402 | — |

TABLE I-continued

| Example No | Compound | S1P1 EC$_{50}$ μM | S1P3 EC$_{50}$ μM |
|---|---|---|---|
| 110 | | 0.136 | — |
| 111 | | 0.054 | — |
| 112 | | 0.806 | — |
| 113 | | 0.002 | 1.37 |
| 114 | | 0.05 | 6.68 |

TABLE I-continued
| Example No | Compound | S1P1 EC$_{50}$ μM | S1P3 EC$_{50}$ μM |
|---|---|---|---|
| 115 | 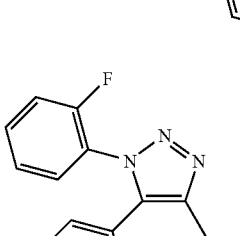 | 0.246 | — |
| 116 | 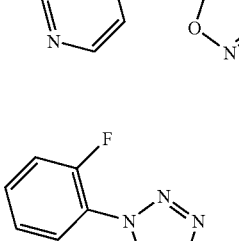 | 0.004 | 0.164 |
| 117 | 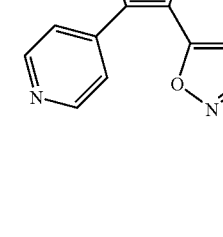 | 0.009 | — |
| 118 | 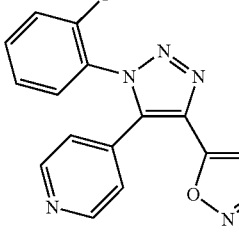 | 0.131 | — |
| 119 | 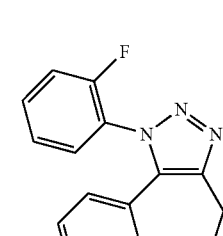 | 1.255 | — |

TABLE I-continued

| Example No | Compound | S1P1 EC$_{50}$ μM | S1P3 EC$_{50}$ μM |
|---|---|---|---|
| 120 | | 0.754 | — |
| 121 | | 0.013 | >20 |
| 122 | | 0.056 | — |
| 123 | | 0.475 | — |
| 124 | | 0.023 | — |

TABLE I-continued

| Example No | Compound | S1P1 EC$_{50}$ μM | S1P3 EC$_{50}$ μM |
|---|---|---|---|
| 125 | | 0.23 | — |
| 126 | | 0.226 | — |
| 127 | | 0.001 | 0.318 |
| 128 | | 0.008 | 2.53 |
| 129 | | 0.01 | 4.56 |

TABLE I-continued

| Example No | Compound | S1P1 EC$_{50}$ μM | S1P3 EC$_{50}$ μM |
|---|---|---|---|
| 130 | | 0.045 | — |
| 131 | | 0.011 | — |
| 132 | | 0.383 | — |
| 133 | | 0.646 | — |
| 134 | | 0.758 | — |

TABLE I-continued
| Example No | Compound | S1P1 EC$_{50}$ μM | S1P3 EC$_{50}$ μM |
|---|---|---|---|
| 135 | 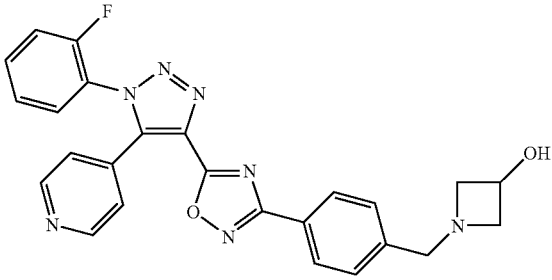 | 0.018 | — |
| 136 | 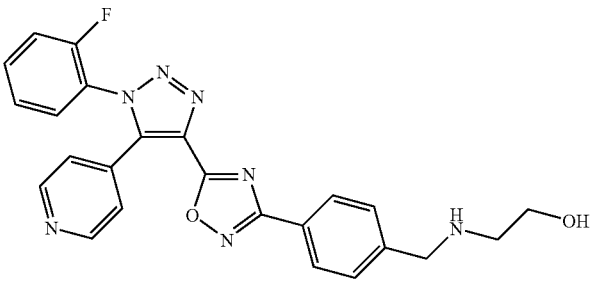 | 0.031 | — |
| 137 | 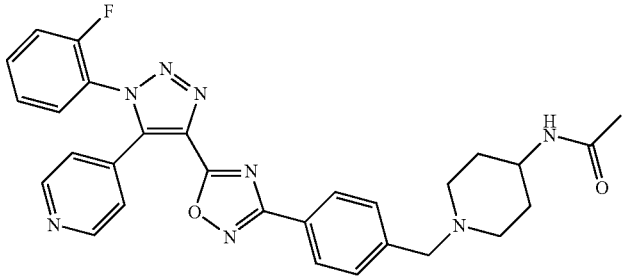 | 0.223 | — |
| 138 | 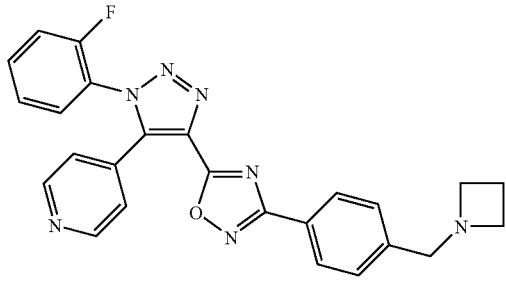 | 0.021 | — |
| 139 | 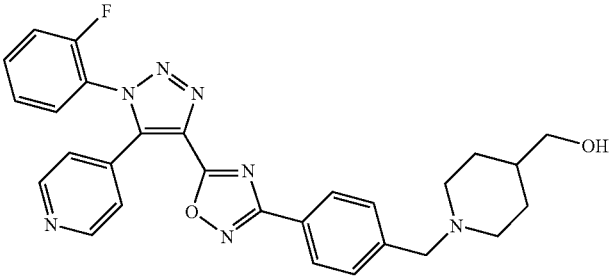 | 0.118 | — |

TABLE I-continued
| Example No | Compound | S1P1 EC$_{50}$ μM | S1P3 EC$_{50}$ μM |
|---|---|---|---|
| 140 | 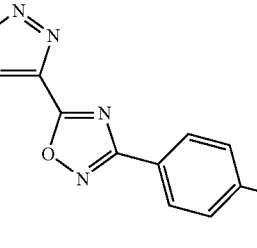 | 0.53 | — |
| 141 | 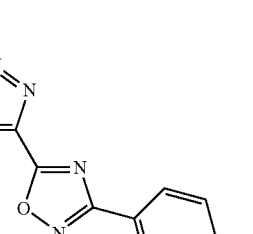 | 0.074 | — |
| 142 | 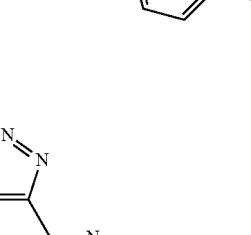 | 0.013 | 0.835 |
| 143 | 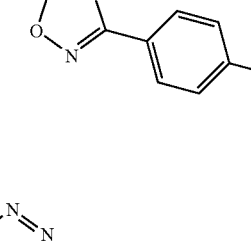 | 0.118 | — |
| 144 | 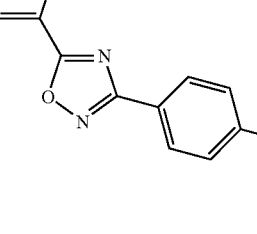 | 0.108 | — |

TABLE I-continued

| Example No | Compound | S1P1 EC$_{50}$ μM | S1P3 EC$_{50}$ μM |
|---|---|---|---|
| 145 | | 0.23 | — |
| 146 | | 0.36 | — |
| 147 | | 0.577 | — |
| 148 | | 0.508 | — |
| 149 | | 0.039 | — |

TABLE I-continued
| Example No | Compound | S1P1 EC$_{50}$ μM | S1P3 EC$_{50}$ μM |
|---|---|---|---|
| 150 | 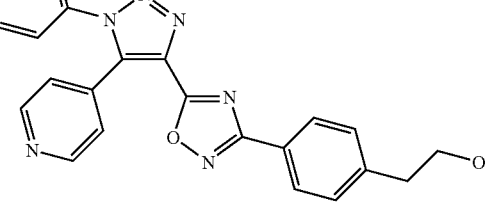 | 0.043 | — |
| 151 | 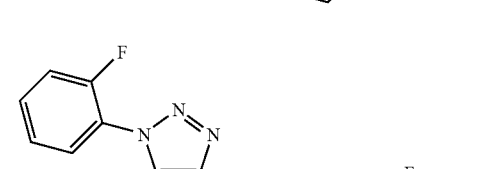 | 0.34 | — |
| 152 | 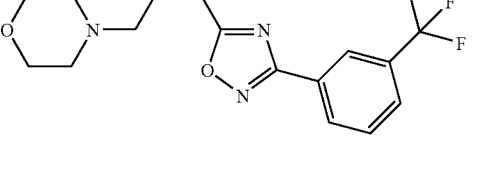 | 0.078 | — |
| 153 | 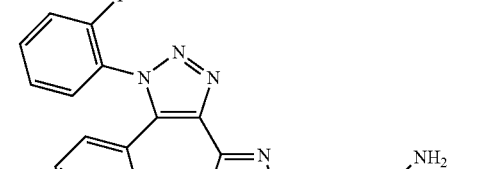 | 0.09 | — |
| 154 | 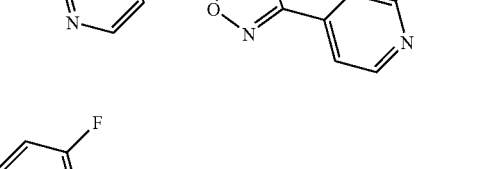 | 0.918 | — |

TABLE I-continued
| Example No | Compound | S1P1 EC$_{50}$ μM | S1P3 EC$_{50}$ μM |
|---|---|---|---|
| 155 | 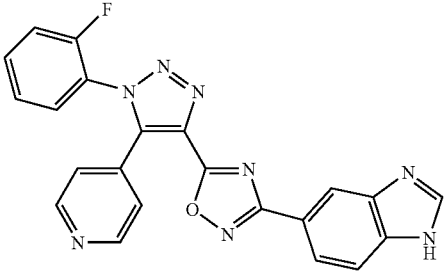 | 0.251 | — |
| 156 | 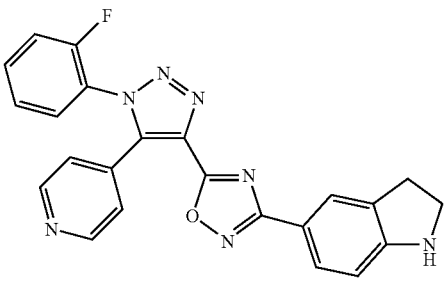 | 0.027 | — |
| 157 | 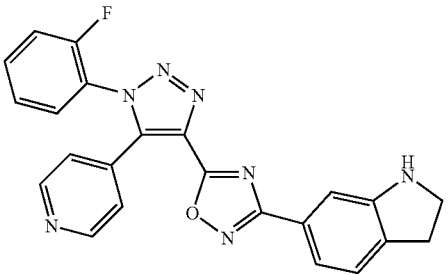 | 0.218 | — |
| 158 | 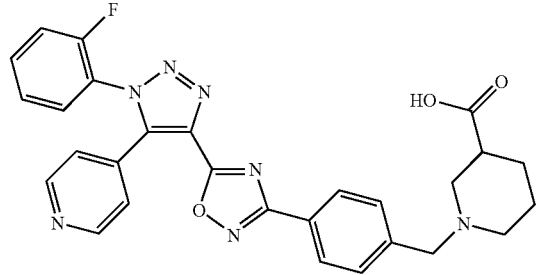 | 0.056 | — |
| 159 | 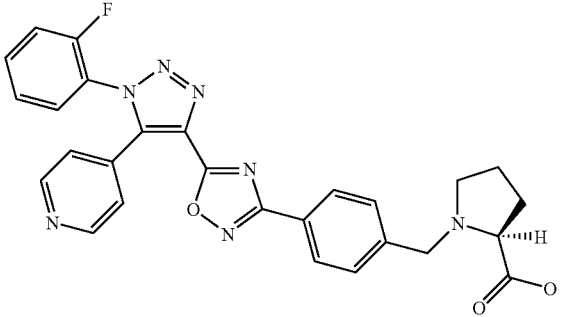 | 0.574 | — |

TABLE I-continued

| Example No | Compound | S1P1 EC$_{50}$ μM | S1P3 EC$_{50}$ μM |
|---|---|---|---|
| 160 | | 0.071 | — |
| 161 | | 0.545 | — |
| 162 | | 0.211 | — |
| 163 | | 0.08 | — |
| 164 | | 0.027 | — |

TABLE I-continued

| Example No | Compound | S1P1 EC$_{50}$ μM | S1P3 EC$_{50}$ μM |
|---|---|---|---|
| 165 | | 0.017 | — |
| 166 | | 0.218 | — |
| 167 | | 0.015 | — |
| 168 | | 0.016 | — |
| 169 Chiral | | 0.008 | — |

TABLE I-continued

| Example No | Compound | S1P1 EC$_{50}$ μM | S1P3 EC$_{50}$ μM |
|---|---|---|---|
| 170 | | 0.004 | — |
| 171 | | 0.011 | — |
| 172 | | 0.005 | — |
| 173 | | 0.24 | — |
| 174 | | 0.162 | — |

TABLE I-continued

| Example No | Compound | S1P1 EC$_{50}$ μM | S1P3 EC$_{50}$ μM |
|---|---|---|---|
| 175 | [structure] | 0.067 | — |
| 176 | [structure] | 0.105 | — |
| 177 | [structure] | 0.742 | — |

Example 179

Animal Models Evaluating the in vivo Efficacy of S1P Agonists

Model of S1P Agonists-induced Lymphopenia in Mice

Female C57BL/6 mice (Elevage Janvier) (8 week old) receive S1P agonists by oral route. Blood is sampled in heparinized (100 IU/kg, ip) mice by intracardiac or retroorbital puncture under isoflurane anesthesia 2 to 120 hrs after drug treatment. The white blood cells (lymphocytes and neutrophils) are counted using a Beckman/Coulter counter. The quality of blood sampling is assessed by counting erythrocytes and platelets. Compounds of Formula (I) are tested according to the above assay and have an ED50 of less than 100 mg/kg, more preferable below 50 mg/kg at 24 hours.

Model of MOG-induced Experimental Autoimmune Encephalomyelytis (EAE) in Mice

EAE was induced in 9 weeks old female mice (C57BL/6, Elevage Janvier) by an immunization against MOG. The mice received Pertussis toxin (Alexis, 300 ng/mouse in 200 μl of PBS) by ip route and 100 μl of an emulsion containing MOG35-55 peptide (NeoMPS, 200 μg/mouse), *Mycobacterium Tuberculosis* (0.25 mg/mouse) in Complete Freund's Adjuvant (DIFCO) by subcutaneous injection into the back. Two days later an additional injection of Pertussis toxin (Alexis, 300 ng/mouse in 200 μl of PBS) was done by ip route. After EAE induction, mice were weighed daily and the neurological impairment was quantified using a 15-points clinical scale assessing the paralysis (tail, hind limbs and fore limbs), the incontinency and the death.

Clinical Score

1—Tail
 Score=0 A normal mouse holds its tail erect when moving.
 Score=1 If the extremity of the tail is flaccid with a tendency to fall.
 Score=2 If the tail is completely flaccid and drags on the table.

2—Hind limbs
 Score=0 A normal mouse has an energetic walk and doesn't drag his paws.
 Score=1 Either one of the following tests is positive:
  a—Flip test: while holding the tail between thumb and index finger, flip the animal on his back and observe the time it takes to right itself. A healthy mouse will turn itself immediately. A delay suggests hind-limb weakness.
  b—Place the mouse on the wire cage top and observe as it crosses from one side to the other. If one or both limbs frequently slip between the bars we consider that there is a partial paralysis.

Score=2 Both previous tests are positive.

Score=3 One or both hind limbs show signs of paralysis but some movements are preserved; for example: the animal can grasp and hold on to the underside of the wire cage top for a short moment before letting go Score=4 When both hind legs are paralyzed and the mouse drags them when moving.

3—Fore limbs:
Score=0 A normal mouse uses his front paws actively for grasping and walking and holds his head erect.
Score=1 Walking is possible but difficult due to a weakness in one or both of the paws, for example, the front paws are considered weak when the mouse has difficulty grasping the underside of the wire top cage. Another sign of weakness is head drooping.
Score=2 When one forelimb is paralyzed (impossibility to grasp and the mouse turns around the paralyzed limb). At this time the head has also lost much of its muscle tone.
Score=3 Mouse cannot move, and food and water are unattainable.

4—Bladder:
Score=0 A normal mouse has full control of his bladder.
Score=1 A mouse is considered incontinent when his lower body is soaked with urine.

5—Death:
Score=15

The final score for each animal is determined by the addition of all the above-mentioned categories. The maximum score for live animals is 10.

At day 12 (first signs of paralysis) the mice were stratified in experimental groups (n=10) according to the clinical score and the body weight loss. The semi-curative treatment started at day 14.

Example 180

Preparation of a Pharmaceutical Formulation

Formulation 1—Tablets
A compound of formula I and related formulae is admixed as a dry powder with a dry gelatin binder in an approximate 1:2 weight ratio. A minor amount of magnesium stearate is added as a lubricant. The mixture is formed into 240-270 mg tablets (80-90 mg of active compound according to the invention per tablet) in a tablet press.

Formulation 2—Capsules
A compound of formula I and related formulae is admixed as a dry powder with a starch diluent in an approximate 1:1 weight ratio. The mixture is filled into 250 mg capsules (125 mg of active compound according to the invention per capsule).

Formulation 3—Liquid
A compound of formula I and related formulae (1250 mg), sucrose (1.75 g) and xanthan gum (4 mg) are blended, passed through a No. 10 mesh U.S. sieve, and then mixed with a previously prepared solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4—Tablets
A compound of formula I and related formulae is admixed as a dry powder with a dry gelatin binder in an approximate 1:2 weight ratio. A minor amount of magnesium stearate is added as a lubricant. The mixture is formed into 450-900 mg tablets (150-300 mg of active compound according to the invention) in a tablet press.

Formulation 5—Injection
A compound of formula I and related formulae is dissolved in a buffered sterile saline injectable aqueous medium to a concentration of approximately 5 mg/mL.

The invention claimed is:
1. A compound according to formula I:

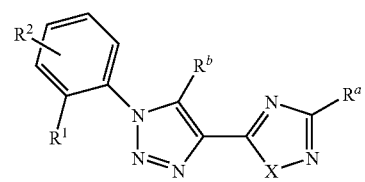

wherein
X is O or S;
$R^1$ denotes H, Hal, $CF_3$, $OCF_3$, CN, or $NO_2$;
$R^2$ is H, A or Hal;
$R^a$ is H, A, Ar, or Het;
$R^b$ is A, Ar, Het, OA, NHA, or $NA_2$, Ar-alkyl, or Het-alkyl;
Hal is F, Cl, Br or I;
A is a branched or linear alkyl having 1 to 12 C-atoms, wherein one or more may be replaced by Hal, $OR^3$, CN, $CO_2R^3$, cycloalkyl having 3 to 7 ring carbon atoms, or $N(R^3)_2$ and wherein one or more non-adjacent $CH_2$-groups may be replaced by O, $NR^3$ or S and/or by —CO—, —$NR^3CO$—, —$CONR^3$—, $NR^3CO_2$—, —$NR^3CONR^3$—, —CH=CH—, —C≡C—groups, or

or denotes cycloalkyl or cycloalkylalkylene having 3-7 ring C atoms;
q is 1, 2, 3, or 4;
Ar denotes a monocyclic or bicyclic, unsaturated or aromatic carbocyclic ring having 6 to 14 carbon atoms which may be unsubstituted or monosubstituted, disubstituted or trisubstituted by a substituent selected from $R^4$ and/or $R^5$;
Ar-alkyl denotes an aryl group linked to the rest of the molecule through a $C_1$-$C_{12}$ alkylene chain;
Het denotes a monocyclic or bicyclic, saturated, unsaturated or aromatic heterocyclic ring having 1 to 4 N, O and/or S atoms which may be unsubstituted or monosubstituted, disubstituted or trisubstituted by a substituent selected from $R^4$ and/or $R^5$; and wherein one or more $CH_2$ groups may be replaced by —CO—;
Het-alkyl denotes a group Het linked to the rest of the molecule through a $C_1$-$C_{12}$ alkylene chain;
$R^4$ and $R^5$ are each independently selected from A, Hal, hydroxy, alkoxy, carboxy, carboxy-alkyl, perfluoro-alkyl, perfluoro-alkoxy, acyl, alkylsulfonyl, sulfonyl, —$SO_2(R^3)_2$, cyano, nitro, amino, amido, alkyl optionally substituted by a carboxy, —$N(R^3)_2$, —$CO(NR^3)_2$, —$OR^3$, $(NR^3)COR^3$, —$CO_2R^3$, —$COR^3$, or Ar-alkyl or Het-alkyl both optionally substituted by A, Hal, an acyl, alkylsulfonyl, carboxy, —$N(R^3)_2$, —$CON(R^3)_2$, —OR³, (NR³)COR³, —CO₂R³, —COR³, —SO₂N(R³)₂, —SO₂alkyl, NR³SO₂alkyl, NR³SO₂alkyl,

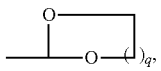

or $C_1$-$C_6$ alkyl;

R³ is H or A;

or a pharmaceutically acceptable tautomer, salt or stereoisomer thereof, including mixtures thereof.

2. The compound according to claim 1, said compound being selected from a compound having the formula IA, IB, IC, ID, IE, IF or IG IA
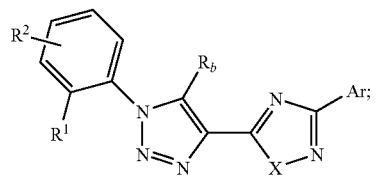

IB
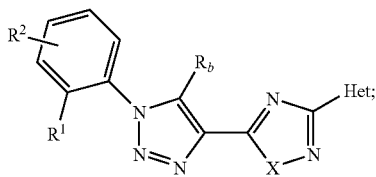

IC
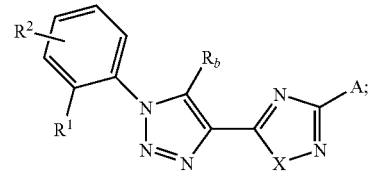

ID
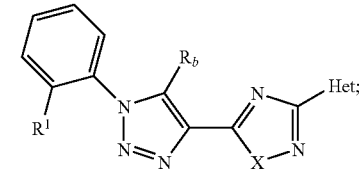

IE
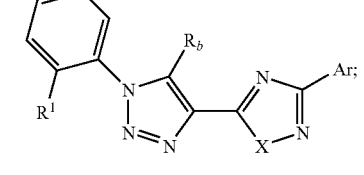

IF
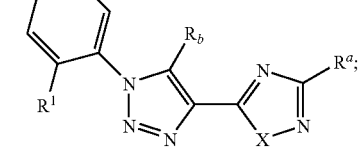

IG
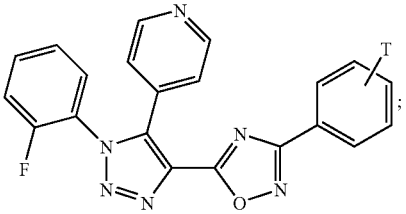

wherein T is Het-alkyl, A, SO₂Me, R⁴ or R⁵ and wherein X, Rᵃ, Rᵇ, R¹, R², R⁴, R⁵ are as defined in claim 1, or a pharmaceutically acceptable tautomer, salt or stereoisomer thereof, including mixtures thereof.

3. The compound according to claim 1, wherein Het is selected from the following groups:

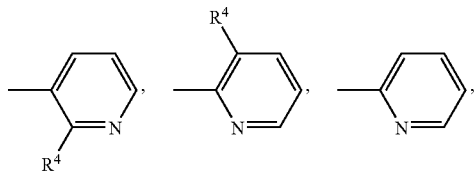

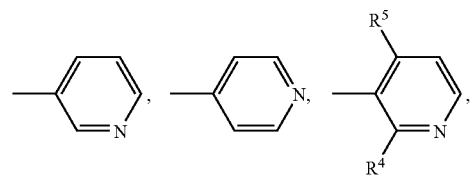

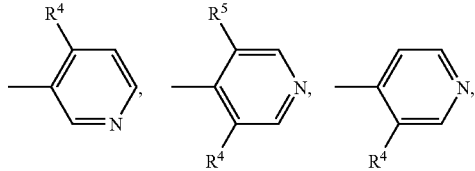

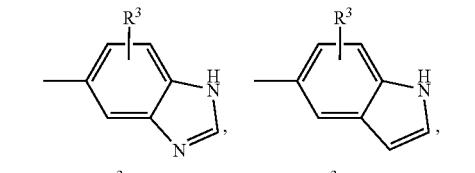

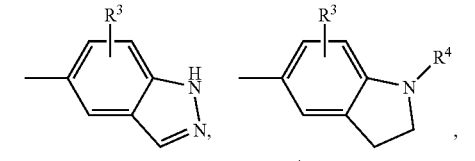

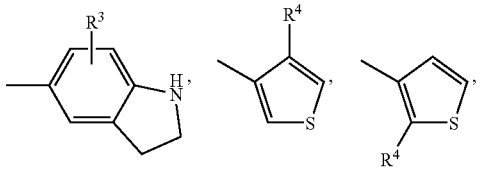

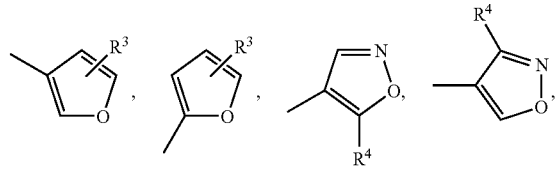

-continued

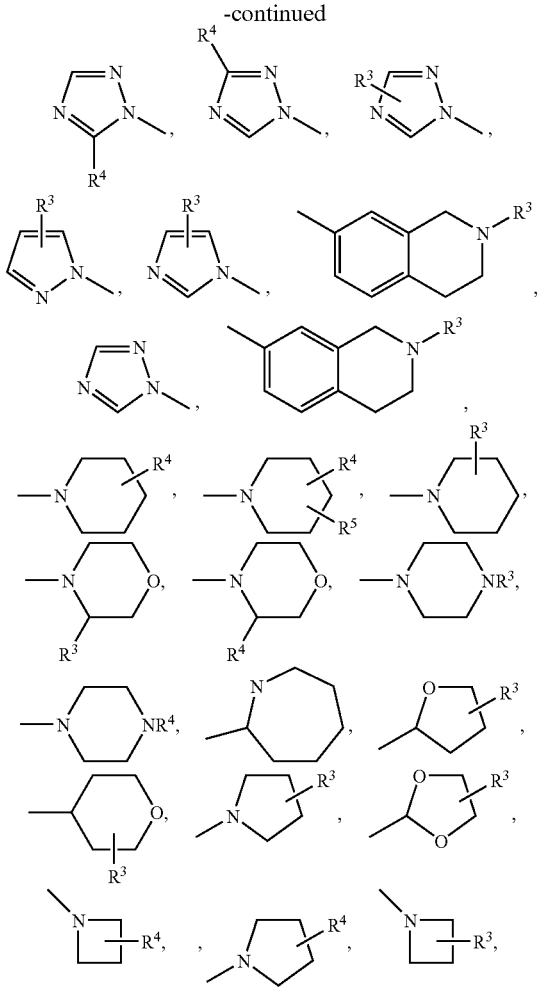

wherein R³, R⁴ and R⁵ are as defined as in claim 1.

4. The compound according to claim 1, wherein R⁴ and R⁵ are selected from the following groups:

Hal, $C_1$-$C_6$alkyl, —CF$_3$, —(CH$_2$)$_n$OR$^3$, —(CH$_2$)$_n$COOR$^3$, —SO$_2$Me, —SO$_2$N(R$^3$)$_2$, —COR$^3$, —CO(NR$^3$)$_2$, —(CH$_2$)$_n$COOtBu, —(CH$_2$)$_n$N(R$^3$)$_2$, —(CH$_2$)$_n$OH, —(CH$_2$)$_n$N(R$^3$)(CH$_2$)$_p$OR$^3$, —(CH$_2$)$_n$N(R$^3$)(CH$_2$)$_p$COOR$^3$, —NHCOR$^3$, NHSO$_2$R$^3$,

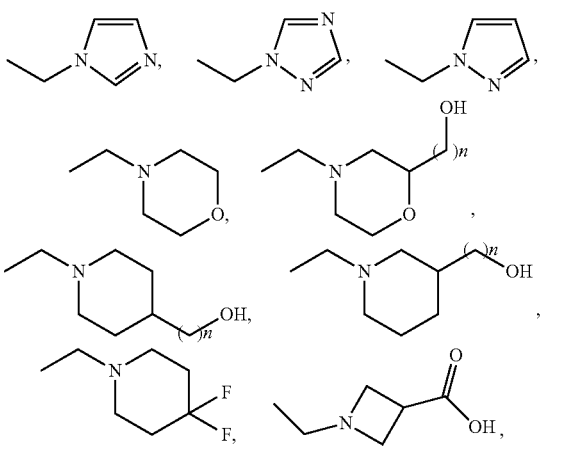

-continued

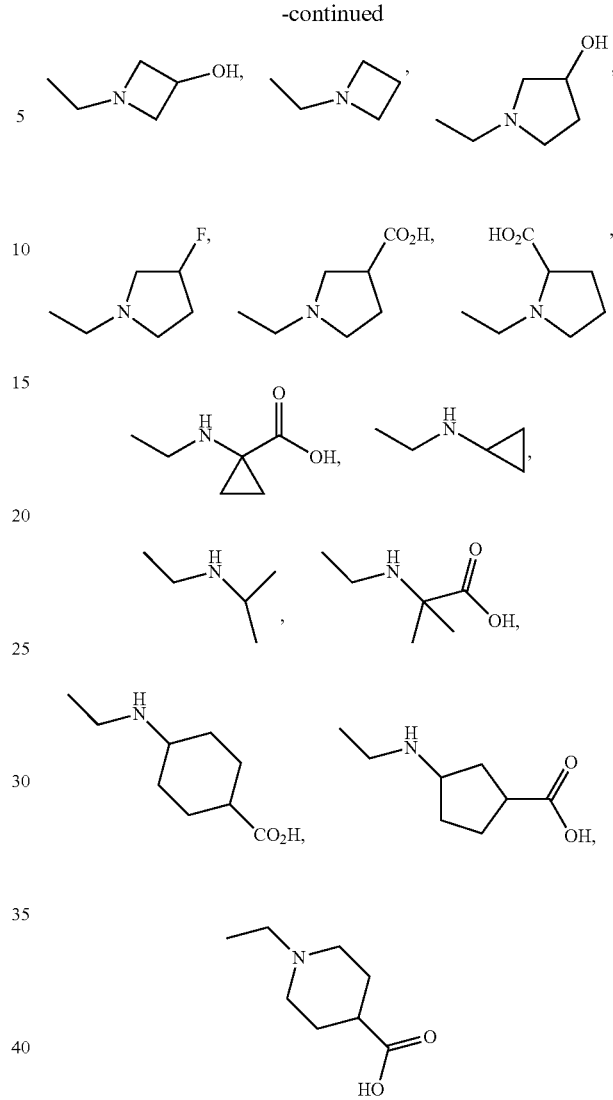

wherein n and p are independently from one other 0,1,2,3 or 4 and R³ is as defined in claim 1.

5. The compound according to claim 1, wherein said compound is selected from:

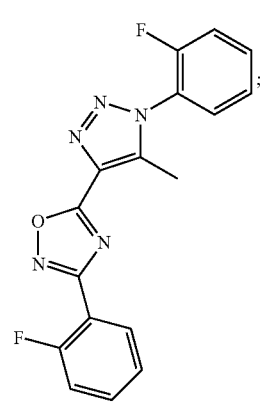

1

295
-continued
2
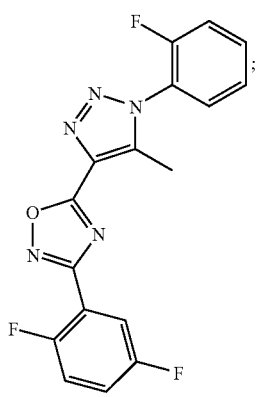
3
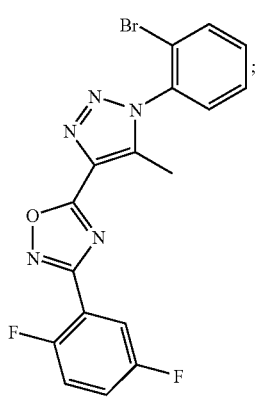
4
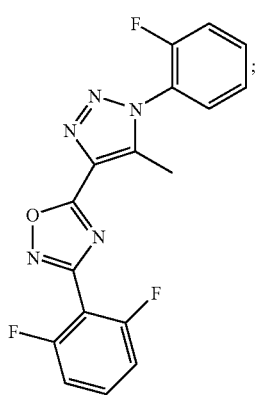
5
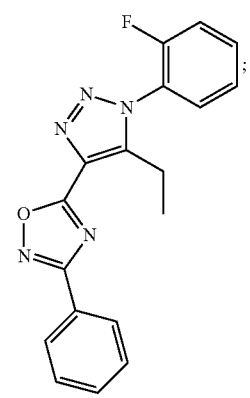
296
-continued
6
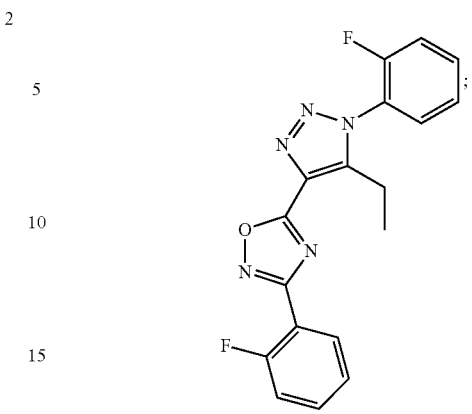
7
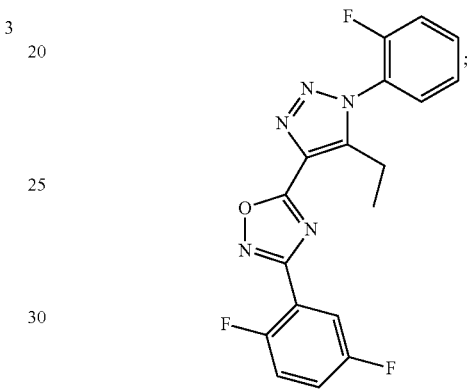
8
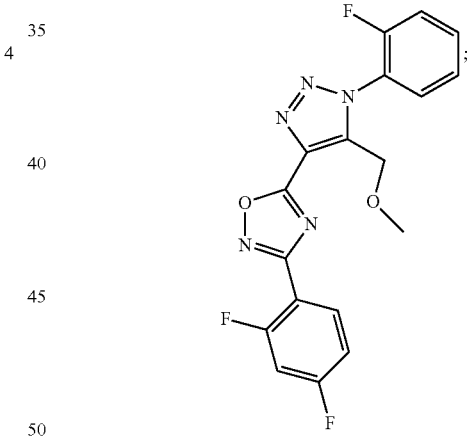
9
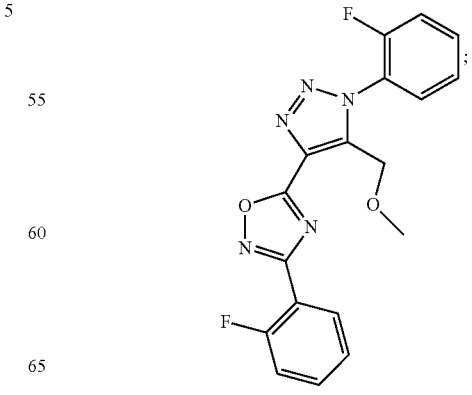

-continued
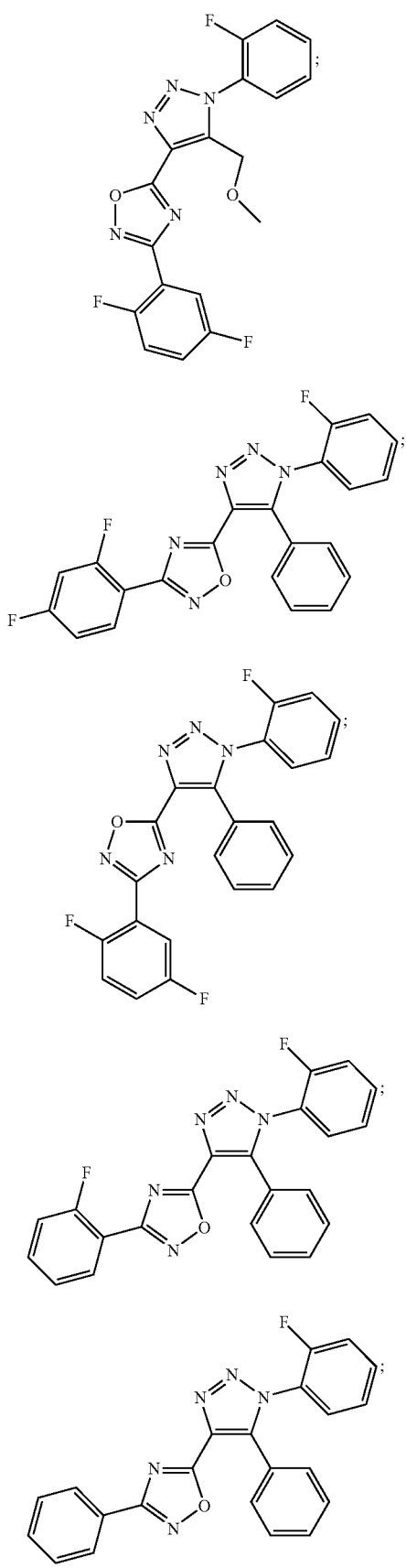
-continued
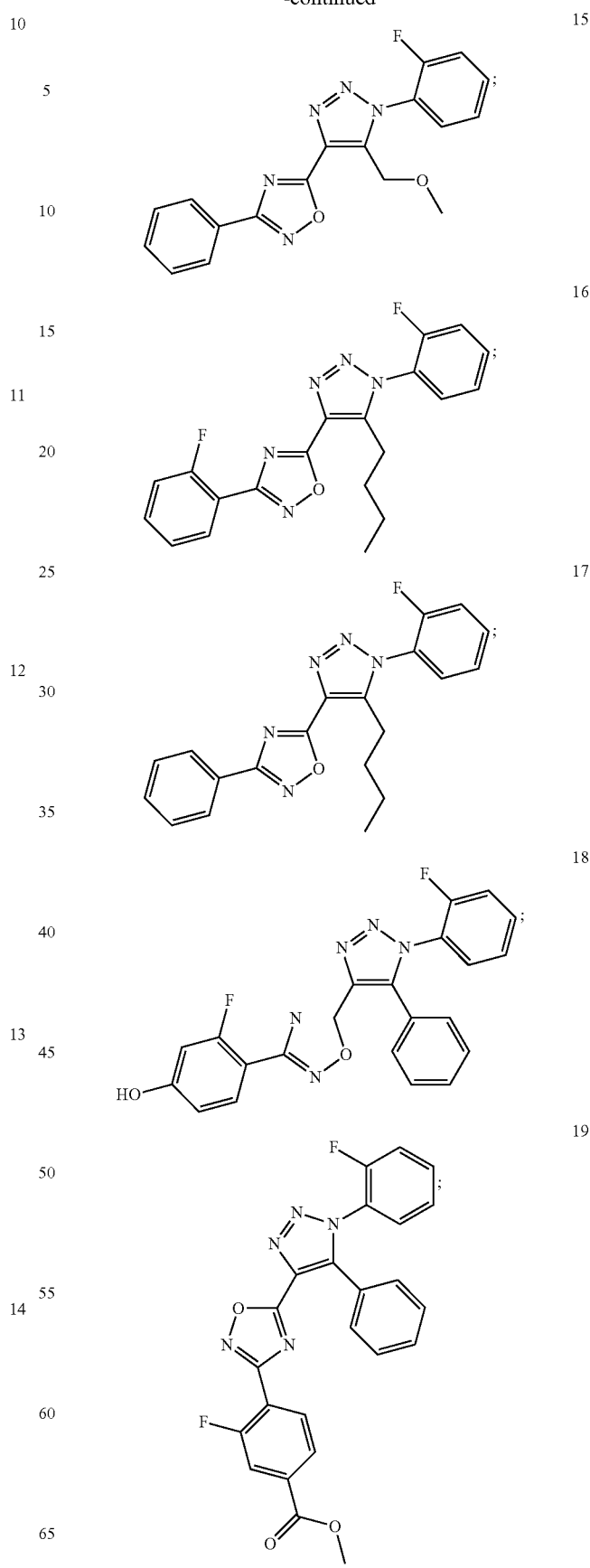

20
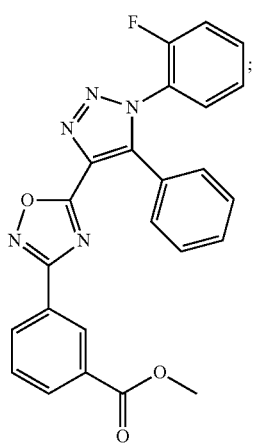
21
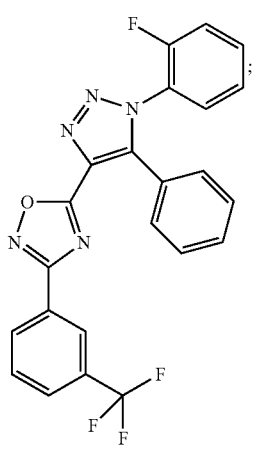
22
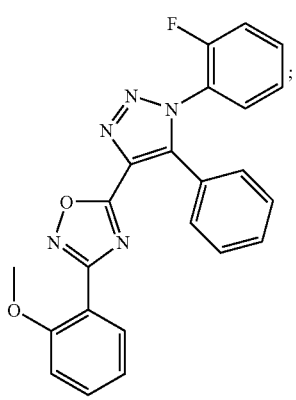
23
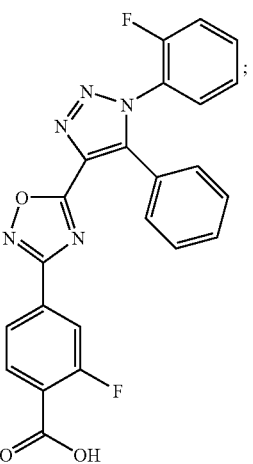
24
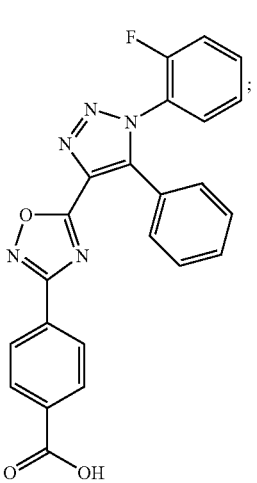
25
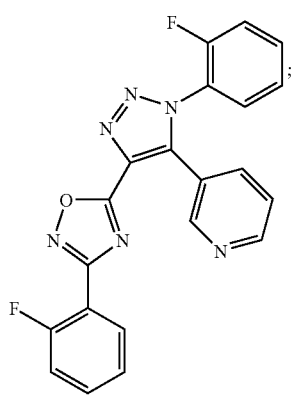

26
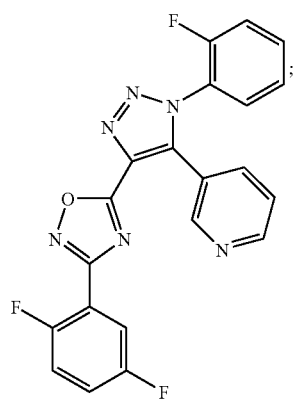
27
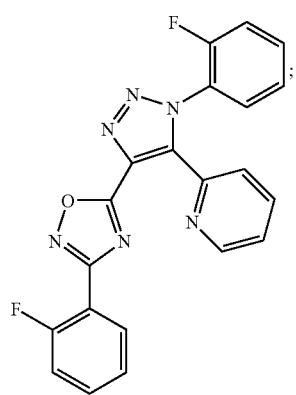
28
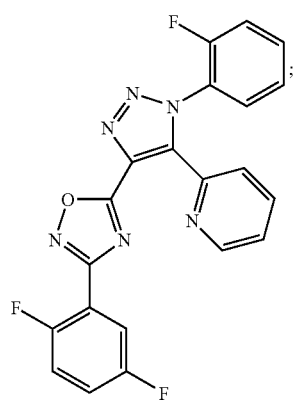
29
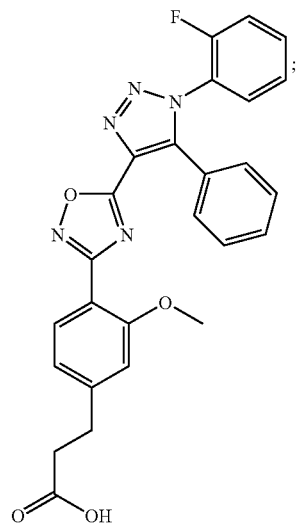
30
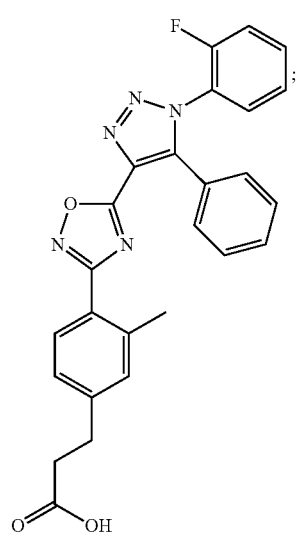
31
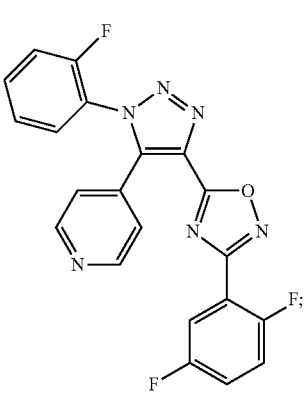

303
-continued
| | |
|---|---|
| 32 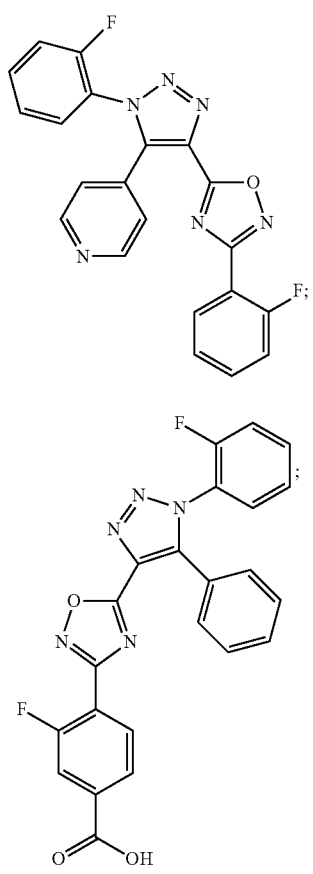 | 36 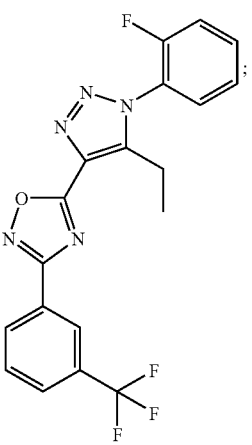 |
| 33 | 37 |
| 34 | 38 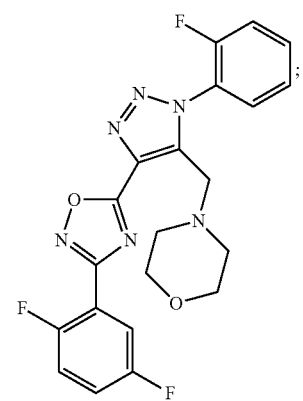 |
| 35 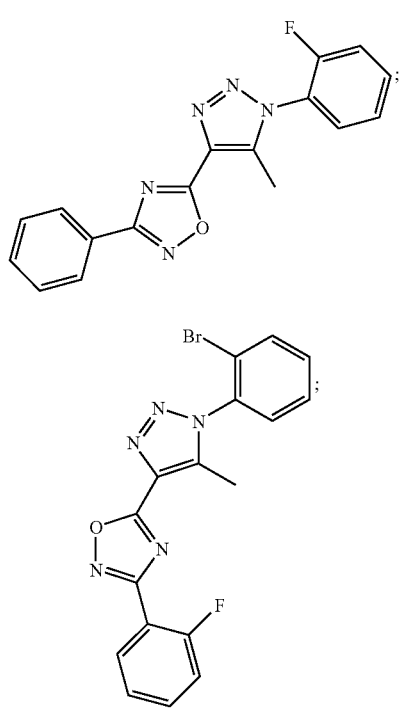 | 39 |
304
-continued 305
-continued
40
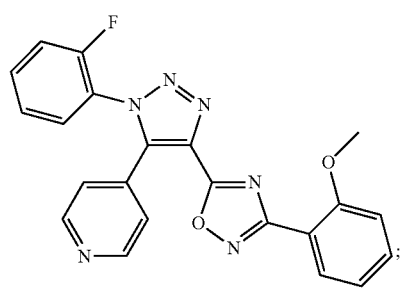
41
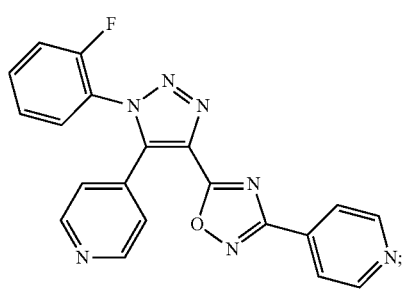
42
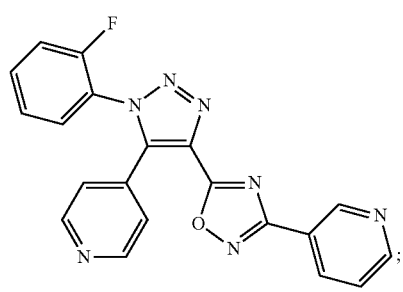
43
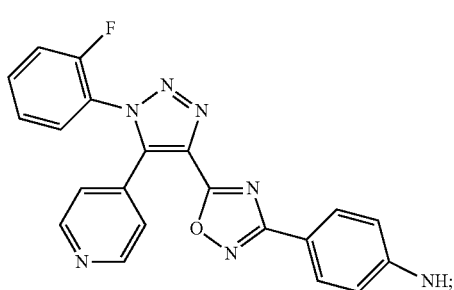
44
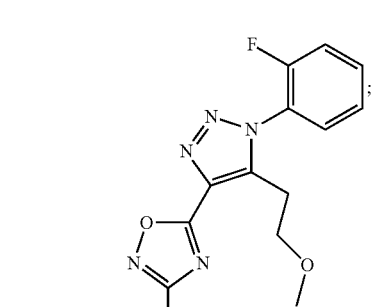
306
-continued
45
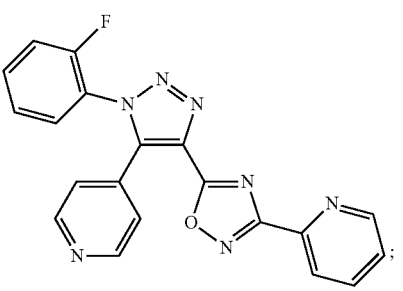
46
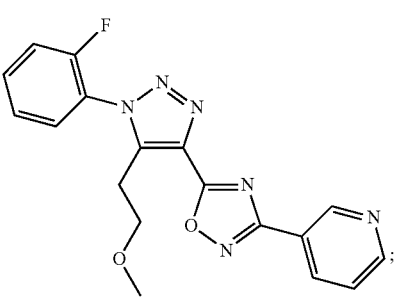
47
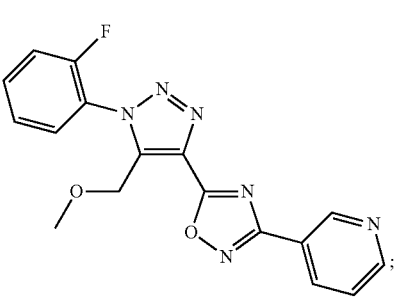
48
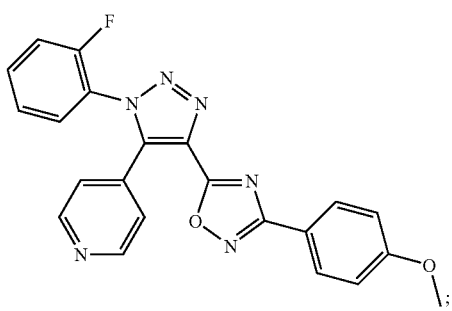
49
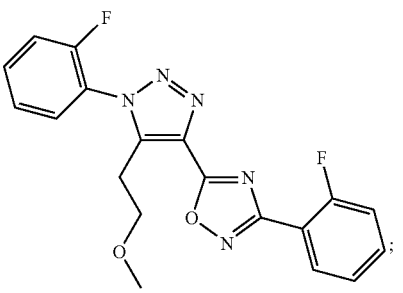

307
-continued
50
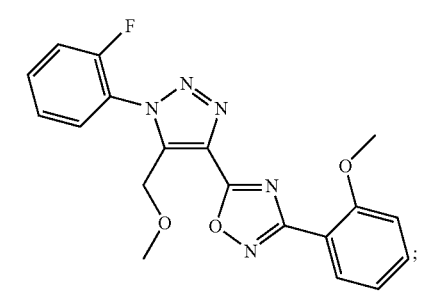
51
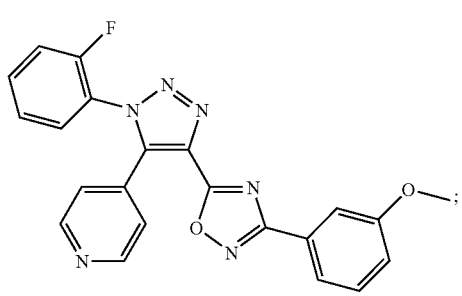
52
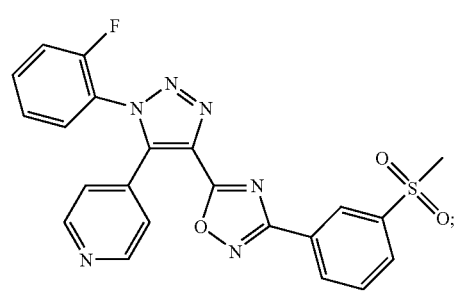
53
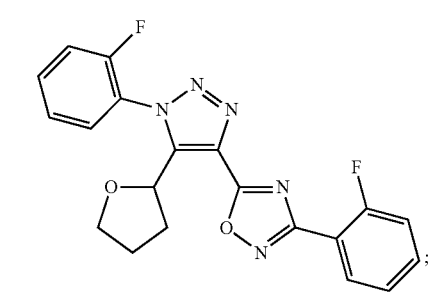
54
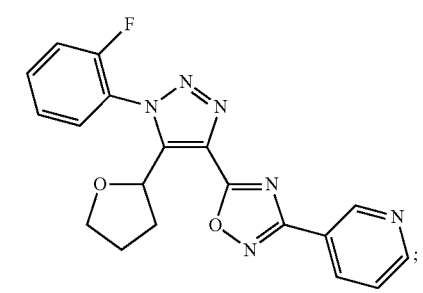
308
-continued
55
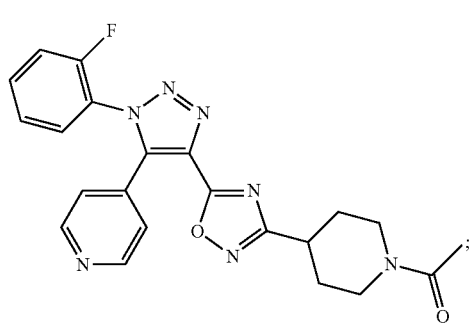
56
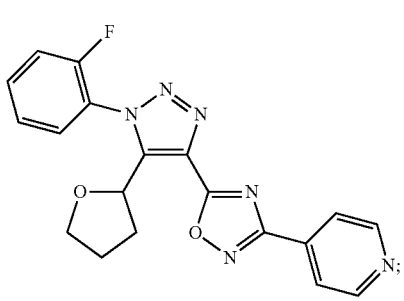
57
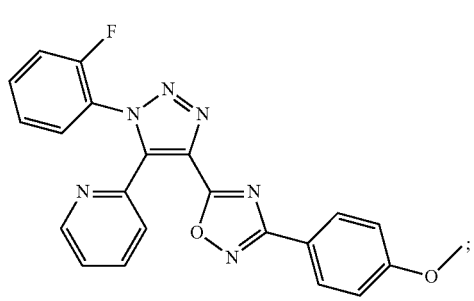
58
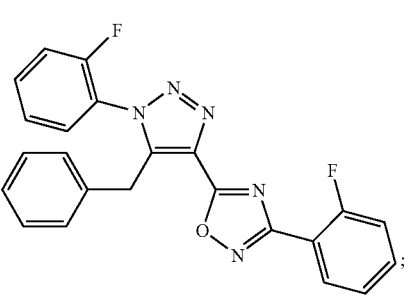
59
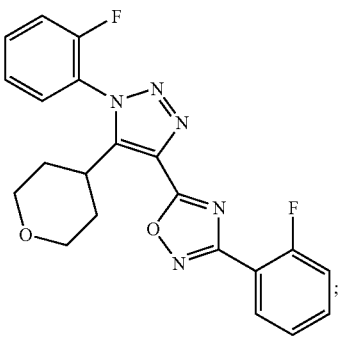

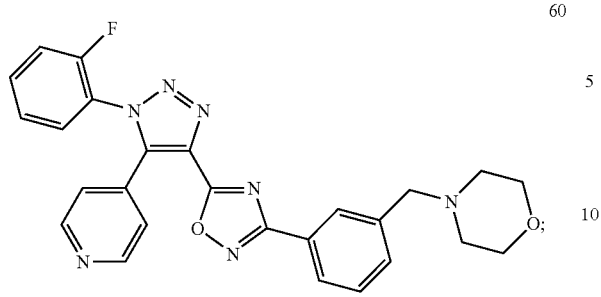
60;
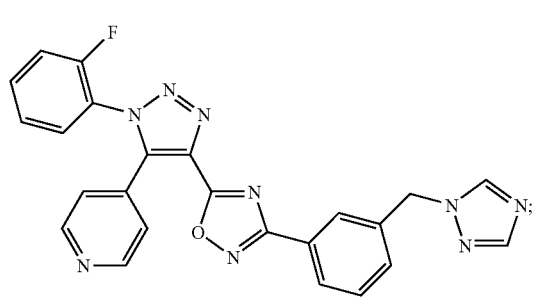
61;
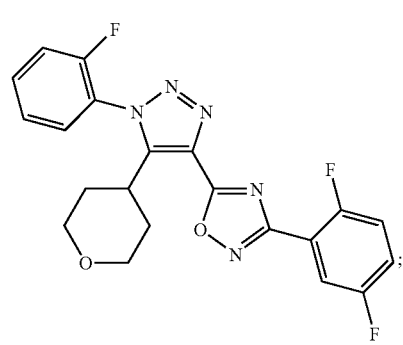
62;
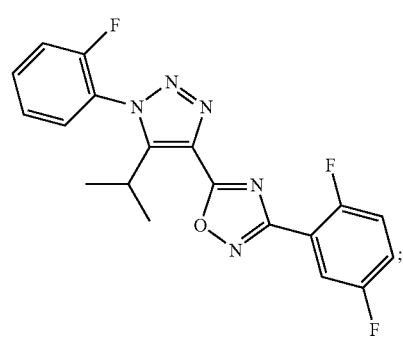
63;
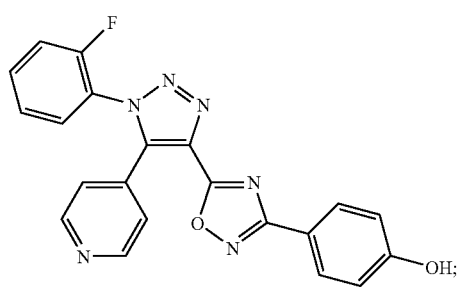
64
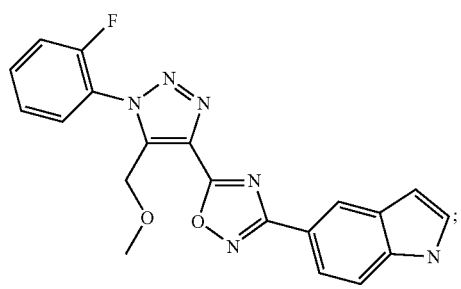
65;
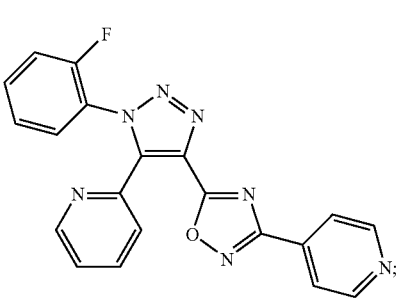
66;
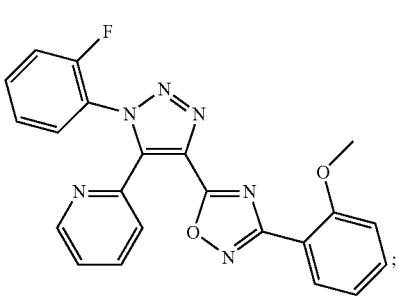
67;
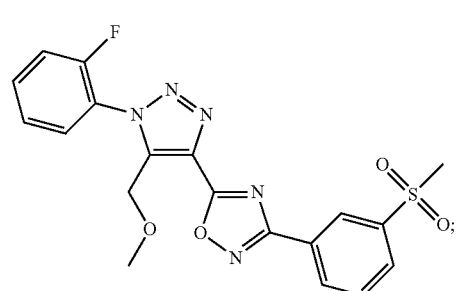
68;
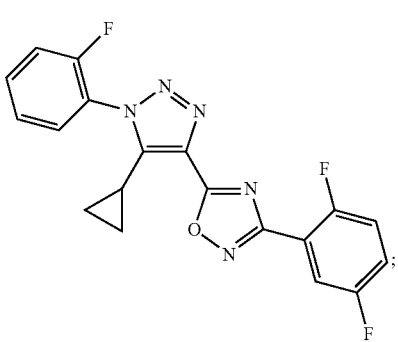
69;

70
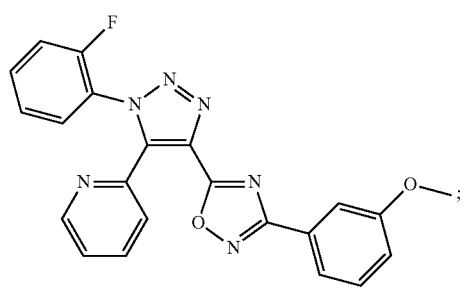
71
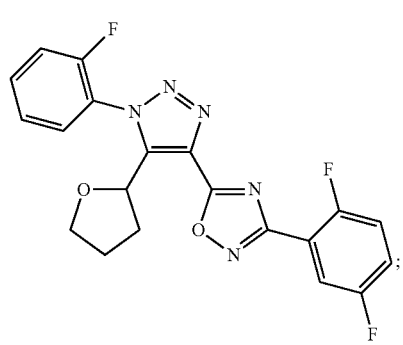
72
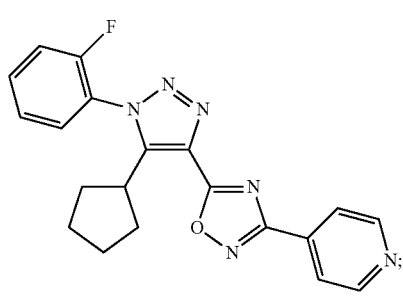
73
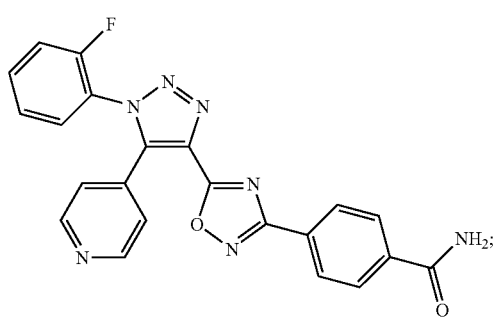
74
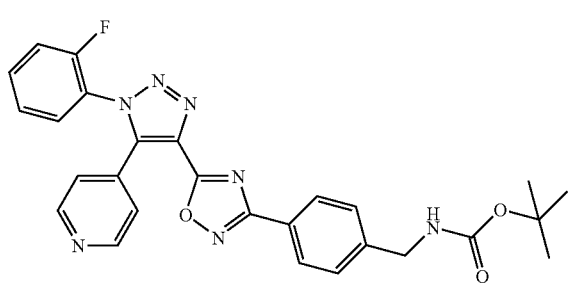
75
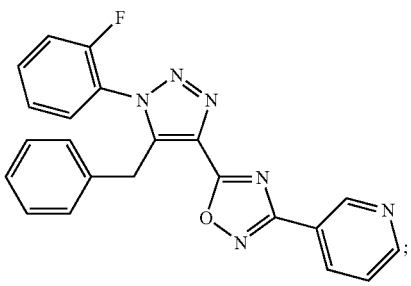
76
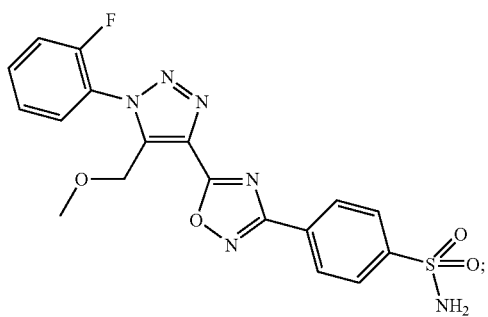
77
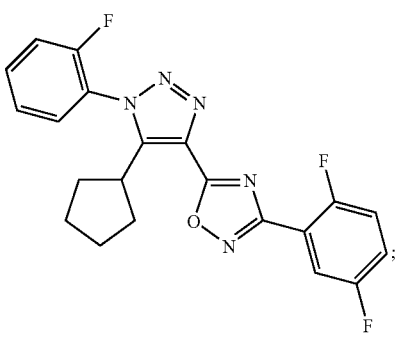
78
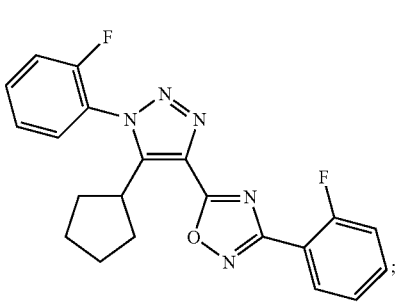
79
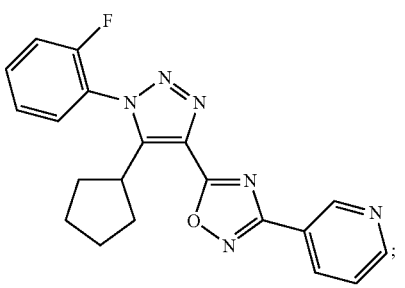

80
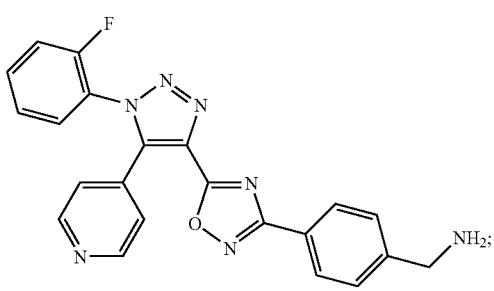
81
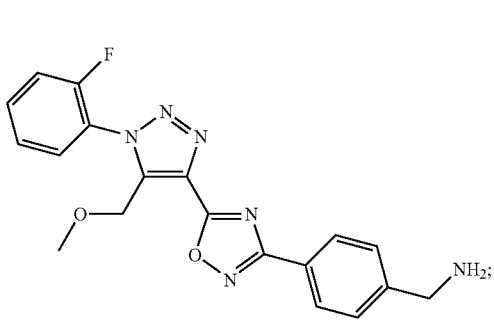
82
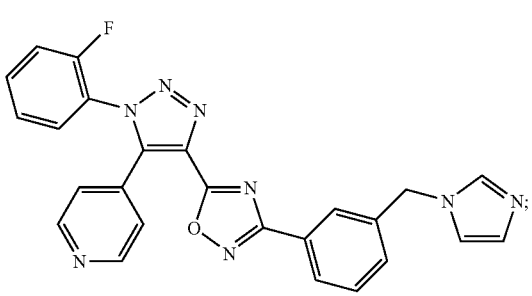
83
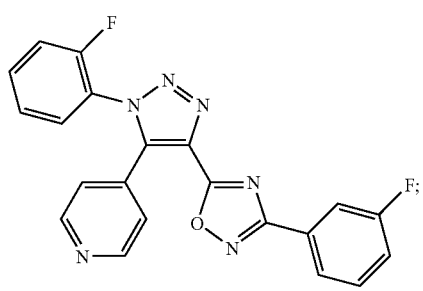
84
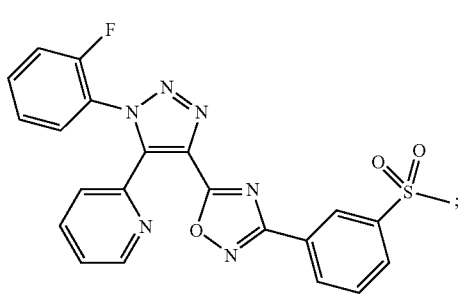
85
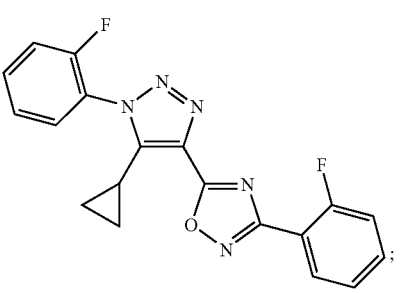
86
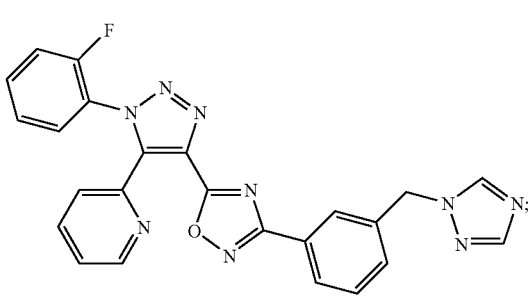
87
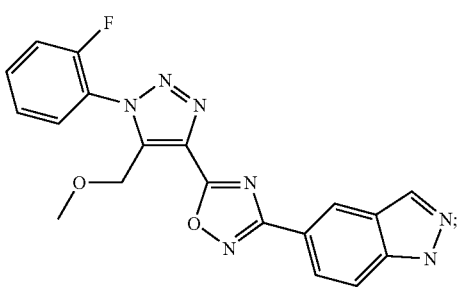
88
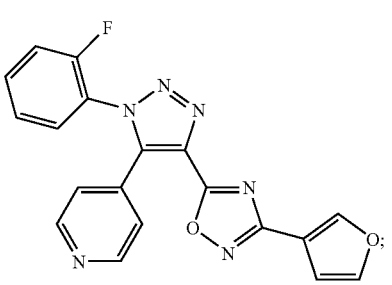
89
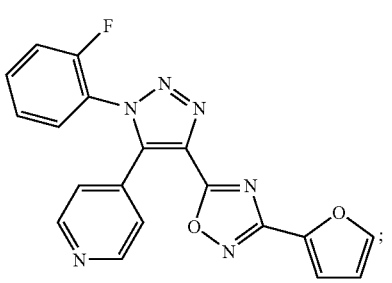

315
-continued
90
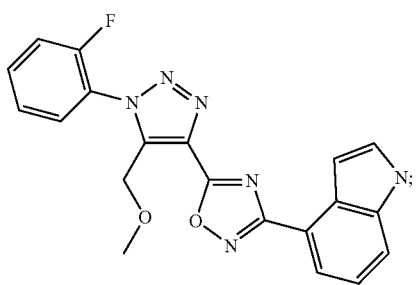
91
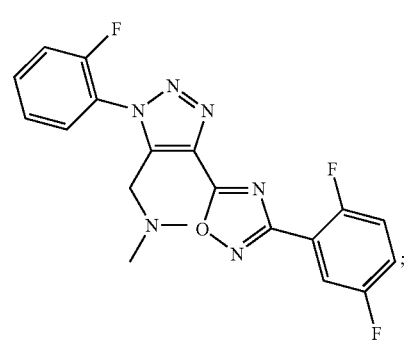
92
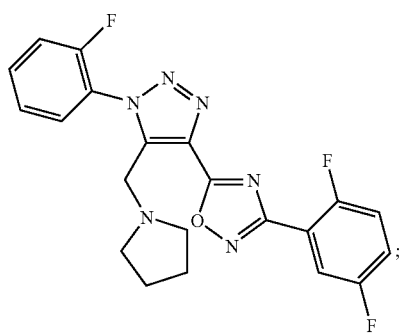
93
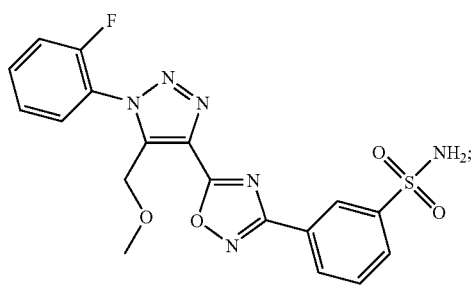
94
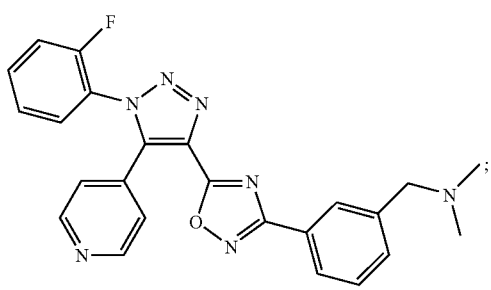
316
-continued
95
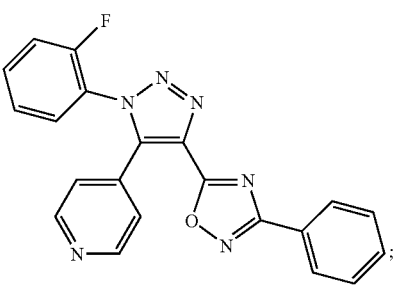
96
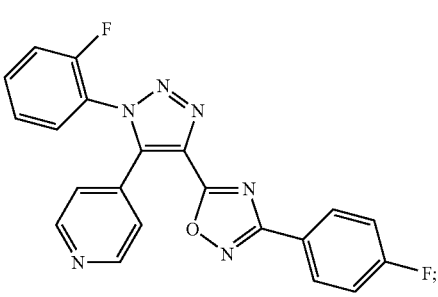
97
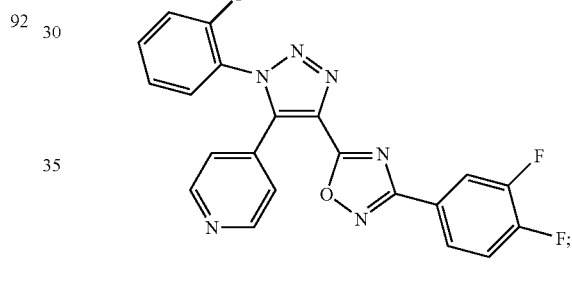
98
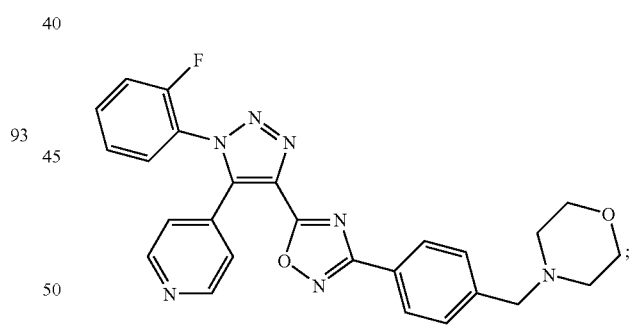
99
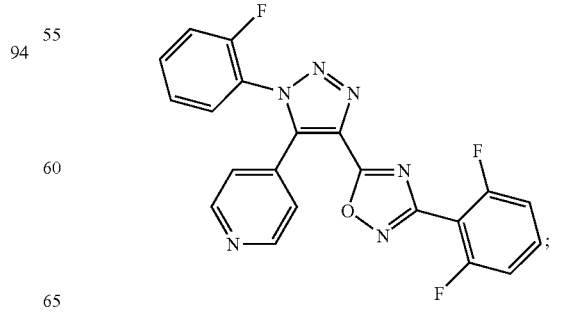

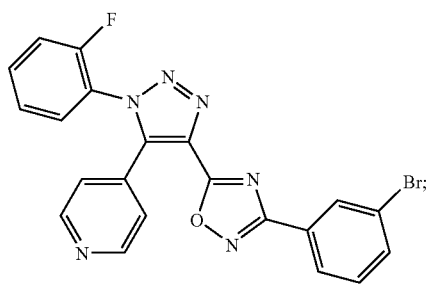
100
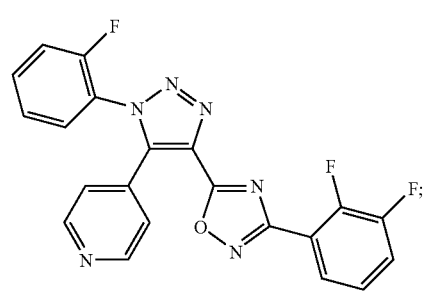
101
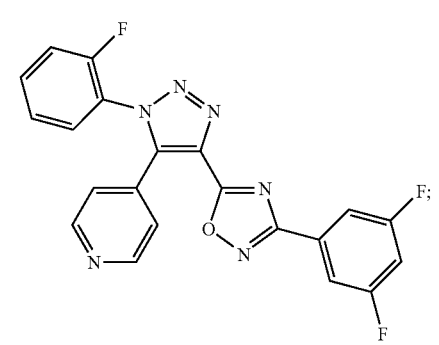
102
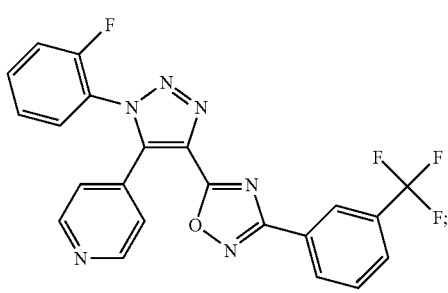
103
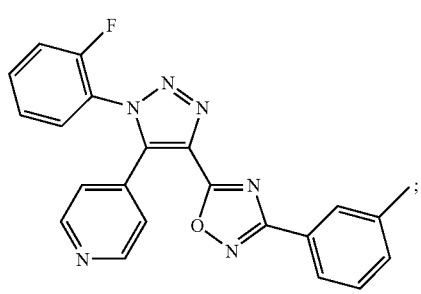
104
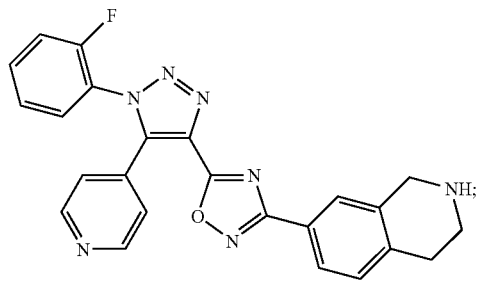
105
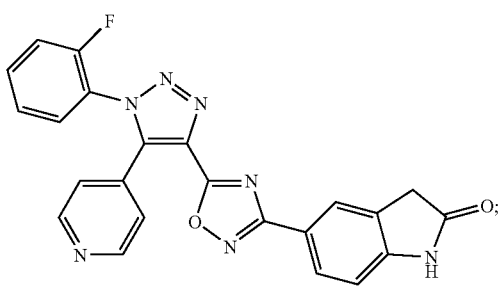
106
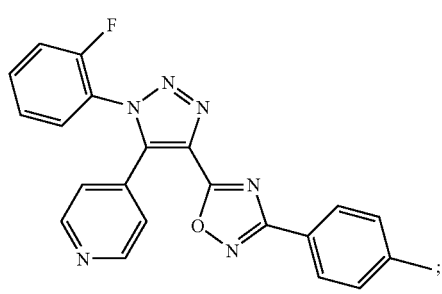
107
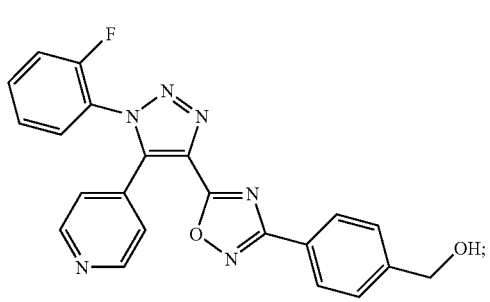
108
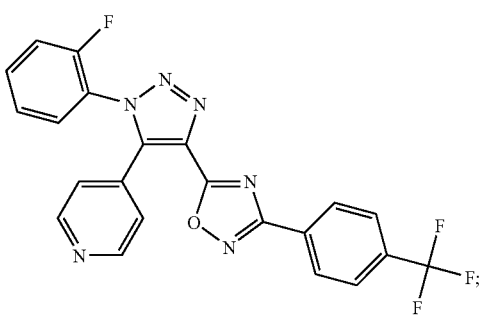
109

319
-continued
110
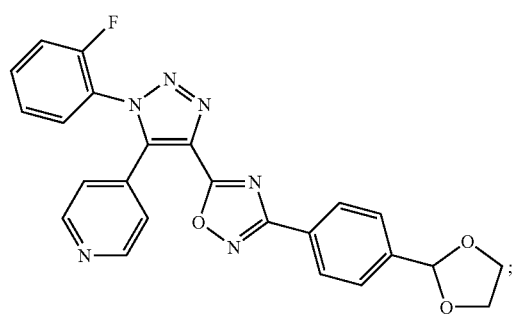
111
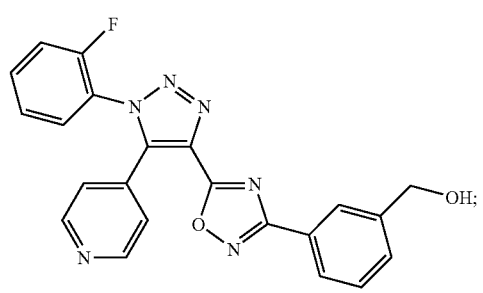
112
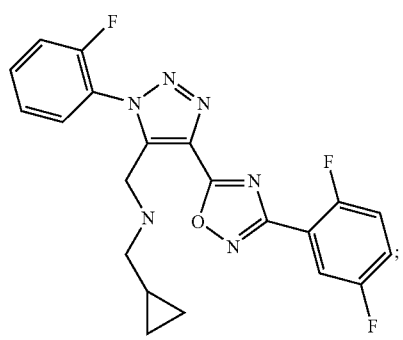
113
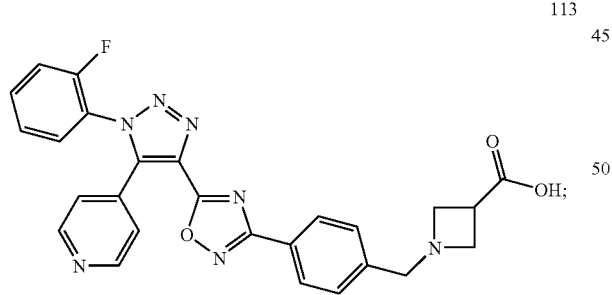
114
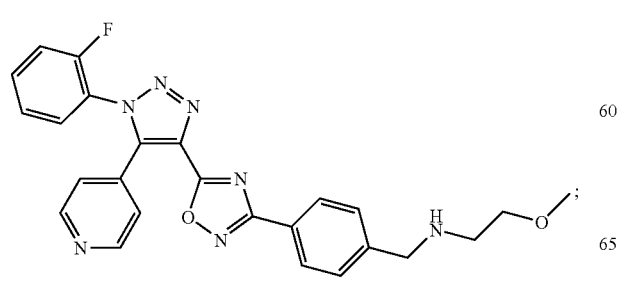
320
-continued
115
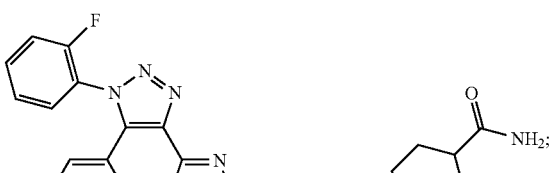
116
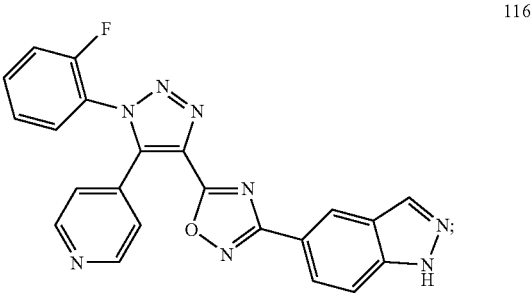
117
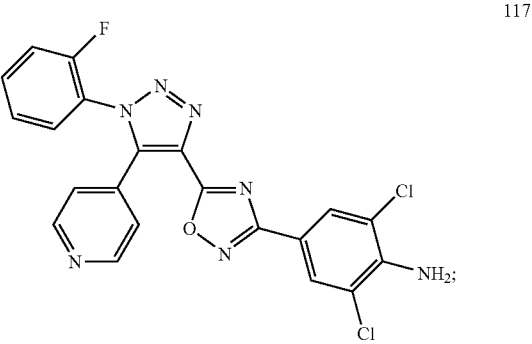
118
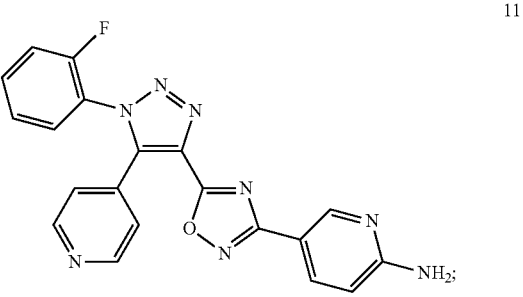
119
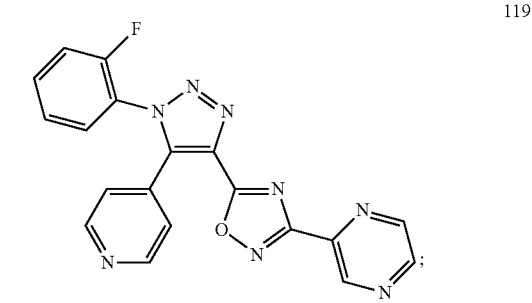

321
-continued
120
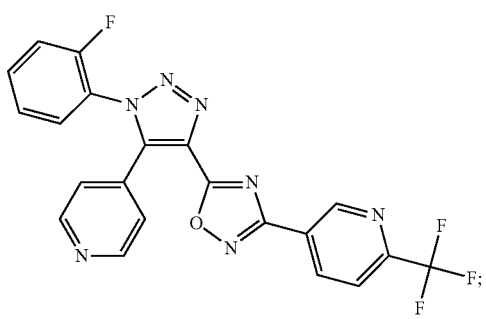
121
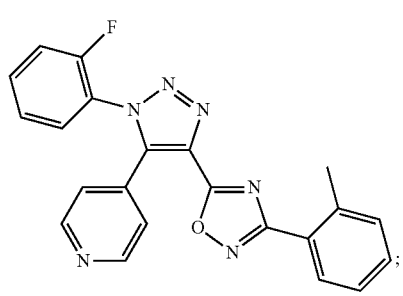
122
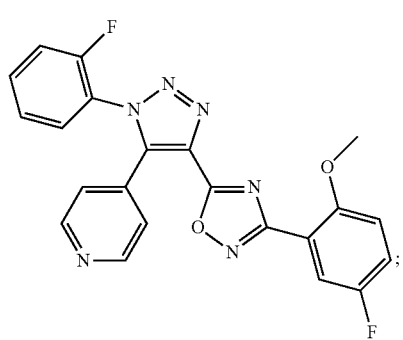
123
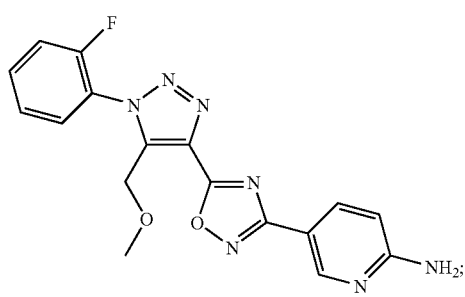
124
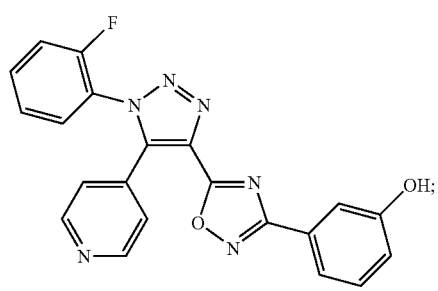
322
-continued
125
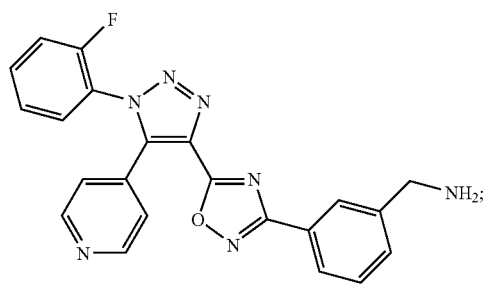
126
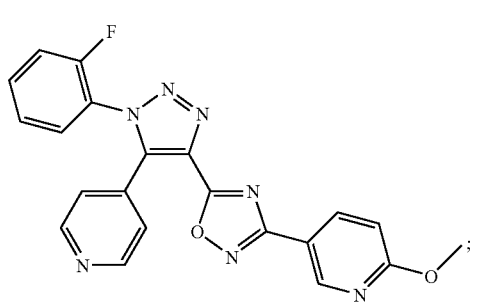
127
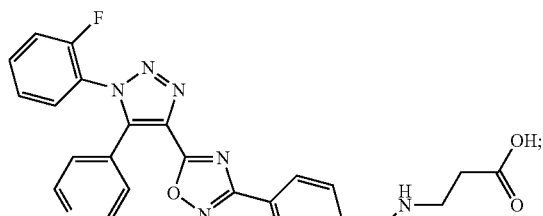
128
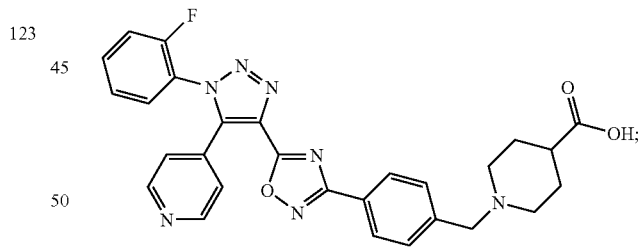
129
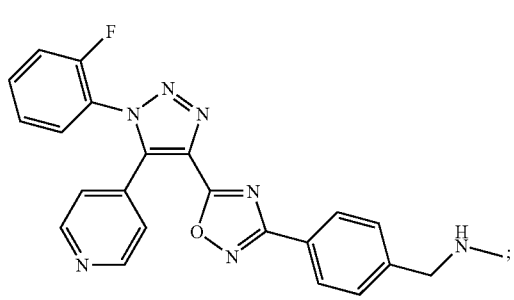

323
-continued
130
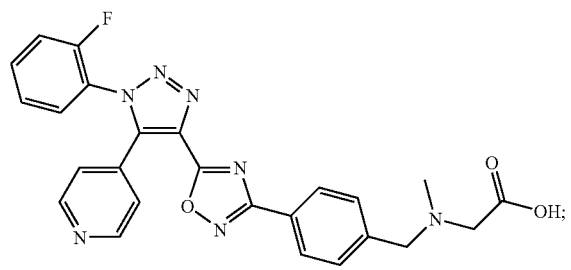
131
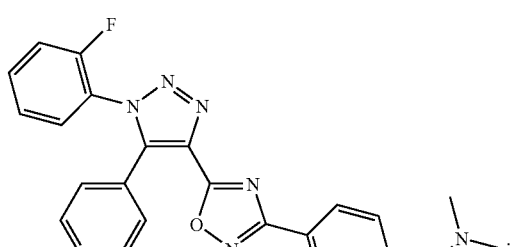
132
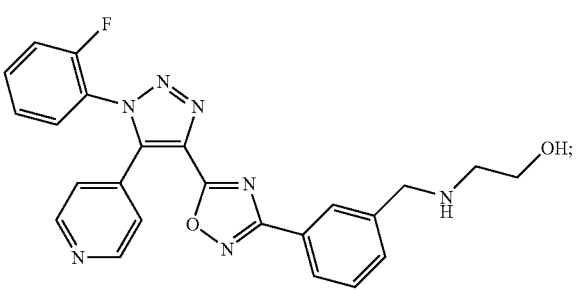
133
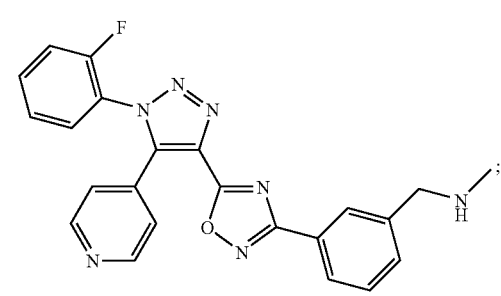
134
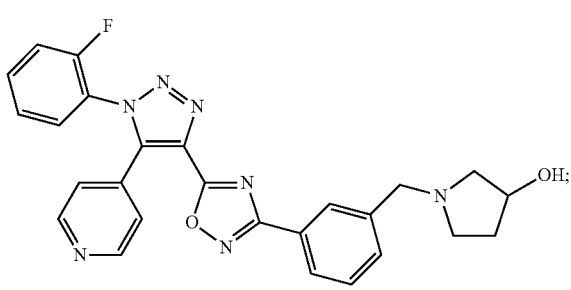
324
-continued
135
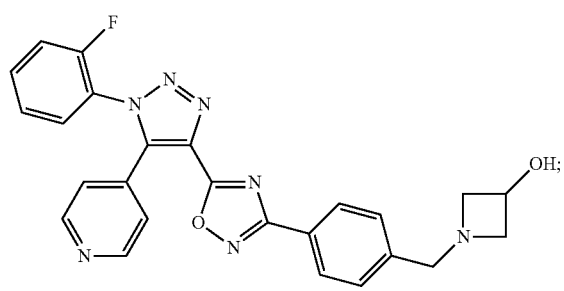
136
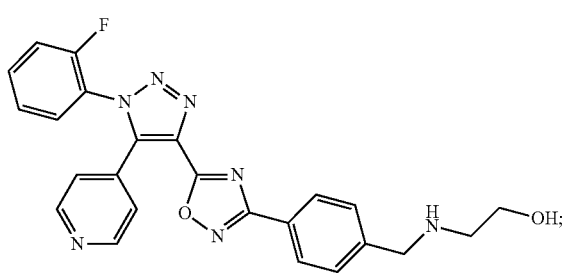
137
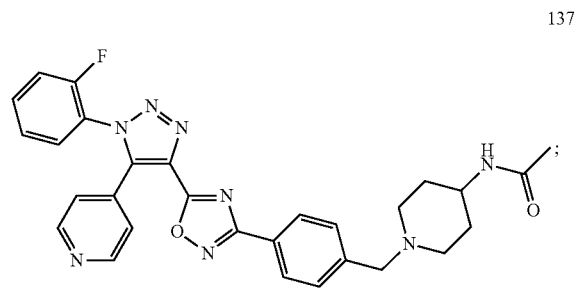
138
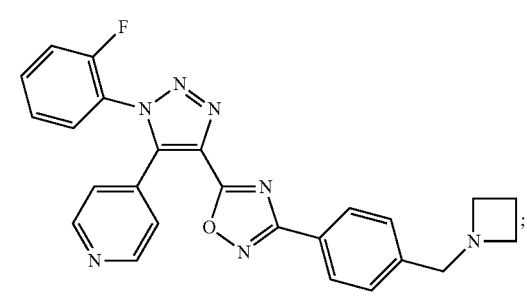
139
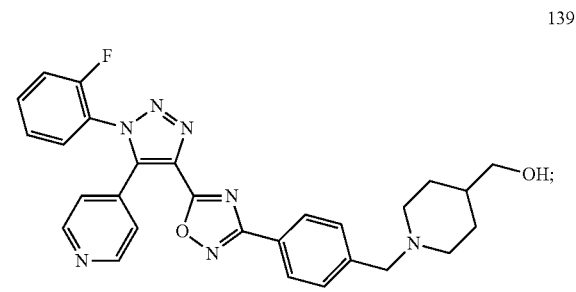

140
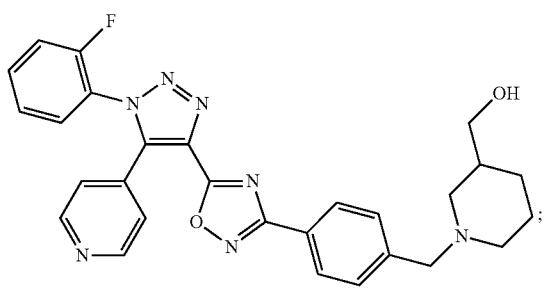
141
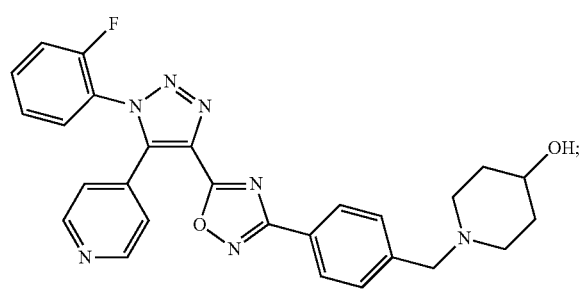
142
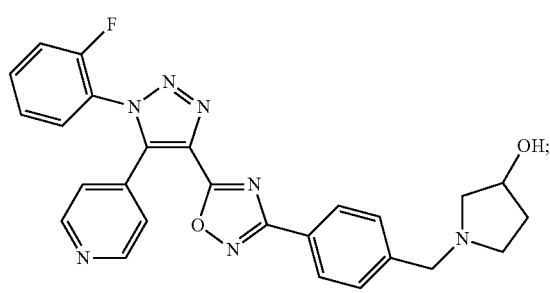
143
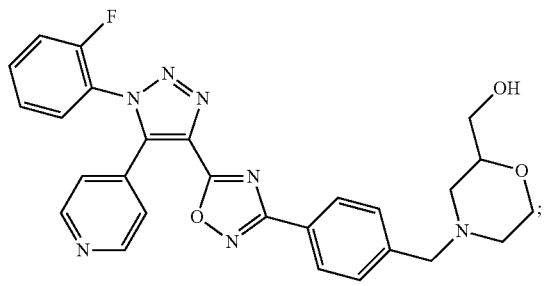
144
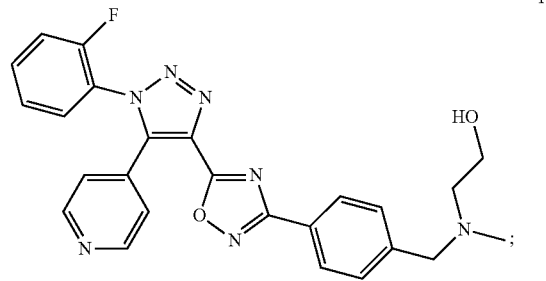
145
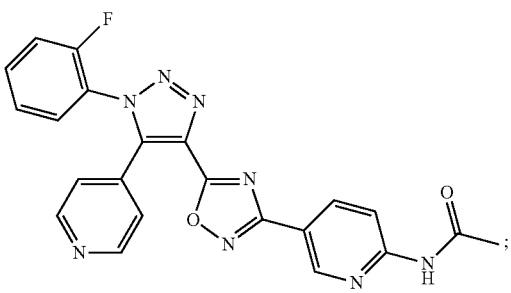
146
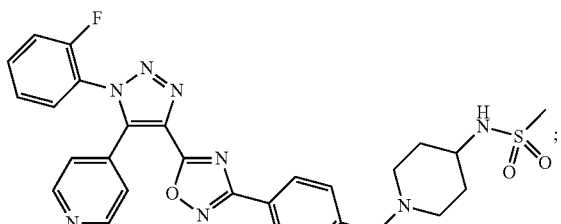
147
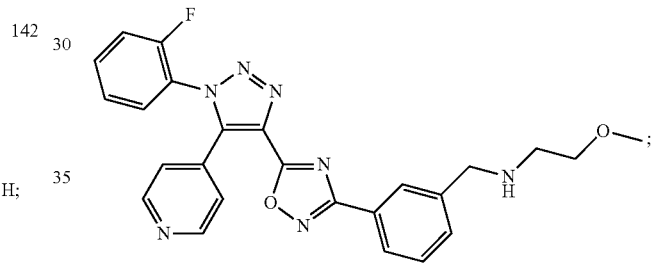
148
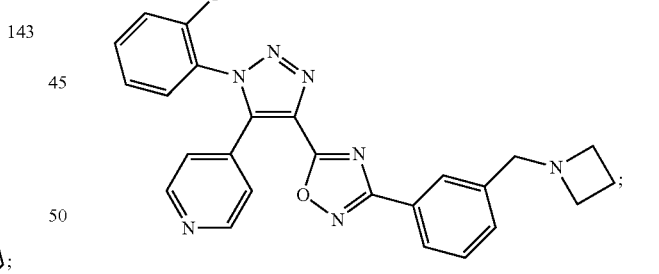
149
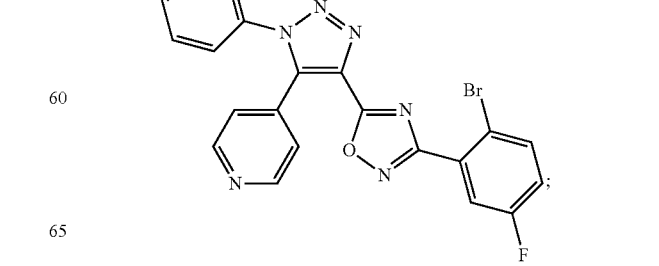

150
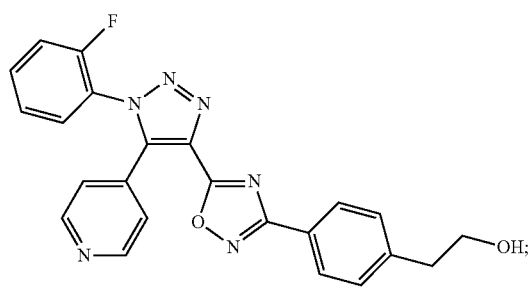
151
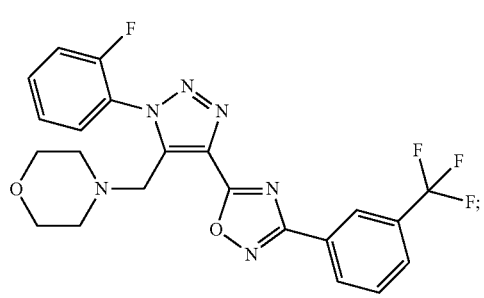
152
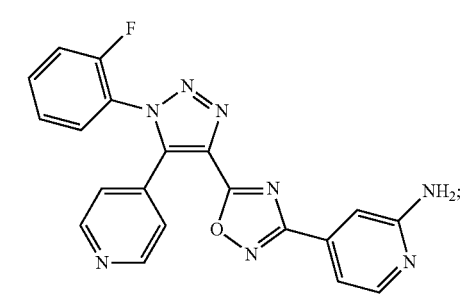
153
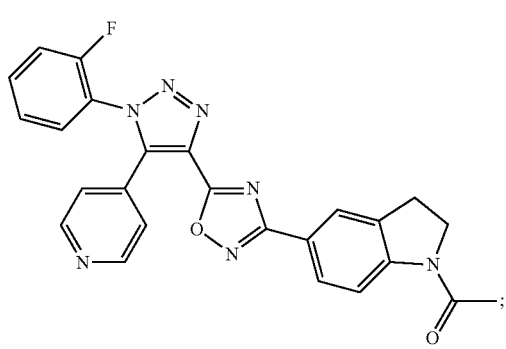
154
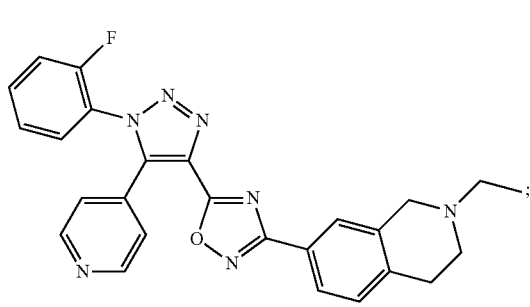
155
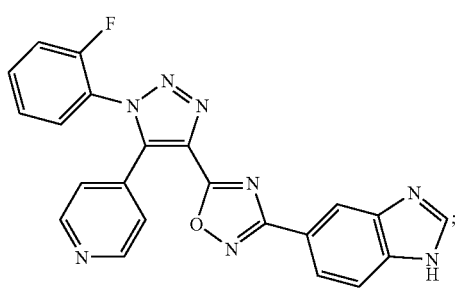
156
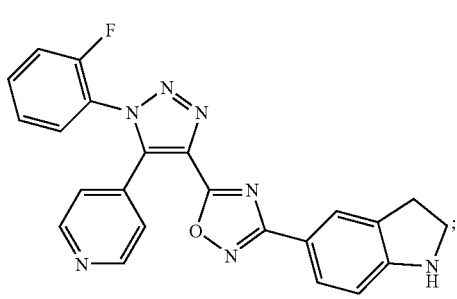
157
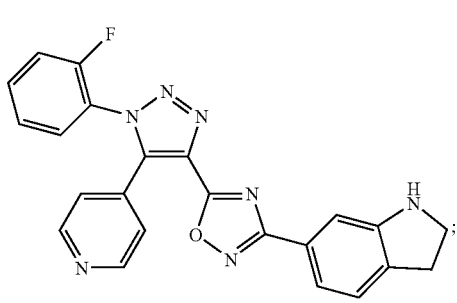
158
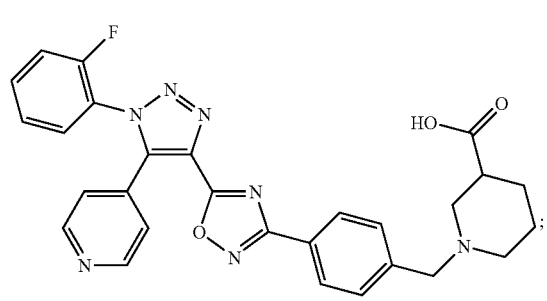
159
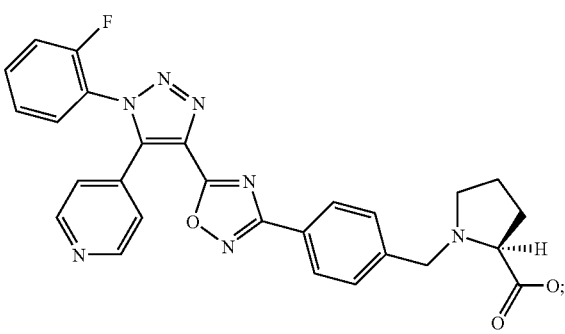

329
-continued
160
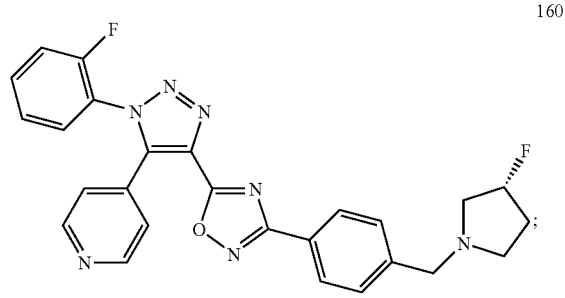
161
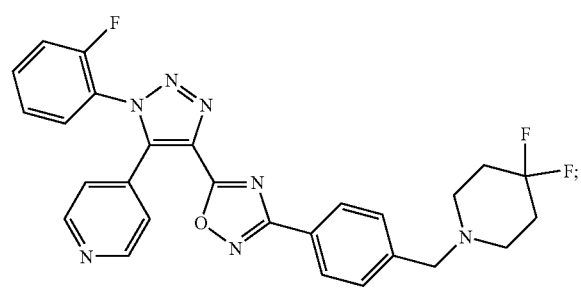
162
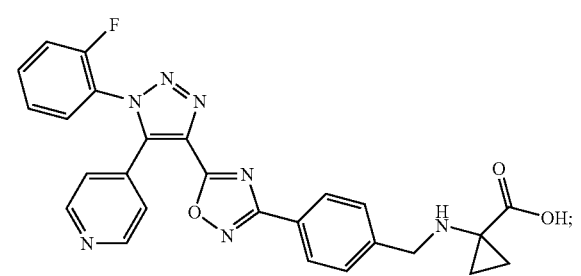
163
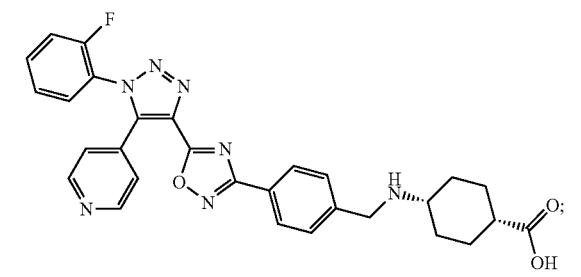
164
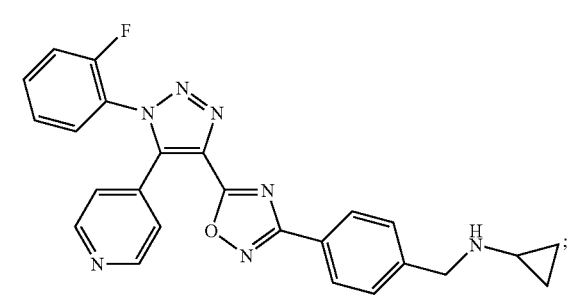
330
-continued
165
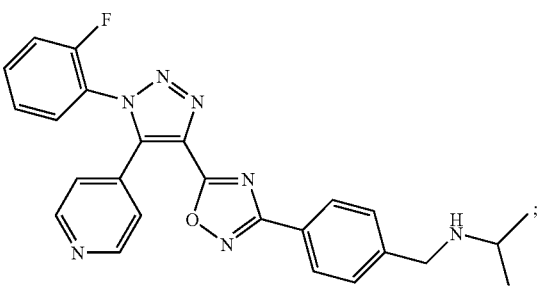
166
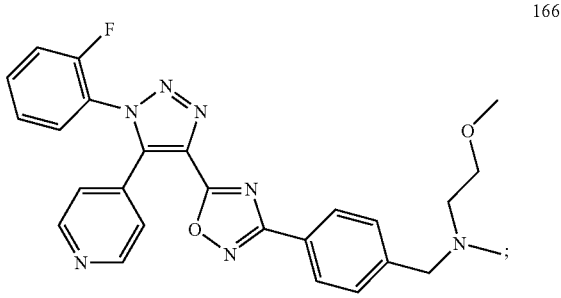
167
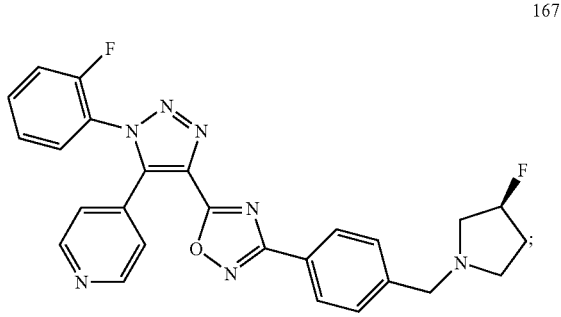
168
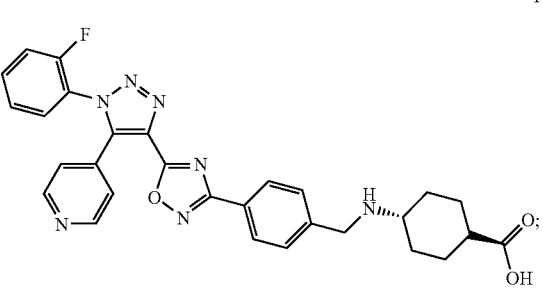
169
Chiral
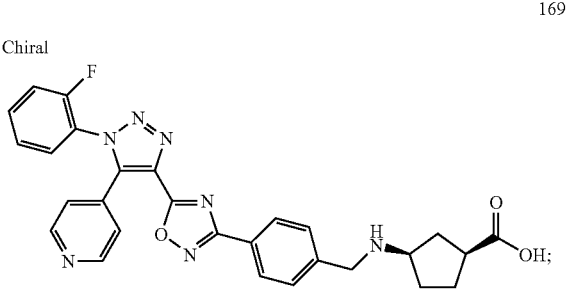

170

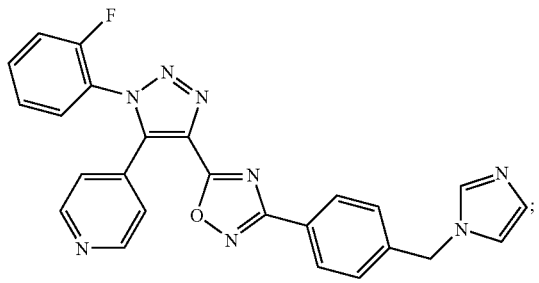

171

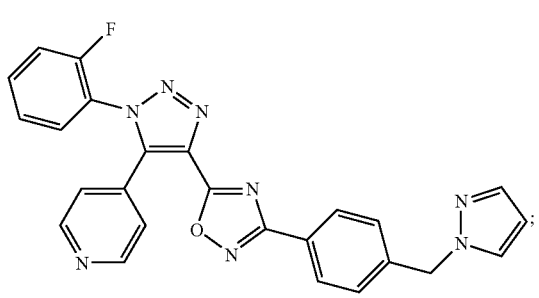

172

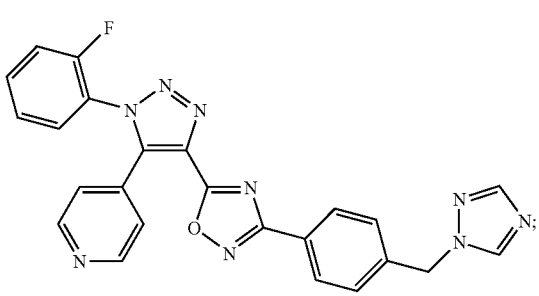

173

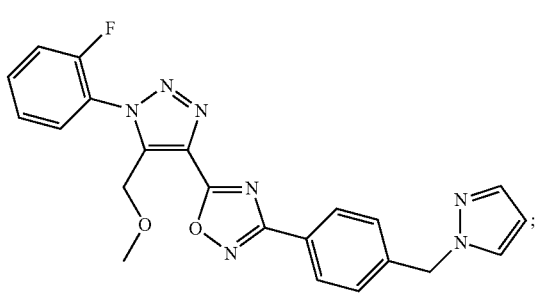

174

175

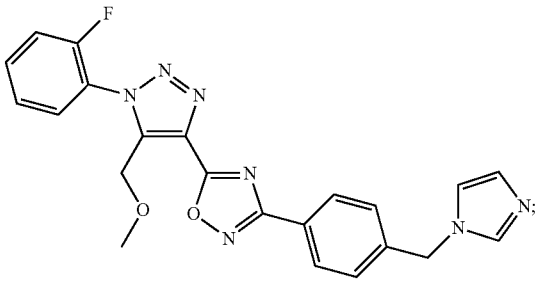

176

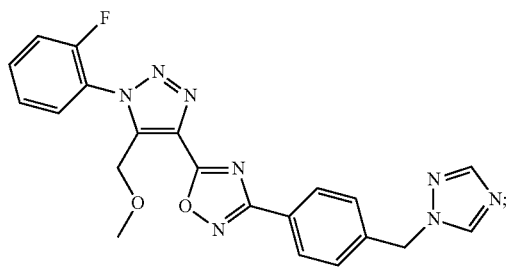

177

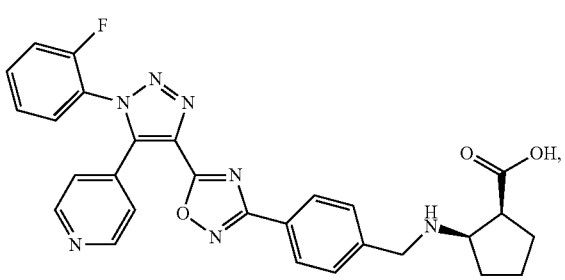

or a pharmaceutically acceptable tautomer, salt and stereoisomer thereof, including mixtures thereof.

6. The compound according to claim 1, wherein A is a branched or linear alkyl having 1 to 12 C-atoms, wherein one to seven H atoms may be replaced by Hal, $OR^3$, CN, $CO_2R^3$, cycloalkyl having 3 to 7 ring carbon atoms, or $N(R^3)_2$ and wherein one to seven non-adjacent $CH_2$-groups may be replaced by O, $NR^3$ or S and/or by —CO—, —$NR^3$CO—, —$CONR^3$—, $NR^3CO_2$—, —$NR^3CONR^3$—, —CH=CH—, —C≡C—, groups, or

or denotes cycloalkyl or cycloalkylalkylene having 3-7 ring C atoms.

7. A pharmaceutical composition comprising at least one compound according to claim 1 or a pharmaceutically acceptable tautomer, salt and stereoisomer thereof, including mixtures thereof, and optionally excipients and/or adjuvants.

8. A pharmaceutical composition comprising at least one compound according to claim 1 or a pharmaceutically acceptable tautomer, salt and stereoisomer thereof, including mixtures thereof, and at least one further active ingredient.

9. A kit comprising at least one compound according to claim 1 or a pharmaceutically acceptable tautomer, salt and stereoisomer thereof, including mixtures thereof, and at least one further active ingredient.

10. A process for the preparation of compounds of formula I according to claim 1, comprising the step of reacting compounds of formula II

(II)

with compounds of formula III or of formula V

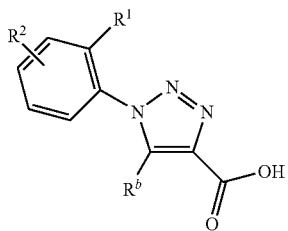
(III)

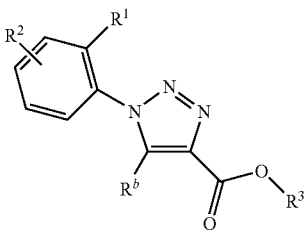
(V)

in the presence or absence of a base and a coupling agent, in a suitable solvent, heating at an elevated temperature to obtain the compound of formula I;

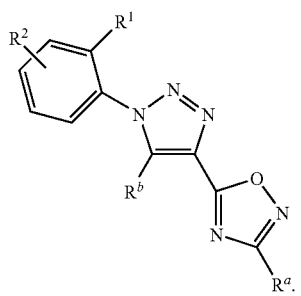
(I)

11. The process according to claim 10, wherein the solvent is chosen from a polar or apolar solvent selected from MeCN, THF, DMF, DCM, toluene or a mixture of them.

12. The process according to claim 10, wherein said heating is performed by microwave radiation.

13. A compound according to formula I:

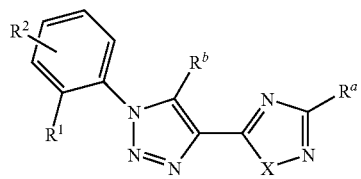
I wherein
X is O or S;
$R^1$ denotes H, Hal, $CF_3$, $OCF_3$, CN, or $NO_2$;
$R^2$ is H, A or Hal;
$R^a$ is H, A, Ar, or Het; provided that $R^3$ is not a benzo[1,3]dioxolyl group, or a phenyl group being unsubstituted or substituted by at least one methyl, F, Cl, OMe and/or OEt, if $R^b$ is a methyl group;
$R^b$ is A, Ar, Het, OA, NHA, or $NA_2$, Ar-alkyl, or Het-alkyl;
Hal is F, Cl, Br, or I;
A is a branched or linerar alkyl having 1 to 12 C-atoms, wherein one or more may be replaced by Hal, $OR^3$, CN, $CO_2R^3$, cycloalkyl having 3 to 7 ring carbon atoms, or $N(R^3)_2$ wherein one or more non-adjacent $CH_2$-groups may be replaced by O, $NR^3$ or S and/or by —CO—, —$NR^3$CO—, —$CONR^3$—, $NR^3CO_2$—, —$NR^3CONR^3$—, —CH=CH—, —C≡C—, groups, or

or denotes cycloalkyl or cycloalkylalkylene having 3-7 ring C atoms;
q is 1, 2, 3, or 4;
Ar denotes a monocylclic or bicyclic, unsaturated or aromatic carbocyclic ring having 6 to 14 carbon atoms which may be unsubstituted or monosubstituted, disubstituted or trisubstituted by a substituent selected from $R^4$ and/or $R^5$;
Ar-alkyl denotes an aryl group linked to the rest of the molecule through a $C_1$-$C_{12}$ alkylene chain;
Het denotes a monocyclic or bicyclic, saturated, unsaturated, or aromatic heterocyclic ring having 1 to 4 N, O and/or S atoms which may be unsubstituted or monosubstituted, disubstituted or trisubstituted by a substituent from $R^4$ and/or $R^5$; and wherein one or more $CH_2$ groups may be replaced by —CO—;
Het-alkyl denotes a group Het linked to the rest of the molecule through a $C_1$-$C_{12}$ alkylene chain;
$R^4$ and $R^5$ are each independently selected from A, Hal, hydroxy, alkoxy, carboxy, carboxy-alkyl, perfluoro-alkyl, perfluoro-alkoxy, acyl, alkylsulfonyl, sulfonyl, —$SO_2(R^3)_2$, cyano, nitro, amino, amido, alkyl optionally substituted by a carboxy, —$N(R^3)_2$, —$CO(NR^3)_2$, —$OR^3$, $(NR^3)COR^3$, —$CO_2R^3$, —$COR^3$, or Ar-alkyl or Het-alkyl both optionally substituted by A, Hal, an acyl, alkylsulfonyl, carboxy, —$N(R^3)_2$, —$CONR(R^3)_2$, —$OR^3$, $(NR^3)COR^3$, —$CO_2R^3$, —$COR^3$, —$SO_2N(R^3)_2$, —$SO_2$alkyl, $NR^3SO_2$alkyl, $NR^3SO_2$alkyl,

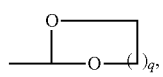
or $C_1$-$C_6$ alkyl;
$R^3$ is H or A;
or a pharmaceutically acceptable tautomer, salt, or stereoisomer thereof, including mixtures thereof.
* * * * *

UNITED STATES PATENT AND TRADEMARK OFFICE
CERTIFICATE OF CORRECTION

PATENT NO.         : 8,202,856 B2
APPLICATION NO.    : 12/809816
DATED              : June 19, 2012
INVENTOR(S)        : Anna Quattropani et al.

Page 1 of 7

It is certified that error appears in the above-identified patent and that said Letters Patent is hereby corrected as shown below:

Title Page,
Item (57) Abstract, "claim 16." should read --claim 1.--.

Column 3,
Line 21, "Crohn's diseases" should read --Crohn's disease--.
Line 40, "The inventions" should read --The invention--.
Line 47, "mycophenolic add" should read --mycophenolic acid--.

Column 6,
Line 3, "Schem 1a" should read --Scheme 1a--.
Line 54, "can be used or" should read --can be used for--.

Signed and Sealed this
Nineteenth Day of February, 2013

Teresa Stanek Rea
*Acting Director of the United States Patent and Trademark Office*

CERTIFICATE OF CORRECTION (continued)
U.S. Pat. No. 8,202,856 B2

Columns 9-10, Scheme 5, "

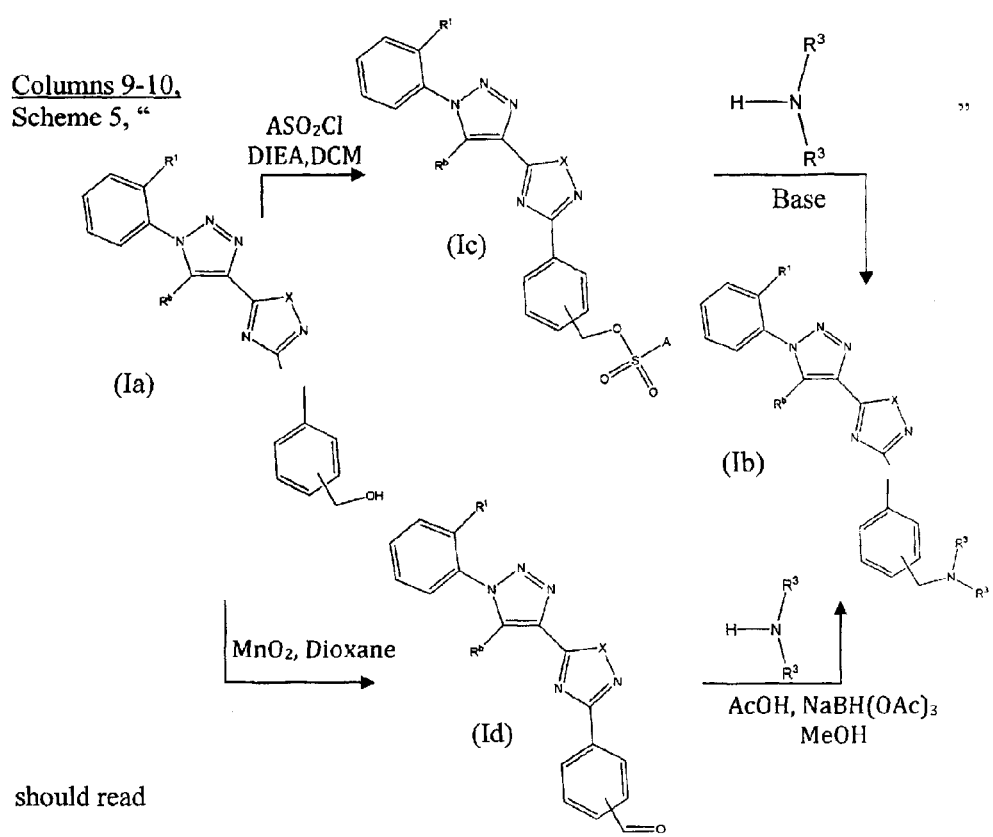

should read

--

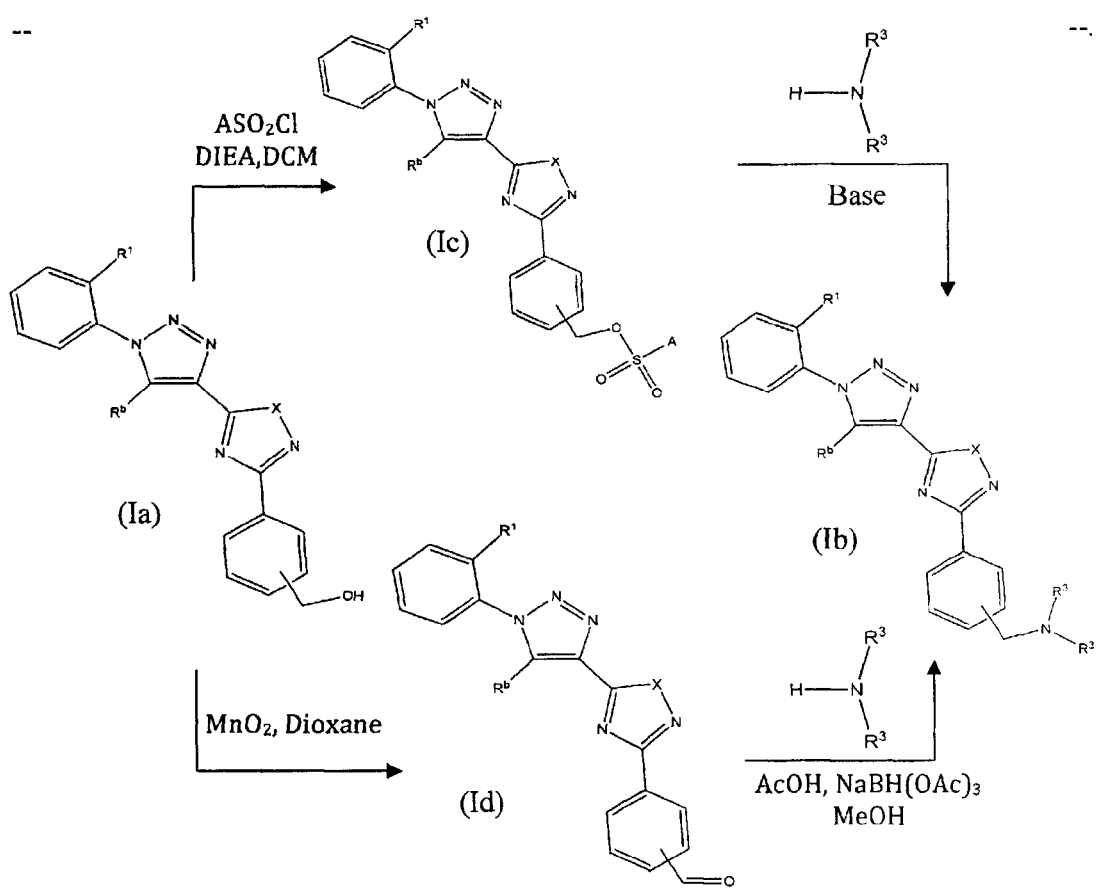

--.

CERTIFICATE OF CORRECTION (continued)
U.S. Pat. No. 8,202,856 B2

Column 19,
Line 3, "of a —COON group" should read --of a —COOH group--.

Column 22,
Line 1, "$R^b$Het," should read --$R^b$, Het,--.

Column 63,
Line 47, "1,2,2-trimethylpropyl" should read --1,2,2-trimethylpropyl.--.

Column 64,
Line 14, "a group —COON" should read --a group —COOH--.

Column 67,
Lines 42-47, "Hal, $C_1$-$C_6$alkyl, —$CF_3$, —$(CH_2)_n OR^3$, —$(CH_2)_n COOR^3$, —$SO_2Me$, —$SO_2N(R^3)_2$, —$COR^S$, —$CO(NR^3)_2$, —$(CH_2)_n COOtBu$, —$(CH_2)_n N(R^3)_2$, —$(CH_2)_n OH$, —$(CH_2)_n N(R^3)(CH_2)_p OR^3$, $(CH_2)_n N(R^3)(CH_2)_p COOR^3$, —$NHCOR^3$, $NHSO_2R^3$, $NHSO_2R^3$, —$(CH_2)_n N(R^3)(CH_2)_p COOR^3$, —$NHCOR^3$, $NHSO_2R^3$, 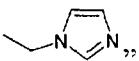
should read --Hal, $C_1$-$C_6$alkyl, —$CF_3$, —$(CH_2)_n OR^3$, —$(CH_2)_n COOR^3$, —$SO_2Me$, —$SO_2N(R^3)_2$, —$COR^3$, —$CO(NR^3)_2$, —$(CH_2)_n COOtBu$, —$(CH_2)_n N(R^3)_2$, —$(CH_2)_n OH$, —$(CH_2)_n N(R^3)(CH_2)_p OR^3$, —$(CH_2)_n N(R^3)(CH_2)_p COOR^3$, —$NHCOR^3$, $NHSO_2R^3$,

 --.

Column 68,
Line 33, "independently from one other" should read --independent from one another--.

Column 73,
Line 28, "as above;" should read --as above.--.
Line 31, "a heterocyclic" should read --a monocyclic saturated heterocyclic--.
Line 43, "is O S and" should read --is O or S, and--.

Column 74,
Line 7, "piperzinyl" should read --piperazinyl--.

Column 75,
Line 43, "$R^b$Het" should read --$R^b$ is Het--.
Line 45, "embodiments" should read --embodiment--.
Line 55, "embodiments" should read --embodiment--.
Line 65, "embodiments" should read --embodiment--.

Column 76,
Line 1, "embodiments" should read --embodiment--.
Line 4, "embodiments" should read --embodiment--.
Line 8, "embodiments" should read --embodiment--.
Line 11, "embodiments" should read --embodiment--.
Line 14, "embodiments" should read --embodiment--.

CERTIFICATE OF CORRECTION (continued)
U.S. Pat. No. 8,202,856 B2

Column 77,
Line 63, "magnesium. salts" should read --magnesium. Salts--.

Column 79,
Line 59, "mycophenolic add;" should read --mycophenolic acid;--.

Column 87,
Line 2, "embodiment" should read --embodiments--.
Lines 4-5, "provide a compound according to any one of embodiment" should read
--provides a compound according to any one of embodiments--.
Line 42, "by 0;" should read --by O;--.

Column 88,
Line 4, "embodiments 14" should read --embodiment 14--.

Column 90,
Line 60, "GTPTS" should read --GTPγS--.

Column 91,
Line 39, "B-ACN" should read --B-ACN.--.

Column 92,
Line 4, "HPLC" should read --UPLC--.

Column 93,
Line 50, "GC/MS R," should read --GC/MS Rt--.

Column 98,
Line 45, "$(M+1-1)^+$." should read --$(M+H)^+$.--.

Column 101,
Line 47, "$(M+1-1)^+$." should read --$(M+H)^+$.--.

Column 106,
Line 65, "(DMSO-d6," should read --(DMSO-$d_6$,--.

Column 109,
Line 40, "4-[amino(hydroxyimino)methyl]benzaide" should read
--4-[amino(hydroxyimino)methyl]benzamide--.

Column 130,
Lines 40-41, "5-5-[5-Butyl-1-(2-fluorophenyl)-1H-1,2,3-triazole-4-yl]-3-(2-
fluorophenyl)-1,2,4-oxadiazole" should read --5-[5-Butyl-1-(2-fluorophenyl)-1H-1,2,3-
triazole-4-yl]-3-(2-fluorophenyl)-1,2,4-oxadiazole--.

Column 143,
Lines 35-36, "sat. eq." should read --sat. aq.--.

Column 145,
Lines 25-46, "

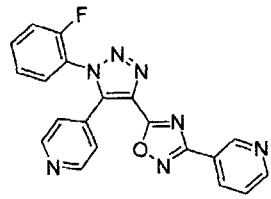

Isobutyl"

should read

--

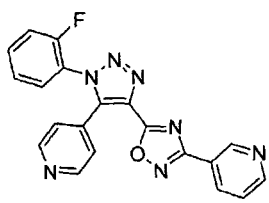

Sodium salt of Intermediate 16 (91.87 mg; 0.30 mmol; 1.00 eq.) was dissolved in anhydrous ACN (5 mL) under nitrogen and the suspension was cooled down to -40°C. Isobutyl--.

Column 153,
Lines 37-38, "(Flrochem" should read --(Fluorochem--.

Column 156,
Line 32, "(CDCl3" should read --(CDCl$_3$--.
Line 65, "(CDCl3" should read --(CDCl$_3$--.

Column 158,
Line 32, "(Flrochem" should read --(Fluorochem--.
Line 33, "(CDCl3" should read --(CDCl$_3$--.
Line 64, "(CDCl3" should read --(CDCl$_3$--.

Column 159,
Line 63, "(CDCl3" should read --(CDCl$_3$--.

Column 161,
Line 28, "(Flrochem" should read --(Fluorochem--.

Column 162,
Line 6, "carbamte" should read --carbamate--.

Column 164,
Line 32, "2.2.5-2.10" should read --2.25-2.10--.

Column 169,
Lines 4-5, "4-{1-(2-fluorophenyl)-4-[3-(3-furyl)-1,2,4-oxadiazol-5-yl]-1H-1,2,3-triazol--yl}pyridine" should read --4-{1-(2-fluorophenyl)-4-[3-(3-furyl)-1,2,4-oxadiazol-5-yl]-1H-1,2,3-triazol-5-yl}pyridine--.

Column 171,
Lines 22-24, "3-(2,5-difluorophenyl)-5-[1-(2-fluorophenyl)-5-(pyrrolidin-1-ylmethyl)-1H-1,2,3-triazol-4-yl]-1,2,4-oxadiazle" should read --3-(2,5-difluorophenyl)-5-[1-(2-fluorophenyl)-5-(pyrrolidin-1-ylmethyl)-1H-1,2,3-triazol-4-yl]-1,2,4-oxadiazole--.

Column 191,
Line 21, "                    " should read --                    --.

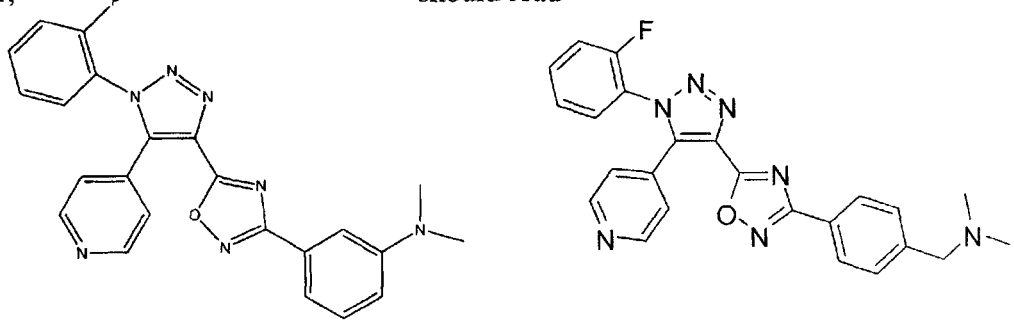

Column 209,
Line 45, "486 (M+HPLC (Method I)" should read --486 (M + H)$^+$. HPLC (Method I)--.

Column 212,
Lines 3-4, "4-(1H-1,2,4-triazol-1-yl)methyl)-N'-hydroxybenzimidamide" should read --4-((1H-1,2,4-triazol-1-yl)methyl)-N'-hydroxybenzimidamide--.

Column 213,
Lines 49-50, "4-(1H-imidazol-1-yl)methyl)-N'-hydroxybenzimidamide" should read --4-((1H-imidazol-1-yl)methyl)-N'-hydroxybenzimidamide--.

Column 214,
Lines 25-26, "4-(1H-1,2,4-triazol-1-yl)methyl)-N'-hydroxybenzimidamide" should read --4-((1H-1,2,4-triazol-1-yl)methyl)-N'-hydroxybenzimidamide--.

Column 215,
Line 7, "35S-GTPTS" should read --35S-GTPγS--.
Line 24, "25 μM or 10 μM" should read --25 pM or 10 pM--.

Column 287,
Line 53, "erythocytes" should read --erythrocytes--.

CERTIFICATE OF CORRECTION (continued)
U.S. Pat. No. 8,202,856 B2

Column 298,
Structure "18",
" 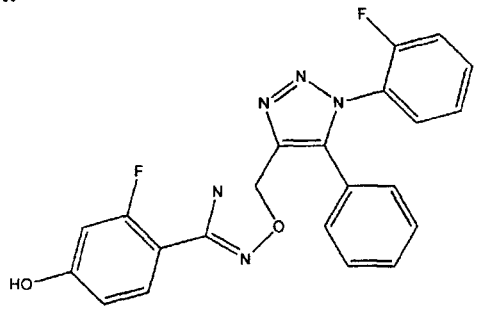 " should read -- 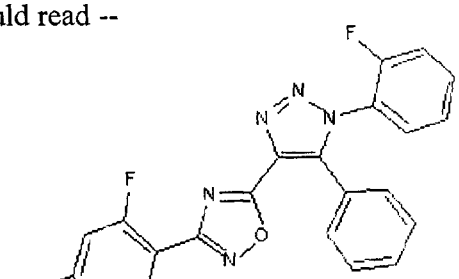 --.

Column 334,
Line 17, "that $R^3$ is not" should read --that $R^a$ is not--.
Line 24, "linerar alkyl" should read --linear alkyl--.